(12) United States Patent
Oku et al.

(10) Patent No.: US 6,573,274 B1
(45) Date of Patent: Jun. 3, 2003

(54) SULFONAMIDE COMPOUNDS AND USES THEREOF AS MEDICINES

(75) Inventors: Teruo Oku, deceased, late of Tokyo (JP), by Noriko Oku, Chikako Oku, Tomohito Oku, heirs; Hiroshi Kayakiri, Suita (JP); Yoshito Abe, Tsukuba (JP); Hitoshi Hamashima, Kyoto (JP); Hitoshi Sawada, Tsukuba (JP); Naoki Ishibashi, Tsukuba (JP); Hiroyuki Setoi, Ibaraki (JP); Noritsugu Yamasaki, Himeji (JP); Takafumi Imoto, Arai (JP); Takahiro Hiramura, Tsukuba (JP)

(73) Assignee: Fujisawa Pharmaceutical Co. Ltd., Osaka (JP)

( * ) Notice: Subject to any disclaimer, the term of this patent is extended or adjusted under 35 U.S.C. 154(b) by 0 days.

(21) Appl. No.: 09/856,172

(22) PCT Filed: Dec. 1, 1999

(86) PCT No.: PCT/JP99/06748

§ 371 (c)(1),
(2), (4) Date: Sep. 12, 2001

(87) PCT Pub. No.: WO00/34277

PCT Pub. Date: Jun. 15, 2000

(30) Foreign Application Priority Data

| Dec. 4, 1998 | (JP) | 10-346175 |
| Dec. 24, 1998 | (JP) | 10-367540 |
| Aug. 9, 1999 | (JP) | 11-259283 |

(51) Int. Cl.[7] .................. A61K 31/437; C07D 47/104
(52) U.S. Cl. .................. 514/303; 546/118
(58) Field of Search .................. 514/303; 546/118

(56) References Cited

U.S. PATENT DOCUMENTS

| 5,215,994 A | 6/1993 | Oku et al. |
| 6,166,219 A | 12/2000 | Yamasaki et al. |
| 6,242,474 B1 | 6/2001 | Yamasaki et al. |
| 6,348,474 B1 | 2/2002 | Kayakiri et al. |

FOREIGN PATENT DOCUMENTS

| EP | 0 503 838 A2 | 9/1992 |
| EP | 0 510 813 A1 | 10/1992 |
| WO | WO 93/19067 | 9/1993 |
| WO | WO 99/00372 | 1/1999 |

OTHER PUBLICATIONS

H. T. Beauchamp, et al., The Journal of Pharmacology and Experimental Therapeutics, vol. 272, No. 2, pp. 612–618, "In Vivo Receptor Occupancy of the Angiotensin II Receptor By Nonpeptide Antagonists: Relationship to in Vitro Affinities and In Vivo Pharmacologic Potency," 1995.

*Primary Examiner*—Charanjit S. Aulakh
(74) *Attorney, Agent, or Firm*—Oblon, Spivak, McClelland, Maier & Neustadt, P.C.

(57) ABSTRACT

The present invention relates to a sulfonamide compound of the formula (I):

(I)

wherein each symbol is as defined in the specification, a salt thereof, and a pharmaceutical composition containing same. This compound can be an effective agent for the prophylaxis and treatment of the diseases curable based on a hypoglycemic action, and the diseases curable based on a cGMP-PDE inhibitory action, a smooth muscle relaxing action, a bronchodilating action, a vasodilating action, a smooth muscle cell inhibitory action and an allergy suppressing action.

45 Claims, No Drawings

SULFONAMIDE COMPOUNDS AND USES THEREOF AS MEDICINES

This application is a 371 of PCT/JP99/06748 filed Dec. 1, 1999, now WO 00/34277 Jun. 15, 2000.

TECHNICAL FIELD

The present invention relates to novel sulfonamide compounds. More particularly, the present invention relates to novel sulfonamide compounds and salts thereof having hypoglycemic activity or PDE-V inhibitory activity. The present invention also relates to a method for producing the above-mentioned sulfonamide compound and salts thereof. Moreover, The present invention relates to pharmaceutical compositions comprising the above-mentioned sulfonamide compound or a salt thereof as an active ingredient.

DISCLOSURE OF THE INVENTION

The present invention aims at providing novel sulfonamide compounds, pharmaceutically acceptable salts thereof and pharmaceutical preparations comprising the above-mentioned sulfonamide compound or a pharmaceutically acceptable salt thereof as an active ingredient, which are used as an agent for the prophylaxis and treatment of impaired glucose tolerance disorder, diabetes (e.g., type II diabetes), gestational diabetes, diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy and the like), insulin resistance syndrome (e.g., insulin receptor abnormality, Rabson-Mendenhall syndrome, leprechaunism, Kobberling-Dunnigan syndrome, Seip syndrome, Lawrence syndrome, Cushing syndrome, acromegaly and the like), polycystic ovary syndrome, hyperlipidemia, atherosclerosis, cardiovascular diseases (e.g., stenocardia, cardiac failure and the like), hyperglycemia (e.g., those characterized by abnormal saccharometabolism such as eating disorders), pancreatitis, osteoporosis, hyperuricemia, hypertension, inflammatory bowel diseases, and skin disorders related to an anomaly of differentiation of epidermic cells; and which, based on the cGMP-PDE (particularly PDE-V) inhibitory action, smooth muscle relaxing action, bronchodilating action, vasodilating action, smooth muscle cell inhibitory action, allergy suppressing action and the like, are used as prophylactic and therapeutic agents for angina pectoris, hypertension, pulmonary hypertension, congestive heart failure, glomerulopathy (e.g., diabetic glomerulosclerosis), tubulointerstitial disorders (e.g., kidney diseases induced by FK506, cyclosporin and the like), renal failure, atherosclerosis, angiostenosis (e.g., after percutaneous arterioplasty), peripheral vascular diseases, cerebral apoplexy, chronic reversible obstructive impairment (e.g., bronchitis, asthma inclusive of chronic asthma and allergic asthma), autoimmune diseases, allergic rhinitis, urticaria, glaucoma, diseases characterized by impaired intestinal motility (e.g., irritable bowel syndrome), impotence (e.g., organic impotence, psychic impotence and the like), nephritis, cancer cachexia, restenosis after PTCA, cachexia (e.g., progressive weight loss due to lipolysis, myolysis, anemia, edema, anorexia and the like in chronic diseases such as cancer, tuberculosis, endocrine diseases and AIDS), and the like.

The sulfonamide compound, which is the novel compound of the present invention, is expressed by the formula (I):

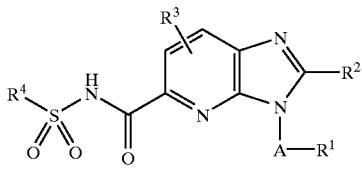

wherein
$R^1$ is an aryl or heterocyclic group substituted by at least one substituent selected from the group consisting of (1) aryl, (2) a heterocyclic group optionally substituted by oxo or halogen, (3) halogen, (4) halo(lower)alkyl, (5) lower alkoxy optionally substituted by cyclo(lower)alkyl, (6) amino optionally substituted by at least one substituent selected from the group consisting of lower alkyl optionally substituted by cyclo(lower)alkyl, protected carboxy, acyl, lower alkylcarbamoyl, and lower alkanesulfonyl, (7) nitro and (8) lower alkynyl optionally substituted by aryl, $R^2$ is a lower alkyl or lower alkoxy, $R^3$ is a hydrogen or lower alkyl, $R^4$ is a lower alkenyl optionally substituted by aryl or heterocyclic group, aryl optionally substituted by carboxy or protected carboxy, lower alkyl optionally substituted by acyloxy, amino optionally substituted by lower alkyl, or heterocyclic group optionally substituted by halogen, and A is a lower alkylene

[hereinafter to be also referred to as the objective compound (I)].

Preferred salts of the objective compound (I) are conventional salts that are non-toxic and acceptable for use as pharmaceuticals. Examples thereof include salts with alkali metal such as sodium and potassium, salts with alkaline earth metal such as calcium and magnesium, salts with inorganic base such as ammonium salt, salts with organic amine such as triethylamine, pyridine, picoline, ethanolamine and triethanolamine, salts with inorganic acid such as hydrochloric acid, hydrobromic acid, sulfuric acid and phosphoric acid, salts with organic carboxylic acid such as formic acid, acetic acid, trifluoroacetic acid, maleic acid and tartaric acid, addition salts with sulfonic acid such as methanesulfonic acid, benzenesulfonic acid and p-toluenesulfonic acid, and salts or acid addition salts with base such as basic or acidic amino acid such as arginine, aspartic acid and glutamic acid.

The objective compound (I) and a salt thereof of the present invention can be produced by the method shown by the following reaction formulas.

PRODUCTION METHOD 1

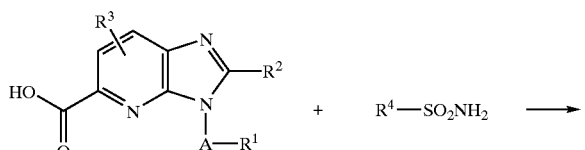

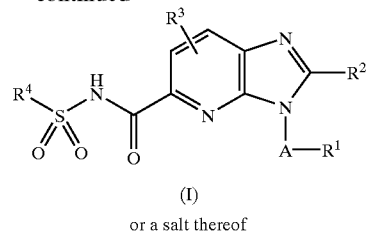

(I)

or a salt thereof wherein each symbol in the formula is as defined above.

The objective compound (I) and a salt thereof of the present invention can be also produced by the method shown by the following reaction formulas.

PRODUCTION METHOD 2

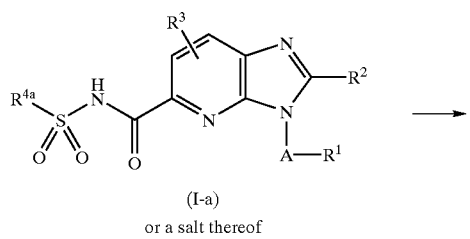

(I-a)

or a salt thereof

↓

(I-b)

or a salt thereof wherein $R^{4a}$ is aryl substituted by at least one protected carboxy, $R^{4b}$ is aryl substituted by at least one carboxy, and other symbols are as defined above.

PRODUCTION METHOD 3

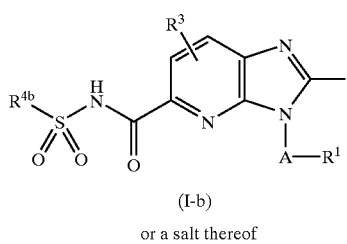

(I-c)

or a salt thereof

↓

(I-d)

or a salt thereof wherein $R^{1a}$ is aryl or heterocyclic group substituted by at least one amino substituted by at least one protected carboxy, $R^{1b}$ is aryl or heterocyclic group substituted by at least one unsubstituted or monosubstituted amino, and other symbols are as defined above.

PRODUCTION METHOD 4

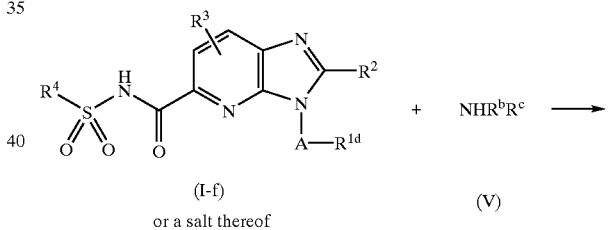

(I-d)               (IV)

or a salt thereof

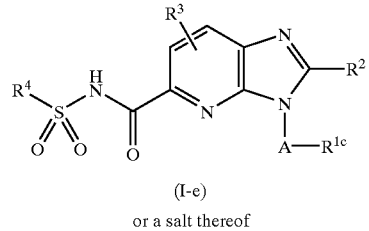

(I-e)

or a salt thereof wherein $R^a$ is hydrogen or lower alkyl optionally substituted by cyclo(lower)alkyl, $R^{1c}$ is aryl or heterocyclic group substituted by at least one amino substituted by at least one lower alkyl optionally substituted by cyclo(lower)alkyl, and other symbols are as defined above.

PRODUCTION METHOD 5

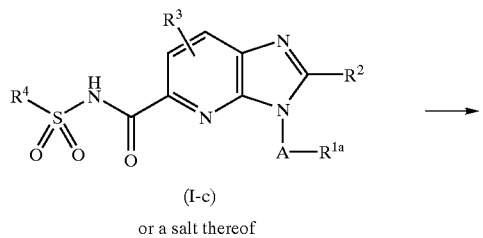

(I-f)              (V)

or a salt thereof

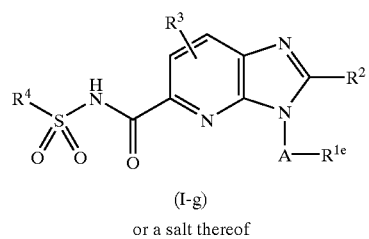

(I-g)

or a salt thereof wherein $R^{1d}$ is aryl or heterocyclic group substituted by at least one halogen, $R^b$ and $R^c$ are each independently hydrogen, lower alkyl optionally substituted by cyclo(lower)alkyl, protected carboxy, acyl or lower alkanesulfonyl, $R^{1e}$ is aryl or heterocyclic group substituted by at least one amino optionally substituted by at least one substituent selected from the group consisting of lower alkyl optionally substituted by cyclo(lower)alkyl, protected carboxy, acyl and lower alkanesulfonyl, and other symbols are as defined above.

PRODUCTION METHOD 6

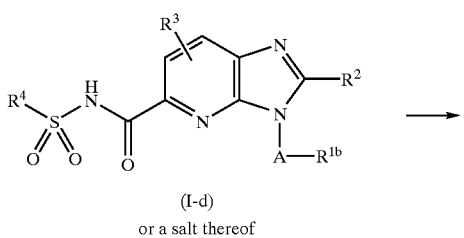

(I-d)
or a salt thereof

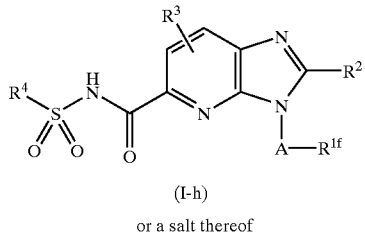

(I-h)
or a salt thereof wherein $R^{1f}$ is aryl or heterocyclic group substituted by at least one amino substituted by at least one acyl, and other symbols are as defined above.

PRODUCTION METHOD 7

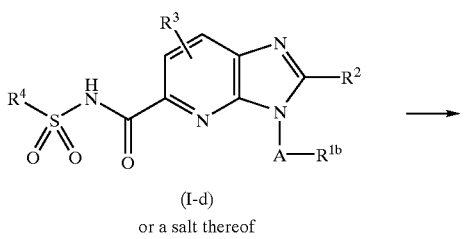

(I-d)
or a salt thereof

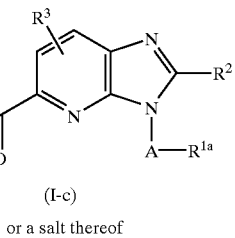

(I-c)
or a salt thereof wherein each symbol in the formula is as defined above.

PRODUCTION METHOD 8

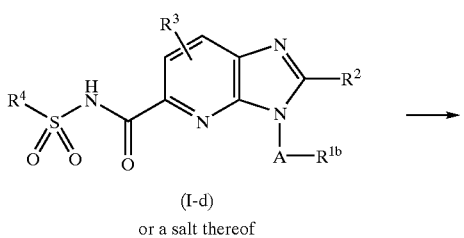

(I-d)
or a salt thereof

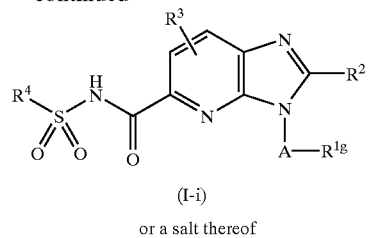

(I-i)
or a salt thereof wherein $R^{1g}$ is aryl or heterocyclic group substituted by at least one amino substituted by at least one lower alkanesulfonyl, and other symbols are as defined above.

Various definitions included in the entire specification are explained in detail in the following.

"Lower" means 1 to 6 carbon atoms, unless otherwise specified.

"Alkyl" and "alkyl moiety" are preferably linear or branched alkyl. Specific examples include methyl, ethyl, 1-propyl, isopropyl, 1-butyl, i-butyl, t-butyl, sec-butyl, 1-pentyl, i-pentyl, sec-pentyl, t-pentyl, methylbutyl, 1,1-dimethylpropyl, 1-hexyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 2,2-dimethylbutyl, 3,3-dimethylbutyl, 1-ethyl-1-methylpropyl, 1-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1,1-dimethylpentyl, 2,2-dimethylpentyl, 3,3-dimethylpentyl, 4,4-dimethylpentyl, 1-propylbutyl, 1-octyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 5-ethylhexyl, 1,1-dimethylhexyl, 2,2-dimethylhexyl, 3,3-dimethylhexyl, 4,4-dimethylhexyl, 5,5-dimethylhexyl, 1-propylpentyl, 2-propylpentyl and the like.

Of these, particularly preferred is alkyl having 1 to 6 carbon atoms.

"Alkenyl" and "alkenyl moiety" are preferably exemplified by linear or branched alkenyl, such as ethenyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl and the like.

Of these, preferred is alkenyl having 2 to 6 carbon atoms, which is more preferably ethenyl.

"Cyclo(lower)alkyl" is cycloalkyl having 3 to 10, preferably 3 to 7, carbon atoms. Preferable examples thereof include cyclopropyl, cyclobutyl, cyclopentyl, cyclohexyl and cycloheptyl, with more preference given to cyclopropyl, cyclobutyl, cyclopentyl and cyclohexyl.

Examples of preferable lower alkylene include methylene, ethylene, propylene, butylene, pentylene, hexylene and the like, with particular preference given to alkylene having up to 4 carbon atoms. Of these, particularly preferred is methylene.

Examples of preferable lower alkynyl include linear or branched alkynyl, such as ethynyl, 1-propynyl, 2-propynyl, 1-butynyl, 2-butynyl, 3-butynyl, 1-pentynyl, 2-pentynyl, 3-pentynyl, 4-pentynyl, 2-methyl-3-butynyl, 1,1-dimethyl-2-butynyl, 1-hexynyl, 5-hexynyl and the like.

Of these, particularly preferred is alkynyl having 2 to 6 carbon atoms, which is more preferably ethynyl.

Lower alkoxy is linear or branched alkyloxy having up to 6 carbon atoms. Prefererable examples thereof include methoxy, ethoxy, 1-propyloxy, i-propyloxy, 1-butyloxy, i-butyloxy, sec-butyloxy, t-butyloxy, 1-pentyloxy, i-pentyloxy, sec-pentyloxy, t-pentyloxy, 2-methylbutoxy, 1-hexyloxy, i-hexyloxy, t-hexyloxy, sec-hexyloxy, 2-methylpentyloxy, 3-methylpentyloxy, 1-ethylbutyloxy, 2-ethylbutyloxy, 1,1-dimethylbutyloxy, 2,2-dimethylbutyloxy, 3,3-dimethylbutyloxy, 1-ethyl-1-methylpropyloxy, and the like.

More preferred is alkoxy having up to 5 carbon atoms, such as methoxy, ethoxy, 1-propyloxy, i-propyloxy, 1-butyloxy, i-butyloxy, sec-butyloxy, t-butyloxy, 1-pentyloxy and the like.

"Lower alkanesulfonyl" is sulfonyl substituted by the above-defined lower alkyl. Preferred is lower alkanesulfonyl having up to 4 carbon atoms, more preferably 1-butanesulfonyl.

Halogen is exemplified by fluorine atom, chlorine atom, bromine atom and iodine atom.

"Halo(lower)alkyl" is a linear or branched alkyl having up to 6 carbon atoms, which is substituted by fluorine atom, chlorine atom, bromine atom or iodine atom, and is preferably a linear or branched alkyl having up to 6 carbon atoms, which is substituted by fluorine atom, chlorine atom or bromine atom. Examples thereof include fluoromethyl, difluoromethyl, trifluoromethyl, chloromethyl, dichloromethyl, trichloromethyl, bromomethyl, dibromomethyl, tribromomethyl, 1-fluoroethyl, 1-chloroethyl, 1-bromoethyl, 2-fluoroethyl, 2-chloroethyl, 2-bromoethyl, 1,2-difluoroethyl, 1,2-dichloroethyl, 1,2-dibromo-ethyl, 2,2,2-trifluoroethyl, heptafluoroethyl, 1-fluoropropyl, 1-chloropropyl, 1-bromopropyl, 2-fluoropropyl, 2-chloropropyl, 2-bromopropyl, 3-fluoropropyl, 3-chloropropyl, 3-bromopropyl, 1,2-difluoropropyl, 1,2-dichloropropyl, 1,2-dibromopropyl, 2,3-difluoropropyl, 2,3-dichloropropyl, 2,3-dibromopropyl, 3,3,3-trifluoropropyl, 2,2,3,3,3-pentafluoropropyl, 2-fluorobutyl, 2-chlorobutyl, 2-bromobutyl, 4-fluorobutyl, 4-chlorobutyl, 4-bromobutyl, 4,4,4-trifluorobutyl, 2,2,3,3,4,4-heptafluorobutyl, perfluorobutyl, 2-fluoropentyl, 2-chloropentyl, 2-bromopentyl, 5-fluoropentyl, 5-chloropentyl, 5-bromopentyl, perfluoropentyl, 2-fluorohexyl, 2-chlorohexyl, 2-bromohexyl, 6-fluorohexyl, 6-chlorohexyl, 6-bromohexyl, perfluorohexyl and the like.

Preferable alkyl of the "lower alkylcarbamoyl" is the above-mentioned lower alkyl.

In the present specification, aryl means unsubstituted aryl or alkyl-substituted aryl. Examples of preferable unsubstituted aryl include $C_6$–$C_{10}$ aryl, such as phenyl, naphthyl and pentalenyl. Of these, preferred is phenyl and naphthyl.

"Alkyl-substituted aryl" means aryl substituted by at least one alkyl. The number of alkyl substituents is preferably 1 to 4. The aryl moiety of "alkyl-substituted aryl" is the same as for the aforementioned unsubstituted aryl, and the "alkyl moiety" is as defined above, which is preferably lower alkyl. Specific examples of preferable alkyl-substituted aryl include tolyl, xylyl, mesityl, ethylphenyl, propylphenyl and the like, with more preference given to p-tolyl.

"Heterocyclic group" is a saturated or unsaturated, heteromonocyclic or heteropolycyclic group having at least one hetero atom, such as oxygen atom, sulfur atom, nitrogen atom and selenium atom. Particularly, unsaturated heteromonocyclic group is preferable. More preferred are the heterocyclic groups described in the below-mentioned (1), (2), (4), (7) and (9), which are still preferably pyridyl, pyrrolyl, pyrrolidinyl, oxazolidinyl, thienyl and furyl.

Heteromonocyclic group includes the following.
(1) Unsaturated 3 to 8-membered (more preferably 5- or 6-membered) heteromonocyclic group having 1 to 4 nitrogen atoms, such as pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl and 2H-1,2,3-triazolyl), tetrazolyl (e.g., 1H-tetrazolyl and 2H-tetrazolyl) and the like.
(2) Saturated 3 to 8-membered (more preferably 5- or 6-membered) heteromonocyclic group having 1 to 4 nitrogen atoms, such as pyrrolidinyl, imidazolidinyl, piperidyl, pyperazinyl and the like.
(3) Unsaturated 3 to 8-membered (more preferably 5- or 6-membered) heteromonocyclic group having 1 or 2 oxygen atoms and 1 to 3 nitrogen atoms, such as oxazolyl, isoxazolyl, oxadiazolyl (e.g., 1,2,4-oxadiazolyl, 1,3,4-oxadiazolyl and 1,2,5-oxadiazolyl) and the like.
(4) Saturated 3 to 8-membered (more preferably 5- or 6-membered) heteromonocyclic group having 1 or 2 oxygen atoms and 1 to 3 nitrogen atoms, such as oxazolidinyl, thiazolidinyl, morpholinyl, sydnonyl and the like.
(5) Unsaturated 3 to 8-membered (more preferably 5- or 6-membered) heteromonocyclic group having 1 or 2 sulfur atoms and 1 to 3 nitrogen atoms, such as thiazolyl, isothiazolyl, thiadiazolyl (e.g., 1,2,3-thiadiazolyl, 1,2,4-thiadiazolyl, 1,3,4-thiadiazolyl and 1,2,5-thiadiazolyl), dihydrothiazinyl and the like.
(6) Saturated 3 to 8-membered (more preferably 5- or 6-membered) heteromonocyclic group having 1 or 2 sulfur atoms and 1 to 3 nitrogen atoms, such as thiazolidinyl and the like.
(7) Unsaturated 3 to 8-membered (more preferably 5- or 6-membered) heteromonocyclic group having 1 or 2 sulfur atoms, such as thienyl, dihydrodithinyl, dihydrodithionyl and the like.
(8) Saturated 3 to 8-membered (more preferably. 5- or 6-membered) heteromonocyclic group having 1 or 2 oxygen atoms, such as tetrahydrofuryl, tetrahydropyranyl and the like.
(9) Unsaturated 3 to 8-membered (more preferably 5- or 6-membered) heteromonocyclic group having one oxygen atom, such as furyl and the like.
(10) Spiroheterocyclic group having 1 or 2 oxygen atoms, such as dioxaspiroundecanyl (e.g., 1,5-dioxaspiro[5,5] undecanyl) and the like.
(11) Unsaturated 3 to 8-membered (more preferably 5- or 6-membered) heteromonocyclic group having one oxygen atom and 1 or 2 sulfur atoms, such as dihydroxathinyl.

Examples of heteropolycyclic group include the following.
(12) Saturated or unsaturated 7 to 12-membered (more preferably 8 to 10-membered) heteropolycyclic (more preferably heterodicyclic) group having 1 to 4 nitrogen atoms.

Specific examples thereof include benzimidazolyl, indolyl, 2,3-dihydrobenzimidazolyl, pyrazolopyrimidinyl (e.g., pyrazolo[1,5-a]pyrimidinyl), tetrahydropyrazolopyrimidinyl (e.g., 4,5,6,7-tetrahydropyrazolo[1,5-a] pyrimidinyl), imidazopyrazolyl (e.g., 4H-imidazo[1,2-b] pyrazolyl), dihydroimidazopyrazolyl (e.g., 2,3-dihydroimidazo[1,2-b]pyrazolyl), imidazopyridyl (e.g., imidazo[1,5-a] (or [1,2-a] or [3,4-a])pyridyl, 1H (or 3H)-imidazo[4,5-b] (or [4,5-c])pyridyl), pyrrolopyridyl (e.g., 1H-pyrrolo[3,2-b]pyridyl), pyrazolopyridyl (e.g., pyrazolo [1,5-a] (or [2,3-a])pyridyl, 1H (or 2H)-pyrazolo[4,3-b] pyridyl), benzopyrazolyl (e.g., 1H (or 2H)-benzo[c] pyrazolyl), dihydrobenzimidazolyl, benzotriazolyl (e.g., benzo[d][1H-1,2,3]triazolyl), indolidinyl, isoindolyl (e.g., 1H-isoindolyl), indazolyl (e.g., 1H (or 2H or 3H)-indazolyl), indolinyl, isoindolinyl, purinyl, quinolidinyl (e.g., 4H-quinolidinyl), isoquinolyl, quinolyl, phthaladinyl, naphthalidinyl (e.g., 1,8-naphthalidinyl), quinoxalinyl, dihydroquinoxalinyl (e.g., 1,2-dihydroquinoxalinyl), tetrahydroquinoxalinyl (e.g., 1,2,3,4-tetrahydroquinoxalinyl), quinazolinyl, dihydroquinazolinyl (e.g., 1,4 (or 3,4)-dihydro-quinazolinyl), tetrahydroquinazolinyl (e.g., 1,2,3,4-tetrahydro-quinazolinyl), cinnolinyl, pteridinyl, pyrazinopyridazinyl (e.g., pyrazino[2,3-d]pyridazinyl), imidazotriazinyl (e.g., imidazo[1,2-b][1,2,4]triazinyl, imidazopyrazinyl (e.g., 1H-imidazo[4,5-b]pyrazinyl), imidazopyrimidine (e.g., 3H-purine and imidazo[1,5-a] (or [3,4-a])pyrimidine), imidazopyridazinyl (e.g., imidazo[2,3-b] (or [3,4-b])pyridazinyl), 1H-1 (or 2)-pyrinedinyl and the like.

(13) Saturated or unsaturated 7 to 12-membered (more preferably 8 to 10-membered) heteropolycyclic (more preferably heterodicyclic) group having 1 to 3 oxygen atoms.

Specific examples thereof include benzofuranyl (e.g., benzo[b] (or [c])furanyl), isobenzofuranyl, furopyridyl, chromenyl (e.g., 2H-chromenyl), chromanyl, isochromanyl, benzoxepinyl (e.g., 3-benzoxepinyl), cyclopentapyranyl (e.g., cyclopenta[b]pyranyl), furopyranyl (e.g., 2H-furo[3,2-b]pyranyl, and the like.

(14) Saturated or unsaturated 7 to 12-membered (more preferably 8 to 10-membered) heteropolycyclic (more preferably heterodicyclic) group having 1 to 3 sulfur atoms.

Specific examples thereof include benzothiophenyl (e.g., benzo[b]thiophenyl), dihydrodithianaphthalenyl (e.g., 4H-1,3-dithianaphthalenyl), dithianaphthalenyl (e.g., 1,4-dithianaphthalenyl) and the like.

(15) Saturated or unsaturated 7 to 12-membered (more preferably 8 to 10-membered) heteropolycyclic (more preferably heterodicyclic) group having 1-to 3 nitrogen atoms and 1 or 2 oxygen atoms.

Specific examples thereof include dioxoloimidazolyl (e.g., 4H-1,3-dioxolo[4,5-d]imidazolyl, benzoxazinyl (e.g., 4H-3,1-benzoxazinyl), pyridoxazinyl (e.g., 5H-pyrid[2,3-d]oxazinyl), pyrazolooxazolyl (e.g., 1H-pyrazolo[4,3-d]oxazolyl), furopyridyl, and the like.

(16) Saturated or unsaturated 7 to 12-membered (more preferably 8 to 10-membered) heteropolycyclic (more preferably heterodicyclic) group having 1 to 3 nitrogen atoms and 1 or 2 sulfur atoms.

Specific examples thereof include thienoimidazolyl (e.g., thieno[2,3-d]imidazolyl), thienopyridyl, dithiadiazaindanyl (e.g., 2,3-dithia-1,5-diazaindanyl) and the like.

(17) Saturated or unsaturated 7 to 12-membered (more preferably 8 to 10-membered) heteropolycyclic (more preferably heterodicyclic) group having 1 to 3 oxygen atoms and 1 or 2 sulfur atoms.

Specific examples thereof include thienofuranyl (e.g., thieno[2,3-b]furanyl), and the like.

(18) Saturated or unsaturated 7 to 12-membered (more preferably 8 to 10-membered) heteropolycyclic (more preferably heterodicyclic) group having 1 nitrogen atom, 1 oxygen atom and 1 sulfur atom.

Specific examples thereof include oxathiolopyrrolyl (e.g., 4H[1,3]-oxathiolo[5,4-b]pyrrolyl, and the like.

(19) Saturated or unsaturated 7 to 12-membered (more preferably 8 to 10-membered) heteropolycyclic (more preferably heterodicyclic) group having 1 or 2 selenium atoms.

Preferred specific examples include benzoselenophenyl (e.g., benzo[b] (or [c])selenophenyl), and the like.

(20) Saturated or unsaturated 7 to 12-membered (more preferably 8 to 10-membered) heteropolycyclic (more preferably heterodicyclic) group having 1 or 2 selenium atoms and 1 to 3 nitrogen atoms.

Specific examples thereof include selenopyridyl (e.g., seleno[3,2-b]pyridyl), and the like.

"Acyl" and "acyl moiety" are exemplified by carbamoyl, liphatic acyl, and acyl having heterocyclic group called to as aromatic acyl or acyl having heterocyclic group called to as heterocyclic acyl. Preferable examples of the above-mentioned acyl include carbamoyl; aliphatic acyl such as lower alkanoyl having 1 to 10, preferably 1 to 6, carbon atoms, (e.g., formyl, acetyl, propanoyl, butanoyl, 2-methylpropanoyl, pentanoyl, 2,2-dimethylpropanoyl, hexanoyl, 3,3-dimethylbutanoyl, heptanoyl, octanoyl, nonanoyl, decanoyl and the like), alkoxycarbonyl (e.g., methoxycarbonyl, ethoxycarbonyl, t-butoxycarbonyl, t-pentyloxycarbonyl, heptyloxycarbonyl and the like), butyloxycarbonyl, alkanesulfonyl (e.g., methanesulfonyl, ethanesulfonyl and the like), and alkoxysulfonyl (e.g., methoxysulfonyl and ethoxysulfonyl); aromatic acyl such as aroyl (e.g., benzoyl, toluoyl, naphthoyl and the like), aryl (lower)alkanoyl (e.g., phenyl(lower)alkanoyl (e.g., phenylacetyl, phenylpropanoyl, phenylbutanoyl, phenylisobutyryl, phenylpentanoyl and phenylhexanoyl) and naphthyl(lower)alkanoyl (e.g., naphthylacetyl, naphthylpropanoyl and naphthylbutanoyl)), aryl(lower)alkenoyl (e.g., phenyl(lower)alkenoyl (e.g., phenylpropenoyl, phenylbutenoyl, phenylmethacryloyl, phenylpentenoyl and phenylhexenoyl) and naphthyl(lower)alkenoyl (e.g., naphthylpropenoyl, naphthylbutenoyl and naphthylpentenoyl)), aryl(lower)alkoxycarbonyl (e.g., phenyl(lower)alkoxycarbonyl (e.g., benzyloxycarbonyl)), aryloxycarbonyl (e.g., phenoxycarbonyl, naphthyloxycarbonyl and the like), aryloxy(lower)alkanoyl (e.g., phenoxyacetyl, phenoxypropionyl and the like), arylcarbamoyl (e.g., phenylcarbamoyl and the like), arylthiocarbamoyl (e.g., phenylthiocarbamoyl and the like), and arylglyoxyloyl (e.g., phenylglyoxyloyl, naphthylglyoxyloyl and the like); heterocyclic acyl such as arenesulfonyl (e.g., benzenesulfonyl and p-toluenesulfonyl), heterocyclecarbonyl; heterocycle(lower)alkanoyl (e.g., thienylacetyl, thienylpropanoyl, thienylbutanoyl, thienylpentanoyl, thienylhexanoyl, thiazolylacetyl, tetrazolylacetyl and the like), heterocycle(lower)alkenoyl (e.g., heterocyclepropenoyl, heterocyclebutenoyl, heterocyclepentenoyl, heterocyclehexenoyl and the like), and heterocycleglyoxyloyl (e.g., thiazolylglyoxyloyl, thienyl-glyoxyloyl and the like); and the like.

More specifically, the preferable heterocycle moiety of the above-mentioned "heterocyclecarbonyl", "heterocycle (lower)alkanoyl", "heterocycle(lower)alkenoyl" and "heterocycleglyoxyloyl" means a saturated or unsaturated heteromonocyclic or heteropolycyclic group having at least one hetero atom such as oxygen atom, sulfur atom, nitrogen atom and the like, with particular preference given to the heterocyclic groups mentioned above.

The aforementioned acyl moiety may have 1 to 10 same or different suitable substituent(s), such as halogen (e.g., fluorine, chlorine, bromine and iodine), hydroxy, nitro, lower alkyl (e.g., methyl, ethyl, propyl, isopropyl, butyl, isobutyl, t-butyl, pentyl and hexyl), amino, protected amino, heterocycle(lower)alkylamino having the above-mentioned heterocycle moiety and lower alkyl moiety, lower alkoxy (e.g., methoxy, ethoxy, propoxy, butyloxy, t-butyloxy, pentyloxy and hexyloxy), carboxy, protected carboxy, N,N-di (lower)alkylamino(lower)alkyl (e.g., N,N-dimethylaminomethyl, N,N-diethylaminomethyl, N,N-dipropylaminomethyl, N,N-dimethylaminoethyl, N,N- diethylaminoethyl, N,N-dipropylaminoethyl, N,N-dimethylaminopropyl, N,N-diethylaminopropyl, N,N-dipropylaminopropyl, N,N-dibutylaminomethyl, N,N-dipentylaminomethyl and N,N-dihexylaminomethyl), hydroxyimino(lower)alkyl (e.g., hydroxyiminomethyl, hydroxyiminoethyl, hydroxyiminopropyl, hydroxyiminobutyl, hydroxyiminopentyl and hydroxyiminohexyl), arylimino(lower)alkyl exemplified by phenylimino(lower)alkyl (e.g., phenyliminomethyl, phenyliminoethyl, phenyliminopropyl, phenyliminobutyl, phenyliminopentyl and phenyliminohexyl), acyl such as lower alkanoyl (e.g., formyl, acetyl, propanoyl, butanoyl, pentanoyl and hexanoyl), hydroxy(lower)alkylheterocycle (lower)alkyl having the above-mentioned lower alkyl moiety and heterocycle moiety, mono- (or di- or tri-)halo(lower)alkyl, and arylamino (e.g., phenylamino).

More preferable "acyl" is the above-mentioned lower alkanoyl.

The preferable acyl moiety of acyloxy is exemplified by acyl moiety defined above, more preferably acetyl.

Preferable example of the protected carboxy is esterified carboxy.

Examples of preferable ester moiety of the esterified carboxy include lower alkyl esters such as methyl ester, ethyl ester, propyl ester, isopropyl ester, butyl ester, isobutyl ester, t-butyl ester, pentyl ester and hexyl ester, and the like. These groups may have at least one appropriate substituent, which is exemplified by lower alkanoyloxy(lower)alkyl ester such as. acetoxymethyl ester, propionyloxymethyl ester, butyryloxymethyl ester, valeryloxymethyl ester, pivaloyloxymethyl ester, hexanoyloxy-methyl ester, 1 (or 2)-acetoxyethyl ester, 1 (or 2 or 3)-acetoxypropyl ester, 1 (or 2, 3 or 4)-acetoxybutyl ester, 1 (or 2)-propionyloxyethyl ester, 1 (or 2 or 3)-propionyloxypropyl ester, 1 (or 2)-butyryloxyethyl ester, 1 (or 2)-isobutyryloxyethyl ester, 1 (or 2)-pivaloyloxyethyl ester, 1 (or 2)-hexanoyl-oxyethyl ester, isobutyryloxymethyl ester, 2-ethylbutyryloxymethyl ester, 3,3-dimethylbutyryloxymethyl ester, 1 (or 2)-pentanoyloxyethyl ester), lower alkanesulfonyl-(lower)alkyl ester (e.g., 2-mesylethyl ester), mono- (or di- or tri-)-halo(lower)alkyl ester (e.g., 2-iodoethyl ester and 2,2,2-trichloroethyl ester), lower alkoxycarbonyloxy(lower)alkyl ester (e.g., methoxycarbonyloxymethyl ester, ethoxycarbonyloxymethyl ester, 2-methoxycarbonyloxyethyl ester, 1-ethoxycarbonyloxyethyl ester and 1-isopropoxycarbonyloxyethyl ester), phthalidylidene(lower)alkyl ester and (5-lower alkyl-2-oxo-1,3-dioxol-4-yl)(lower)alkyl ester (e.g., (5-methyl-2-oxo-1,3-dioxol-4-yl)methyl ester, (5-ethyl-2-oxo-1,3-dioxol-4-yl)methyl ester and (5-propyl-2-oxo-1,3-dioxol-4-yl)ethyl ester); lower alkenyl ester (e.g., vinyl ester and allyl ester); lower alkynyl ester (e.g., ethynyl ester and propynyl ester); aryl(lower)alkyl ester optionally having at least one suitable substituent, such as mono- (or di- or tri-)phenyl(lower)alkyl ester optionally having at least one suitable substituent, which is exemplified by benzyl ester, 4-methoxybenzyl ester, 4-nitrobenzyl ester, phenylethyl ester, trityl ester, benzhydryl ester, bis(methoxyphenyl)methyl ester, 3,4-dimethoxybenzyl ester and 4-hydroxy-3,5-di-t-butylbenzyl ester; aryl ester optionally having at least one suitable substituent, such as phenyl ester, 4-chlorophenyl ester, tolyl ester, t-butylphenyl ester, xylyl ester, mesityl ester and cumenyl ester; cyclo(lower)alkyl ester (e.g., cyclohexyl ester); phthalidyl ester; and the like.

When the above-mentioned substituents are substituted, the number of the substituents is preferably 1 to 4, unless particularly specified.

Preferable examples of the objective compound (I) are the compound of the formula (I) wherein $R^1$ is pyridyl optionally substituted by at least one substituent selected from the group consisting of (1) aryl, (2) a heterocyclic group, (3) halogen, (4) halo(lower)alkyl, (5)lower alkoxy optionally substituted by cyclo(lower)alkyl, (6) amino optionally substituted by at least one substituent selected from the group consisting of lower alkyl optionally substituted by cyclo(lower)alkyl, and protected carboxy, acyl and lower alkanesulfonyl, (7) nitro, and (8) lower alkynyl optionally substituted by aryl, and a salt thereof.

Of the objective compounds, another particularly preferable compound has the following formula (IA):

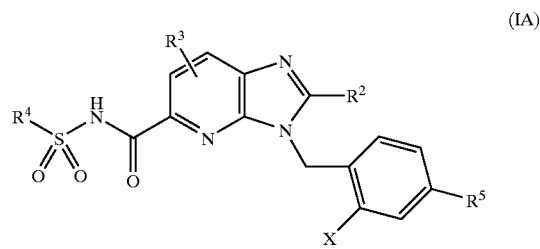

(IA)

wherein $R^2$ is lower alkyl or lower alkoxy,
$R^3$ is hydrogen or lower alkyl,
$R^4$ is lower alkenyl optionally substituted by aryl or heterocyclic group, aryl optionally substituted by carboxy or protected carboxy, lower alkyl optionally substituted by acyloxy, amino optionally substituted by lower alkyl, or heterocyclic group optionally substituted by halogen,
$R^5$ is pyrrolyl, furyl, or amino substituted by protected carboxy optionally substituted by lower alkyl, and
X is halogen,
and a salt thereof.

Particularly preferable groups are as follows.
$R^1$: 3-chloro-4-biphenylyl, 2-chloro-4-methoxyphenyl, 2-chloro-4-ethoxyphenyl, 2-chloro-4-(1-propoxy)phenyl, 2-chloro-4-isopropoxyphenyl, 2-chloro-4-(1-butoxy)phenyl, 2-chloro-4-(1-pentyloxy)phenyl, 2-chloro-4-((cyclopentylmethyl)oxy)phenyl, 2-chloro-4-ethoxyphenyl, 2-chloro-4-(N-(tert-butoxycarbonyl)-N-methylamino)phenyl, 2-chloro-4-(methylamino)phenyl, 2-chloro-4-(ethylmethylamino)phenyl, 2-chloro-4-(methyl-(1-propyl)amino)-phenyl, 4-(1-butyl)methylamino-2-chlorophenyl, 2-chloro-4-(dimethylamino)phenyl, 2-chloro-4-(ethylmethylamino)phenyl, 2-chloro-4-((1-butyl)methylamino)phenyl, 2-chloro-4-(methyl-(1-pentyl)amino)phenyl, 2-chloro-4-(N-(cyclohexylmethyl)-methylamino)phenyl, 4-bromo-2-chlorophenyl, 3-chloro-5-(trifluoromethyl)-2-pyridyl, 2-chloro-4-(2-furyl)phenyl, 2-chloro-4-(N-(ethoxycarbonyl)-N-methylamino)phenyl, 2-chloro-4-(N-(tert-butoxycarbonyl)-N-ethylamino)phenyl, 2-chloro-4-(N-(pivaloyl)-N-methylamino)phenyl, 2-chloro-4-(ethylamino)phenyl,2-chloro-4-(diethylamino)phenyl, 2-chloro-4-(1-pentylethylamino)-phenyl, 2,6-dichloro-3-pyridyl, 2-chloro-4-(cyclohexylmethyloxy)-phenyl, 2-chloro-4-(1-pyrrolyl)phenyl, (2,4-dichloro-5-nitro)-phenyl, (2,4-dichloro-5-(N,N-dimethylamino))phenyl, (4-(N-(1-butanesulfonyl)-N-methylamino)-2-chlorophenyl, 2-chloro-4-(N-methyl-N-(1-propoxycarbonyl)amino)phenyl, 2-chloro-4-(N-methyl-N-(isopropoxycarbonyl)amino)phenyl, 4-(N-

(tert-butoxycarbonyl)-amino)-2-chlorophenyl, 2-chloro-4-(ethoxycarbonylamino)phenyl, 2-chloro-4-(N-valerylamino)phenyl, 4-(N-(1-butanesulfonyl)amino)-2-chlorophenyl, 2-chloro-4-(N-(t-butylacetyl)amino)phenyl, $R^2$: methyl, ethyl, ethoxy, $R^3$: hydrogen, methyl, $R^4$: (E)-2-(4-pyridyl)vinyl, 1-pentyl, 1-butyl, 4-methylphenyl, 1-propylamino, 1-butylamino, (E)-2-(phenyl)vinyl, 5-bromo-2-thienyl, 5-chloro-2-thienyl, 4-ethoxycarbonylphenyl, 4-carboxyphenyl, 4-acetoxybutyl, $R^5$: N-(tert-butoxycarbonyl)-N-methylamino, 2-furyl, N-(ethoxycarbonyl)-N-methylamino, N-(tert-butoxycarbonyl)-N-ethylamino, 1-pyrrolyl, N-methyl-N-(isopropoxycarbonyl)amino, N-methyl-N-(isopropoxycarbonyl) amino, N-(tert-butoxycarbonyl) amino, ethoxycarbonylamino, A: methylene, X: chlorine.

Preferable objective compounds (I) are as follows.

3-(2-chloro-4-phenylbenzyl)-2-methyl-5-[(E)-[2-(4-pyridyl)ethene]sulfonylcarbamoyl]-3H-imidazo[4,5-b]pyridine, 5-[(4-acetoxybutane)sulfonylcarbamoyl]-3-(2-chloro-4-phenylbenzyl)-2-methyl-3H-imidazo[4,5-b]pyridine, 3-(2-chloro-4-phenylbenzyl)-2-methyl-5-[(4-ethoxycarbonylbenzene)sulfonylcarbamoyl]-3H-imidazo[4,5-b]pyridine, 3-(2-chloro-4-phenylbenzyl)-2-methyl-5-[(4-carboxybenzene)sulfonylcarbamoyl]-3H-imidazo[4,5-b]pyridine, 3-(2-chloro-4-methoxybenzyl)-2-methyl-5-(1-pentanesulfonylcarbamoyl)-3H-imidazo[4,5-b]pyridine, 5-(1-butanesulfonylcarbamoyl)-3-(2-chloro-4-methoxybenzyl)-2-methyl-3H-imidazo[4,5-b]pyridine, 3-(2-chloro-4-methoxybenzyl)-2-methyl-5-[(4-methylbenzene)sulfonylcarbamoyl]-3H-imidazo[4,5-b]pyridine, 3-(2-chloro-4-ethoxybenzyl)-2-methyl-5-(1-pentanesulfonylcarbamoyl)-3H-imidazo[4,5-b]pyridine, 5-(1-butanesulfonylcarbamoyl)-3-(2-chloro-4-ethoxybenzyl)-2-methyl-3H-imidazo[4,5-b]pyridine, 3-(2-chloro-4-ethoxybenzyl)-2-methyl-5-((1-propylaminosulfonyl)carbamoyl)-3H-imidazo[4,5-b]pyridine, 5-((1-butylaminosulfonyl)carbamoyl)-3-(2-chloro-4-ethoxybenzyl)-2-methyl-3H-imidazo[4,5-b]pyridine, 3-(2-chloro-4-(1-propoxy)benzyl)-2-methyl-5-(1-pentanesulfonylcarbamoyl)-3H-imidazo[4,5-b]pyridine, 5-(1-butanesulfonylcarbamoyl)-3-(2-chloro-4-(1-propoxy)benzyl)-2-methyl-3H-imidazo[4,5-b]pyridine, 3-(2-chloro-4-isopropoxybenzyl)-2-methyl-5-(1-pentanesulfonylcarbamoyl)-3H-imidazo[4,5-b]pyridine, 5-(1-butanesulfonylcarbamoyl)-3-(2-chloro-4-isopropoxybenzyl)-2-methyl-3H-imidazo[4,5-b]pyridine, 3-(2-chloro-4-isopropoxybenzyl)-2-methyl-5-[(4-methylbenzene)sulfonylcarbamoyl]-3H-imidazo[4,5-b]pyridine, 3-(2-chloro-4-(1-butoxy)benzyl)-2-methyl-5-(1-pentanesulfonylcarbamoyl)-3H-imidazo[4,5-b]pyridine, 5-(1-butanesulfonylcarbamoyl)-3-(2-chloro-4-(1-butoxy)benzyl)-2-methyl-3H-imidazo[4,5-b]pyridine, 3-(2-chloro-4-(1-butoxy)benzyl)-2-methyl-5-[(4-methylbenzene)sulfonylcarbamoyl]-3H-imidazo[4,5-b]pyridine, 3-(2-chloro-4-(1-pentyloxy)benzyl)-2-methyl-5-(1-pentanesulfonylcarbamoyl)-3H-imidazo[4,5-b]pyridine, 5-(1-butanesulfonylcarbamoyl)-3-(2-chloro-4-(1-pentyloxy)benzyl)-2-methyl-3H-imidazo[4,5-b]pyridine, 3-(2-chloro-4-(1-pentyloxy)benzyl)-2-methyl-5-((E)-(2-phenylethene)sulfonylcarbamoyl)-3H-imidazo[4,5-b]pyridine, 5-[(5-bromothiophen-2-yl)sulfonylcarbamoyl]-3-[2-chloro-4-(1-pentyloxy)benzyl]-2-methyl-3H-imidazo[4,5-b]pyridine, 3-[2-chloro-4-(1-pentyloxy)benzyl]-2-methyl-5-[(5-chlorothiophen-2-yl)sulfonylcarbamoyl]-3H-imidazo[4,5-b]pyridine, 5-((1-propylaminosulfonyl)carbamoyl)-3-(2-chloro-4-(1-pentyloxy)benzyl)-2-methyl-3H-imidazo[4,5-b]pyridine, 5-((1-butylaminosulfonyl)carbamoyl)-3-(2-chloro-4-(1-pentyloxy)benzyl)-2-methyl-3H-imidazo[4,5-b]pyridine, 3-(2-chloro-4-((cyclopentylmethyl)oxy)benzyl)-2-methyl-5-(1-pentanesulfonylcarbamoyl)-3H-imidazo[4,5-b]pyridine, 5-(1-butanesulfonylcarbamoyl)-3-(2-chloro-4-((cyclopentylmethyl)oxy)benzyl)-2-methyl-3H-imidazo[4,5-b]pyridine, 3-(2-chloro-4-ethoxybenzyl)-2-ethyl-5-(1-pentanesulfonylcarbamoyl)-3H-imidazo[4,5-b]pyridine, 3-(2-chloro-4-ethoxybenzyl)-2-ethyl-5-[(4-methylbenzene)sulfonylcarbamoyl]-3H-imidazo[4,5-b]pyridine, 3-(2-chloro-4-(1-propoxy)benzyl)-2-ethyl-5-(1-pentanesulfonylcarbamoyl)-3H-imidazo[4,5-b]pyridine, 3-(2-chloro-4-(1-propoxy)benzyl)-2-ethyl-5-[(4-methylbenzene)sulfonylcarbamoyl]-3H-imidazo[4,5-b]pyridine, 3-(2-chloro-4-(1-pentyloxy)benzyl)-2-ethyl-5-(1-pentanesulfonylcarbamoyl)-3H-imidazo[4,5-b]pyridine, 3-(2-chloro-4-(1-pentyloxy)benzyl)-2-ethyl-5-[(4-methylbenzene)sulfonylcarbamoyl]-3H-imidazo[4,5-b]pyridine, 3-(2-chloro-4-(1-propoxy)benzyl)-2,7-dimethyl-5-(1-pentanesulfonylcarbamoyl)-3H-imidazo[4,5-b]pyridine, 5-(1-butanesulfonylcarbamoyl)-3-[2-chloro-4-(1-propoxy)benzyl]-2,7-dimethyl-3H-imidazo[4,5-b]pyridine, 3-(2-chloro-4-(1-propoxy)benzyl)-2,7-dimethyl-5-[(4-methylbenzene)sulfonylcarbamoyl]-3H-imidazo[4,5-b]pyridine, 3-[2-chloro-4-(1-pentyloxy)benzyl]-2,7-dimethyl-5-(1-pentanesulfonylcarbamoyl)-3H-imidazo[4,5-b]pyridine, 5-(1-butanesulfonylcarbamoyl)-3-[2-chloro-4-(1-pentyloxy)benzyl]-2,7-dimethyl-3H-imidazo[4,5-b]pyridine, 3-[2-chloro-4-(1-pentyloxy)benzyl]-2,7-dimethyl-5-[(4-methylbenzene)sulfonylcarbamoyl]-3H-imidazo[4,5-b]pyridine, 3-(4-(N-(tert-butoxycarbonyl)-N-methylamino)-2-chlorobenzyl)-2-methyl-5-(1-pentanesulfonylcarbamoyl)-3H-imidazo[4,5-b]pyridine, 3-(2-chloro-4-(methylamino)benzyl)-2-methyl-5-(1-pentanesulfonylcarbamoyl)-3H-imidazo[4,5-b]pyridine, 3-(2-chloro-4-(ethylmethylamino)benzyl)-2-methyl-5-(1-pentanesulfonylcarbamoyl)-3H-imidazo[4,5-b]pyridine, 3-(2-chloro-4-(methyl-(1-propyl)amino)benzyl)-2-methyl-5-(1-pentanesulfonylcarbamoyl)-3H-imidazo[4,5-b]pyridine, 3-(4-((1-butyl)methylamino)-2-chlorobenzyl)-2-methyl-5-(1-pentanesulfonylcarbamoyl)-3H-imidazo[4,5-b]pyridine, 3-(4-(N-(tert-butoxycarbonyl)-N-methylamino)-2-chlorobenzyl)-2-methyl-5-((4-methylbenzene)sulfonylcarbamoyl)-3H-imidazo[4,5-b]pyridine, 3-(2-chloro-4-(methylamino)benzyl)-2-methyl-5-((4-methylbenzene)sulfonylcarbamoyl)-3H-imidazo[4,5-b]pyridine, 3-(2-chloro-4-(dimethylamino)benzyl)-2-methyl-5-((4-methylbenzene)sulfonylcarbamoyl)-3H-imidazo[4,5-b]pyridine, 3-(2-chloro-4-(ethylmethylamino)benzyl)-2-methyl-5-((4-methylbenzene)sulfonylcarbamoyl)-3H-imidazo[4,5-b]pyridine, 3-(2-chloro-4-(methyl-(1-propyl)amino)benzyl)-2-methyl-5-((4-methylbenzene)sulfonylcarbamoyl)-3H-imidazo[4,5-b]pyridine, 3-(2- chloro-4-((1-butyl)methylamino)benzyl)-2-methyl-5-((4-methylbenzene)sulfonylcarbamoyl)-3H-imidazo[4,5-b]pyridine, 3-(2-chloro-4-(methyl-(1-pentyl)amino)benzyl)-2-methyl-5-(1-pentanesulfonylcarbamoyl)-3H-imidazo[4,5-b]pyridine, 3-(2-chloro-4-(N-(cyclohexylmethyl)methylamino)benzyl)-2-methyl-5-(1-pentanesulfonylcarbamoyl)-3H-imidazo[4,5-b]pyridine, 3-(2-chloro-4-(N-(cyclohexylmethyl)methylamino)benzyl)-2-methyl-5-((4-methylbenzene)sulfonylcarbamoyl)-3H-imidazo[4,5-b]pyridine, 3-(4-bromo-2-chlorobenzyl)-2,7-dimethyl)-5-[(4-methylbenzene)sulfonylcarbamoyl]-3H-imidazo[4,5-b]pyridine, 3-(2-chloro-4-(ethylmethylamino)benzyl)-2,7-dimethyl-5-[(4-methylbenzene)sulfonylcarbamoyl]-3H-imidazo[4,5-b]pyridine, 3-[(3-chloro-5-(trifluoromethyl)-2-pyridyl)methyl]-2-methyl-5-(1-pentanesulfonylcarbamoyl)-3H-imidazo[4,5-b]pyridine, 3-[(3-chloro-5-(trifluoromethyl)-2-pyridyl)methyl]-2-methyl-5-[(4-methylbenzene)sulfonylcarbamoyl]-3H-imidazo[4,5-b]pyridine, 3-(2-chloro-4-phenylbenzyl)-2-ethoxy-5-(1-pentanesulfonylcarbamoyl)-3H-imidazo[4,5-b]pyridine, 3-(2-chloro-4-phenylbenzyl)-2-methyl-5-[(1-propylaminosulfonyl)carbamoyl]-3H-imidazo[4,5-b]pyridine, 3-[(3-chloro-5-(trifluoromethyl)-2-pyridyl)methyl]-2,7-dimethyl-5-[(4-methylbenzene)sulfonylcarbamoyl]-3H-imidazo[4,5-b]pyridine, 3-[(2,6-dichloro-3-pyridyl)methyl]-2-methyl-5-(1-pentanesulfonylcarbamoyl)-3H-imidazo[4,5-b]pyridine, 3-[(2,6-dichloro-3-pyridyl)methyl]-2-methyl-5-[(4-methylbenzene)sulfonylcarbamoyl]-3H-imidazo[4,5-b]pyridine, 3-(2-chloro-4-(methyl(pivaloyl)amino)benzyl)-2-methyl-5-(1-pentanesulfonylcarbamoyl)-3H-imidazo[4,5-b]pyridine, 3-(4-(N-(ethoxycarbonyl)-N-methylamino)-2-chlorobenzyl)-2-methyl-5-(1-pentanesulfonylcarbamoyl)-3H-imidazo[4,5-b]pyridine, 5-(1-butanesulfonylcarbamoyl)-3-(2-chloro-4-(1-pentyloxy)benzyl)-2-ethyl-3H-imidazo[4,5-b]pyridine, 5-(1-butanesulfonylcarbamoyl)-3-(2-chloro-4-(cyclohexylmethyloxy)benzyl)-2-ethyl-3H-imidazo[4,5-b]pyridine, 3-(2-chloro-4-(cyclohexylmethyloxy)benzyl)-2-ethyl-5-(1-pentanesulfonylcarbamoyl)-3H-imidazo[4,5-b]pyridine, 5-(1-butanesulfonylcarbamoyl)-3-[2-chloro-4-(2-furyl)benzyl]-2-methyl-3H-imidazo[4,5-b]pyridine, 3-[2-chloro-4-(2-furyl)benzyl]-2-methyl-5-(1-pentanesulfonylcarbamoyl)-3H-imidazo[4,5-b]pyridine, 3-[2-chloro-4-(2-furyl)benzyl]-2-methyl-5-[(4-methylbenzene)sulfonylcarbamoyl]-3H-imidazo[4,5-b]pyridine, 3-[4-(N-(tert-butoxycarbonyl)-N-ethylamino)-2-chlorobenzyl]-2-methyl-5-(1-pentanesulfonylcarbamoyl)-3H-imidazo[4,5-b]pyridine, 3-(4-(N-(tert-butoxycarbonyl)-N-ethylamino)-2-chlorobenzyl)-2-methyl-5-((4-methylbenzene)sulfonylcarbamoyl)-3H-imidazo[4,5-b]pyridine, 3-(2-chloro-4-(ethylamino)benzyl)-2-methyl-5-((4-methylbenzene)sulfonylcarbamoyl)-3H-imidazo[4,5-b]pyridine, 3-(2-chloro-4-(N,N-diethylamino)benzyl)-2-methyl-5-((4-methylbenzene)sulfonylcarbamoyl)-3H-imidazo[4,5-b]pyridine, 3-(2-chloro-4-(N-ethyl-N-(1-pentyl)amino)benzyl)-2-methyl-5-((4-methylbenzene)sulfonylcarbamoyl)-3H-imidazo[4,5-b]pyridine, 3-(4-(N-(tert-butoxycarbonyl)-N-methylamino)-2-chlorobenzyl)-2,7-dimethyl-5-(1-pentanesulfonylcarbamoyl)-3H-imidazo[4,5-b]pyridine, 3-(4-(N-(tert-butoxycarbonyl)-N-methylamino)-2-chlorobenzyl)-2,7-dimethyl-5-((4-methylbenzene)sulfonylcarbamoyl)-3H-imidazo[4,5-b]pyridine, 3-(2-chloro-4-(methylamino)benzyl)-2,7-dimethyl-5-((4-methylbenzene)sulfonylcarbamoyl)-3H-imidazo[4,5-b]pyridine, 3-(2-chloro-4-(N-methyl-N-propylamino)benzyl)-2,7-dimethyl-5-((4-methylbenzene)sulfonylcarbamoyl)-3H-imidazo[4,5-b]pyridine, 3-[4-(N-(tert-butoxycarbonyl)-N-ethylamino)-2-chlorobenzyl]-2,7-dimethyl-5-(1-pentanesulfonylcarbamoyl)-3H-imidazo[4,5-b]pyridine, 3-[4-(N-(tert-butoxycarbonyl)-N-ethylamino)-2-chlorobenzyl]-2,7-dimethyl-5-((4-methylbenzene)sulfonylcarbamoyl)-3H-imidazo[4,5-b]pyridine, 3-(2-chloro-4-(1-pyrrolyl)benzyl)-2-methyl-5-(1-pentanesulfonylcarbamoyl)-3H-imidazo[4,5-b]pyridine, 3-(2-chloro-4-(1-pyrrolyl)benzyl)-2-methyl-5-((4-methylbenzene)sulfonylcarbamoyl)-3H-imidazo[4,5-b]pyridine, 3-[2-chloro-4-(cyclohexylmethyloxy)benzyl]-2-methyl-5-(1-pentanesulfonylcarbamoyl)-3H-imidazo[4,5-b]pyridine sodium salt, 3-[2-chloro-4-(2-furyl)benzyl]-2,7-dimethyl-5-(1-pentanesulfonylcarbamoyl)-3H-imidazo[4,5-b]pyridine, 3-[2-chloro-4-(2-furyl)benzyl]-2,7-dimethyl-5-[(4-methylbenzene)sulfonylcarbamoyl]-3H-imidazo[4,5-b]pyridine, 3-[2-chloro-4-(2-furyl)benzyl]-2,7-dimethyl-5-(1-butanesulfonylcarbamoyl)-3H-imidazo[4,5-b]pyridine, 3-(2,4-dichloro-5-nitrobenzyl)-2-methyl-5-(1-pentanesulfonylcarbamoyl)-3H-imidazo[4,5-b]pyridine, 3-(2,4-dichloro-5-nitrobenzyl)-2-methyl-5-[(4-methylbenzene)sulfonylcarbamoyl]-3H-imidazo[4,5-b]pyridine, 3-[2,4-dichloro-5-(N,N-dimethylamino)benzyl]-2-methyl-5-(1-pentanesulfonylcarbamoyl)-3H-imidazo[4,5-b]pyridine, 3-[2,4-dichloro-5-(N,N-dimethylamino)benzyl]-2-methyl-5-[(4-methylbenzene)sulfonylcarbamoyl]-3H-imidazo[4,5-b]pyridine, 3-(4-(N-(1-butanesulfonyl)-N-methylamino)-2-chlorobenzyl)-2-methyl-5-((4-methylbenzene)sulfonylcarbamoyl)-3H-imidazo[4,5-b]pyridine, 3-(4-(N-(tert-butoxycarbonyl)-N-methylamino)-2-chlorobenzyl)-2-methyl-5-(1-pentanesulfonylcarbamoyl)-3H-imidazo[4,5-b]pyridine sodium salt, 3-(2-chloro-4-(N-methyl-N-(1-propoxycarbonyl)amino)benzyl)-2-methyl-5-(1-pentanesulfonylcarbamoyl)-3H-imidazo[4,5-b]pyridine, 3-(2-chloro-4-(N-methyl-N-(isopropoxycarbonyl)amino)benzyl)-2-methyl-5-(1-pentanesulfonylcarbamoyl)-3H-imidazo[4,5-b]pyridine, 3-(4-(N-(tert-butoxycarbonyl)amino)-2-chlorobenzyl)-2-methyl-5-(1-pentanesulfonylcarbamoyl)-3H-imidazo[4,5-b]pyridine, 3-(2-chloro-4-(ethoxycarbonylamino)benzyl)-2-methyl-5-(1-pentanesulfonylcarbamoyl)-3H-imidazo[4,5-b]pyridine, 3-(2-chloro-4-(N-valerylamino)benzyl)-2-methyl-5-[(4-methylbenzene)sulfonylcarbamoyl]-3H-imidazo[4,5-b]pyridine, 3-(4-(N-(1-butanesulfonyl)amino)-2-chlorobenzyl)-2-methyl-5-[(4-methylbenzene)sulfonylcarbamoyl]-3H-imidazo[4,5-b]pyridine, 3-(2-chloro-4-(N-(t-butylacetyl)amino)benzyl)-2-methyl-5-[(4-methylbenzene)sulfonylcarbamoyl]-3H-imidazo[4,5-b]pyridine, 3-(2-chloro-4-(N-(isopropoxycarbonyl)amino)benzyl)-2-methyl-5-((E)-1-penten-1-ylsulfonylcarbamoyl)-3H-imidazo[4,5-b]pyridine, 5-(1-butanesulfonylcarbamoyl)-3-(2-chloro-4-(N-(isopropoxycarbonyl)amino)benzyl)-2-methyl-3H- imidazo[4,5-b]pyridine, 3-(2-chloro-4-(N-ethoxycarbonyl-N-methylamino)benzyl)-2-methyl-5-((E)-1-penten-1-ylsulfonylcarbamoyl)-3H-imidazo[4,5-b]pyridine, 5-(1-butanesulfonylcarbamoyl)-3-(2-chloro-4-(N-ethoxycarbonyl-N-methylamino)benzyl)-2-methyl-3H-imidazo[4,5-b]pyridine, 3-(4-amino-2-chlorobenzyl)-2-methyl-5-(1-pentanesulfonylcarbamoyl)-3H-imidazo[4,5-b]pyridine, 3-(4-(N-(1-propoxycarbonyl)amino)-2-chlorobenzyl)-2-methyl-5-(1-pentanesulfonylcarbamoyl)-3H-imidazo[4,5-b]pyridine, 3-(4-(N-(isopropoxycarbonyl)amino)-2-chlorobenzyl)-2-methyl-5-(1-pentanesulfonylcarbamoyl)-3H-imidazo[4,5-b]pyridine, 5-(1-butanesulfonylcarbamoyl)-3-(4-(N-t-butoxycarbonylamino)-2-chlorobenzyl)-2-methyl-3H-imidazo[4,5-b]pyridine, 3-(4-amino-2-chlorobenzyl)-5-(1-butanesulfonylcarbamoyl)-2-methyl-3H-imidazo[4,5-b]pyridine, 3-(4-ethoxycarbonylamino-2-chlorobenzyl)-2-methyl-5-(1-butanesulfonylcarbamoyl)-3H-imidazo[4,5-b]pyridine, 3-(4-(N-t-butoxycarbonylamino)-2-chlorobenzyl)-2-methyl-5-((E)-1-penten-1-ylsulfonylcarbamoyl)-3H-imidazo[4,5-b]pyridine, 3-(4-amino-2-chlorobenzyl)-2-methyl-5-((E)-1-penten-1-ylsulfonylcarbamoyl)-3H-imidazo[4,5-b]pyridine, 3-(4-ethoxycarbonylamino-2-chlorobenzyl)-2-methyl-5-((E)-1-penten-1-ylsulfonylcarbamoyl)-3H-imidazo[4,5-b]pyridine, 3-(4-(N-(tert-butoxycarbonyl)-N-methylamino)-2-chlorobenzyl)-2-methyl-5-((E)-1-penten-1-ylsulfonylcarbamoyl)-3H-imidazo[4,5-b]pyridine, 3-(2-chloro-4-(3-(1-propyl)ureido)benzyl)-2-methyl-5-[(4-methylbenzene)sulfonylcarbamoyl]-3H-imidazo[4,5-b]pyridine, 3-(4-(1-methyl-3-(1-propyl)ureido)-2-chlorobenzyl)-2-methyl-5-((4-methylbenzene)sulfonylcarbamoyl)-3H-imidazo[4,5-b]pyridine, 3-(2-chloro-4-(2-oxo-1-pyrrolidinyl)benzyl)-2-methyl-5-((4-methylbenzene)sulfonylcarbamoyl)-3H-imidazo[4,5-b]pyridine, 3-(2-chloro-4-(2-oxo-1,3-oxazolidin-3-yl)benzyl)-2-methyl-5-((4-methylbenzene)sulfonylcarbamoyl)-3H-imidazo[4,5-b]pyridine, 3-(2-chloro-4-(((2-(4-methylbenzene)sulfonylcarbamoyloxy)-ethyl)amino)benzyl)-2-methyl-5-((4-methylbenzene)sulfonyl-carbamoyl)-3H-imidazo[4,5-b]pyridine, 3-[(4-chloro-1,2-dimethyl-1H-benzimidazol-5-yl)methyl]-2-methyl5-(1-pentanesulfonylcarbamoyl)-3H-imidazo[4,5-b]pyridine, 3-[(4-chloro-1,2-dimethyl-1H-benzimidazol-5-yl)methyl]-2-methyl-5-[(4-methylbenzene)sulfonylcarbamoyl]-3H-imidazo[4,5-b]pyridine, 3-((6-chloro-1,2-dimethyl-1H-benzimidazol-5-yl)methyl)-2-methyl-5-((4-methylbenzene)sulfonylcarbamoyl)-3H-imidazo[4,5-b]pyridine, 3-[(3,5-dichloropyridin-2-yl)methyl]-2-methyl-5-(1-pentanesulfonylcarbamoyl)-3H-imidazo[4,5-b]pyridine, 3-[(3,5-dichloropyridin-2-yl)methyl]-2-methyl-5-[(4-methylbenzene)sulfonylcarbamoyl]-3H-imidazo[4,5-b]pyridine, 3-((3,5-dichloropyridin-2-yl)methyl)-2,7-dimethyl-5-((4-methylbenzenesulfonyl)carbamoyl)-3H-imidazo[4,5-b]pyridine, 3-((3,5-dichloropyridin-2-yl)methyl)-2,7-dimethyl-5-(((E)-2-phenylethenesulfonyl)carbamoyl)-3H-imidazo[4,5-b]pyridine, 3-[(2-chloro-6-phenylpyridin-3-yl)methyl]-2-methyl-5-(1-pentanesulfonylcarbamoyl)-3H-imidazo[4,5-b]pyridine, 3-[(2-chloro-6-phenylpyridin-3-yl)methyl]-2-methyl-5-[(4-methylbenzene)sulfonylcarbamoyl]-3H-imidazo[4,5-b]pyridine, 3-[(5-(N-(tert-butoxycarbonyl)amino)-3-chloropyridin-2-yl)methyl]-2-methyl-5-(1-pentanesulfonylcarbamoyl)-3H-imidazo[4,5-b]pyridine, 3-[(5-(N-(tert-butoxycarbonyl)amino)-3-chloropyridin-2-yl)methyl]-2-methyl-5-((E)-1-penten-1-ylsulfonylcarbamoyl)-3H-imidazo[4,5-b]pyridine, 3-[(5-(N-(tert-butoxycarbonyl)amino)-3-chloropyridin-2-yl)methyl]-2-methyl-5-[(4-methylbenzene)sulfonylcarbamoyl]-3H-imidazo[4,5-b]pyridine, 3-[(3-chloro-5-(N-(ethoxycarbonyl)amino)pyridin-2-yl)methyl]-2-methyl-5-(1-pentanesulfonylcarbamoyl)-3H-imidazo[4,5-b]pyridine, 3-[(3-chloro-5-(N-(ethoxycarbonyl)amino)pyridin-2-yl)methyl]-2-methyl-5-((E)-1-penten-1-ylsulfonylcarbamoyl)-3H-imidazo[4,5-b]pyridine, 3-[(3-chloro-5-(N-(ethoxycarbonyl)amino)pyridin-2-yl)methyl]-2-methyl-5-[(4-methylbenzene)sulfonylcarbamoyl]-3H-imidazo[4,5-b]pyridine, 3-[(5-(N-(isopropoxycarbonyl)amino)-3-chloropyridin-2-yl)methyl]-2-methyl-5-(1-pentanesulfonylcarbamoyl)-3H-imidazo[4,5-b]pyridine, 3-[(5-(N-(isopropoxycarbonyl)amino)-3-chloropyridin-2-yl)methyl]-2-methyl-5-((E)-1-penten-1-ylsulfonylcarbamoyl)-3H-imidazo[4,5-b]pyridine, 3-[(5-(N-(isopropoxycarbonyl)amino)-3-chloropyridin-2-yl)methyl]-2-methyl-5-((4-methylbenzene)sulfonylcarbamoyl)-3H-imidazo[4,5-b]pyridine, 3-((2,4-dichloropyridin-5-yl)methyl)-2-methyl-5-(1-pentanesulfonylcarbamoyl)-3H-imidazo[4,5-b]pyridine, 3-((2,4-dichloropyridin-5-yl)methyl)-2-methyl-5-((4-methylbenzene)sulfonylcarbamoyl)-3H-imidazo[4,5-b]pyridine, 3-(2-chloro-4-(phenylethynyl)benzyl)-2,7-dimethyl-5-(1-pentanesulfonylcarbamoyl)-3H-imidazo[4,5-b]pyridine sodium salt, 3-[2-chloro-4-(5-chlorothiophen-2-yl)benzyl]-2-methyl-5-(1-pentanesulfonylcarbamoyl)-3H-imidazo[4,5-b]pyridine sodium salt, 3-(2-chloro-4-(phenylethynyl)benzyl)-2,7-dimethyl-5-[(4-methylbenzene)sulfonylcarbamoyl]-3H-imidazo[4,5-b]pyridine sodium salt, 5-[(5-bromothiophen-2-yl)sulfonylcarbamoyl]-3-(2-chloro-4-phenylbenzyl)-2,7-dimethyl-3H-imidazo[4,5-b]pyridine sodium salt, 3-[2-chloro-4-(1-pentyloxy)benzyl]-2-methyl-5-[(4-methylbenzene)sulfonylcarbamoyl]-3H-imidazo[4,5-b]pyridine sodium salt, 3-(4-(N-(ethoxycarbonyl)-N-methylamino)-2-chlorobenzyl)-2-methyl-5-(1-pentanesulfonylcarbamoyl)-3H-imidazo[4,5-b]pyridine, and 3-(4-(N-(benzyloxycarbonyl)-N-methylamino)-2-chlorobenzyl)-2-methyl-5-(1-pentanesulfonylcarbamoyl)-3H-imidazo[4,5-b]pyridine.

The production methods of the objective compound (I) are explained in detail in the following.

PRODUCTION METHOD 1

The objective compound (I) and a salt thereof can be produced by reacting compound (II) or reactive derivative at carboxy thereof or a salt thereof with compound (III) or a salt thereof.

Preferable salts of compound (II), reactive derivative at carboxy thereof and compound (III) are exemplified by those shown with regard to compound (I).

Preferable reactive derivative at carboxy of compound (II) indludes acid halide, acid anhydride inclusive of intramolecular acid anhydride, intermolecular acid anhydride and mixed acid anhydride, active amide, active ester and the like. Preferable examples thereof include acid chloride, acid azide, mixed acid anhydride with acid such as substituted phosphoric acid (e.g., dialkylphosphoric acid, phenylphosphoric acid, diphenylphosphoric acid, dibenzylphosphoric acid and halogenated phosphoric acid), dialklphosphinic acid, sulfurous acid, thiosulfuric acid, sulfuric acid, sulfonic acid (e.g., methanesulfonic acid), aliphatic carboxylic acid (e.g., acetic acid, propionic acid, butyric acid, isobutyric acid, pivalic acid, pentanoic acid, isopentanoic acid, 2-ethylbutyric acid and trichloroacetic acid), aromatic carboxylic acid (e.g., benzoic acid), and the like; symmetric acid anhydride; active amide with imidazole, 4-substituted imidazole, dimethylpyrazole, triazole or tetrazole; active ester (e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenylthio ester, p-cresylthio ester, carboxymethylthio ester, pyranyl ester, pyridyl ester, piperidyl ester and 8-quinolylthio ester); esters with N-hydroxy compound (e.g., N,N-dimethylhydroxylamine, 1-hydroxy-2-1H-pyridone, N-hydroxysuccinimide and 1-hydroxy-1H-benzotriazole); and the like. These reactive derivatives can be appropriately selected according to the kind of compound (II) to be used.

The reaction generally proceeds in a conventional solvent such as water, alcohol (e.g., methanol and ethanol), acetone, dioxane, acetonitrile, chloroform, methylene chloride, ethylene chloride, tetrahydrofuran, ethyl acetate, N,N-dimethylformamide, pyridine and a mixture thereof, or in any other solvent which does not adversely affect the reaction. These conventional solvents may be used alone or in combination.

When compound (II) is used in the form of a free acid or a salt thereof in this reaction, the reaction is preferably carried out in the presence of a conventional condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonylbis(2-methyl-imidazole), pentamethyleneketene-N-cyclohexylimine, diphenylketene-N-cyclohexylimine, ethoxyacetylene, 1-alkoxy-1-chloroethylene, trialkyl phosphite, ethyl polyphosphorate, isopropyl polyphosphate, phosphorous oxychloride (phosphoryl chloride), phosphorus trichloride, diphenylphosphoryl azide, diphenyl chlorophosphate, diphenylphosphinic chloride, thionyl chloride, oxalyl chloride, lower alkyl haloformate (e.g., ethyl chloroformate and isopropyl chloroformate), triphenylphosphine, 2-ethyl-7-hydroxybenzisoxazolium salt, intramolecular salt of 2-ethyl-5-(m-sulfophenyl)-isoxazolium hydroxide, 1-(p-chlorobenzenesulfonyloxy)-6-chloro-1H-benzotriazole, and so-called Vilsmeier reagent (prepared by the reaction of N,N-dimethylformamide with thionyl chloride, phosgene, trichloromethyl chloroformate, phosphorous oxychloride, or the like), and the like.

The reaction can be carried out in the presence of an inorganic or organic base such as alkali metal bicarbonate, tri(lower)alkylamine, pyridine, 4-dimethylaminopyridine, N-(lower)alkylmorpholine, N,N-di(lower)alkylaniline (e.g., N,N-dimethylaniline), N,N-di(lower)alkylbenzylamine, and the like.

The reaction temperature is not particularly limited, and the reaction is generally carried out under cooling to heating.

PRODUCTION METHOD 2

The objective compound (I-b) and a salt thereof can be produced by subjecting compound (I-a) or a salt thereof to elimination of carboxy-protecting group.

The preferable salts of compound (I-a) and (I-b) are exemplified by those shown with regard to compound (I).

This reaction is carried out according to a conventional method such as hydrolysis and the like.

Hydrolysis is preferably carried out in the presence of a base or an acid inclusive of Lewis acid. Examples of preferable base include inorganic base and organic base such as alkali metal (e.g., lithium, sodium, potassium and the like), alkaline earth metal (magnesium, calcium and the like), and hydroxide, carbonate and bicarbonate thereof, trialkylamine (e.g., trimethylamine, triethylamine and the like), picoline, 1,5-diazabicyclo-[4.3.0]non-5-ene, 1,4-diazabicyclo[2.2.2]octane, 1,8-diazabicyclo[5.4.0]undec-7-ene and the like. Preferable acid includes organic acid (e.g., formic acid, acetic acid, propionic acid, trichloroacetic acid, trifluoroacetic acid and the like), inorganic acid (e.g., hydrochloric acid, hydrobromic acid, hydroiodic acid, sulfuric acid and the like) and Lewis acid (boron tribromide and the like).

The reaction generally proceeds in a solvent such as water, alcohol (e.g., methanol, ethanol and the like), xylene, diethyleneglycol monomethyl ether, methylene chloride, tetrahydrofuran, mixtures thereof and the like, or any other solvent that does not adversely affect the reaction. A liquid base or acid can be also used as a solvent. The reaction temperature is not particularly limited and the reaction generally proceeds under cooling to heating.

PRODUCTION METHOD 3

Compound (I-d) and a salt thereof can be produced by subjecting compound (I-c) or a salt thereof to elimination of amino-protecting group.

The preferable salts of compound (I-c) and (I-d) are exemplified by those shown with regard to compound (I).

This reaction can be carried out in essentially the same manner as in Production Method 2, and therefore, the method of reaction and reaction conditions (e.g., solvent, reaction temperature and the like) are to be referred to those disclosed for Production Method 2.

PRODUCTION METHOD 4

The objective compound (I-e) and a salt thereof can be prepared by adding compound (IV) to compound (I-d) or a salt thereof by reduction.

The preferable salts of compound (I-d) and (I-e) are exemplified by those shown with regard to compound (I).

The reduction can be carried out in chemical reduction and catalytic reduction, which may be carried out by a conventional method.

The preferable reducing agent used in the chemical reduction is, for example, metal such as tin, zinc and iron, a combination of such a metal and/or a metal compound such as chromium chloride and chromium acetate, and an organic acid or inorganic acid such as formic acid, acetic acid, propionic acid, trifluoroacetic acid, p-toluenesulfonic acid, hydrochloric acid and hydrobromic acid, a combination of the aforementioned metal and/or metal compound and a base (e.g., ammonia, ammonium chloride, sodium hydroxide and the like), metal hydride compound such as aluminum hydride compound (e.g., lithium aluminum hydride, alminium sodium hydride, aluminum hydride, trimethoxy aluminum lithium hydride, tri-t-butoxy aluminum hydride and the like), borohydride compound (e.g., sodium borohydride, lithium borohydride, sodium cyanoborohydride, tetramethyl ammonium borohydride, borane, diborane and the like) and the like, phosphorus compound (phosphorus trichloride, phosphorus tribromide, triphenylphosphine, triethylphosphine and the like) and the like.

The preferable reducing agent used in the catalytic reduction is conventional one, for example, platinum catalyst such as platinum plate, platinum sponge, platinum black, platinum colloid, platinum oxide and platinum wire, palladium catalyst such as palladium sponge, palladium black, palladium oxide, palladium carbon, palladium colloid, palladium-barium sulfate and palladium-barium carbonate, nickel catalyst such as reduing nickel, nickel oxide and Raney nickel, cobalt catalyst such as reducing cobalt and Raney cobalt, iron catalyst such as reducing iron and Raney iron, copper catalyst such as reducing copper, Raney copper and Ullmann copper, and the like.

The reducion is generally carried out in a solvent. Examples of the solvent used include conventional solvent such as water, alcohol (e.g., methanol, ethanol, propanol and the like), acetonitrile, diethyl ether, dioxane, N,N-dimethylformamide, tetrahydrofuran, liquid base or acid, and a mixed solvent thereof, and any other solvents that do not adversely affect the reaction. A liquid base or acid can be also used as a solvent. The reaction temperature is not particularly limited and the reaction generally proceeds under cooling to heating.

PRODUCTION METHOD 5

The objective compound (I-g) and a salt thereof can be produced by substituting the halogen of compound (I-f) or a salt thereof with compound (V).

The preferable salts of compound (I-f) and (I-g) are exemplified by those shown with regard to compound (I).

This reaction is preferably carried out in the presence of potassium tert-butylate or a base such as the above-mentioned inorganic or organic base. The reaction is preferably carried out in the presence of a catalyst such as tris(dibenzilideneacetone)-dipalladium(O), (R)-(+)-BINAP [2,2'-bis(diphenylphosphino)-1,1'-binaphthyl] and the like.

While the reaction temperature is not particularly limited, the reaction is preferably carried out from under room temperature to heating, and the reaction can be also carried out in the presence of a solvent such as toluene, which does not adversely affect the reaction.

PRODUCTION METHOD 6

The objective compound (I-h) and a salt thereof can be produced by acylation of compound (I-d) or a salt thereof.

The preferable salts of compound (I-f) are exemplified by those shown with regard to compound (I).

When objective compound (I-f) is to be obtained by acylation, compound (I-d) having terminal amino is reacted with an acylating agent. Examples of the acylating agent include lower alkanecarbonyl halide (e.g., pivaloyl chloride) and lower alkanecarbonic anhydride. The solvent may be dichloromethane, tetrahydrofuran and the like, and the reaction proceeds from under ice-cooling to room temperature.

PRODUCTION METHOD 7

The objective compound (I-c) and a salt thereof can be produced by introducing an amino-protecting group into compound (I-d) or a salt thereof Examples of the amino-protecting group include halogenated lower alkanecarbonate derivative (e.g., ethyl chlorocarbonate) and lower alkanecarbonic anhydride. The solvent may be dichloromethane, tetrahydrofuran and the like, and the reaction proceeds from under ice-cooling to room temperature.

PRODUCTION METHOD 8

The objective compound (I-i) and a salt thereof can be produced by sulfonamidation of compound (I-d) or a salt thereof.

The preferable salts of compound (I-i) are exemplified by those shown with regard to compound (I).

When the objective compound (I-i) is obtained by sulfonamidation, compound (I-d) having terminal amino is reacted with lower alkanesulfonyl halide (e.g., butanesulfonyl chloride), lower alkanesulfonic anhydride and the like. The solvent may be dichloromethane, tetrahydrofuran and the like, and the reaction proceeds from under ice-cooling to room temperature.

The aforementioned compounds can be converted to preferable salts as necessary by a conventional method (e.g., the method described in Example 85 to be mentioned later). All of them can be purified as necessary according to a conventional method for purifying an organic compound (i.e., recrystallization, column chromatography, thin layer chromatography, high performance liquid chromatography and the like). The compound can be identified by NMR spectrum analysis, mass spectrum analysis, IR spectrum analysis, elemental anlysis, melting point measurement and the like.

The compound of the present invention may have one or more chrial centers and, therefore, may be presented in enantiomers or diastereomers. Some compounds having alkenyl may be present as a cis or trans isomer. In bose case, the present invention encompasses mixtures thereof and respective isomers.

The inventive compound and a salt thereof may be in the form of a solvate, which is also encompassed in the present invention. The solvate is preferably exemplified by hydrate and ethanol solvate.

The pharmaceutical data of compound (I) are shown in the following to demonstrate the utility of the objective compound (I).

EXPERIMENTAL EXAMPLE 1

Blood Sugar Level Depressing Activity in db/db Mice

Test Compound

Compound A 3-(2-Chloro-4-(1-propoxy)benzyl)-2,7-dimethyl-5-[(4-methylbenzene)sulfonylcarbamoyl]-3H-imidazo[4,5-b]pyridine (Compound of Example 37)

Animal to be Used

Female C57BL/KsJ-dbm db+/db+, C57BL/KsJ-dbm +m/+m (Jackson Laboratory) mice (5 weeks old) were purchased and subjected to the test after 2–3 weeks of acclimating period.

Drug Administration

The test drug was mixed with a powder diet (CE-2, Clea Japan, Inc.) in a mortar. In the case of administration in 100 mg/kg, the mixing proportion was 0.1%, in the case of 30 mg/kg, the proportion was 0.03% and in the case of 10 mg/kg, the proportion was 0.01%. The diet was changed twice a week for each group. The amount of the diet given and the amount left were recorded and the diet intake was calculated by determining the difference.

Test Schedule

The female db/db mice were grouped according to body weight, blood sugar level and triglyceride concentration in plasma. Then, the drug-mixed diet was given for 14 days, during which period the mice were 8 to 10 weeks of age. At day 7 and day 14 in the morning, blood was taken from orbital venous plexus using a heparinized glass capillary tube (Chase Heparinized Capillary Tube), and centrifuged to give plasma fractions. The blood sugar level, triglyceride concentration in plasma and insulin concentration in plasma were measured at day 0 and day 14, and blood sugar level and triglyceride concentration in blood were measured at day 7. Body weight was measured at day 0, day 7 and day 14. After final blood sampling, the mice were sacrificed with $CO_2$ gas.

Measurement Method

Blood sugar level was measured using 10–15 μl of plasma and in accordance with glucose oxidase method (glucose CII-Test Wako, Wako Pure Chemicals Co., Ltd.). The triglyceride concentration in plasma was measured using 10–15 μl of plasma and in accordance with GPO-p-chlorophenol method (triglyceride G-Test Wako) or GPO-DAOS method (triglyceride E-Test Wako). The measurement was done promptly after blood sampling. The insulin concentration in plasma was measured using 20 μl of plasma (preservable at −20° C.) and in accordance with an antibody method (Phadesef Insulin RIA kit, Kabi Pharmacia).

Result

Using the difference between db/db mice control group and +/+ mice in blood sugar level and triglyceride concentration in plasma as 100%, the proportion (%) of decrease in the blood sugar level and triglyceride concentration in plasma of the group administered with the test drug was determined. The results are shown in Table 1.

TABLE 1

| Test compound | Dose (mg/kg) | Blood sugar decrease (%) |
| --- | --- | --- |
| Compound A | 1 | 97 |

The compound (I) of the present invention can be used for therapeutic purposes in the form of a pharmaceutical preparation. This pharmaceutical preparation contains any one of the compounds (I) as an active ingredient in admixture with a pharmaceutically acceptable organic or inorganic excipient which is a solid, semi-solid or liquid and which is suitable for oral, parenteral or external (local) administration. Examples of the pharmaceutical preparation include capsules, tablets, sugar coating tablets, granules, suppositories, liquid, lotion, suspension,. emulsion, ointment, gel and the like. When desired, these preparations may contain adjuvant, auxiliary substance, stabilizer, moistening agent, emulsifier, buffering agent, and other conventional additives. While the dose of the compound (I) varies depending on the age and symptom of patients, compound (I) may be administered for the therapy of the above-mentioned diseases in an average single dose amount of about 0.1 mg, 1 mg, 10 mg, 50 mg, 100 mg, 250 mg, 500 mg or 1000 mg. In general, its daily dose may be about 0.1 mg/patient to about 1000 mg/patient.

The present invention is described in more detail by way of the following Preparation Examples and Examples.

PREPARATION EXAMPLE 1-1

To a solution of diisopropylamine (7.4 ml) in tetrahydrofuran (36 ml) was added dropwise a 1.6 M solution (30 ml) of 1-butyllithium in n-hexane under a nitrogen atmosphere at an inside temperature of from −62° C. to −48° C. over 5 minutes. After stirring for 30 min under ice-cooling, a solution of N-tert-butylmethanesulfonamide (3.63 g) in tetrahydrofuran (15 ml) was added dropwise at an inside temperature of from −60° C. to −50° C. over 5 minutes. After stirring for 1 hr under ice-cooling, the mixture was cooled to an inner temperature of −60° C. again. 4-Formylpyridine (2.74 ml) was added dropwise and after stirring at room temperature for 5 hr, the mixture was left standing overnight. Water (250 ml) was gradually added to the reaction mixture under ice-cooling, and the mixture was extracted 4 times with ethyl acetate. The organic layers were combined and dried over magnesium sulfate and concentrated to dryness under reduced pressure to give N-tert-butyl-2-hydroxy-2-(4-pyridyl)ethanesulfonamide (7.02 g) as a brown oil.

MASS (ESI): m/z 259 (M+1).

PREPARATION EXAMPLE 1-2

A mixture of N-tert-butyl-2-hydroxy-2-(4-pyridyl) ethanesulfonamide (6.62 g), acetic anhydride (13.2 ml) and pyridine (26.4 ml) was stirred at room temperature for 1.5 hr. To the reaction mixture was added 1,8-diazabicyclo[5.4.0]undec-7-ene (9.58 ml), and the mixture was stirred in an oil bath at 100° C. for 40 min. The reaction mixture was concentrated to dryness under reduced pressure. The residue was dissolved in ethyl acetate and washed with saturated brine. Th aqueous layer was extracted with ethyl acetate and organic layers were combined, dried over magnesium sulfate and concentrated to dryness under reduced pressure. The residue was purified by silica gel column chromatography (n-hexane:ethyl acetate=1:1) to give (E)-N-tert-butyl-2-(4-pyridyl)ethenesulfonamide (3.91 g) as a pale-yellow solid.

$^1$H-NMR (CDCl$_3$): 1.38 (9H, s), 6.99 (1H, d, J=16 Hz), 7.33 (2H, d, J=6 Hz), 7.39 (1H, d, J=16 Hz), 8.68 (2H, d, J=6 Hz). MASS (ESI): m/z 241 (M+1).

PREPARATION EXAMPLE 1-3

(E)-N-tert-Butyl-2-(4-pyridyl)ethenesulfonamide (3.8 g) was dissolved in trifluoroacetic acid (38 ml) and the mixture was stirred in an oil bath at 50° C. for 4 hr. The reaction mixture was concentrated to dryness under reduced pressure. The residue was dissolved in trifluoroacetic acid (19 ml) and stirred in an oil bath at 50° C. for 45 min. The reaction mixture was concentrated to dryness under reduced pressure and the residue was partitioned between chloroform:methanol (9:1) and a saturated aqueous solution of sodium hydrogen carbonate. The aqueous layer was extracted twice with chloroform:methanol (9:1) and once with ethyl acetate. The aqueous layer was saturated with sodium chloride and extracted 4 times with ethyl acetate. All extracts with ethyl acetate were combined, dried over magnesium sulfate, and concentrated to dryness under reduced pressure. The residue was powdered from diethyl ether to give (E)-2-(4-pyridyl)ethenesulfonamide (2.34 g) as a pale-brown powder.

$^1$H-NMR (DMSO-d$_6$): 7.27 (2H, s), 7.31 (1H, d, J=16 Hz), 7.55 (1H, d, J=16 Hz), 7.67 (2H, d, J=6 Hz), 8.63 (2H, d, J=6 Hz). MASS (ESI): m/z 183 (M−1).

PREPARATION EXAMPLE 2-1

To a solution of diisopropylamine (3.7 ml) in tetrahydrofuran (18 ml) was added dropwise a 1.6 M solution (15 ml) of 1-butyllithium in n-hexane under a nitrogen atmosphere at an inside temperature of from −62° C. to −48° C. over 5 minutes. After stirring for 30 min under ice-cooling, a solution of N-tert-butylmethanesulfonamide(3.63 g) in tetrahydrofuran (12 ml) was added dropwise at an inside temperature of from −63° C. to −59° C. over 5 minutes. After stirring for 1 hr under ice-cooling, the mixture was cooled to an inner temperature of −60° C. again. 1-Bromo-3-(tert-butyldimethylsilyloxy)propane (3.35 ml) was added dropwise and the mixture was stirred overnight at room temperature. The reaction mixture was partitioned between ethyl acetate and saturated brine and the organic layer was dried over magnesium sulfate and concentrated to dryness under reduced pressure. The residue was purified by silica gel column chromatography (n-hexane:ethyl acetate=9:1) to give N-tert-butyl-4-(tert-butyl-dimethylsilyloxy) butanesulfonamide (618 mg) as a pale-yellow oil.

$^1$H-NMR (CDCl$_3$): 0.07 (6H, s), 0.89 (9H, s), 1.38 (9H, s), 1.64 (2H, m), 1.90 (2H, m), 3.08 (2H, t, J=6 Hz), 3.64 (2H, t, J=6 Hz), 4.05 (1H, br s). MASS (ESI): m/z 322 (M−1).

PREPARATION EXAMPLE 2-2

N-tert-Butyl-4-(tert-butyldimethylsilyloxy) butanesulfonamide (515 mg) was dissolved in tetrahydrofuran (2.0 ml), a 1N solution (3.2 ml) of tetrabutylammonium fluoride in tetrahydrofuran was added and the mixture was left standing for 2 hr. The reaction mixture was partitioned between ethyl acetate and 1N hydrochloric acid saturated with sodium chloride. The aqueous layer was extracted twice with ethyl acetate. The organic layers were combined, dried over magnesium sulfate, and concentrated to dryness under reduced pressure to give a crude product (1.17 g) of N-tert-butyl-4-hydroxybutanesulfonamide as a pale-yellow oil. This was used in the next reaction without further purification.

PREPARATION EXAMPLE 2-3

A crude product (1.17 g) of N-tert-butyl-4-hydroxybutanesulfonamide was dissolved in pyridine (3.0 ml) and acetic anhydride (1.5 ml) was added, and the mixture was left standing at room temperature for 1 hr. The reaction mixture was concentrated to dryness under reduced pressure and the residue was partitioned between ethyl acetate and 1N hydrochloric acid. The organic layer was washed once with water and once with saturated brine, dried over magnesium sulfate and concentrated to dryness under reduced pressure to give N-tert-butyl-4-acetoxybutanesulfonamide (425 mg) as a pale-yellow oil.

$^1$H-NMR (CDCl$_3$): 1.38 (9H, s), 1.78 (2H, m), 1.90 (2H, m), 2.05 (3H, s), 3.08 (2H, t, J=6 Hz), 4.10 (2H, t, J=6 Hz), 4.05 (1H, br s). MASS (ESI): m/z 322 (M−1).

PREPARATION EXAMPLE 2-4

N-tert-Butyl-4-acetoxybutanesulfonamide (425 mg) was dissolved in trifluoroacetic acid (4.3 ml), and the mixture was stirred at room temperature for 4 hr and concentrated to dryness under reduced pressure. The residue was purified by silica gel column chromatography (chloroform:methanol= 49:1) to give 4-acetoxybutanesulfonamide (347 mg) as a brown oil.

$^1$H-NMR (CDCl$_3$): 1.80 (2H, m), 1.96 (2H, m), 2.08 (3H, s), 3.16 (2H, t, J=6 Hz), 4.11 (2H, t, J=6 Hz), 4.77 (2H, br s). MASS (ESI): m/z 194 (M−1).

PREPARATION EXAMPLE 3-1

To a suspension of tetrakis(triphenylphosphine)palladium (213 mg) in toluene (7 ml) was added 2-chloro-4-iodotoluene (2.33 g) at room temperature. The mixture was stirred at room temperature for 30 min, and a solution of phenylboronic acid (1.35 g) in ethanol (2 ml) and 2 M aqueous sodium carbonate solution (9.25 ml) were added to this mixture, which was followed by reflux under heating. After 3 hr, the reaction mixture was cooled and the organic layer was separated. The aqueous layer was extracted with hexane (4 ml). The organic layers were combined, washed with saturated aqueous sodium hydrogen carbonate solution (4 ml) and saturated brine (4 ml), and dried over anhydrous magnesium sulfate. After filtration, the filtrate was concentrated. To the residue (2.11 g) were added hexane (10 ml) and silica gel (4 g) and the mixture was stirred at room temperature for 1 hr. Silica gel was filtered off and the filtrate was concentrated to give 2-chloro-4-phenyltoluene as a pale-brown oil (1.86 g, 99.4%).

$^1$H-NMR (CDCl$_3$): 2.40 (3H, s), 7.23–7.60 (8H, m).

PREPARATION EXAMPLE 3-2

In the same manner as in Preparation Example 4-2 to be mentioned later, 2-chloro-4-phenylbenzylbromide was obtained as colorless crystals (3.22 g) from 2-chloro-4-phenyltoluene (3.6 g).

$^1$H-NMR (CDCl$_3$): 4.64 (2H, s), 7.35–7.63 (8H, m). m.p. 73–74° C.

PREPARATION EXAMPLE 3-3

In the same manner as in Preparation Example 4-5 to be mentioned later, 6-bromo-2-[N-(2-chloro-4-phenylbenzyl) acetamido]-3-nitropyridine (1.6 g) was obtained as amorphous from 2-(acetamido)-6-bromo-3-nitropyridine (1.0 g) and 2-chloro-4-phenylbenzylbromide (1.1 g).

$^1$H-NMR (CDCl$_3$): 2.25 (3H, br s), 5.42 (2H, br s), 7.32–7.70 (9H, m), 8.11 (1H,d, J=8 Hz). MASS (ESI): m/z 458 (M−1).

PREPARATION EXAMPLE 3-4

To a solution of 2-[N-acetyl-N-(2-chloro-4-phenylbenzyl)]-amino-6-bromo-3-nitropyridine (3.56 g) in acetic acid (7.1 ml) and ethanol (34 ml) was added iron powder (1.73 g) at room temperature under a nitrogen flow and the mixture was refluxed under heating. One hour later, the reaction mixture was cooled and dichloromethane:methanol=5:1 (17.5 ml) was added, which was followed by stirring at room temperature for 15 min. The reaction mixture was filtered through celite and washed 10 times with dichloromethane (7 ml). The filtrate was concentrated and subjected to azeotropic distillation once with toluene. To the residue were added dichloromethane (17.5 ml) and saturated aqueous sodium hydrogen carbonate solution (20 ml) and the mixture was stirred at room temperature for 10 min. This mixture was filtered through celite and washed 10 times with dichloromethane (7 ml). The organic layer was separated and washed with saturated brine. The organic layer was dried over anhydrous magnesium sulfate. After filtration, the filtrate was concentrated to give the residue as a colorless solid (3.39 g). This was suspended in methanol (17 ml), heated and stirred at room temperature for 30 min. The crystals were filtrated, washed 4 times with methanol (3.4 ml) and dried under reduced pressure at 50° C. for 2 hr to give 5-bromo-3-(2-chloro-4-phenylbenzyl)-2-methyl-3H-imidazo[4,5-b]pyridine as pale-yellow crystals (2.8 g, 87.8%).

$^1$H-NMR (CDCl$_3$): 2.61 (3H, s), 5.62 (2H, s), 6.71 (1H, d, J=8 Hz), 7.32–7.55(7H, m), 7.68 (1H, s), 7.92 (1H, d, J=8 Hz). MASS (ESI): m/z 414 (M−1).

PREPARATION EXAMPLE 3-5

In the same manner as in Preparation Example 12-2 to be mentioned later, methyl 3-(2-chloro-4-phenylbenzyl)-2-methyl-3H-imidazo[4,5-b]pyridine-5-carboxylate (504 mg) was obtained as pale-yellow crystals from 5-bromo-3-(2-chloro-4-phenylbenzyl)-2-methyl-3H-imidazo[4,5-b]pyridine (822 mg).

$^1$H-NMR (CDCl$_3$): 2.60 (3H, s), 4.00 (3H, s), 5.73 (2H, s), 6.71 (1H, d, J=8 Hz), 7.30–7.54 (6H, m), 7.67 (1H, br s), 8.10 (1H, d, J=8 Hz), 8.18 (1H, d, J=8 Hz). MASS (ESI): m/z 392 (M+1). m.p. 200–201° C.

PREPARATION EXAMPLE 3-6

In the same manner as in Preparation Example 14-7 to be mentioned later, 3-(2-chloro-4-phenylbenzyl)-2-methyl-3H-imidazo[4,5-b]pyridine-5-carboxylic acid (403 mg) was obtained as colorless crystals from methyl 3-(2-chloro-4-phenylbenzyl)-2-methyl-3H-imidazo[4,5-b]pyridine-5-carboxylate (500 mg).

$^1$H-NMR (DMSO-d$_6$): 2.55 (3H , s), 5.65 (2H, s), 6.60 (1H, d, J=8 Hz), 7.33–7.55 (3H, m), 7.65 (2H, br d, J=8 Hz), 7.85 (1H, d, J=1 Hz), 8.00 (1H, d, J=8 Hz), 8.11 (1H, d, J=8 Hz). MASS (ESI): m/z 376 (M−1). m.p. 238–243° C.

PREPARATION EXAMPLE 4-1

Acetic anhydride (430 mg) and pyridine (416 mg) were added to a solution of 3-chloro-4-methylphenol (500 mg) in ether (5.0 ml), and the mixture was stirred at room temperature for 2 hr. The reaction mixture was washed once with 1N hydrochloric acid and twice with saturated brine, dried over magnesium sulfate, and concentrated to dryness under reduced pressure to give 4-acetoxy-2-chlorotoluene as a pale-yellow oil (645 mg).

$^1$H-NMR (CDCl$_3$): 2.30 (3H, s), 2.36 (3H, s), 6.90 (1H, dd, J=8,2 Hz), 7.12 (1H, d, J=2 Hz), 7.22 (1H, d, J=8 Hz).

PREPARATION EXAMPLE 4-2

To a solution of 4-acetoxy-2-chlorotoluene (13.4 g) in carbon tetrachloride (134 ml) were added N-bromosuccinimide (12.9 g) and 2,2'-azobis(4-methoxy-2,4-dimethylvaleronitrile) (1.12 g), and the mixture was refluxed under heating for 2.5 hr. The reaction mixture was concentrated to dryness under reduced pressure. To the residue was added hexane (270 ml) and the mixture was stirred at room temperature for 10 min. The insoluble matter was filtered off and washed with hexane. The filtrate and washing were combined and washed 3 times with saturated aqueous sodium hydrogen carbonate solution and once with saturated brine. The organic layer was dried over magnesium sulfate and concentrated to dryness under reduced pressure. The residue was crystallized from hexane to give 4-acetoxy-2-chlorobenzylbromide as colorless crystals (11.3 g).

$^1$H-NMR (CDCl$_3$): 2.30 (3H, s), 4.58 (2H, s), 7.02 (1H, dd, J=8,2 Hz), 7.18 (1H, d, J=2 Hz), 7.44 (1H, d, J=8 Hz).

PREPARATION EXAMPLE 4-3

To a suspension of 2,6-dibromo-3-nitropyridine (5.00 g) in ethanol (10 ml) was added a solution (6.8 M, 15 ml) of ammonium/ethanol at room temperature, and the mixture was stirred at room temperature for 19 hr in a sealed container. Water (25 ml) was added to the reaction mixture, and the precipitate was collected by filtration and washed with ethanol. This was suspended in ethanol (55 ml), heated, and allowed to cool. The precipitate was collected by filtration to give 2-amino-6-bromo-3-nitropyridine as a yellow powder (3.19 g).

$^1$H-NMR (DMSO-d$_6$): 6.89 (1H, d, J=8 Hz), 8.24 (1H, d, J=8 Hz), 8.25(2H, br s). MASS (ESI): m/e 216,218 (M−H)$^-$.

PREPARATION EXAMPLE 4-4

To a suspension of 2-amino-6-bromo-3-nitropyridine (23.9 g) in acetic acid (48 ml) were added acetic anhydride (48 ml) and sulfuric acid (2.9 ml), and the mixture was heated at 65° C. for 40 min. The reaction mixture once became homogeneous and a product soon precipitated to give a suspension. The reaction mixture was allowed to cool and poured into cold water (480 ml), which was followed by stirring for 30 min. The precipitate was collected by filtration and washed with water to give a crude product. This was suspended in ether (60 ml) and collected by filtration to give 2-(acetamido)-6-bromo-3-nitropyridine as a pale-yellow powder (27.2 g).

$^1$H-NMR (CDCl$_3$): 2.54 (3H s), 7.33 (1H, d, J=8 Hz), 8.33 (1H, d, J=8 Hz), 9.95 (1H, br s). MASS (ESI): m/e 258,260 (M−H)$^-$.

PREPARATION EXAMPLE 4-5

To a solution of 2-acetamido-6-bromo-3-nitropyridine (203 mg) in N,N-dimethylformamide (2.34 ml) was added sodium hydride (60%, 34.3 mg) under ice-cooling, and the mixture was stirred for 1 hr. 4-Acetoxy-2-chlorobenzylbromide (288 mg) was added, and the mixture was stirred for 30 min under ice-cooling and at room temperature for 1 hr. Ethyl acetate (350 ml) and water (700 ml) were added to the reaction mixture under ice-cooling, and the mixture was partitioned. The organic layer was washed with water and saturated aqueous sodium chloride solution, dried over anhydrous magnesium sulfate, filtered and concentrated. The residue was purified by flash silica gel column chromatography and eluted with hexane/ethyl acetate=4/1–3/1. The eluate was concentrated under reduced pressure to give 2-[N-(4-acetoxy-2-chlorobenzyl) acetamido]-6-bromo-3-nitropyridine as an oil (256 mg).

$^1$H-NMR (CDCl$_3$): 2.22 (3H, br s), 2.29 (3H, s), 5.37 (2H, br s), 7.02 (1H, dd, J=1,8 Hz), 7.19 (1H, br s), 7.50 (1H, br s), 7.64 (1H, d, J=8 Hz), 8.10 (1H, d, J=8 Hz).

PREPARATION EXAMPLE 4-6

To a solution of 2-[N-(4-acetoxy-2-chlorobenzyl) acetamido]-6-bromo-3-nitropyridine (1.28 g) in ethanol (13 ml) were added acetic acid (1.5 ml) and reduced iron powder (646 mg), and the mixture was refluxed under heating at 110° C. for 15 hr. After allowing to cool, chloroform/methanol=10/1 (15 ml) was added and the mixture was stirred under ice-cooling. The insoluble matter was filtered off and the filtrate was concentrated. A saturated aqueous sodium hydrogen carbonate solution (5 ml) and chloroform/methanol=10/1 (15 ml) were added to make the mixture alkaline, and the precipitated insoluble matter was filtered off. The residue was repeatedly eluted with chloroform/ methanol=5/1–2/1–1/1. The organic layer of the filtrate was washed with saturated aqueous sodium hydrogen carbonate solution and saturated brine, dried over anhydrous magnesium sulfate, filtered and concentrated. To the resulting crystals was added ethyl acetate (8 ml), and the mixture was heated and stirred at room temperature. The crystals were collected by filtration and dried under reduced pressure to give 5-bromo-3-(2-chloro-4-hydroxybenzyl)-2-methyl-3H-imidazo[4,5-b]pyridine as colorless crystals (1.04 g).

$^1$H-NMR (DMSO-d$_6$): 2.46 (3H, s), 5.40 (2H, s), 6.53 (1H, d, J=8 Hz), 6.66 (1H, dd, J=1,8 Hz), 6.91 (1H, d, J=1 Hz), 7.44 (1H, d, J=8 Hz), 7.97 (1H, d, J=8 Hz).

PREPARATION EXAMPLE 4-7

In the same manner as in Preparation Example 12-2 to be mentioned later, methyl 3-(2-chloro-4-hydroxybenzyl)-2-methyl-3H-imidazo[4,5-b]pyridine-5-carboxylate was obtained as pale-gray crystals (272 mg) from 5-bromo-3-(2-chloro-4-hydroxybenzyl)-2-methyl-3H-imidazo[4,5-b]pyridine (400 mg).

$^1$H-NMR (DMSO-d$_6$): 2.52 (3H, s), 3.86 (3H, s), 5.50 (2H, s), 6.50 (1H, d, J=8 Hz), 6.64 (1H, dd, J=8,2 Hz), 6.92 (1H, d, J=2 Hz), 8.04 (1H, d, J=8 Hz), 8.16 (1H, d, J=8 Hz), 10.00 (1H, br s).

PREPARATION EXAMPLE 4-8

In the same manner as in Preparation Example 14-6, methyl 3-(2-chloro-4-methoxybenzyl)-2-methyl-3H-imidazo[4,5-b]pyridine-5-carbxylate was obtained as bright yellow crystals (536 mg) from methyl 3-(2-chloro-4-hydroxybenzyl)-2-methyl-3H-imidazo[4,5-b]pyridine-5-carboxylate (560 mg) and methyl iodide (359 mg).

$^1$H-NMR (CDCl$_3$): 2.54 (3H, s), 3.77 (3H, s), 4.00 (3H, s), 5.62 (2H, s), 6.66 (2H, s), 6.97 (1H, d, J=1 Hz), 8.05 (1H, d, J=8 Hz), 8.14 (1H, d, J=8 Hz). MASS (ESI): m/z 346 (M+1).

PREPARATION EXAMPLE 4-9

In the same manner as in Preparation Example 14-7 to be mentioned later, 3-(2-chloro-4-methoxybenzyl)-2-methyl-3H-imidazo[4,5-b]pyridine-5-carboxylic acid (83 mg) was obtained as a pale-yellow powder from methyl 3-(2-chloro-4-methoxybenzyl)-2-methyl-3H-imidazo[4,5-b]pyridine-5-carboxylate (78 mg).

$^1$H-NMR (DMSO-d$_6$): 2.50 (3H, s), 3.55 (3H, s), 5.53 (2H, s), 6.58 (1H, d, J=8 Hz), 6.81 (1H, dd, J=8 and 2 Hz), 7.13 (1H, d, J=2 Hz), 7.99 (1H, d, J=8 Hz), 8.11 (1H, d, J=8 Hz). MASS (ESI): m/e 330 (M–H)$^-$.

PREPARATION EXAMPLE 5-1

In the same manner as in Preparation Example 14-6 to be mentioned later, methyl 3-(2-chloro-4-ethoxybenzyl)-2-methyl-3H-imidazo[4,5-b]pyridine-5-carboxylate was obtained as thin yellow crystals (578 mg) from methyl 3-(2-chloro-4-hydroxybenzyl)-2-methyl-3H-imidazo[4,5-b]pyridine-5-carboxylate (560 mg) and ethyl iodide (395 mg).

$^1$H-NMR (CDCl$_3$): 1.39 (3H, t, J=7 Hz), 2.53 (3H, s), 3.98 (2H, q, J=7 Hz), 4.00 (3H, s), 5.62 (2H, s), 6.64 (2H, s), 6.96 (1H, s), 8.05 (1H, d, J=8 Hz), 8.14 (1H, d, J=8 Hz). MASS (ESI): m/z 360 (M+1).

PREPARATION EXAMPLE 5-2

In the same manner as in Preparation Example 14-7 to be mentioned later, 3-(2-chloro-4-ethoxy)benzyl-2-methyl-3H-imidazo[4,5-b]pyridine-5-carboxylic acid was obtained as colorless crystals (380 mg) from methyl 3-(2-chloro-4-ethoxy)benzyl-2-methyl-3H-imidazo[4,5-b]pyridine-5-carboxylate (376 mg).

$^1$H-NMR (DMSO-d$_6$): 1.21 (3H, t, J=7.5 Hz), 2.52 (3H, s), 2.99 (2H, q, J=7.5 Hz), 5.57 (2H, s), 6.50 (1H, d, J=8 Hz), 7.15 (1H, dd, J=8, 1 Hz), 7.47 (1H, d, J=1 Hz), 8.00 (1H, d, J=8 Hz), 8.13 (1H, d, J=8 Hz).

PREPARATION EXAMPLE 6-1

In the same manner as in Preparation Example 14-6 to be mentioned later, methyl 3-[2-chloro-4-(1-propoxy)benzyl]-2-methyl-3H-imidazo[4,5-b]pyridine-5-carboxylate was obtained as colorless crystals (220 mg) from methyl 3-[2-chloro-4-hydroxybenzyl]-2-methyl-3H-imidazo[4,5-b]pyridine-5-carboxylate (240 mg).

$^1$H-NMR (CDCl$_3$): 1.01 (3H, t, J=7 Hz), 1.70–1.85 (2H, m), 2.53 (3H, s), 3.86 (2H, t, J=7 Hz), 4.00 (3H, s), 5.61 (2H, s), 6.63 (2H, s), 6.96 (1H, br s), 8.04 (1H, d, J=8 Hz), 8.13 (1H, d, J=8 Hz). MASS (ESI): m/z 374 (M+1).

PREPARATION EXAMPLE 6-2

In the same manner as in Preparation Example 14-7 to be mentioned later, 3-[2-chloro-4-(1-propoxy)benzyl]-2-methyl-3H-imidazo[4,5-b]pyridine-5-carboxylic acid was obtained as colorless crystals (205 mg) from methyl 3-[2-chloro-4-(1-propoxy)benzyl]-2-methyl-3H-imidazo[4,5-b]pyridine-5-carboxylate (247 mg).

$^1$H-NMR (DMSO-d$_6$): 0.93 (3H, t, J=7 Hz), 1.62–1.76 (2H, m), 2.51 (3H, s), 3.91 (2H, t, J=7 Hz), 5.54 (2H, s), 6.56 (1H, d, J=8 Hz), 6.81 (1H, dd, J=8, 2 Hz), 7.13 (1H, d, J=2 Hz), 8.00 (1H, d, J=8 Hz), 8.11(1H, d, J=8 Hz). MASS (ESI): m/z 358 (M–1).

PREPARATION EXAMPLE 7-1

In the same manner as in Preparation Example 14-6 to be mentioned later, methyl 3-(2-chloro-4-isopropoxybenzyl)-2-methyl-3H-imidazo[4,5-b]pyridine-5-carboxylate was obtained as thin yellow crystals (635 mg) from methyl 3-(2-chloro-4-hydroxybenzyl)-2-methyl-3H-imidazo[4,5-b]pyridine-5-carboxylate (687 mg) and 2-iodopropane (528 mg).

$^1$H-NMR (CDCl$_3$): 1.30 (6H, d, J=7 Hz), 2.54 (3H, s), 4.00 (3H, s), 4.48 (1H, sept, J=7 Hz), 5.61 (2H, s), 6.62 (2H, s), 6.95 (1H, s), 8.05 (1H, d, J=8 Hz), 8.14 (1H, d, J=8 Hz). MASS (ESI): m/z 374 (M+1).

PREPARATION EXAMPLE 7-2

In the same manner as in Preparation Example 14-7 to be mentioned later, 3-(2-chloro-4-isopropoxybenzyl)-2-methyl-3H-imidazo[4,5-b]pyridine-5-carboxylic acid (66 mg) was obtained as pale-yellow powder from methyl 3-(2-chloro-4-isopropoxybenzyl)-2-methyl-3H-imidazo[4,5-b]pyridine-5-carboxylate (67 mg).

$^1$H-NMR (DMSO-d$_6$): 1.23 (6H, d, J=7 Hz), 2.50 3H, s), 4.60 (1H, sept, J=7 Hz), 5.53 (2H, s), 6.52 (1H, d, J=8 Hz), 6.79 (1H, dd, J=8 and 2 Hz), 7.11 (1H, d, J=2 Hz), 8.01 (1H, d, J=8 Hz), 8.12 (1H, d, J=8 Hz). MASS (ESI): m/e 358 (M–H)$^-$.

PREPARATION EXAMPLE 8-1

In the same manner as in Preparation Example 14-6 to be mentioned later, methyl 3-(4-(1-butoxy)-2-chlorobenzyl)-2-methyl-3H-imidazo[4,5-b]pyridine-5-carboxylate was obtained as thin green crystals (778 mg) from methyl 3-(2-chloro-4-hydroxybenzyl)-2-methyl-3H-imidazo[4,5-b]pyridine-5-carboxylate (800 mg) and 1-iodobutane (666 mg).

$^1$H-NMR (CDCl$_3$): 0.96 (3H, t, J=7 Hz), 1.40–1.52 (2H, m), 1.68–1.80 (2H, m), 2.53 (3H, s), 3.90 (2H, t, J=7 Hz), 4.00 (3H, s), 5.62 (2H, s), 6.64 (2H, s), 6.96 (1H, s), 8.05 (1H, d, J=8 Hz), 8.14 (1H, d, J=8 Hz). MASS (ESI): m/z 388 (M+1).

PREPARATION EXAMPLE 8-2

In the same manner as in Preparation Example 14-7 to be mentioned later, 3-(4-(1-butoxy)-2-chlorobenzyl)-2-methyl-3H-imidazo[4,5-b]pyridine-5-carboxylic acid (90 mg) was obtained as a pale-yellow powder from methyl 3-(4-(1-butoxy)-2-chlorobenzyl)-2-methyl-3H-imidazo[4,5-b]pyridine-5-carboxylate (90 mg).

$^1$H-NMR (DMSO-d$_6$): 0.90 (3H, t, J=7 Hz), 1.30–1.48 (2H, m), 1.57–1.71 (2H, m), 2.50 (3H, s), 3.94 (2H, t, J=7 Hz), 5.54 (2H, s), 6.53 (1H, d, J=8 Hz), 6.80 (1H, dd, J=8 and 2 Hz), 7.13 (1H, d, J=2 Hz), 8.00 (1H, d, J=8 Hz), 8.11 (1H, d, J=8 Hz). MASS (ESI): m/e 372 (M−H)$^-$.

PREPARATION EXAMPLE 9-1

In the same manner as in Preparation Example 14-6 to be mentioned later, methyl 3-[2-chloro-4-(1-pentyloxy)benzyl]-2-methyl-3H-imidazo[4,5-b]pyridine-5-carboxylate was obtained as colorless crystals (247 mg) from methyl 3-[2-chloro-4-hydroxybenzyl]-2-methyl-3H-imidazo[4,5-b]pyridine-5-carboxylate (240 mg).

$^1$H-NMR (CDCl$_3$): 0.92 (3H, brt, J=7 Hz), 1.29–1.48 (4H, m), 1.69–1.81 (2H, m), 2.53 (3H, s), 3.89 (2H, t, J=7 Hz), 4.00 (3H, s), 5.61 (2H, s), 6.63 (2H, s), 6.96 (1H, br s), 8.04 (1H, d, J=8 Hz), 8.13 (1H, d, J=8 Hz). MASS (ESI): m/z 402 (M+1).

PREPARATION EXAMPLE 9-2

In the same manner as in Preparation Example 14-7 to be mentioned later, 3-[2-chloro-4-(1-pentyloxy)benzyl]-2-methyl-3H-imidazo[4,5-b]pyridine-5-carboxylic acid was obtained as colorless crystals (208 mg) from methyl 3-[2-chloro-4-(1-pentyloxy)benzyl]-2-methyl-3H-imidazo[4,5-b]pyridine-5-carboxylate (247 mg).

$^1$H-NMR (DMSO-d$_6$): 0.87 (3H, t, J=7 Hz), 1.27–1.41 (6H, m), 1.61–1.72 (2H, m), 2.50 (3H, s), 3.94 (2H, t, J=7 Hz), 5.53 (2H, s), 6.55 (1H, d, J=8 Hz), 6.80 (1H, dd, J=8, 2 Hz), 7.13 (1H, d, J=2 Hz), 8.00 (1H, d, J=8 Hz), 8.12 (1H, d, J=8 Hz). MASS (ESI): m/z 386 (M−1).

PREPARATION EXAMPLE 10-1

In the same manner as in Preparation Example 14-6 to be mentioned later, methyl 3-[2-chloro-4-(cyclopentylmethyloxy)benzyl]-2-methyl-3H-imidazo[4,5-b]pyridine-5-carboxylate was obtained as colorless amorphous (83 mg) from methyl 3-[2-chloro-4-hydroxybenzyl]-2-methyl-3H-imidazo[4,5-b]pyridine-5-carboxylate (240 mg).

$^1$H-NMR (CDCl$_3$): 1.22–1.41 (3H, m), 1.50–1.70 (3H, m), 1.75–1.90 (2H, m), 2.33 (1H, m), 2.53 (3H, s), 3.77 (2H, d, J=5 Hz), 4.00 (3H, s), 5.62 (2H, s), 6.64 (2H, s), 6.97 (1H, br s), 8.05 (1H, d, J=8 Hz), 8.14 (1H, d, J=8 Hz). MASS (ESI): m/z 414 (M+1).

PREPARATION EXAMPLE 10-2

In the same manner as in Preparation Example 14-7 to be mentioned later, 3-[2-chloro-4-(cyclopentylmethyloxy)benzyl]-2-methyl-3H-imidazo[4,5-b]pyridine-5-carboxylic acid was obtained as colorless crystals (72 mg) from methyl 3-[2-chloro-4-(cyclopentylmethyloxy)benzyl]-2-methyl-3H-imidazo[4,5-b]pyridine-5-carboxylate (82 mg).

$^1$H-NMR (CDCl$_3$): 1.24–1.41 (3H, m), 1.50–1.70 (3H, m), 1.75–1.90 (2H, m), 2.33 (1H, m), 2.64 (3H, s), 3.79 (2H, d, J=5 Hz), 5.53 (2H, s), 6.67 (1H, d, J=8 Hz), 6.70 (1H, dd, J=8, 2 Hz), 7.00 (1H, d, J=2 Hz), 8.15 (1H, d, J=8 Hz), 8.21 (1H, d, J=8 Hz). MASS (ESI): m/z 398 (M−1).

PREPARATION EXAMPLE 11-1

A mixture of 2-amino-6-bromo-3-nitropyridine (4.5 g), propionic acid anhydride (12.2 ml), propionic acid (12.2 ml) and conc. sulfuric acid (101 mg) was stirred in an oil bath at 65° C. for 30 min, and left standing overnight. Water (122 ml) was added to the reaction mixture under ice-cooling, and stirred at the same temperature for 30 min. The precipitate was collected by filtration, washed with water, suspended in diisopropyl ether (20 ml) and stirred at room temperature for 30 min. The precipitate was stirred and washed with diisopropyl ether to give 6-bromo-3-nitro-2-(propionylamino)pyridine (5.59 g) as a pale-brown powder.

$^1$H-NMR (CDCl$_3$): 1.27 (3H, t, J=6 Hz), 2.78 (2H, q, J=6 Hz), 7.34 (1H, d, J=8 Hz), 8.32 (1H, d, J=8 Hz), 9.86 (1H, br, s). MASS (ESI): m/z 275 (M+1).

PREPARATION EXAMPLE 11-2

In the same manner as in Preparation Example 4-5, 2-[N-(4-acetoxy-2-chlorobenzyl)propionylamino]-6-bromo-3-nitropyridine was obtained as a pale-yellow powder (7.06 g) from 6-bromo-3-nitro-2-(propionylamino)pyridine (5.59 g) and 4-acetoxy-2-chlorobenzylbromide (8.06 g).

$^1$H-NMR (CDCl$_3$): 1.13 (3H, t, J=6 Hz), 2.29 (3H, s), 2.42 (2H, br s), 5.34 (2H, br s), 7.02 (1H, dd, J=8, 2 Hz), 7.17 (1H, br s), 7.50 (1H, br s), 7.63 (1H, d, J=8 Hz), 8.10 (1H, d, J=8 Hz). MASS (ESI): m/z 458 (M+1).

PREPARATION EXAMPLE 11-3

In the same manner as in Preparation Example 4-6, 5-bromo-3-(2-chloro-4-hydroxybenzyl)-2-ethyl-3H-imidazo[4,5-b]pyridine was obtained as colorless crystals (440 mg) from 2-[N-(4-acetoxy-2-chlorobenzyl)propionylamino]-6-bromo-3-nitropyridine (695 mg).

$^1$H-NMR (DMSO-d$_6$): 1.24 (3H, t, J=7 Hz), 2.76 (2H, q, J=7 Hz), 5.40 (2H, s), 6.49 (1H, d, J=8 Hz), 6.65 (1H, dd, J=1, 8 Hz), 6.90 (1H, d, J=1 Hz), 7.45 (1H, d, J=8 Hz), 8.00 (1H, d, J=8 Hz). MASS (ESI): m/z 366,368 (M+1).

PREPARATION EXAMPLE 11-4

In the same manner as in Preparation Example 14-6 to be mentioned later, 5-bromo-3-(2-chloro-4-ethoxybenzyl)-2-ethyl-3H-imidazo[4,5-b]pyridine was obtained as thin yellow crystals (928 mg) from 5-bromo-3-(2-chloro-4-hydroxybenzyl)-2-ethyl-3H-imidazo[4,5-b]pyridine (1.1 g) and ethyl iodide (936 mg).

$^1$H-NMR (CDCl$_3$): 1.36 (3H, t, J=7 Hz), 1.39 (3H, t, J=7 Hz), 2.75 (2H, q, J=7 Hz), 3.98 (2H, q, J=7 Hz), 5.49 (2H, s), 6.55 (1H, d, J=8 Hz), 6.65 (1H, dd, J=1,8 Hz), 6.95 (1H, d, J=1 Hz), 7.37 (1H, d, J=8 Hz), 7.88 (1H, d, J=8 Hz). MASS (ESI): m/z 394,396 (M+1).

PREPARATION EXAMPLE 11-5

In the same manner as in Preparation Example 12-2 to be mentioned later, methyl 3-(2-chloro-4-ethoxybenzyl)-2- ethyl-3H-imidazo[4,5-b]pyridine-5-carboxylate was obtained as colorless crystals (697 mg) from 5-bromo-3-(2-chloro-4-ethoxybenzyl)-2-ethyl-3H-imidazo[4,5-b]pyridine (908 mg).

$^1$H-NMR (CDCl$_3$): 1.37–1.42 (6H, m), 2.80 (2H, q, J=7 Hz), 3.91–4.02 (5H, m), 5.62 (2H, s), 6.58 (1H, d, J=8 Hz), 6.63 (1H, dd, J=1,8 Hz), 6.95 (1H, d, J=1 Hz), 8.09 (1H, d, J=8 Hz), 8.14 (1H, d, J=8 Hz). MASS (ESI): m/z 374 (M+1).

PREPARATION EXAMPLE 11-6

In the same manner as in Preparation Example 14-7 to be mentioned later, 3-(2-chloro-4-ethoxybenzyl)-2-ethyl-3H-imidazo[4,5-b]pyridine-5-carboxylic acid was obtained as colorless crystals (369 mg) from methyl 3-(2-chloro-4-ethoxybenzyl)-2-ethyl-3H-imidazo[4,5-b]pyridine-5-carboxylate (407 mg).

$^1$H-NMR (DMSO-d$_6$): 1.26 (3H, t, J=7 Hz), 1.29 (3H, t, J=7 Hz), 2.81 (2H, q, J=7 Hz), 4.01 (2H, q, J=7 Hz), 5.55 (2H, s), 6.53 (1H, d, J=8 Hz), 6.80 (1H, dd, J=1,8 Hz), 7.12 (1H, d, J=1 Hz), 8.01 (1H, d, J=8 Hz), 8.15 (1H, d, J=8 Hz). MASS (ESI): m/z 358 (M−1).

PREPARATION EXAMPLE 12-1

In the same manner as in Preparation Example 14-6 to be mentioned later, 5-bromo-3-(2-chloro-4-(1-propoxy)benzyl)-2-ethyl-3H-imidazo[4,5-b]pyridine was obtained as thin yellow crystals (1.10 g) from 5-bromo-3-(2-chloro-4-hydroxybenzyl)-2-ethyl-3H-imidazo[4,5-b]pyridine (1.1 g) and (1-propyl)iodide (663 mg).

$^1$H-NMR (CDCl$_3$): 1.01 (3H, t, J=7 Hz), 1.36 (3H, t, J=7 Hz), 1.71–1.85 (2H, m), 2.75 (2H, q, J=7 Hz), 3.87 (2H, t, J=7 Hz), 5.49 (2H, s), 6.54 (1H, d, J=8 Hz), 6.65 (1H, dd, J=1,8 Hz), 6.96 (1H, d, J=1 Hz), 7.37 (1H, d, J=8 Hz), 7.88 (1H, d, J=8 Hz). MASS (ESI): m/z 408,410 (M+1).

PREPARATION EXAMPLE 12-2

N,N-Dimethylformamide (6 ml), triethylamine(0.85 ml), 1,3-bis(diphenylphosphino)propane (346 mg), palladium (II) acetate (188 mg) and methanol (4 ml) were added to 5-bromo-3-(2-chloro-4-(1-propoxy)benzyl)-2-ethyl-3H-imidazo[4,5-b]pyridine (1.07 g) and the mixture was stirred for 8 hr while heating to 85° C. in a 10 atm. carbon monoxide atmosphere. After cooling with ice, water (20 ml) was added to the reaction mixture and the reaction mixture was stirred at room temperature. The precipitated crystals were collected by filtration, washed with water and air-dried. This was applied to silica gel column chromatography, eluted with hexane/ethyl acetate=1/1, and concentrated under reduced pressure. Methanol (5 ml) was added to the obtained crystals and heated on a hot water bath. The mixture was stirred under ice-cooling, and the precipitate was collected by filtration and washed with cooled methanol to give methyl 3-(2-chloro-4-(1-propoxy)benzyl)-2-ethyl-3H-imidazo[4,5-b]pyridine-5-carboxylate as bright yellow crystals (816 mg).

$^1$H-NMR (CDCl$_3$): 1.01 (3H, t, J=7 Hz), 1.38 (3H, t, J=7 Hz), 1.70–1.85 (2H, m), 2.80 (2H, q, J=7 Hz), 3.86 (2H, t, J=7 Hz), 4.00 (3H, s), 5.62 (2H, s), 6.58 (1H, d, J=8 Hz), 6.68 (1H, dd, J=1, 8 Hz), 6.96 (1H, d, J=1 Hz), 8.09 (1H, d, J=8 Hz), 8.14 (1H, d, J=8 Hz). MASS (ESI): m/z 388 (M+1).

PREPARATION EXAMPLE 12-3

In the same manner as in Preparation Example 14-7 to be mentioned later, 3-(2-chloro-4-(1-propoxy)benzyl)-2-ethyl-3H-imidazo[4,5-b]pyridine-5-carboxylic acid was obtained as colorless crystals (620 mg) from methyl 3-(2-chloro-4-(1-propoxy)benzyl)-2-ethyl-3H-imidazo[4,5-b)pyridine-5-carboxylate (789 mg).

$^1$H-NMR (CDCl$_3$): 1.02 (3H, t, J=7 Hz), 1.44 (3H, t, J=7 Hz), 1.71–1.86 (2H, m), 2.90 (2H, q, J=7 Hz), 3.88 (2H, t, J=7 Hz), 5.54 (2H, s), 6.60 (1H, d, J=8 Hz), 6.38 (1H, dd, J=1, 8 Hz), 7.00 (1H, d, J=1 Hz), 8.15–8.24 (2H, m). MASS (ESI): m/z 372 (M−1).

PREPARATION EXAMPLE 13-1

In the same manner as in Preparation Example 14-6 to be mentioned later, 5-bromo-3-(2-chloro-4-(1-pentyloxy)benzyl)-2-ethyl-3H-imidazo[4,5-b]pyridine was obtained as thin yellow crystals (789 mg) from 5-bromo-3-(2-chloro-4-hydroxybenzyl)-2-ethyl-3H-imidazo[4,5-b]pyridine (1.1 g) and (1-pentyl)iodide (772 mg).

$^1$H-NMR (CDCl$_3$): 0.92 (3H, t, J=7 Hz), 1.28–1.48 (7H, m), 1.66–1.82 (2H, m), 2.75 (2H, q, J=7 Hz), 3.90 (2H, t, J=7 Hz), 5.49 (2H, s), 6.55 (1H, d, J=8 Hz), 6.65 (1H, dd, J=1,8 Hz), 6.95 (1H, d, J=1 Hz), 7.37 (1H, d, J=8 Hz), 7.86 (1H, d, J=8 Hz). MASS (ESI): m/z 436,438 (M+1).

PREPARATION EXAMPLE 13-2

In the same manner as in Preparation Example 12-2, methyl 3-(2-chloro-4-(1-pentyloxy)benzyl)-2-ethyl-3H-imidazo[4,5-b]pyridine-5-carboxylate was obtained as colorless crystals (537 mg) from 5-bromo-3-(2-chloro-4-(1-pentyloxy)benzyl)-2-ethyl-3H-imidazo[4,5-b]pyridine (772 mg).

$^1$H-NMR (CDCl$_3$): 0.85–0.98 (3H, m), 1.29–1.49 (7H, m), 1.68–1.82 (2H, m), 2.80 (2H, q, J=7 Hz), 3.90 (2H, t, J=7 Hz), 4.00 (3H, s), 5.62 (2H, s), 6.53–6.66 (2H, m), 6.95 (1H, d, J=1 Hz), 8.05–8.16 (2H, m). MASS (ESI): m/z 416 (M+1).

PREPARATION EXAMPLE 13-3

In the same manner as in Preparation Example 14-7 to be mentioned later, 3-(2-chloro-4-(1-pentyloxy)benzyl)-2-ethyl-3H-imidazo[4,5-b]pyridine-5-carboxylic acid was obtained as colorless crystals (428 mg) from methyl 3-(2-chloro-4-(1-pentyloxy)benzyl)-2-ethyl-3H-imidazo[4,5-b]pyridine-5-carboxylate (525 mg).

$^1$H-NMR (CDCl$_3$): 0.92 (3H, t, J=7 Hz), 1.30–1.50 (7H, m), 1.70–1.82 (2H, m), 2.90 (2H, q, J=7 Hz), 3.91 (2H, t, J=7 Hz), 5.53 (2H, s), 6.60 (1H, d, J=8 Hz), 6.68 (1H, dd, J=1, 8 Hz), 7.00 (1H, d, J=1 Hz), 8.15–8.25 (2H, m). MASS (ESI): m/z 400 (M−1).

PREPARATION EXAMPLE 14-1

To a solution of 2,7-dimethyl-1H-imidazo[4,5-b]pyridine (4.29 g) in chloroform (43 ml) was added m-chloroperbenzoic acid (80%, 7.55 g) at room temperature and the mixture was refluxed under heating for 1 hr. After allowing to cool to room temperature, the reaction mixture was directly purified by silica gel column chromatography (chloroform/methanol=9/1) and powdered with ethyl acetate to give 2,7-dimethyl-1H-imidazo[4,5-b]pyridine-4-oxide as a brown powder (4.61 g).

$^1$H-NMR (DMSO-d$_6$): 2.46 (3H, s), 2.52 (3H, s), 6.93 (1H, d, J=5 Hz), 7.98 (1H, d, J=5 Hz).

PREPARATION EXAMPLE 14-2

A mixture of 2,7-dimethyl-3H-imidazo[4,5-b]pyridine-4-oxide (4.45 g), chloroform (4.5 ml) and phosphorus oxychloride (25.4 ml) was stirred at 80° C. for 3 hr and concentrated to dryness under reduced pressure. The residue was poured into ice (75 g) and neutralized with aqueous ammonia under ice-cooling. After stirring at room temperature for 30 min, the precipitated solid was collected by filtration and washed with water to give 5-chloro-2,7-dimethyl-3H-imidazo[4,5-b]pyridine as a gray powder (3.66 g).

$^1$H-NMR (DMSO-$d_6$): 2.49 (3H, s), 2.52 (3H, s), 7.08 (1H, s).

PREPARATION EXAMPLE 14-3

In the same manner as in Preparation Example 16-3 to be mentioned later, methyl 2,7-dimethyl-3H-imidazo[4,5-b]pyridine-5-carboxylate was obtained as colorless crystals (264 mg, 46.7%) from 5-chloro-2,7-dimethyl-3H-imidazo[4,5-b]pyridine (500 mg).

$^1$H-NMR (DMSO-$d_6$): 2.56 (6H, s), 3.87 (3H, s), 7.78 (1H, s). MASS (ESI): m/z 206 (M+1).

PREPARATION EXAMPLE 14-4

A mixture of methyl 2,7-dimethyl-3H-imidazo[4,5-b]pyridine-5-carboxylate (2.70 g), 4-acetoxy-2-chlorobenzylbromide (4.85 g), potassium carbonate (2.73 g) and N,N-dimethylformamide (27 ml) was stirred at room temperature for 5 hr and left standing overnight. The reaction mixture was partitioned between ethyl acetate and saturated brine, and the resulting precipitate was collected by filtration and washed with water and ethyl acetate to give methyl 3-(4-acetoxy-2-chlorobenzyl)-2,7-dimethyl-3H-imidazo[4,5-b]pyridine-5-carboxylate (6.0 g) as a pale-brown powder. The mother liquor and washing were combined and the organic layer was separated, dried over magnesium sulfate and concentrated to dryness under reduced pressure. The residue was powdered from diethyl ether to give the second lot (680 mg) as a pale-brown powder.

$^1$H-NMR (CDCl$_3$): 2.24 (3H, s), 2.53 (3H, s), 2.63 (3H, s), 3.84 (3H, s), 5.56 (2H, s), 6.58 (1H, d, J=8 Hz), 7.01 (1H, dd, J=8, 2 Hz), 7.46 (1H, d, J=2 Hz), 7.88 (1H, s). MASS (ESI): m/z 388 (M+1).

PREPARATION EXAMPLE 14-5

A mixture of methyl 3-(4-acetoxy-2-chlorobenzyl)-2,7-dimethyl-3H-imidazo[4,5-b]pyridine-5-carboxylate (6.5 g), conc. sulfuric acid (3.0 ml) and methanol (60 ml) was refluxed under heating for 1.5 hr. The reaction mixture was diluted with chloroform (60 ml) and saturated aqueous sodium hydrogen carbonate solution was gradually added under ice-cooling. The organic layer was separated, dried over magnesium sulfate and concentrated to dryness under reduced pressure. The residue was washed with diethyl ether to give methyl 3-(2-chloro-4-hydroxybenzyl)-2,7-dimethyl-3H-imidazo[4,5-b]pyridine-5-carboxylate (3.81 g) as a pale-yellow powder.

$^1$H-NMR (CDCl$_3$): 2.49 (3H, s), 2.62 (3H, s), 3.86 (3H, s), 5.46 (2H, s), 6.44 (1H, d, J=8 Hz), 6.64 (1H, dd, J=8, 2 Hz), 6.91 (1H, d, J=2 Hz), 7.88 (1H, s), 9.99 (1H, br s). MASS (ESI): m/z 346 (M+1).

PREPARATION EXAMPLE 14-6

A mixture of methyl 3-(2-chloro-4-hydroxybenzyl)-2,7-dimethylimidazo[4,5-b]pyridine-5-carboxylate (500 mg), 1-iodopropane (295 mg), potassium carbonate (300 mg) and N,N-dimethylformamide (5.0 ml) was stirred at 60° C. for 3 hr. The reaction mixture was partitioned between ethyl acetate and water, and the organic layer was washed twice with water and once with saturated brine, dried over magnesium sulfate, and concentrated to dryness under reduced pressure. The residue was powdered from diethyl ether to give methyl 3-(2-chloro-4-(1-propoxy)benzyl)-2,7-dimethylimidazo[4,5-b]pyridine-5-carboxylate (490 mg) as a pale-yellow powder.

$^1$H-NMR (CDCl$_3$): 1.01 (3H, t, J=6 Hz), 1.78 (2H, m), 2.53 (3H, s), 2.73 (3H, s), 3.86 (2H, t, J=6 Hz), 3.99 (3H, s), 5.59 (2H, s), 6.58 (1H, d, J=8 Hz), 6.64 (1H, dd, J=8, 2 Hz), 6.96 (1H, d, J=2 Hz), 7.97 (1H, s). MASS (ESI): m/z 388 (M+1).

PREPARATION EXAMPLE 14-7

To a suspension of methyl 3-(2-chloro-4-(1-propoxy)benzyl)-2,7-dimethyl-3H-imidazo[4,5-b]pyridine-5-carboxylate (475 mg) in 1,4-dioxane was added 1N aqueous sodium hydroxide solution, and the mixture was heated to 60° C. and stirred for 30 min. It was air cooled and adjusted to pH 4 by dropwise addition of 1N hydrochloric acid. Water (25 ml) was added and the mixture was stirred at room temperature. The precipitated crystals were collected by filtration and dried under reduced pressure at 60° C. Thereto was added acetonitrile (3 ml) and the mixture was heated and stirred at room temperature. The crystals were collected by filtration and dried under reduced pressure at 60° C. to give 3-(2-chloro-4-(1-propoxy)benzyl)-2,7-dimethyl-3H-imidazo[4,5-b]pyridine-5-carboxylic acid as thin yellow crystals (426 mg).

$^1$H-NMR (CDCl$_3$): 1.02 (3H, t, J=7 Hz), 1.71–1.85 (2H, m), 2.62 (3H, s), 2.75 (3H, s), 3.88 (2H, t, J=7 Hz), 5.50 (2H, s), 6.61 (1H, d, J=8 Hz), 6.68 (1H, dd, J=1, 8 Hz), 6.99 (1H, d, J=1 Hz), 8.03 (1H, s). MASS (ESI): m/z 374 (M+1).

PREPARATION EXAMPLE 15-1

In the same manner as in Preparation Example 14-6, methyl 3-[2-chloro-4-(1-pentyloxy)benzyl]-2,7-dimethyl-3H-imidazo[4,5-b]pyridine-5-carboxylate was obtained as a pale-yellow solid (1.17 g) from methyl 3-[2-chloro-4-hydroxybenzyl]-2,7-dimethyl-3H-imidazo[4,5-b]pyridine-5-carboxylate (1.05 g) and 1-iodopentane (662 mg).

$^1$H-NMR (CDCl$_3$): 0.92 (3H, t, J=7 Hz), 1.30–1.47 (4H, m), 1.69–1.81 (2H, m), 2.53 (3H, s), 2.72 (3H, s), 3.89 (2H, t, J=7 Hz), 3.99 (3H, s), 5.59 (2H, s), 6.56–6.67 (2H, m), 6.96 (1H, d, J=1 Hz), 7.26 (1H, s), 7.97 (1H, s). MASS (ESI): m/z 416 (M+1).

PREPARATION EXAMPLE 15-2

In the same manner as in Preparation Example 14-7, 3-[2-chloro-4-(1-pentyloxy)benzyl]-2,7-dimethyl-3H-imidazo[4,5-b]pyridine-5-carboxylic acid was obtained as colorless crystals (1.02 g) from methyl 3-[2-chloro-4-(1-pentyloxy)benzyl]-2,7-dimethyl-3H-imidazo[4,5-b]pyridine-5-carboxylate (1.15 g).

$^1$H-NMR (DMSO-$d_6$): 0.87 (3H, t, J=7 Hz), 1.24–1.43 (4H, m), 1.62–1.74 (2H, m), 2.49 (3H, s), 2.62 (3H, s), 3.94 (2H, t, J=7 Hz), 5.52 (2H, s), 6.50 (1H, d, J=8 Hz), 6.80 (1H, dd, J=8, 2 Hz), 7.13 (1H, d, J=2 Hz), 7.86 (1H, s). MASS (ESI): m/z 400 (M−1).

PREPARATION EXAMPLE 16-1

To a suspension of 2-amino-6-bromo-3-nitropyridine (21.8 g) in ethanol (220 ml)—water (22 ml) was added iron powder (39.0 g) at room temperature. Conc. hydrochloric acid (0.8 ml) was added and the mixture was gradually heated with stirring to start the reaction. The mixture was refluxed under heating for 2 hr, and an insoluble matter was removed by filtration while hot. The solvent was evaporated under reduced pressure, and water (200 ml) and active charcoal were added to the resulting solid, which was followed by heating. The insoluble matter was removed by filtration while hot, and water was evaporated under reduced pressure from the filtrate to give 2,3-diamino-6-bromopyridine (9.00 g) as a green brown powder. To the resulting solid from the above reaction were added ethanol (100 ml)—water (100 ml) and the mixture was heated for dissolution. The insoluble matter was removed by filtration. The solvent was evaporated under reduced pressure, and the residue was purified by silica gel column chromatography (hexane/ethyl acetate=1/3) to further give the objective compound (8.25 g) as a black-powder.

$^1$H-NMR (DMSO-d$_6$): 4 78 (2H, br s), 5.80 (2H, br s), 6.47 (1H, d, J=8 Hz), 6.61 (1H, d, J=8 Hz). MASS (ESI): m/e 188,190 (M+H)$^+$.

PREPARATION EXAMPLE 16-2

2,3-Diamino-6-bromopyridine (8.16 g) and triethyl orthoacetate (12.0 ml) were mixed in acetic acid (41 ml), and the mixture was refluxed under heating for 29 hr. After allowing to cool, the solvent was evaporated under reduced pressure to give a crude product (10 g). This was dissolved in a sufficient amount of dichloromethane and anhydrous potassium carbonate and active charcoal were added. The mixture was stirred at room temperature. The insoluble matter was removed by filtration and the solvent was evaporated to give 5-bromo-2-methyl-1H-imidazo[4,5-b]pyridine (7.59 g) as a pale-yellow powder.

$^1$H-NMR (DMSO-d$_6$): 2.51 (3H, s), 7.31 (1H, d, J=8 Hz), 7.82 (1H, d, J=8 Hz). MASS (ESI): m/e 212,214 (M+H)$^+$.

PREPARATION EXAMPLE 16-3

Palladium acetate (1.18 g), 1,3-bis(diphenylphosphino) propane (2.31 g) and 5-bromo-2-methyl-1H-imidazo[4,5-b]pyridine (3.72 g) were charged in an autoclave, and N,N-dimethylformamide (18.6 ml), methanol (14.9 ml) and triethylamine (5.4 ml) were added. The mixture was stirred at 85° C. for 14 hr in a 10 atm. carbon monoxide atmosphere. The reaction mixture was allowed to cool and the solvent was evaporated. Methanol (60 ml) was added to the residue and heated, and the insoluble matter was filtered off while hot. The filtrate was concentrated to give methyl 2-methyl-1H-imidazo[4,5-b]pyridine-5-carboxylate (2.95 g) as a white powder.

$^1$H-NMR (CDCl$_3$): 2.82 (3H, s), 4.05 (3H, s), 8.04 (1H, d, J=8 Hz), 8.10 (1H, d, J=8 Hz). MASS (ESI): m/e 192 (M+H)$^+$.

PREPARATION EXAMPLE 16-4

3-Chloro-4-methylaniline (100.0 g) was dissolved in tetrahydrofuran (500 ml) and di-tert-butyl dicarbonate (200.0 g) was added. The mixture was refluxed under heating for 3 hr. The reaction mixture was concentrated under reduced pressure, and the residue was dissolved in ethyl acetate (1300 ml) and washed successively with 10% aqueous citric acid solution (500 ml), saturated aqueous sodium hydrogen carbonate solution (500 ml) and saturated brine (500 ml). The organic layer was dried over anhydrous magnesium sulfate and concentrated under reduced pressure. To the residue was added hexane (300 ml) and the precipitated crystals were collected by filtration to give N-(tert-butoxycarbonyl)-3-chloro-4-methylaniline (150.4 g) as colorless crystals.

$^1$H-NMR (CDCl$_3$): 1.53 (9H, s), 2.31 (3H, s), 6.40 (1H, s), 7.05–7.13 (2H, m), 7.48 (1H, s).

PREPARATION EXAMPLE 16-5

N-(tert-Butoxycarbonyl)-3-chloro-4-methylaniline (60.0 g) was dissolved in N,N-dimethylformamide (300 ml) and 60% sodium hydride (10.4 g) was gradually added under ice-cooling over 10 min. The reaction mixture was stirred at room temperature for 30 min and methyl iodide (38.8 g) was added dropwise over 15 min under ice-cooling. The reaction mixture was stirred at room temperature for 2 hr and concentrated under reduced pressure. Water (500 ml) was added and the mixture was extracted with ethyl acetate (500 ml). The organic layer was washed successively with water (500 ml), saturated aqueous sodium hydrogen carbonate solution (500 ml) and saturated brine (500 ml). The organic layer was dried over anhydrous magnesium sulfate and concentrated under reduced pressure. The residue was subjected to silica gel column chromatography and eluted with hexane:ethyl acetate=9:1. The objective fraction was concentrated under reduced pressure to give N-(tert-butoxycarbonyl)-3-chloro-N,4-dimethylaniline as a pale-yellow oil (62.7 g).

$^1$H-NMR (CDCl$_3$): 1.46 (9H, s), 2.34 (3H, s), 3.26 (3H, s), 7.04 (1H, dd, J=8, 2 Hz), 7.16 (1H, d, J=8 Hz), 7.24 (1H, d, J=2 Hz).

PREPARATION EXAMPLE 16-6

N-(tert-Butoxycarbonyl)-3-chloro-N,4-dimethylaniline (62.6 g) was dissolved in carbon tetrachloride (310 ml), and N-bromosuccinimide (52.3 g) and 2,2'-azobis(4-methoxy-2,4-dimethylvaleronitrile) (3.77 g) were added. The mixture was stirred at 55° C. for 2 hr and 75° C. for 1 hr, and hexane (500 ml) was added. The mixture was stirred under ice-cooling for 1 hr. The reaction mixture was filtered, and the filtrate was concentrated under reduced pressure. The residue was diluted with ethyl acetate (310 ml) and washed successively with saturated aqueous sodium hydrogen carbonate solution (500 ml) and saturated brine (500 ml). The organic layer was dried over anhydrous magnesium sulfate and concentrated under reduced pressure to give 4-bromomethyl-N-(tert-butoxycarbonyl)-N-methyl-3-chloroaniline as a brown oil (75.6 g).

$^1$H-NMR (CDCl$_3$): 1.48 (9H, s), 3.25 (3H, s), 4.57 (2H, s), 7.17 (1H, dd, J=8, 2 Hz), 7.33 (1H, d, J=2 Hz), 7.38 (1H, d, J=8 Hz).

PREPARATION EXAMPLE 16-7

In the same manner as in Preparation Example 18-4 to be mentioned later, methyl 3-(4-(N-(t-butoxycarbonyl)-N-methylamino)-2-chlorobenzyl)-2-methyl-3H-imidazo[4,5-b]pyridine-5-carboxylate (7.14 g) was obtained as colorless crystals and methyl 1-(4-(N-(tert-butoxycarbonyl)-N-methylamino)-2-chlorobenzyl)-2-methyl-1H-imidazo[4,5-b]pyridine-5-carboxylate (8.0 g) as a pale-brown powder, from methyl 2-methyl-3H-imidazo[4,5-b]pyridine-5-carboxylate (10.0 g) and 4-bromomethyl-N-(tert-butoxycarbonyl)-N-methyl-3-chloroaniline (23.6 g).
Methyl 3-(4-(N-(t-butoxycarbonyl)-N-methylamino)-2-chlorobenzyl)-2-methyl-3H-imidazo[4,5-b]pyridine-5-carboxylate:

$^1$H-NMR (CDCl$_3$): 1.45 (9H, s), 2.55 (3H, s), 3.22 (3H, s), 4.00 (3H, s), 5.65 (2H, s), 6.58 (1H, d, J=8 Hz), 7.00 (1H, dd, J=8, 2 Hz), 7.39 (1H, d, J=2 Hz), 8.06 (1H, d, J=8 Hz), 8.14 (1H, d, J=8 Hz).

Methyl 1-(4-(N-(tert-butoxycarbonyl)-N-methylamino)-2-chlorobenzyl)-2-methyl-1H-imidazo[4,5-b]pyridine-5-carboxylate:

$^1$H-NMR (CDCl$_3$): 1.47 (9H, s), 2.67 (3H, s), 3.24 (3H, s), 4.03 (3H, s), 5.42 (2H, s), 6.45 (1H, d, J=8 Hz), 7.03 (1H, dd, J=8, 2 Hz), 7.45 (1H, d, J=2 Hz), 7.55 (1H, d, J=8 Hz), 8.06 (1H, d, J=8 Hz).

PREPARATION EXAMPLE 16-8

In the same manner as in Preparation Example 14-7, 3-(4-(N-(tert-butoxycarbonyl)-N-methylamino)-2-chlorobenzyl)-2-methyl-3H-imidazo[4,5-b]pyridine-5-carboxylic acid (7.14 g) was obtained as a colorless powder from methyl 3-(4-(N-(tert-butoxycarbonyl)-N-methylamino)-2-chlorobenzyl)-2-methyl-3H-imidazo[4,5-b]pyridine-5-carboxylate (10.0 g).

$^1$H-NMR (CDCl$_3$): 1.47 (9H, s), 2.64 (3H, s), 3.24 (3H, s), 5.57 (2H, s), 6.59 (1H, d, J=8 Hz), 7.06 (1H, dd, J=8, 2 Hz), 7.43 (1H, d, J=2 Hz), 8.17 (1H, d, J=8 Hz), 8.23 (1H, d, J=8 Hz).

PREPARATION EXAMPLE 17-1

Methyl 3-(4-(N-(tert-butoxycarbonyl)-N-methylamino)-2-chlorobenzyl)-2-methyl-3H-imidazo[4,5-b]pyridine-5-carboxylate (234 mg) was dissolved in dichloromethane (3 ml) and 4N hydrochloric acid (ethyl acetate solution) (2 ml) was added. The mixture was stirred at room temperature for 1 hr. The reaction mixture was concentrated under reduced pressure and ethyl acetate was added. The precipitated crystals were collected by filtration and concentrated under reduced pressure with heating to give methyl 3-(2-chloro-4-(methylamino)benzyl)-2-methyl-3H-imidazo[4,5-b]pyridine-5-carboxylate dihydrochloride (215 mg) as pale-red crystals.

$^1$H-NMR (DMSO-d$_6$): 2.67 (3H, s), 3.91 (3H, s), 5.56 (2H, s), 6.56 (1H, dd, J=8, 2 Hz), 6.78–6.82 (2H, m), 8.15 (1H, d, J=8 Hz), 8.31 (1H, d, J=8 Hz).

PREPARATION EXAMPLE 17-2

Methyl 3-(2-chloro-4-(methylamino)benzyl)-2-methyl-3H-imidazo[4,5-b]pyridine-5-carboxylate dihydrochloride (169 mg) was suspended in methanol (2 ml) and valeraldehyde (70 mg) and sodium cyanoborohydride (51 mg) were added. The mixture was stirred at room temperature for 4 hr. To the reaction mixture was added 1N hydrochloric acid and the mixture was stirred for 1 hr. Saturated aqueous sodium hydrogen carbonate solution was added to neutralize the solution and the mixture was extracted with ethyl acetate. The organic layer was washed successively with saturated aqueous sodium hydrogen carbonate solution and saturated brine, dried over anhydrous magnesium sulfate and concentrated under reduced pressure. The residue was subjected to silica gel column chromatography and eluted with chloroform:methanol=100:1. The objective fraction was concentrated under reduced pressure to give methyl 3-(2-chloro-4-(methyl-(1-pentyl)amino)benzyl)-2-methyl-3H-imidazo[4,5-b]pyridine-5-carboxylate (179 mg) as a pale-yellow oil.

$^1$H-NMR (CDCl$_3$): 0.89 (3H, t, J=7 Hz), 1.20–1.42 (4H, m), 1.46–1.57 (2H, m), 2.56 (3H, s), 2.88 (3H, s), 3.23 (2H, t, J=7 Hz), 4.00 (3H, s), 5.59 (2H, s), 6.39 (1H, dd, J=8, 2 Hz), 6.62–6.67 (2H, m), 8.04 (1H, d, J=8 Hz), 8.13 (1H, d, J=8 Hz).

PREPARATION EXAMPLE 17-3

In the same manner as in Preparation Example 14-7, 3-(2-chloro-4-(methyl-(1-pentyl)amino)benzyl)-2-methyl-3H-imidazo[4,5-b]pyridine-5-carboxylic acid was obtained as a pale-yellow powder (180 mg) from methyl 3-(2-chloro-4-(methyl-(1-pentyl)amino)benzyl)-2-methyl-3H-imidazo[4,5-b]pyridine-5-carboxylate (150 mg).

$^1$H-NMR (CDCl$_3$): 0.88 (3H, t, J=7 Hz), 1.22–1.55 (6H, m), 2.61 (3H, s), 2.87 (3H, s), 3.22 (2H, br s), 5.48 (2H, s), 6.40 (1H, br s), 6.62 (2H, br s), 8.10 (2H, br s).

PREPARATION EXAMPLE 18-1

To a solution of 3-chloro-4-methylaniline (7.08 g) in methanol (35 ml) were added cyclohexanecarbaldehyde (5.33 g) and sodium cyanoborohydride (3.78 g) under ice-cooling and the mixture was stirred at room temperature. After one hour, the reaction mixture was concentrated and water and saturated brine were added. The mixture was extracted 3 times with ethyl acetate. The organic layers were combined, washed with saturated brine and dried over anhydrous magnesium sulfate. The solvent was evaporated and the residue was purified by column chromatography (silica gel, hexane/ethyl acetate=15/1) to give 3-chloro-N-cyclohexylmethyl-4-methylaniline as a pale-yellow oil (9.64 g).

$^1$H-NMR (CDCl$_3$): 0.86–1.35 (5H, m), 1.45–1.89 (6H, m), 2.23 (3H, s), 2.90 (2H, d, J=7 Hz), 3.63 (1H, br s), 6.40 (1H, dd, J=8 and 2 Hz), 6.59 (1H, d, J=2 Hz), 6.97 (1H, d, J=8 Hz). MASS (ESI): m/e 238 (M+H)$^+$.

PREPARATION EXAMPLE 18-2

In the same manner as in Preparation Example 16-4, N-(tert-butoxycarbonyl)-3-chloro-N-cyclohexylmethyl-4-methylaniline (13.68 g) was obtained as a pale-yellow oil from 3-chloro-N-cyclohexylmethyl-4-methylaniline (9.63 g) and di-tert-butyl dicarbonate (9.74 g).

$^1$H-NMR (CDCl$_3$): 0.82–1.27 (5H, m), 1.34–1.78 (6H, m), 1.43 (9H, s), 2.35 (3H, s), 3.46 (2H, d, J=7 Hz), 6.99 (1H, d, J=8 Hz), 7.17 (1H, d, J=8 Hz), 7.19 (1H, s).

PREPARATION EXAMPLE 18-3

In the same manner as in Preparation Example 16-6, 4-bromomethyl-N-(tert-butoxycarbonyl)-3-chloro-N-(cyclohexylmethyl)aniline was obtained as a pale-yellow oil (16.83 g) from N-(tert-butoxycarbonyl)-3-chloro-N-cyclohexylmethyl-4-methylaniline (13.60 g).

$^1$H-NMR (CDCl$_3$): 0.80–1.77 (11H, m), 1.44 (9H, s), 3.49 (2H, d, J=7 Hz), 4.58 (2H, s), 7.10 (1H, dd, J=8 and 2 Hz), 7.27 (1H, d, J=2 Hz), 7.38 (1H, d, J=8 Hz).

PREPARATION EXAMPLE 18-4

To a suspension of methyl 2-methylimidazo[4,5-b]pyridine-5-carboxylate (954 mg) in N,N-dimethylformamide (9.6 ml) was added sodium hydride (in 70% mineral oil, 203 mg) under ice-cooling, and the mixture was stirred for 30 min. To this reaction mixture was added 4-bromomethyl-N-(tert-butoxycarbonyl)-3-chloro-N-(cyclohexylmethyl)aniline (2.70 g) and the mixture was stirred overnight at room temperature. The reaction mixture was poured into water and the resulting product was extracted twice with ethyl acetate. The organic layers were combined, washed successively with water and saturated brine, and dried over anhydrous magnesium sulfate. The solvent was evaporated and two kinds of isomers—methyl 3-(4-(N-(tert-butoxycarbonyl)-N-(cyclohexylmethyl) amino)-2-chlorobenzyl)-2-methyl-3H-imidazo[4,5-b] pyridine-5-carboxylate (495 mg) and methyl 1-(4-(N-(tert-butoxycarbonyl)-N-(cyclohexylmethyl)amino)-2-chlorobenzyl)-2-methyl-1H-imidazo[4,5-b]pyridine-5-carboxylate (827 mg)—were separated by silica gel column chromatography (chloroform/ethyl acetate=2/1) as white or pale-yellow powders.

Methyl 3-(4-(N-(tert-Butoxycarbonyl)-N-(cyclohexylmethyl)amino)-2-chlorobenzyl)-2-methyl-3H-imidazo[4,5-b]pyridine-5-carboxylate:

$^1$H-NMR (CDCl$_3$): 0.77–1.76 (11H, m), 1.43 (9H, s), 2.54 (3H, s), 3.46 (2H, d, J=7 Hz), 4.00 (3H, s), 5.66 (2H, s), 6.59 (1H, d, J=8 Hz), 6.95 (1H, dd, J=8 and 2 Hz), 7.33 (1H, d, J=2 Hz), 8.07 (1H, d, J=8 Hz), 8.15 (1H, d, J=8 Hz). MASS (ESI): m/e 527 (M+H)$^+$.

Methyl 1-(4-(N-(tert-Butoxycarbonyl)-N-(cyclohexylmethyl)amino)-2-chlorobenzyl)-2-methyl-1H-imidazo[4,5-b]pyridine-5-carboxylate:

$^1$H-NMR (CDCl$_3$): 0.80–1.78 (11H, m), 1.43 (9H, s), 2.66 (3H, s), 3.47 (2H, d, J=7 Hz), 4.03 (3H, s), 5.42 (2H, s), 6.45 (1H, d, J=8 Hz), 6.99 (1H, dd, J=8 and 2 Hz), 7.38 (1H, d, J=2 Hz), 7.57 (1H, d, J=8 Hz), 8.08 (1H, d, J=8 Hz). MASS (ESI): m/e 527 (M+H)$^+$.

PREPARATION EXAMPLE 18-5

In the same manner as in Example 42 to be mentioned later, methyl 3-(2-chloro-4-(N-(cyclohexylmethyl)amino) benzyl)-2-methyl-3H-imidazo[4,5-b]pyridine-5-carboxylate (260 mg) was obtained as a white powder from methyl 3-(4-(N-(tert-butoxycarbonyl)-N-(cyclohexylmethyl) amino)-2-chlorobenzyl)-2-methyl-3H-imidazo[4,5-b] pyridine-5-carboxylate (384 mg).

$^1$H-NMR (CDCl$_3$): 0.82–1.90 (11H, m), 2.55 (3H, s), 2.89 (2H, d, J=7 Hz), 4.00 (3H, s), 5.57 (2H, s), 6.30 (1H, dd, J=8 and 2 Hz), 6.58 (1H, d, J=8 Hz), 6.60 (1H, d, J=2 Hz), 8.04 (1H, d, J=8 Hz), 8.13 (1H, d, J=8 Hz). MASS (ESI): m/e 427 (M+H)$^+$.

PREPARATION EXAMPLE 18-6

In the same manner as in Preparation Example 17-2, methyl 3-(2-chloro-4-(N-(cyclohexylmethyl)methylamino) benzyl)-2-methyl-3H-imidazo[4,5-b]pyridine-5-carboxylate (230 mg) was obtained as a white powder from methyl 3-(2-chloro-4-(N-(cyclohexylmethyl)amino)benzyl)-2-methyl-3H-imidazo[4,5-b]pyridine-5-carboxylate (255 mg).

$^1$H-NMR (CDCl$_3$): 0.80–1.32 (6H, m), 1.52–1.80 (5H, m), 2.56 (3H, s), 2.90 (3H, s), 3.06 (2H, d, J=7 Hz), 4.00 (3H, s), 5.58 (2H, s), 6.37 (1H, dd, J=9 and 2 Hz), 6.63 (1H, d, J=9 Hz), 6.63 (1H, d, J=2 Hz), 8.03 (1H, d, J=8 Hz), 8.12 (1H, d, J=8 Hz). MASS (ESI): m/e 441 (M+H)$^+$.

PREPARATION EXAMPLE 18-7

In the same manner as in Preparation Example 14-7, 3-(2-chloro-4-(N-(cyclohexylmethyl)methylamino)benzyl)-2-methyl-3H-imidazo[4,5-b]pyridine-5-carboxylic acid (219 mg) was obtained as a white powder from methyl 3-(2-chloro-4-(N-(cyclohexylmethyl)methylamino)benzyl)-2-methyl-3H-imidazo[4,5-b]pyridine-5-carboxylate (221 mg).

$^1$H-NMR (CDCl$_3$): 0.80–1.30 (6H, m), 1.46–1.82 (5H, m), 2.66 (3H, s), 2.92 (3H, s), 3.08 (2H, d, J=7 Hz), 5.49 (2H, s), 6.41 (1H, dd, J=9 and 2 Hz), 6.65 (1H, d, J=2 Hz), 6.67 (1H, d, J=9 Hz), 8.13 (1H, d, J=8 Hz), 8.19 (1H, d, J=8 Hz). MASS (ESI): m/e 425 (M–H)$^-$.

PREPARATION EXAMPLE 19-1

To a solution of 4-bromo-2-chlorobenzyl alcohol (3.56 g) and anhydrous triethylamine (3 ml) in anhydrous dichloromethane (36 ml) was added dropwise methanesulfonyl chloride (1.4 ml) under a nitrogen flow under ice-cooling. The mixture was stirred for 1 hr and the reaction mixture was washed with water, saturated aqueous sodium hydrogen carbonate solution and saturated brine, and dried over anhydrous magnesium sulfate. The filtrate was concentrated to give 4-bromo-2-chloro-1-(methanesulfonyloxymethyl) benzene as a pale-brown solid (4.77 g).

$^1$H-NMR (CDCl$_3$): 3.03 (3H, s), 5.29 (2H, s), 7.37 (1H, d, J=8 Hz), 7.47 (1H, dd, J=8, 1 Hz), 7.60 (1H, d, J=1 Hz). MASS (ESI): m/e 298 (M–1).

PREPARATION EXAMPLE 19-2

In the same manner as in Preparation Example 4-5, methyl 3-(4-bromo-2-chlorobenzyl)-2,7-dimethyl-3H-imidazo[4,5-b]pyridine-5-carboxylate was obtained as colorless crystals (950 mg) from methyl 2,7-dimethyl-3H-imidazo[4,5-b]pyridine-5-carboxylate (550 mg) and 4-bromo-2-chloro-1-(methanesulfonyloxymethyl)benzene (963 mg).

$^1$H-NMR (CDCl$_3$): 2.52 (3H, s), 2.73 (3H, s), 3.98 (3H, s), 5.59 (2H, s), 6.49 (1H, d, J=8 Hz), 7.22 (1H, d, J=8 Hz), 7.60 (1H, s), 7.99 (1H, d, J=8 Hz).

PREPARATION EXAMPLE 19-3

In the same manner as in Preparation Example 14-7, 3-(4-bromo-2-chlorobenzyl)-2,7-dimethyl-3H-imidazo[4,5-b]pyridine-5-carboxylic acid was obtained as colorless crystals (870 mg) from methyl 3-(4-bromo-2-chlorobenzyl)-2,7-dimethyl-3H-imidazo[4,5-b]pyridine-5-carboxylate (950 mg).

$^1$H-NMR (DMSO-d$_6$): 2.49 (3H, s), 2.62 (3H, s), 5.55 (2H, s), 6.47 (1H, d, J=8 Hz), 7.34 (1H, dd, J=8, 1 Hz), 7.85 (1H, d, J=1 Hz).

PREPARATION EXAMPLE 20-1

In the same manner as in Preparation Example 18-4, methyl 3-[(3-chloro-5-(trifluoromethyl)-2-pyridyl)methyl]-2-methyl-3H-imidazo[4,5-b]pyridine-5-carboxylate (399 mg) was obtained as a pale-brown solid and methyl 1-[(3-chloro-5-(trifluoromethyl)-2-pyridyl)methyl]-2-methyl-1H-imidazo[4,5-b]pyridine-5-carboxylate (245 mg) as a brown solid, from methyl 2-methyl-3H-imidazo[4,5-b]pyridine-5-carboxylate (500 mg) and 3-chloro-2-(chloromethyl)-5-(trifluoromethyl)pyridine (662 mg). methyl 3-[(3-chloro-5-(trifluoromethyl)-2-pyridyl)methyl]-2-methyl-3H-imidazo [4,5-b]pyridine-5-carboxylate:

$^1$H-NMR (CDCl$_3$): 2.56 (3H, s), 3.97 (3H, s), 5.84 (2H, s), 7.98 (1H, br s), 8.06 (1H, d, J=8 Hz), 8.12 (1H, d, J=8 Hz), 8.51 (1H, br s). MASS (ESI): m/z 385 (M+1).

Methyl 1-[(3-Chloro-5-(trifluoromethyl)-2-pyridyl)methyl]-2-methyl-1H-imidazo[4,5-b]pyridine-5-carboxylate:

$^1$H-NMR (CDCl$_3$): 2.72 (3H, s), 4.02 (3H, s), 5.62 (2H, s), 7.62 (1H, d, J=8 Hz), 8.01 (1H, br s), 8.07 (1H, d, J=8 Hz), 8.60 (1H, br s). MASS (ESI): m/z 385 (M+1).

PREPARATION EXAMPLE 20-2

In the same manner as in Preparation Example 14-7, 3-[(3-chloro-5-(trifluoromethyl)-2-pyridyl)methyl]-2-methyl-3H-imidazo[4,5-b]pyridine-5-carboxylic acid was obtained as a colorless solid (271 mg) from methyl 3-[(3- chloro-5-(trifluoromethyl)-2-pyridyl)methyl]-2-methyl-3H-imidazo[4,5-b]pyridine-5-carboxylate (395 mg).

¹H-NMR (DMSO-d₆): 2.51 (3H, s), 3.97 (3H, s), 5.89 (2H, s), 7.98 (1H, br s), 8.09 (1H, d, J=8 Hz), 8.60 (1H, d, J=1 Hz), 8.73 (1H, br s). MASS (ESI): m/z 369 (M−1).

PREPARATION EXAMPLE 21-1

To a solution of 6-bromo-2-[N-(2-chloro-4-phenylbenzyl) acetamido]-3-nitropyridine (15.4 g) in dioxane (150 ml) was added 1N aqueous sodium hydroxide solution (43.5 ml) at room temperature and the mixture was heated to 50° C. The mixture was stirred for 3 hr, ice-cooled, and neutralized with 1N hydrochloric acid. Water (300 ml) was added and the precipitated crystals were collected by filtration and dried under reduced pressure to give 6-bromo-2-[N-(2-chloro-4-phenylbenzyl)amino]-3-nitropyridine (13.8 g) as yellow crystals.

¹H-NMR (CDCl₃): 4.94 (2H, d, J=5 Hz), 6.82 (1H, d, J=8 Hz), 7.32–7.61 (6H, m), 7.63 (1H, d, J=1 Hz), 8.23 (1H, d, J=8 Hz), 8.76 (1H, br s).

PREPARATION EXAMPLE 21-2

To a solution of 6-bromo-2-[N-(2-chloro-4-phenylbenzyl)-amino]-3-nitropyridine (13.5 g) in acetic acid (27 ml) and ethanol (81 ml) was added iron powder (7.2 g) at room temperature under a nitrogen flow, and the mixture was refluxed under heating. After 2 hr, the reaction mixture was cooled, filtered through celite, and washed with ethyl acetate. The filtrate was concentrated and subjected to azeotropic distillation twice with toluene. Ethyl acetate and saturated aqueous sodium hydrogen carbonate solution were added to the residue and the mixture was stirred at room temperature for 10 min. This mixture was filtered through celite and washed with ethyl acetate. The organic layer was separated, washed with saturated brine and dried over anhydrous magnesium sulfate. After filtration, the filtrate was concentrated and the residue was applied to flash silica gel column chromatography (silica gel, 400 ml) and eluted with hexane:ethyl acetate=5:1–3:1–2:1 to give 3-amino-6-bromo-2-[N-(2-chloro-4-phenylbenzyl)amino]pyridine (10.6 g) as a black gum.

¹H-NMR (CDCl₃): 3.14 (2H, br s), 4.75 (2H, s), 6.67 (1H, d, J=8 Hz), 6.73 (1H, d, J=8 Hz), 7.33–7.49 (4H, m), 7.51–7.64 (4H, m). MASS (ESI): m/z 388 (M+1).

PREPARATION EXAMPLE 21-3

A mixture of 3-amino-6-bromo-2-(N-(2-chloro-4-phenylbenzyl)amino)pyridine (1.85 g), tetraethoxymethane (4.3 g) and acetic acid (18.5 ml) was stirred at room temperature overnight and at 70° C. for 7 hr. The reaction mixture was concentrated to dryness under reduced pressure, and toluene was added, which was followed by concentration under reduced pressure. The residue was dissolved in ethyl acetate and washed twice with saturated aqueous sodium hydrogen carbonate solution and once with saturated brine. The organic layer was dried over magnesium sulfate and concentrated to dryness under reduced pressure. The residue was applied to silica gel column (n-hexane:ethyl acetate=9:1) to give a single product (55 mg) of 5-bromo-3-(2-chloro-4-phenylbenzyl)-2-ethoxy-3H-imidazo[4,5-b]pyridine and a mixture (977 mg) with a by product each as pale-brown amorphous.

¹H-NMR (CDCl₃): 1.43 (3H, t, J=7 Hz), 4.60 (2H, q, J=7 Hz), 5.41 (2H, s), 6.94 (1H, d, J=8 Hz), 7.25–7.67 (9H). MASS (ESI): m/z 444 (M+H).

PREPARATION EXAMPLE 21-4

5-Bromo-3-(2-chloro-4-phenylbenzyl)-2-ethoxy-3H-imidazo[4,5-b]pyridine (57 mg) was dissolved in N,N-dimethylformamide (1.3 ml) and tert-butyl alcohol (1.0 ml) and triethylamine (30.4 mg), 1,3-bis(diphenylphosphino) propane (17 mg) and palladium (II) acetate (9.3 mg) were successively added. The mixture was stirred under a 10 atm. carbon monoxide atmosphere at 85° C. for 48 hr. The insoluble matter was filtered off and washed with chloroform. The filtrate and washing were combined and concentrated to dryness under reduced pressure. The residue was purified by thin layer chromatography (chlorofozm:methanol=19:1) to give 3-(2-chloro-4-phenylbenzyl)-2-ethoxy-3H-imidazo[4,5-b]pyridine-5-carboxylic acid (43 mg) as a brown oil.

¹H-NMR (CDCl₃): 1.52 (3H, t, J=7 Hz), 4.72 (2H, q, J=7 Hz), 5.45 (2H, s), 7.07 (1H, d, J=8 Hz), 7.33–7.72 (7H), 7.92 (1H, d, J=8 Hz), 8.13 (1H, d, J=8 Hz).

PREPARATION EXAMPLE 22-1

In the same manner as in Preparation Example 4-5, methyl 3-[(3-chloro-5-(trifluoromethyl)-2-pyridyl)methyl]-2,7-dimethyl-3H-imidazo[4,5-b]pyridine-5-carboxylate was obtained as a colorless solid (487 mg) from methyl 2,7-dimethyl-3H-imidazo[4,5-b]pyridine-5-carboxylate (300 mg) and 3-chloro-2-(chloromethyl)-5-(trifluoromethyl) pyridine (370 mg).

¹H-NMR (CDCl₃): 2.55 (3H, s), 2.74 (3H, s), 3.96 (3H, s), 5.82 (2H, s), 7.95 (1H, br s), 7.98 (1H, d, J=1 Hz), 8.51 (1H, br s).

PREPARATION EXAMPLE 22-2

In the same manner as in Preparation Example 14-7, 3-[(3-chloro-5-(trifluoromethyl)-2-pyridyl)methyl]-2,7-dimethyl-3H-imidazo[4,5-b]pyridine-5-carboxylic acid was obtained as a colorless solid (398 mg) from methyl 3-[(3-chloro-5-(trifluoromethyl)-2-pyridyl)methyl]-2,7-dimethyl-3H-imidazo(4,5-b]pyridine-5-carboxylate (450 mg).

¹H-NMR (DMSO-d₆): 2.51 (3H, s), 2.62 (3H, s), 5.86 (2H, s), 7.83 (1H, br s), 8.60 (1H, br s), 8.74 (1H, br s). MASS (ESI): m/z 383 (M−1).

PREPARATION EXAMPLE 23-1

Lithium aluminum hydride (1.78 g) was suspended in dry tetrahydrofuran (10 ml), and 2,6-dichloronicotinic acid was added under ice-cooling at an inside temperature of not more than 10° C. The mixture was stirred under ice-cooling for 1 hr and 28% aqueous amonia was added dropwise to the reaction mixture until foams disappeared. Methanol was added and the mixture was stirred at room temperature for 3 hr, and filtered through celite. The mother liquor was concentrated and the residue was applied to flash silica gel column chromatography (silica gel, 200 ml) and eluted with chloroform:ethyl acetate=8:1 to give 2,6-dichloro-3-hydroxymethylpyridine as colorless crystals (2.89 g).

¹H-NMR (CDCl₃): 2.11 (1H, t, J=7 Hz), 4.77 (2H, d, J=7 Hz), 7.32 (1H, d, J=8 Hz), 7.87 (1H, d, J=8 Hz). MASS (ESI): m/z 176 (M−1).

PREPARATION EXAMPLE 23-2

In the same manner as in Preparation Example 19-1, 2,6-dichloro-3-(methanesulfonyloxymethyl)pyridine was obtained as a pale-brown oil (1.3 g) from 2,6-dichloro-3-hydroxymethylpyridine (900 mg).

¹H-NMR (CDCl₃): 3.11 (3H, s), 5.31 (2H, s), 7.36 (1H, d, J=8 Hz), 7.83 (1H, d, J=8 Hz).

PREPARATION EXAMPLE 23-3

In the same manner as in Preparation Example 18-4, methyl 3-[(2,6-dichloro-3-pyridyl)methyl]-2-methyl-3H-imidazo[4,5-b]pyridine-5-carboxylate was obtained as colorless crystals (684 mg), and methyl 1-[(2,6-dichloro-3-pyridyl)methyl]-2-methyl-3H-imidazo[4,5-b]pyridine-5-carboxylate as a brown solid (297 mg), from methyl 2-methyl-3H-imidazo[4,5-b]pyridine-5-carboxylate (700 mg) and 2,6-dichloro-3-(methanesulfonyloxymethyl)pyridine (1.03 g).
Methyl 3-[(2,6-Dichloro-3-pyridyl)methyl]-2-methyl-3H-imidazo[4,5-b]pyridine-5-carboxylate:
 ¹H-NMR (CDCl₃): 2.61 (3H, s), 4.00 (3H, s), 5.63 (2H, s), 7.15 (1H, d, J=8 Hz), 7.18 (1H, d, J=8 Hz), 8.07 (1H, d, J=8 Hz), 8.15 (1H, d, J=8 Hz). MASS (ESI): m/z 351 (M+1).
Methyl 1-[(2,6-Dichloro-3-pyridyl)methyl]-2-methyl-3H-imidazo[4,5-b]pyridine-5-carboxylate:
 ¹H-NMR (CDCl₃): 2.66 (3H, s), 4.03 (3H, s), 5.42 (2H, s), 6.74 (1H, d, J=8 Hz), 7.19 (1H, d, J=8 Hz), 7.56 (1H, d, J=8 Hz), 8.11 (1H, d, J=8 Hz). MASS (ESI): m/z 351 (M+1).

PREPARATION EXAMPLE 23-4

In the same manner as in Preparation Example 14-7, 3-[(2,6-dichloro-3-pyridyl)methyl]-2-methyl-3H-imidazo[4,5-b]pyridine-5-carboxylic acid was obtained as a colorless solid (578 mg) from methyl 3-[(2,6-dichloro-3-pyridyl)methyl]-2-methyl-3H-imidazo[4,5-b]pyridine-5-carboxylate (665 mg).
 ¹H-NMR (DMSO-d₆): 2.56 (3H, s), 5.60 (2H, s), 7.23 (1H, d, J=8 Hz), 7.46 (1H, d, J=8 Hz), 8.01 (1H, d, J=8 Hz), 8.13 (1H, d, J=8 Hz). MASS (ESI): m/z 335 (M−1).

PREPARATION EXAMPLE 24-1

In the same manner as in Preparation Example 14-6, 5-bromo-3-(2-chloro-4-(cyclohexylmethyloxy)benzyl)-2-ethyl-3H-imidazo[4,5-b]pyridine was obtained as colorless crystals (886 mg) from 5-bromo-3-(2-chloro-4-hydroxybenzyl)-2-ethyl-3H-imidazo[4,5-b]pyridine (790 mg) and (bromomethyl)cyclohexane (763 mg).
 ¹H-NMR (CDCl₃): 0.94–1.90 (14H, m), 2.75 (2H, q, J=7 Hz), 3.69 (2H, d, J=7 Hz), 5.49 (2H, s), 6.53 (1H, d, J=8 Hz), 6.65 (1H, dd, J=1, 8 Hz), 6.95 (1H, d, J=1 Hz), 7.37 (1H, d, J=8 Hz), 7.87 (1H, d, J=8 Hz). MS(ESI): m/z 462, 464 (M+1).

PREPARATION EXAMPLE 24-2

In the same manner as in Preparation Example 12-2, methyl 3-(2-chloro-4-(cyclohexylmethyloxy)benzyl)-2-ethyl-3H-imidazo-[4,5-b]pyridine-5-carboxylate was obtained as pale-yellow crystals (549 mg) from 5-bromo-3-(2-chloro-4-(cyclohexylmethyloxy)benzyl)-2-ethyl-3H-imidazo[4,5-b]pyridine (760 mg).
 ¹H-NMR (CDCl₃): 0.94–1.34 (6H, m), 1.38 (3H, t, J=7 Hz), 1.65–1.87 (5H, m), 2.80 (2H, q, J=7 Hz), 3.69 (2H, d, J=7 Hz), 4.00 (3H, s), 5.62 (2H, s), 6.58 (1H, d, J=8 Hz), 6.62 (1H, dd, J=1, 8 Hz), 6.95 (1H, d, J=1 Hz), 8.10 (1H, d, J=8 Hz), 8.14 (1H, d, J=8 Hz). MS(ESI): m/z 442 (M+1).

PREPARATION EXAMPLE 24-3

In the same manner as in Preparation Example 14-7, 3-(2-chloro-4-(cyclohexylmethyloxy)benzyl)-2-ethyl-3H-imidazo[4,5-b]pyridine-5-carboxylic acid was obtained as colorless crystals (453 mg) from methyl 3-(2-chloro-4-(cyclohexylmethyloxy)benzyl)-2-ethyl-3H-imidazo[4,5-b]pyridine-5-carboxylate (532 mg).
 ¹H-NMR (CDCl₃): 0.94–1.38 (6H, m), 1.44 (3H, t, J=7 Hz), 1.64–1.88 (5H, m), 2.90 (2H, q, J=7 Hz), 3.71 (2H, d, J=7 Hz), 5.53 (2H, s), 6.60 (1H, d, J=8 Hz), 6.67 (1H, dd, J=1, 8 Hz), 7.00 (1H, d, J=1 Hz), 8.16–8.24 (2H, m). MS(ESI): m/z 426 (M−1).

PREPARATION EXAMPLE 25-1

In the same manner as in Preparation Example 14-4, methyl 3-(2-chloro-4-iodobenzyl)-2-methyl-3H-imidazo[4,5-b]pyridine-5-carboxylate (163 mg) and methyl 1-(2-chloro-4-iodobenzyl)-2-methyl-1H-imidazo[4,5-b]pyridine-5-carboxylate (108 mg) were obtained each as a pale-brown powder from methyl 2-methyl-3H-imidazo[4,5-b]pyridine-5-carboxylate (150 mg) and 2-chloro-4-iodobenzylbromide (780 mg).
Methyl 3-(2-Chloro-4-iodobenzyl)-2-methyl-3H-imidazo[4,5-b]pyridine-5-carboxylate:
 ¹H-NMR (CDCl₃): 2.54 (3H, s), 3.99 (3H, s), 5.62 (2H, s), 6.37 (1H, d, J=8 Hz), 7.43 (1H, d, J=8 Hz), 7.80 (1H, s), 8.08 (1H, d, J=8 Hz), 8.16 (1H, d, J=8 Hz).
Methyl 1-(2-Chloro-4-iodobenzyl)-2-methyl-1H-imidazo[4,5-b]pyridine-5-carboxylate:
 ¹H-NMR (CDCl₃): 2.65 (3H, s), 4.03 (3H, s), 5.38 (2H, s), 6.20 (1H, d, J=8 Hz), 7.48 (1H, d, J=8 Hz), 7.53 (1H, d, J=8 Hz), 7.83 (1H, s), 8.09 (1H, d, J=8 Hz).

PREPARATION EXAMPLE 25-2

To a suspension of tetrakis(triphenylphosphine)palladium (0) (262 mg) in N,N-dimethylformamide (20 ml) were added methyl 3-(2-chloro-4-iodobenzyl)-2-methyl-3H-imidazo[4,5-b]pyridine-5-carboxylate (2.00 g), furan-2-boric acid (608 mg) and potassium carbonate (1.88 g) at room temperature in a nitrogen atmosphere. After heating at 80° C. for 12 hr, the reaction mixture was ice-cooled and water was added. The precipitated powder was collected by filtration and washed with water. This powder was dried and applied to flash silica gel column chromatography (silica gel, 150 ml) and eluted with chloroform:ethyl acetate=10:1–5:1–3:1 to give a pale-brown solid (1.66 g). This was crystallized from methanol to give methyl 3-[2-chloro-4-(2-furyl)benzyl]-2-methyl-3H-imidazo[4,5-b]pyridine-5-carboxylate as colorless crystals (1.58 g).
 ¹H-NMR (CDCl₃): 2.55 (3H, s), 4.00 (3H, s), 5.69 (2H, s), 6.47 (1H, m), 6.63–6.27 (2H, m), 7.38 (1H, dd, J=8, 1 Hz), 7.47 (1H, d, J=1 Hz), 7.75 (1H, d, J=1 Hz), 8.07 (1H, d, J=8 Hz), 8.16 (1H, d, J=8 Hz). MASS (ESI): m/z 382 (M+1).

PREPARATION EXAMPLE 25-3

In the same manner as in Preparation Example 14-7, 3-[2-chloro-4-(2-furyl)benzyl]-2-methyl-3H-imidazo[4,5-b]pyridine-5-carboxylic acid was obtained as colorless solid (1.44 g) from methyl 3-[2-chloro-4-(2-furyl)benzyl]-2-methyl-3H-imidazo[4,5-b]pyridine-5-carboxylate (1.57 g).
 ¹H-NMR (DMSO-d₆): 2.55 (3H, s), 4.00 (3H, s), 5.69 (2H, s), 6.47 (1H, m), 6.63–6.27 (2H, m), 7.38 (1H, dd, J=8, 1 Hz), 7.47 (1H, d, J=1 Hz), 7.75 (1H, d, J=1 Hz), 8.07 (1H, d, J=1 Hz), 8.16 (1H, d, J=1 Hz). MASS (ESI): m/z 369 (M−1).

PREPARATION EXAMPLE 26-1

In the same manner as in Preparation Example 16-5, N-(tert-butoxycarbonyl)-3-chloro-N-ethyl-4-methylaniline (11.8 g) was obtained as a pale-yellow oil from N-(tert-butoxycarbonyl)-3-chloro-4-methylaniline (10.0 g) and ethyl iodide (7.10 g).

$^1$H-NMR (CDCl$_3$): 1.13 (3H, t, J=7 Hz), 1.44 (9H, s), 2.35 (3H, s), 3.64 (2H, q, J=7 Hz), 6.98 (1H, dd, J=8, 2 Hz), 7.16–7.20 (2H, m).

PREPARATION EXAMPLE 26-2

In the same manner as in Preparation Example 16-6, 4-bromomethyl-N-(tert-butoxycarbonyl)-3-chloro-N-ethylaniline (14.1 g) was obtained as a brown oil from N-(tert-butoxycarbonyl)-3-chloro-N-ethyl-4-methylaniline (11.7 g). This substance was used in the next reaction without further purification.

PREPARATION EXAMPLE 26-3

In the same manner as in Preparation Example 14-4, methyl 3-(4-(N-(tert-butoxycarbonyl)-N-ethylamino)-2-chlorobenzyl)-2-methyl-3H-imidazo[4,5-b]pyridine-5-carboxylate (534 mg) was obtained as pale-orange crystals, and methyl 1-(4-(N-(tert-butoxycarbonyl)-N-ethylamino)-2-chlorobenzyl)-2-methyl-1H-imidazo[4,5-b]pyridine-5-carboxylate (701 mg) as a pale-orange powder, from methyl 2-methyl-3H-imidazo[4,5-b]pyridine-5-carboxylate (950 mg) and 4-bromomethyl-N-(tert-butoxycarbonyl)-3-chloro-N-ethylaniline (2.25 g).

Methyl 3-(4-(N-(tert-Butoxycarbonyl)-N-ethylamino)-2-chlorobenzyl)-2-methyl-3H-imidazo[4,5-b]pyridine-5-carboxylate:

$^1$H-NMR (CDCl$_3$): 1.13 (3H, t, J=7 Hz), 1.44 (9H, s), 2.54 (3H, s), 3.63 (3H, q, J=7 Hz), 4.00 (3H, s), 5.66 (2H, s), 6.60 (1H, d, J=8 Hz), 6.95 (1H, dd, J=8, 2 Hz), 7.34 (1H, d, J=2 Hz), 8.07 (1H, d, J=8 Hz), 8.15 (1H, d, J=8 Hz).

Methyl 1-(4-(N-(tert-Butoxycarbonyl)-N-ethylamino)-2-chlorobenzyl)-2-methyl-1H-imidazo[4,5-b]pyridine-5-carboxylate:

$^1$H-NMR (CDCl$_3$): 1.14 (3H, t, J=7 Hz), 1.44 (9H, s), 2.66 (3H, s), 3.64 (2H, q, J=7 Hz), 4.02 (3H, s), 5.42 (2H, s), 6.45 (1H, d, J=8 Hz), 6.99 (1H, dd, J=8, 2 Hz), 7.39 (1H, d, J=2 Hz), 7.56 (1H, d, J=8 Hz), 8.07 (1H, d, J=8 Hz).

PREPARATION EXAMPLE 26-4

In the same manner as in Preparation Example 14-7, 3-(4-(N-(tert-butoxycarbonyl)-N-ethylamino)-2-chlorobenzyl)-2-methyl-3H-imidazo[4,5-b]pyridine-5-carboxylic acid (535 mg) was obtained as a pale-yellow powder from methyl 3-(4-(N-(tert-butoxycarbonyl)-N-ethylamino)-2-chlorobenzyl)-2-methyl-3H-imidazo[4,5-b]pyridine-5-carboxylate (514 mg).

$^1$H-NMR (DMSO-d$_6$): 1.03 (3H, t, J=7 Hz), 1.37 (9H, s), 2.52 (3H, s), 3.59 (2H, q, J=7 Hz), 5.61 (2H, s), 6.55 (1H, d, J=8 Hz), 7.11 (1H, dd, J=8, 2 Hz), 7.49 (1H, d, J=2 Hz), 8.01 (1H, d, J=8 Hz), 8.14 (1H, d, J=8 Hz).

PREPARATION EXAMPLE 27-1

In the same manner as in Preparation Example 4-5, methyl 3-(4-(N-(tert-butoxycarbonyl)-N-methylamino)-2-chlorobenzyl)-2,7-dimethyl-3H-imidazo[4,5-b]pyridine-5-carboxylate (1.26 g) was obtained as a pale-yellow powder from methyl 2,7-dimethyl-3H-imidazo[4,5-b]pyridine-5-carboxylate (800 mg) and 4-bromomethyl-N-(tert-butoxycarbonyl)-3-chloro-N-methylaniline (1.96 g).

$^1$H-NMR (CDCl$_3$): 1.45 (9H, s), 2.54 (3H, s), 2.73 (3H, s), 3.21 (3H, s), 3.99 (3H, s), 5.63 (2H, s), 6.55 (1H, d, J=8 Hz), 6.98 (1H, dd, J=8, 2 Hz), 7.39 (1H, d, J=2 Hz), 7.97 (1H, s). MASS (ESI): m/z 459 (M+H)$^+$.

PREPARATION EXAMPLE 27-2

In the same manner as in Preparation Example 14-7, 3-(4-(N-(tert-butoxycarbonyl)-N-methylamino)-2-chlorobenzyl)-2,7-dimethyl-3H-imidazo[4,5-b]pyridine-5-carboxylic acid (805 mg) was obtained as a pale-yellow powder from methyl 3-(4-(N-(tert-butoxycarbonyl)-N-methylamino)-2-chlorobenzyl)-2,7-dimethyl-3H-imidazo[4,5-b]pyridine-5-carboxylate (900 mg).

$^1$H-NMR (DMSO-d$_6$): 1.38 (9H, s), 2.51 (3H, s), 2.63 (3H, s), 3.15 (3H, s), 5.57 (2H, s), 6.50 (1H, d, J=8 Hz), 7.15 (1H, dd, J=8, 2 Hz), 7.55 (1H, d, J=2 Hz), 7.87 (1H, s). MASS (ESI): m/z 443 (M−H)$^-$.

PREPARATION EXAMPLE 28-1

In the same manner as in Preparation Example 4-5, methyl 3-[4-(N-(tert-butoxycarbonyl)-N-ethylamino)-2-chlorobenzyl]-2,7-dimethyl-3H-imidazo[4,5-b]pyridine-5-carboxylate (846 mg) was obtained as a brown oil from methyl 2,7-dimethyl-3H-imidazo[4,5-b]pyridine-5-carboxylate (400 mg) and 4-(N-(tert-butoxycarbonyl)-N-ethylamino)-2-chlorobenzyl bromide (816 mg).

$^1$H-NMR (CDCl$_3$): 1.13 (3H, t, J=6 Hz), 1.44 (9H, s), 2.54 (3H, s), 2.74 (3H, s), 3.62 (2H, q, J=6 Hz), 3.99 (3H, s), 5.64 (2H, s), 6.55 (1H, d, J=8 Hz), 6.94 (1H, dd, J=8, 2 Hz), 7.34 (1H, d, J=2 Hz), 7.97 (1H, s).

PREPARATION EXAMPLE 28-2

In the same manner as in Preparation Example 14-7, 3-[4-(N-(tert-butoxycarbonyl)-N-ethylamino)-2-chlorobenzyl]-2,7-dimethyl-3H-imidazo[4,5-b]pyridine-5-carboxylic acid (658 mg) was obtained as a brown powder from methyl 3-[4-(N-(tert-butoxycarbonyl)-N-ethylamino)-2-chlorobenzyl]-2,7-dimethyl-3H-imidazo[4,5-b]pyridine-5-carboxylate (828 mg).

$^1$H-NMR (CDCl$_3$): 1.15 (3H, t, J=6 Hz), 1.44 (9H, s), 2.62 (3H, s), 2.76 (3H, s), 3.65 (2H, q, J=6 Hz), 5.55 (2H, s), 6.56 (1H, d, J=8 Hz), 7.00 (1H, dd, J=8, 2 Hz), 7.39 (1H, d, J=2 Hz), 8.06 (1H, s). MASS (ESI): m/z 459 (M).

PREPARATION EXAMPLE 29-1

In the same manner as in Preparation Example 19-1, 2-chloro-1-methanesulfonyloxymethyl-4-nitrobenzene (3.56 g) was obtained as brown crystals from 2-chloro-4-nitrobenzyl alcohol (2.5 g) and methanesulfonyl chloride (1.68 g).

$^1$H-NMR (CDCl$_3$): 3.12 (3H, s), 5.40 (2H, s), 7.73 (1H, d J=8 Hz), 8.18 (1H, dd, J=2,8 Hz), 8.79 (1H, s).

PREPARATION EXAMPLE 29-2

In the same manner as in Preparation Example 18-4, methyl 3-(2-chloro-4-nitrobenzyl)-2-methyl-3H-imidazo[4,5-b]pyridine-5-carboxylate (1.02 g) was obtained as white crystals, and methyl 1-(2-chloro-4-nitrobenzyl)-2-methyl-1H-imidazo[4,5-b]pyridine-5-carboxylate (330 mg) as pale-brown crystals, from methyl 2-methyl-3H-imidazo[4,5-b]pyridine-5-carboxylate (2.00 g) and 2-chloro-1-methanesulfonyloxymethyl-4-nitrobenzene (3.06 g).

Methyl 3-(2-Chloro-4-nitrobenzyl)-2-methyl-3H-imidazo[4,5-b]pyridine-5-carboxylate:

$^1$H-NMR (CDCl$_3$): 2.55 (3H, s), 3.99 (3H, s), 5.73 (2H, s), 6.80 (1H, d, J=8 Hz), 7.97 (1H, d, J=8 Hz), 8.08 (1H, d, J=8 Hz), 8.16 (1H, d, J=8 Hz), 8.33 (1H, s).

Methyl 1-(2-Chloro-4-nitrobenzyl)-2-methyl-1H-imidazo[4,5-b]pyridine-5-carboxylate:

$^1$H-NMR (CDCl$_3$): 2.65 (3H, s), 4.03 (3H, s), 5.51 (2H, s), 6.62 (1H, d, J=8 Hz), 7.53 (1H, d, J=8 Hz), 8.01 (1H, dd, J=2,8 Hz), 8.10 (1H, d, J=8 Hz), 8.39 (1H, d, J=2 Hz).

PREPARATION EXAMPLE 29-3

Methyl 3-(2-chloro-4-nitrobenzyl)-2-methyl-3H-imidazo[4,5-b]pyridine-5-carboxylate (705 mg) was suspended in ethanol (6 ml) and reduced iron (655 mg) and acetic acid (2.11 ml) were added, which was followed by refluxing under heating for 3 hr. The reaction mixture was filtered through celite, and the filtrate was concentrated under reduced pressure. To the residue was added saturated aqueous sodium hydrogen carbonate solution to make the residue alkaline and extracted with ethyl acetate. The organic layer was washed successively with saturated aqueous sodium hydrogen carbonate solution and saturated brine, dried over anhydrous magnesium sulfate and filtrated. The filtrate was concentrated under reduced pressure to give methyl 3-(4-amino-2-chlorobenzyl)-2-methyl-3H-imidazo[4,5-b]pyridine-5-carboxylate (608 mg) as a white powder.

$^1$H-NMR (CDCl$_3$): 2.53 (3H, s), 3.75 (2H, s), 4.00 (3H, s), 5.67 (2H, s), 6.40 (1H, dd, J=2,8 Hz), 6.54 (1H, dd, J=1,8 Hz), 6.72 (1H, d, J=1 Hz), 8.02 (1H, d, J=8 Hz), 8.12 (1H, d, J=8 Hz).

PREPARATION EXAMPLE 29-4

Methyl 3-(4-amino-2-chlorobenzyl)-2-methyl-3H-imidazo[4,5-b]pyridine-5-carboxylate (1.00 g) was dissolved in acetic acid (5.0 ml) and 2,5-dimethoxytetrahydrofuran (420 mg) was added, which was followed by refluxing under heating for 2 hr. The reaction mixture was concentrated under reduced pressure and the residue was applied to silica gel column chromatography and eluted with chloroform:ethyl acetate=3:1. The objective fraction was concentrated under reduced pressure and ethyl acetate (10.0 ml) was added to the residue. After heating, the mixture was allowed to cool and the precipitated crystals were collected by filtration to give methyl 3-(2-chloro-4-(1-pyrrolyl)benzyl)-2-methyl-3H-imidazo[4,5-b]pyridine-5-carboxylate (641 mg) as colorless crystals.

$^1$H-NMR (CDCl$_3$): 2.58 (3H, s), 4.00 (3H, s), 5.69 (2H, s), 6.34 (2H, t, J=2 Hz), 6.74 (1H, d, J=8 Hz), 7.03 (2H, t, J=2 Hz), 7.14 (1H, dd, J=8, 2 Hz), 7.49 (1H, d, J=2 Hz), 8.08 (1H, d, J=8 Hz), 8.16 (1H, d, J=8 Hz). MASS (ESI): m/z 381 (M+H)$^+$.

PREPARATION EXAMPLE 29-5

In the same manner as in Preparation Example 14-7, 3-(2-chloro-4-(1-pyrrolyl)benzyl)-2-methyl-3H-imidazo[4,5-b]pyridine-5-carboxylic acid(426 mg) was obtained as a pale-yellow powder from methyl 3-(2-chloro-4-(1-pyrrolyl)benzyl)-2-methyl-3H-imidazo[4,5-b]pyridine-5-carboxylate (450 mg).

$^1$H-NMR (DMSO-d$_6$): 2.55 (3H, s), 5.63 (2H, s), 6.26 (2H, t, J=2 Hz), 6.67 (1H, d, J=8 Hz), 7.41 (2H, t, J=2 Hz), 7.47 (1H, dd, J=8, 2 Hz), 7.87 (1H, d, J=2 Hz), 8.02 (1H, d, J=8 Hz), 8.15 (1H, d, J=8 Hz). MASS (ESI): m/z 365 (M−H)$^−$.

PREPARATION EXAMPLE 30-1

In the same manner as in Preparation Example 14-4, methyl 3-(2-chloro-4-iodobenzyl)-2,7-dimethyl-3H-imidazo[4,5-b]pyridine-5-carboxylate (6.42 g) was obtained as a white powder from methyl 2,7-dimethyl-3H-imidazo[4,5-b]pyridine-5-carboxylate (3.00 g) and 2-chloro-4-iodobenzyl bromide (7.00 g).

$^1$H-NMR (DMSO-d$_6$): 2.51 (3H, s), 2.63 (3H, s), 3.85 (3H, s), 5.50 (2H, s), 6.30 (1H, d, J=8 Hz), 7.58 (1H, d, J=8 Hz), 7.88 (1H, s), 7.95 (1H, s).

PREPARATION EXAMPLE 30-2

In the same manner as in Preparation Example 25-2, methyl 3-[2-chloro-4-(2-furyl)benzyl]-2,7-dimethyl-3H-imidazo[4,5-b]pyridine-5-carboxylate was obtained as colorless crystals (1.58 g) from methyl 3-[(2-chloro-4-iodo)benzyl]-2,7-dimethyl-3H-imidazo[4,5-b]pyridine-5-carboxylate (2.00 g) and furan-2-boric acid (608 mg).

$^1$H-NMR (CDCl$_3$): 2.54 (3H, s), 2.74 (3H, s), 3.99 (3H, s), 5.66 (2H, s), 6.46 (1H, m), 6.61 (1H, d, J=8 Hz), 6.64 (1H, d, J=5 Hz), 7.37 (1H, dd, J=8, 1 Hz), 7.46 (1H, d, J=1 Hz), 7.74 (1H, d, J=1 Hz), 7.98 (1H, s). MASS (ESI): m/z 395 (M+1).

PREPARATION EXAMPLE 30-3

In the-same manner as in Preparation Example 14-7, 3-[2-chloro-4-(2-furyl)benzyl]-2,7-dimethyl-3H-imidazo[4,5-b]pyridine-5-carboxylic acid was obtained as a colorless solid (1.07 g) from methyl 3-[2-chloro-4-(2-furyl)benzyl]-2,7-dimethyl-3H-imidazo[4,5-b]pyridine-5-carboxylate (1.17 g).

$^1$H-NMR (DMSO-d$_6$): 2.52 (3H, s), 2.64 (3H, s), 5.61 (2H, s), 6.56–6.63 (2H, m), 7.06 (1H, d, J=5 Hz), 7.54 (1H, dd, J=8, 1 Hz), 7.77 (1H, d, J=1 Hz), 7.85–7.90 (2H, m). MASS (ESI): m/z 380 (M−1).

PREPARATION EXAMPLE 31-1

To a solution of 2,4-dichlorobenzaldehyde (3.5 g) in sulfuric acid (15 ml) was added dropwise fuming nitric acid under ice-cooling at not more than 10° C. over 15 min. The mixture was stirred under ice-cooling for 1 hr and the reaction mixture was poured into ice (50 g). The aqueous layer was extracted with ethyl acetate, and the organic layer was washed with water and saturated brine. The organic layer was dried over anhydrous magnesium sulfate. After filtration, the filtrate was concentrated to give pale-yellow crystals (4.39 g). This was recrystallized from isopropyl ether to give 2,4-dichloro-5-nitrobenzaldehyde as pale-yellow crystals (3.50 g).

$^1$H-NMR (CDCl$_3$): 7.73 (1H, s), 8.44 (1H, s).

PREPARATION EXAMPLE 31-2

To a solution of 2,4-dichloro-5-nitrobenzaldehyde (2.0 g) in ethanol (20 ml) was added sodium borohydride (688 mg) under ice-cooling. After 1 hr, water was added to the reaction mixture and extracted with ethyl acetate. The organic layer was washed with water and saturated brine, and dried over anhydrous magnesium sulfate. After filtration, the filtrate was concentrated to give a pale-yellow solid (2.07 g). This was applied to flash silica gel column chromatography (silica gel, 80 ml) and eluted with hexane:ethyl acetate= 10:1–5:1 to give 2,4-dichloro-5-nitrobenzyl alcohol as pale-yellow crystals (1.97 g).

$^1$H-NMR (CDCl$_3$): 2.08 (1H, t, J=5 Hz), 4.82 (2H, d, J=5 Hz), 7.57 (1H, s) 8.15 (1H, s).

PREPARATION EXAMPLE 31-3

In the same manner as in Preparation Example 19-1, 2,4-dichloro-1-methanesulfonyloxymethyl-5-nitrobenzene was obtained as a colorless oil (2.75 g) from 2,4-dichloro-5-nitrobenzyl alcohol (1.96 g).

$^1$H-NMR (CDCl$_3$): 3.14 (3H, s), 5.33 (2H, s), 7.67 (1H, s), 8.08 (1H, s).

PREPARATION EXAMPLE 31-4

In the same manner as in Preparation Example 14-4, methyl 3-[(2,4-dichloro-5-nitro)benzyl]-2-methyl-3H-imidazo[4,5-b]pyridine-5-carboxylate was obtained as colorless crystals (2.19 g) and methyl 1-[(2,4-dichloro-5-nitro)benzyl]-2-methyl-3H-imidazo[4,5-b]pyridine-5-carboxylate as pale-yellow amorphous (473 mg), from methyl 2-methyl-3H-imidazo[4,5-b]pyridine-5-carboxylate (1.69 g).
Methyl 3-[(2,4-Dichloro-5-nitro)benzyl]-2-methyl-3H-imidazo[4,5-b]pyridine-5-carboxylate:
$^1$H-NMR (CDCl$_3$): 2.64 (3H, s), 4.00 (3H, s), 5.64 (2H, s), 7.57 (1H, s), 6.68 (1H, s), 8.08 (1H, d, J=8 Hz), 8.16 (1H, d, J=8 Hz). MASS (ESI): m/z 395 (M+1).
Methyl 1-[(2,4-Dichloro-5-nitro)benzyl]-2-methyl-3H-imidazo[4,5-b]pyridine-5-carboxylate:
$^1$H-NMR (CDCl$_3$): 2.68 (3H, s), 4.03 (3H, s), 5.46 (2H, s), 7.11 (1H, s), 7.54 (1H, d, J=8 Hz), 7.73 (1H, s), 8.11 (1H, d, J=8 Hz). MASS (ESI): m/z 395 (M+1).

PREPARATION EXAMPLE 31-5

In the same manner as in Preparation Example 14-7, 3-[(2,4-dichloro-5-nitro)benzyl]-2-methyl-3H-imidazo[4,5-b]pyridine-5-carboxylic acid was obtained as a colorless solid (382 mg) from methyl 3-[(2,4-dichloro-5-nitro)benzyl]-2-methyl-3H-imidazo[4,5-b]pyridine-5-carboxylate (450 mg).
$^1$H-NMR (DMSO-d$_6$): 2.57 (3H, s), 2.64 (3H, s), 5.66 (2H, s), 7.58 (1H, s), 8.00 (1H, d, J=8 Hz), 8.13 (1H, d, J=8 Hz), 8.16 (1H, s). MASS (ESI): m/z 381 (M−1).

PREPARATION EXAMPLE 32-1

In the same manner as in Preparation Example 29-3, methyl 3-[(5-amino-2,4-dichloro)benzyl]-2-methyl-3H-imidazo[4,5-b]pyridine-5-carboxylate was obtained as colorless crystals (1.25 g) from methyl 3-[(2,4-dichloro-5-nitro)benzyl]-2-methyl-3H-imidazo[4,5-b]pyridine-5-carboxylate (1.5 g).
$^1$H-NMR (CDCl$_3$): 2.51 (3H, s), 3.94 (3H, s), 4.23 (2H, br s), 5.47 (2H, s), 6.02 (1H, s), 7.25 (1H, s), 7.26 (1H, s), 8.01 (1H, d, J=8 Hz), 8.04 (1H, d, J=8 Hz). MASS (ESI): m/z 365 (M+1).

PREPARATION EXAMPLE 32-2

To a solution of methyl 3-[(5-amino-2,4-dichloro)benzyl]-2-methyl-3H-imidazo[4,5-b]pyridine-5-carboxylate (500 mg) in formic acid (5 ml) was added 37% formalin (1.03 ml) at room temperature and the mixture was refluxed under heating. After 30 min, the reaction mixture was concentrated and chloroform and saturated aqueous sodium hydrogen carbonate solution were added to the residue. The organic layer was separated and the aqueous layer was extracted with chloroform. The organic layers were combined and dried over anhydrous magnesium sulfate. After filtration, the filtrate was concentrated and the residue was applied to flash silica gel column chromatography (silica gel, 50 ml) and eluted with chloroform:ethyl acetate=5:1 to give methyl 3-[(2,4-dichloro-5-(N,N-dimethylamino))benzyl]-2-methyl-3H-imidazo[4,5-b]pyridine-5-carboxylate as a colorless solid (489 mg).
$^1$H-NMR (CDCl$_3$): 2.58 (6H, s), 2.62 (3H, s), 4.01 (3H, s), 5.60 (2H, s), 6.70 (1H, s), 7.41 (1H, s), 8.06 (1H, d, J=8 Hz), 8.15 (1H, d, J=8 Hz). MASS (ESI): m/z 393 (M+1).

PREPARATION EXAMPLE 32-3

In the same manner as in Preparation Example 14-7, 3-[(2,4-dichloro-5-(N,N-dimethylamino))benzyl]-2-methyl-3H-imidazo[4,5-b]pyridine-5-carboxylic acid was obtained as a colorless solid (410 mg) from methyl 3-[(2,4-dichloro-5-(N,N-dimethylamino))-benzyl]-2-methyl-3H-imidazo[4,5-b]pyridine-5-carboxylate (470 mg).
$^1$H-NMR (DMSO-d$_6$): 2.54 (6H, s), 2.59 (3H, s), 5.56 (2H, s), 6.76 (1H, s), 7.60 (1H, s), 8.00 (1H, d, J=8 Hz), 8.12 (1H, d, J=8 Hz). MASS (ESI): m/z 377 (M−1).

PREPARATION EXAMPLE 33-1

A mixture of methyl 3-(4-amino-2-chlorobenzyl)-2-methyl-3H-imidazo[4,5-b]pyridine-5-carboxylate (300 mg), di-tert-butyl dicarbonate (476 mg), pyridine(143 mg), 4-dimethylaminopyridine (22 mg) and tetrahydrofuran (1.5 ml) was refluxed under heating for 2 hr. The reaction mixture was partitioned between ethyl acetate and water. The organic layer was separated, washed with water and saturated brine, dried over magnesium sulfate, and concentrated to dryness under reduced pressure. The residue was purified by silica gel column chromatography (eluted with chloroform) to give methyl 3-[4-(N,N-bis-(tert-butoxycarbonyl)-amino)-2-chlorobenzyl]-2-methyl-3H-imidazo[4,5-b]pyridine-5-carboxylate (420 mg) as a pale-yellow oil.
$^1$H-NMR (CDCl$_3$): 1.42 (18H, s), 2.50 (3H, s), 4.00 (3H, s), 5.69 (2H, s), 6.64 (1H, d, J=8 Hz), 6.92 (1H, dd, J=8, 2 Hz), 7.29 (1H, d, J=2 Hz), 8.06 (1H, d, J=8 Hz), 8.15 (1H, d, J=8 Hz).

PREPARATION EXAMPLE 33-2

Methyl 3-(4-(N,N-bis-(tert-butoxycarbonyl)amino)-2-chlorobenzyl)-2-methyl-3H-imidazo[4,5-b]pyridine-5-carboxylate (391 mg) was dissolved in 1,4-dioxane (4 ml). 1N Aqueous sodium hydroxide solution (3.7 ml) was added and the mixture was stirred at room temperature for 2 days and at 80° C. for 2 hr. To the reaction mixture was added 1N hydrochloric acid to adjust the pH to 4. Water (40 ml) was added and the precipitated crystals were collected by filtration to give 3-(4-(N-(tert-butoxycarbonyl)-amino)-2-chlorobenzyl)-2-methyl-3H-imidazo[4,5-b]pyridine-5-carboxylic acid (261 mg) as pale-yellow crystals.
$^1$H-NMR (DMSO-d$_6$): 1.46 (9H, s), 2.50 (3H, s), 5.54 (2H, s), 6.57 (1H, d, J=8 Hz), 7.23 (1H, dd, J=8, 2 Hz), 7.73 (1H, d, J=2 Hz), 8.00 (1H, d, J=8 Hz), 8.12 (1H, d, J=8 Hz), 9.61 (1H, s).

PREPARATION EXAMPLE 34-1

In the same manner as in Example 65 to be mentioned later, methyl 3-(2-chloro-4-(ethoxycarbonylamino)benzyl)-2-methyl-3H-imidazo[4,5-b]pyridine-5-carboxylate (315 mg) was obtained as a pale-yellow powder from methyl 3-(4-amino-2-chlorobenzyl)-2-methyl-3H-imidazo[4,5-b]pyridine-5-carboxylate (300 mg).
$^1$H-NMR (CDCl$_3$): 1.29 (3H, t, J=7 Hz), 2.53 (3H, s), 3.99 (3H, s), 4.21 (2H, q, J=7 Hz), 5.60 (2H, s), 6.53 (1H, d, J=8 Hz), 6.97 (1H, dd, J=8, 2 Hz), 7.68 (1H, d, J=2 Hz), 8.06 (1H, d, J=8 Hz), 8.14 (1H, d, J=8 Hz). MASS (ESI): m/z 403 (M+1).

PREPARATION EXAMPLE 34-2

In the same manner as in Preparation Example 14-7, 3-(2-chloro-4-(ethoxycarbonylamino)benzyl)-2-methyl-3H-imidazo[4,5-b]pyridine-5-carboxylic acid (319 mg) was obtained as a pale-yellow powder from methyl 3-(2-chloro-4-(ethoxycarbonylamino)-benzyl)-2-methyl-3H-imidazo[4,5-b]pyridine-5-carboxylate (312 mg).

¹H-NMR (CDCl₃): 1.31 (3H, t, J=7 Hz), 2.63 (3H, s), 4.22 (2H, q, J=7 Hz), 5.55 (2H, s), 6.62 (1H, d, J=8 Hz), 7.06 (1H, dd, J=8, 2 Hz), 7.72 (1H, d, J=2 Hz), 8.16 (1H, d, J=8 Hz), 8.22 (1H, d, J=8 Hz). MASS (ESI): m/z 387 (M−1).

PREPARATION EXAMPLE 35-1

To a solution of methyl 3-(4-amino-2-chlorobenzyl)-2-methyl-3H-imidazo[4,5-b]pyridine-5-carboxylate (300 mg) in dichloromethane (3.0 ml) was added triethylamine (110 mg). To this suspension was added valeryl chloride (115 mg) under ice-cooling and the mixture was stirred for 30 min and at room temperature for 7 hr. Water was added to the reaction mixture and extracted twice with chloroform. The combined organic layer was washed with saturated aqueous sodium hydrogen carbonate solution and saturated brine, dried over anhydrous magnesium sulfate, filtrated, and concentrated under reduced pressure. Hexane was added to the residue. The mixture was crystallized, collected by filtration, and dried under reduced pressure to give methyl 3-(2-chloro-4-(N-velerylamino)benzyl)-2-methyl-3H-imidazo[4,5-b]pyridine-5-carboxylate as thin yellow crystals (328 mg).

¹H-NMR (CDCl₃): 0.88 (3H, t, J=7 Hz), 1.28–1.42 (2H, m), 1.62–1.73 (2H, m), 2.34 (2H, t, J=7 Hz), 2.52 (3H, s), 3.99 (3H, s), 5.54 (2H, s), 6.33 (1H, d, J=8 Hz), 7.07 (1H, dd, J=1, 8 Hz), 7.87 (1H, d, J=1 Hz), 8.10 (1H, d, J=8 Hz), 8.16 (1H, d, J=8 Hz). MASS (ESI): m/z 415 (M+1).

PREPARATION EXAMPLE 35-2

In the same manner as in Preparation Example 14-7, 3-(2-chloro-4-(N-valerylamino)benzyl)-2-methyl-3H-imidazo[4,5-b]pyridine-5-carboxylic acid was obtained as bright yellow crystals (236 mg) from methyl 3-(2-chloro-4-(N-valerylamino)benzyl)-2-methyl-3H-imidazo[4,5-b]pyridine-5-carboxylate (300 mg).

¹H-NMR (DMSO-d₆): 0.88 (3H, t, J=7 Hz), 1.22–1.37 (2H, m), 1.49–1.61 (2H, m), 2.28 (2H, t, J=7 Hz), 2.51 (3H, s), 5.56 (2H, s), 6.57 (1H, d, J=8 Hz), 7.26 (1H, dd, J=1, 8 Hz), 8.00 (1H, d, J=1 Hz), 8.01 (1H, d, J=8 Hz), 8.13 (1H, d, J=8 Hz). MASS (ESI): m/z 399 (M−1).

PREPARATION EXAMPLE 36-1

To a solution of methyl 3-(4-amino-2-chlorobenzyl)-2-methyl-3H-imidazo[4,5-b]pyridine-5-carboxylate (300 mg) in dichloromethane (3.0 ml) was added pyridine (143 mg). To this suspension was added 1-butanesulfonyl chloride (156 mg) under ice-cooling and the mixture was stirred for 5 min and at room temperature for 7 hr. Water was added to the reaction mixture and extracted twice with chloroform. The combined organic layer was washed with saturated aqueous sodium hydrogen carbonate solution and saturated brine, dried over anhydrous magnesium sulfate, filtrated, and concentrated under reduced pressure. Methanol was added to the residue. The mixture was crystallized, collected by filtration, and dried under reduced pressure to give methyl 3-(4-(N-(1-butanesulfonyl)amino)-2-chlorobenzyl)-2-methyl-3H-imidazo[4,5-b]pyridine-5-carboxylate as ochroid crystals (287 mg).

¹H-NMR (CDCl₃): 0.90 (3H, t, J=7 Hz), 1.35–1.49 (2H, m), 1.74–1.86 (2H, m), 2.53 (3H, s), 3.10–3.17 (2H, m), 3.99 (3H, s), 5.61 (2H, s), 6.34 (1H, d, J=8 Hz), 6.90 (1H, dd, J=1, 8 Hz), 7.31 (1H, d, J=1 Hz), 8.07 (1H, d, J=8 Hz), 8.13 (1H, d, J=8 Hz). MASS (ESI): m/z 451 (M+1).

PREPARATION EXAMPLE 36-2

In the same manner as in Preparation Example 14-7, 3-(4-(N-(1-butanesulfonyl)amino)-2-chlorobenzyl)-2-methyl-3H-imidazo[4,5-b]pyridine-5-carboxylic acid was obtained as ochroid crystals (235 mg) from methyl 3-(4-(N-(1-butanesulfonyl)amino)-2-chlorobenzyl)-2-methyl-3H-imidazo[4,5-b]pyridine-5-carboxylate (265 mg).

¹H-NMR (DMSO-d₆): 0.81 (3H, t, J=7 Hz), 1.25–1.40 (2H, m), 1.54–1.66 (2H, m), 3.07–3.15 (2H, m), 3.57 (3H, s), 5.56 (2H, s), 6.60 (1H, d, J=8 Hz), 7.05 (1H, dd, J=1, 8 Hz), 7.34 (1H, d, J=1 Hz), 8.00 (1H, d, J=8 Hz), 8.12 (1H, d, J=8 Hz). MASS (ESI): m/z 435 (M−1).

PREPARATION EXAMPLE 37-1

In the same manner as in Preparation Example 35-1, methyl 3-(2-chloro-4-(N-(t-butylacetyl)amino)benzyl)-2-methyl-3H-imidazo[4,5-b]pyridine-5-carboxylate was obtained as thin yellow crystals (346 mg) from methyl 3-(4-amino-2-chlorobenzyl)-2-methyl-3H-imidazo[4,5-b]pyridine-5-carboxylate (300 mg) and t-butylacetyl chloride (128 mg).

¹H-NMR (CDCl₃): 1.06 (9H, s), 2.20 (2H, s), 2.49 (3H, s), 3.99 (3H, s), 5.53 (2H, s), 6.35 (1H, d, J=8 Hz), 7.05 (1H, dd, J=1, 8 Hz), 7.95 (1H, d, J=1 Hz), 8.05 (1H, d, J=8 Hz), 8.15 (1H, d, J=8 Hz). MASS (ESI): m/z 429 (M+1).

PREPARATION EXAMPLE 37-2

In the same manner as in Preparation Example 14-7, 3-(2-chloro-4-(N-(t-butylacetyl)amino)benzyl)-2-methyl-3H-imidazo[4,5-b]pyridine-5-carboxylic acid was obtained as thin yellow crystals (346 mg) from methyl 3-(2-chloro-4-(N-(t-butylacetyl)amino)-benzyl)-2-methyl-3H-imidazo [4,5-b]pyridine-5-carboxylate (320 mg).

¹H-NMR (DMSO-d₆): 0.99 (9H, s), 2.16 (2H, s), 3.57 (3H, s), 5.56 (2H, s), 6.55 (1H, d, J=8 Hz), 7.25 (1H, dd, J=1, 8 Hz), 8.00 (1H, d, J=8 Hz), 8.01 (1H, d, J=1 Hz), 8.11 (1H, d, J=8 Hz). MASS (ESI): m/z 415 (M+1).

PREPARATION EXAMPLE 38-1

In the same manner as in Preparation Example 4-5, 2-(N-acetyl-N-(4-(N,N-bis-(tert-butoxycarbonyl)amino)-2-chlorobenzyl)-amino)-6-bromo-3-nitropyridine (2.30 g) was obtained as pale-yellow amorphous from 2-acetamido-6-bromo-3-nitropyridine (1.00 g) and 4-(N,N-bis(tert-butoxycarbonyl)amino)-2-chlorobenzylbromide (2.10 g).

¹H-NMR (CDCl₃): 1.42 (18H, s), 2.19 (3H, br. s), 5.38 (2H, br. s), 7.06 (1H, d, J=8 Hz), 7.21 (1H, br. s), 7.49 (1H, br. s), 7.62 (1H, d, J=8 Hz), 8.10 (1H, d, J=8 Hz).

PREPARATION EXAMPLE 38-2

In the same manner as in Preparation Example 4-6, a crude product (2.01 g) of 3-(4-(N,N-bis-(tert-butoxycarbonyl)amino)-2-chlorobenzyl)-5-bromo-2-methyl-3H-imidazo[4,5-b]pyridine was obtained as a pale-yellow oil from 2-(N-acetyl-N-(4-(N,N-bis-(tert-butoxycarbonyl)amino)-2-chlorobenzyl)amino)-6-bromo-3-nitropyridine (2.01 g).

PREPARATION EXAMPLE 38-3

A crude product (1.90 g) of 3-(4-(N,N-bis-(tert-butoxycarbonyl)amino)-2-chlorobenzyl)-5-bromo-2-methyl-3H-imidazo[4,5-b]pyridine was dissolved in 1,4-dioxane (19 ml) and 1N aqueous sodium hydroxide solution (7.0 ml) was added, which was followed by refluxing under heating for 8 hr. The mixture was allowed to cool, neutralized and stirred at room temperature for 30 min. The precipitate was collected by filtration, and washed with water to give 3-(4-(N-(tert-butoxycarbonyl)amino)-2-chlorobenzyl)-5-bromo-2-methyl-3H-imidazo[4,5-b]pyridine (1.45 g) as a pale-gray powder.

$^1$H-NMR (CDCl$_3$): 1.50 (9H, s), 2.47 (3H, s), 5.50 (2H, s), 6.49 (1H, br. s), 6.55 (1H, d, J=8 Hz), 6.93 (1H, dd, J=8, 2 Hz), 7.37 (1H, d, J=8 Hz), 7.72 (1H, br. s), 7.83 (1H, d, J=8 Hz). MS (ESI): m/z 452 (M+1).

PREPARATION EXAMPLE 38-4

In the same manner as in Preparation Example 12-2, methyl 3-(4-(N-(tert-butoxycarbonyl)amino)-2-chlorobenzyl)-2-methyl-3H-imidazo[4,5-b]pyridine-5-carboxylate (621 mg) was obtained as pale-yellow amorphous from 3-(4-(N-(tert-butoxycarbonyl)amino)-2-chlorobenzyl)-5-bromo-2-methyl-3H-imidazo[4,5-b]pyridine (500 mg).

$^1$H-NMR (CDCl$_3$): 1.50 (9H, s), 2.54 (3H, s), 4.00 (3H, s), 5.61 (2H, s), 6.56 (1H, d, J=8 Hz), 6.60 (1H, br. s), 6.91 (1H, dd, J=8, 2 Hz), 7.72 (1H, br. s), 8.05 (1H, d, J=8 Hz), 8.14 (1H, d, J=8 Hz). MS (ESI): m/z 431 (M+1).

PREPARATION EXAMPLE 38-5

In the same manner as in Preparation Example 17-1, methyl 3-(4-amino-2-chlorobenzyl)-2-methyl-3H-imidazo[4,5-b]pyridine-5-carboxylate dihydrochloride was obtained as pale-yellow crystals (415 mg) from methyl 3-(4-(N-(tert-butoxycarbonyl)amino)-2-chlorobenzyl)-2-methyl-3H-imidazo[4,5-b]pyridine-5-carboxylate (539 mg).

$^1$H-NMR (DMSO-d$_6$): 2.62 (3H, s), 3.89 (3H, s), 5.55 (2H, s), 6.65–6.79 (2H, m), 7.06 (1H, s), 8.10 (1H, d, J=8 Hz), 8.25 (1H, d, J=8 Hz).

PREPARATION EXAMPLE 38-6

In the same manner as in Example 65 to be mentioned later, methyl 3-(2-chloro-4-(N-(isopropoxycarbonyl)amino)benzyl)-2-methyl-3H-imidazo[4,5-b]pyridine-5-carboxylate was obtained as pale-yellow crystals (310 mg) from methyl 3-(4-amino-2-chlorobenzyl)-2-methyl-3H-imidazo[4,5-b]pyridine-5-carboxylate dihydrochloride (390 mg) and isopropyl chlorocarbonate (173 mg).

$^1$H-NMR (CDCl$_3$): 1.28 (6H, d, J=7 Hz), 2.53 (3H, s), 3.99 (3H, s), 4.95–5.05 (1H, m), 5.62 (2H, s), 6.58 (1H, d, J=8 Hz), 6.98 (1H, dd, J=8 Hz), 7.70 (1H, s), 8.05 (1H, d, J=8 Hz), 8.15 (1H, d, J=8 Hz). MS (ESI): m/z 417 (M+1).

PREPARATION EXAMPLE 39

In the same manner as in Preparation Example 14-7, 3-(2-chloro-4-(N-(isopropoxycarbonyl)amino)benzyl)-2-methyl-3H-imidazo[4,5-b]pyridine-5-carboxylic acid was obtained as pale-yellow crystals (178 mg) from methyl 3-(2-chloro-4-(N-(isopropoxycarbonyl)amino)benzyl)-2-methyl-3H-imidazo[4,5-b]pyridine-5-carboxylate (300 mg).

$^1$H-NMR (DMSO-d$_6$): 1.23 (6H, d, J=7 Hz), 2.50 (3H, overlapped with DMSO-d$_6$), 4.80–4.94 (1H, m), 5.55 (2H, s), 6.58 (1H, d, J=8 Hz), 7.25 (1H, dd, J=1, 8 Hz), 7.71 (1H, s), 8.00 (1H, d, J=8 Hz), 8.12 (1H, d, J=8 Hz).

PREPARATION EXAMPLE 40-1

To a mixture of methyl 3-(2-chloro-4-(methylamino)benzyl)-2-methyl-3H-imidazo[4,5-b]pyridine-5-carboxylate dihydrochloride (418 mg), pyridine (396 mg) and tetrahydrofuran (4.2 ml) was added dropwise ethyl chlorocarbonate (0.115 ml) under ice-cooling and the mixture was stirred at room temperature for 6 hr. The reaction mixture was partitioned between ethyl acetate and water. The organic layer was washed with saturated brine, dried over magnesium sulfate, and concentrated to dryness under reduced pressure. The residue was pulverized in diethyl ether to give methyl 3-(2-chloro-4-(N-ethoxycarbonyl-N-methylamino)benzyl)-2-methyl-3H-imidazo[4,5-b]pyridine-5-carboxylate (340 mg) as a white powder.

$^1$H-NMR (CDCl$_3$): 1.25 (3H, t, J=6 Hz), 2.56 (3H, s), 3.26 (3H, s), 4.00 (3H, s), 4.18 (2H, q, J=6 Hz), 5.65 (2H, s), 6.60 (1H, d, J=8 Hz), 7.02 (1H, dd, J=8, 2 Hz), 7.40 (1H, d, J=2 Hz), 8.07 (1H, d, J=8 Hz), 8.15 (1H, d, J=8 Hz). MS (ESI): m/z 417 (M+1).

PREPARATION EXAMPLE 40-2

In the same manner as in Preparation Example 14-7, 3-(2-chloro-4-(N-ethoxycarbonyl-N-methylamino)benzyl)-2-methyl-3H-imidazo[4,5-b]pyridine-5-carboxylic acid (287 mg) was obtained as a white powder from methyl 3-(2-chloro-4-(N-ethoxycarbonyl-N-methylamino)benzyl)-2-methyl-3H-imidazo[4,5-b]pyridine-5-carboxylate (335 mg).

$^1$H-NMR (CDCl$_3$): 1.26 (3H, t, J=6 Hz), 2.65 (3H, s), 3.26 (3H, s), 4.19 (2H, q, J=6 Hz), 5.57 (2H, s), 6.60 (1H, d, J=8 Hz), 7.08 (1H, dd, J=8, 2 Hz), 7.45 (1H, d, J=2 Hz), 8.18 (1H, d, J=8 Hz), 8.24 (1H, d, J=8 Hz).

PREPARATION EXAMPLE 41-1

In the same manner as in Example 117 to be mentioned later, methyl 3-(2-chloro-4-(3-(n-propyl)ureido)benzyl)-2-methyl-3H-imidazo[4,5-b]pyridine-5-carboxylate was obtained as a yellow solid (220 mg) from methyl 3-(4-amino-2-chlorobenzyl)-2-methyl-3H-imidazo[4,5-b]pyridine-5-carboxylate (300 mg) and n-propyl isocyanate (93 mg).

$^1$H-NMR (CDCl$_3$): 0.86 (3H, t, J=7 Hz), 1.42–1.58 (2H, m), 2.49 (3H, s), 3.15–3.25 (2H, m), 3.97 (3H, s), 5.49 (2H, s), 5.92 (1H, d, J=8 Hz), 6.84 (1H, dd, J=1, 8 Hz), 7.32 (1H, d, J=1 Hz), 8.11 (1H, d, J=8 Hz), 8.17 (1H, d, J=8 Hz). MS (ESI): m/z 416 (M+1).

PREPARATION EXAMPLE 41-2

In the same manner as in Preparation Example 14-7, 3-(2-chloro-4-(3-(n-propyl)ureido)benzyl)-2-methyl-3H-imidazo[4,5-b]pyridine-5-carboxylic acid was obtained as yellow crystals (136 mg) from methyl 3-(2-chloro-4-(3-(n-propyl)ureido)benzyl)-2-methyl-3H-imidazo[4,5-b]pyridine-5-carboxylate (215 mg).

$^1$H-NMR (DMSO-d$_6$): 0.85 (3H, t, J=7 Hz), 1.35–1.50 (2H, m), 2.50 (3H, overlapped with DMSO-d$_6$), 2.96–3.07 (2H, m), 5.53 (2H, s), 6.50 (1H, d, J=8 Hz), 7.00 (1H, dd, J=1, 8 Hz), 7.85 (1H, d, J=1 Hz), 8.00 (1H, d, J=8 Hz), 8.12 (1H, d, J=8 Hz). MS (ESI): m/z 400 (M−1).

PREPARATION EXAMPLE 42-1

Methyl 3-(4-amino-2-chlorobenzyl)-2-methyl-3H-imidazo[4,5-b]pyridine-5-carboxylate (450 mg) was suspended in N,N-dimethylformamide (5 ml) and 1-(3-(dimethylamino)propyl)-3-ethylcarbodiimide hydrochloride (391 mg), 1-hydroxybenzotriazole (276 mg) and 4-bromobutanoic acid (318 mg) were added, which was followed by stirring at room temperature for 24 hr. Water (50 ml) was added to the reaction mixture under ice-cooling and the precipitated crystals were collected by filtration and dried under reduced pressure with heating to give methyl 3-(4-((4-bromobutyryl)amino)-2-chlorobenzyl)-2-methyl-3H-imidazo[4,5-b]pyridine-5-carboxylate (436 mg) as pale-yellow crystals.

$^1$H-NMR (CDCl$_3$-CD$_3$OD): 2.10–2.20 (2H, m), 2.53 (2H, t, J=7 Hz), 3.63 (2H, t, J=7 Hz), 4.00 (3H, s), 5.62 (2H, s), 6.51 (1H, d, J=8 Hz), 7.18 (1H, dd, J=8, 2 Hz), 7.87 (1H, d, J=2 Hz), 8.06 (1H, d, J=8 Hz), 8.15 (1H, d, J=8 Hz).

PREPARATION EXAMPLE 42-2

Methyl 3-(4-((4-bromobutyryl)amino)-2-chlorobenzyl)-2-methyl-3H-imidazo[4,5-b]pyridine-5-carboxylate (425 mg) was dissolved in N,N-dimethylformamide (5 ml) and potassium carbonate (245 mg) was added, which was followed by stirring at 60° C. for 2 hr. Water was added to the reaction mixture under ice-cooling and the mixture was extracted with ethyl acetate. The organic layer was washed successively with water, saturated aqueous sodium hydrogen carbonate solution and saturated brine, dried over anhydrous magnesium sulfate, and concentrated under reduced pressure. Ethanol (10 ml) was added to the residue, and the mixture was heated and allowed to cool. The precipitated crystals were collected by filtration and dried under reduced pressure with heating to give methyl 3-(2-chloro-4-(2-oxotetrahydro-1H-pyrrol-1-yl)benzyl)-2-methyl-3H-imidazo[4,5-b]pyridine-5-carboxylate (235 mg) as pale-yellow crystals.

$^1$H-NMR (CDCl$_3$): 2.11–2.22 (2H, m), 2.54 (3H, s), 2.61 (2H, t, J=7 Hz), 3.80 (2H, t, J=7 Hz), 4.00 (3H, s), 5.66 (2H, s), 6.67 (1H, d, J=8 Hz), 7.31 (1H, dd, J=8, 2 Hz), 7.88 (1H, d, J=2 Hz), 8.06 (1H, d, J=8 Hz), 8.14 (1H, d, J=8 Hz).

PREPARATION EXAMPLE 42-3

In the same manner as in Preparation Example 14-7, 3-(2-chloro-4-(2-oxotetrahydro-1H-pyrrol-1-yl)benzyl)-2-methyl-3H-imidazo[4,5-b]pyridine-5-carboxylic acid (194 mg) was obtained as pale-yellow crystals from methyl 3-(2-chloro-4-(2-oxotetrahydro-1H-pyrrol-1-yl)benzyl)-2-methyl-3H-imidazo[4,5-b]pyridine-5-carboxylate (215 mg).

$^1$H-NMR (DMSO-d$_6$): 1.98–2.09 (2H, m), 2.47–2.52 (5H, m), 3.78 (2H, t, J=7 Hz), 5.60 (2H, s), 6.64 (1H, d, J=8 Hz), 7.40 (1H, dd, J=8, 2 Hz), 7.98–8.02 (2H, m), 8.13 (1H, d, J=8 Hz).

PREPARATION EXAMPLE 43-1

In the same manner as in Example 65, methyl 3-(2-chloro-4-((2-chloroethoxycarbonyl)amino)benzyl)-2-methyl-3H-imidazo[4,5-b]pyridine-5-carboxylate (471 mg) was obtained as yellow crystals from methyl 3-(4-amino-2-chlorobenzyl)-2-methyl-3H-imidazo[4,5-b]pyridine-5-carboxylate (450 mg) and 2-chloroethyl chlorocarbonate (253 mg).

$^1$H-NMR (CDCl$_3$): 2.59 (3H, s), 3.70 (2H, t, J=7 Hz), 3.98 (3H, s), 4.41 (2H, t, J=7 Hz), 5.60 (2H, s), 6.48 (1H, d, J=8 Hz), 7.01 (1H, dd, J=8, 2 Hz), 7.64 (1H, d, J=2 Hz), 8.11 (1H, d, J=8 Hz), 8.18 (1H, d, J=8 Hz).

PREPARATION EXAMPLE 43-2

Methyl 3-(2-chloro-4-((2-chloroethoxycarbonyl)amino)-benzyl)-2-methyl-3H-imidazo[4,5-b]pyridine-5-carboxylate (240 mg) was dissolved in methanol (3 ml) and a 28% solution (159 mg) of sodium methylate in methanol was added at room temperature, which was followed by stirring at 60° C. for 2 hr. The reaction mixture was neutralized with 1N hydrochloric acid under ice-cooling. A saturated aqueous sodium hydrogen carbonate solution was added and the mixture was extracted with chloroform. The organic layer was washed with saturated brine, dried over anhydrous magnesium sulfate, and concentrated under reduced pressure. Ethyl acetate (5 ml) was added to the residue and the mixture was heated and allowed to cool. The precipitated crystals were collected by filtration and dried under reduced pressure with heating to give methyl 3-(2-chloro-4-(2-oxo-1,3-oxazolidin-3-yl)benzyl)-2-methyl-3H-imidazo[4,5-b]pyridine-5-carboxylate (121 mg) as yellow crystals.

$^1$H-NMR (CDCl$_3$): 2.54 (3H, s), 3.98–4.03 (5H, m), 4.49 (2H, t, J=7 Hz), 5.66 (2H, s), 6.71 (1H, d, J=8 Hz), 7.21 (1H, dd, J=8, 2 Hz), 7.80 (1H, d, J=2 Hz), 8.06 (1H, d, J=8 Hz), 8.14 (1H, d, J=8 Hz).

PREPARATION EXAMPLE 43-3

In the same manner as in Preparation Example 14-7, a mixture of 3-(2-chloro-4-(2-oxo-1,3-oxazolidin-3-yl) benzyl)-2-methyl-3H-imidazo[4,5-b]pyridine-5-carboxylic acid and methyl 3-(2-chloro-4-((2-hydroxyethyl)amino) benzyl)-2-methyl-3H-imidazo-[4,5-b]pyridine-5-carboxylate was obtained as a pale-yellow powder from methyl 3-(2-chloro-4-(2-oxo-1,3-oxazolidin-3-yl)-benzyl)-2-methyl-3H-imidazo[4,5-b]pyridine-5-carboxylate (277 mg).

PREPARATION EXAMPLE 44-1

Fuming nitric acid (26 ml) was cooled to −35° C. and stirred. Methyl 4-acetamido-2-chlorobenzoate (6.5 g) was added at from −35° C. to −25° C., and the mixture was stirred for 3 hr. The reaction mixture was ice-cooled and H$_2$O (260 ml) was poured therein, which was followed by stirring. The resulting crystals were collected by filtration, washed with water and dried with air. This was applied to flash silica gel column chromatography (silica gel 100 g) to give methyl 4-acetamido-2-chloro-5-nitrobenzoate as thin yellow crystals (5.32 g) and methyl 4-acetamido-2-chloro-3-nitrobenzoate as a yellow solid (ca. 1.7 g, 22% yield). Methyl 4-Acetamido-2-chloro-5-nitrobenzoate $^1$H-NMR (CDCl$_3$): 2.34 (3H, s), 3.96 (3H, s), 8.83 (1H, s), 9.06 (1H, s). MS (ESI): m/z 271 (M−1).

Methyl 4-Acetamido-2-chloro-3-nitrobenzoate $^1$H-NMR (CDCl$_3$): 2.23 (3H, s), 3.96 (3H, s), 7.99 (1H, d, J=8 Hz), 8.36 (1H, d, J=8 Hz). MS (ESI): m/z 271 (M−1).

PREPARATION EXAMPLE 44-2

In the same manner as in Preparation Example 16-5, methyl 4-(N-acetyl-N-methylamino)-2-chloro-3-nitrobenzoate was obtained as pale-yellow crystals (1.41 g) from methyl 4-(N-acetylamino)-2-chloro-3-nitrobenzoate (1.67 g).

$^1$H-NMR (CDCl$_3$): 1.88 (3H, s), 3.17 (3H, s), 4.00 (3H, s), 7.35 (1H, d, J=8 Hz), 8.05 (1H, d, J=8 Hz).

PREPARATION EXAMPLE 44-3

In the same manner as in Preparation Example 4-6, methyl 4-chloro-1,2-dimethyl-1H-benzimidazole-5-carboxylate was obtained as a colorless solid (1.09 g) from methyl 4-(N-acetyl-N-methylamino)-2-chloro-3-nitrobenzoate (1.39 g).

$^1$H-NMR (CDCl$_3$): 2.67 (3H, s), 3.76 (3H, s), 3.96 (3H, s), 7.20 (1H, d, J=8 Hz), 7.83 (1H, d, J=8 Hz). MASS (ESI): m/z 239 (M+1).

PREPARATION EXAMPLE 44-4

To a solution of methyl 4-chloro-1,2-dimethyl-1H-benzimidazole-5-carboxylate (1.07 g) in anhydrous tetrahydrofuran (11 ml) was added portionwise lithium borohydride (198 mg) at room temperature and the mixture was stirred for 2 hr and heated to 60° C. Thereafter, lithium borohydride (99 mg) was added 3 times at 1 hr intervals. The reaction mixture was ice-cooled and adjusted to pH 2 with 1N hydrochloric acid. The mixture was stirred at room temperature for 30 min, and chloroform was added to the mixture. The precipitated crystals were collected by filtration to give 4-chloro-5-hydroxymethyl-1,2-dimethyl-1H-benzimidazole as colorless crystals (487 mg). The filtrate was extracted 6 times with chloroform:methanol=5:1. The organic layer was dried over anhydrous magnesium sulfate, filtrated and concentrated. The residue was crystallized from isopropyl ether to give the objective product as colorless crystals (417 mg).

$^1$H-NMR (DMSO-$d_6$): 2.54 (3H, s), 3.73 (3H, s), 4.66 (2H, d, J=5 Hz), 5.26 (1H, d, J=5 Hz), 7.35 (1H, d, J=8 Hz), 7.44 (1H, d, J=8 Hz). MASS (ESI): m/z 211 (M+1).

PREPARATION EXAMPLE 44-5

In the same manner as in Preparation Example 19-1, 4-chloro-5-chloromethyl-1,2-dimethyl-1H-benzimidazole was obtained as a pale-yellow solid (1.20 g) from 4-chloro-5-hydroxymethyl-1,2-dimethyl-1H-benzimidazole (885 mg).

$^1$H-NMR (CDCl$_3$): 2.75 (3H, s), 3.78 (3H, s), 4.87 (2H, s), 7.24 (1H, d, J=8 Hz), 7.39 (1H, d, J=8 Hz). MASS (ESI): m/z 229 (M+1).

PREPARATION EXAMPLE 44-6

In the same manner as in Preparation Example 18-4, methyl 3-[(4-chloro-1,2-dimethyl-1H-benzimidazol-5-yl)methyl]-2-methyl-3H-imidazo[4,5-b]pyridine-5-carboxylate was obtained as a colorless solid (465 mg), and methyl 1-[(4-chloro-1,2-dimethyl-1H-benzimidazol-5-yl)methyl]-2-methyl-3H-imidazo[4,5-b]pyridine-5-carboxylate as a colorless solid (510 mg), from methyl 2-methyl-3H-imidazo[4,5-b]pyridine-5-carboxylate (720 mg) and 4-chloro-5-chloromethyl-1,2-dimethyl-1H-benzimidazole (949 mg). methyl 3-[(4-chloro-1,2-dimethyl-1H-benzimidazol-5-yl)methyl]-2-methyl-3H-imidazo[4,5-b]pyridine-5-carboxylate:

$^1$H-NMR (CDCl$_3$): 2.51 (3H, s), 2.66 (3H, s), 3.70 (3H, s), 4.01 (3H, s), 5.85 (2H, s), 6.70 (1H, d, J=8 Hz), 7.04 (1H, d, J=8 Hz), 8.05 (1H, d, J=8 Hz), 8.15 (1H, d, J=8 Hz). MASS (ESI): m/z 384 (M+1). Methyl 1-[(4-Chloro-1,2-dimethyl-1H-benzimidazol-5-yl)methyl]-2-methyl-3H-imidazo[4,5-b]pyridine-5-carboxylate:

$^1$H-NMR (CDCl$_3$): 2.67 (3H, s), 2.69 (3H, s), 3.72 (3H, s), 4.02 (3H, s), 5.60 (2H, s), 6.46 (1H, d, J=8 Hz), 7.05 (1H, d, J=8 Hz), 7.55 (1H, d, J=8 Hz), 8.04 (1H, d, J=8 Hz). MASS (ESI): m/z 384 (M+1).

PREPARATION EXAMPLE 44-7

In the same manner as in Preparation Example 14-7, 3-[(4-chloro-1,2-dimethyl-1H-benzimidazol-5-yl)methyl]-2-methyl-3H-imidazo[4,5-b]pyridine-5-carboxylic acid was obtained as colorless crystals (370 mg) from methyl 3-[(4-chloro-1,2-dimethyl-1H-benzimidazol-5-yl)methyl]-2-methyl-3H-imidazo[4,5-b]pyridine-5-carboxylate (450 mg).

$^1$H-NMR (DMSO-$d_6$): 2.48 (3H, s), 2.59 (3H, s), 3.72 (3H, s), 5.75 (2H, s), 6.60 (1H, d, J=8 Hz), 7.40 (1H, d, J=8 Hz), 8.01 (1H, d, J=8 Hz), 8.14 (1H, d, J=8 Hz). MASS (ESI): m/z 368 (M−1).

PREPARATION EXAMPLE 45-1

In the same manner as in Preparation Example 16-5, methyl 4-(N-acetyl-N-methylamino)-2-chloro-5-nitrobenzoate was obtained as pale-yellow crystals (1.19 g) from methyl 4-acetamido-2-chloro-5-nitrobenzoate (1.5 g).

$^1$H-NMR (CDCl$_3$): 1.87 (3/2H, s), 2.26 (3/2H, s), 3.22 (3/2H, s), 3.46 (3/2H, s), 3.98 (3/2H, s), 4.01 (3/2H, s), 7.43 (1/2H, s), 7.53 (1/2H, s), 8.51 (1/2H, s), 8.56 (1/2H, s). MS (ESI): m/z 287 (M+1).

PREPARATION EXAMPLE 45-2

In the same manner as in Preparation Example 4-6, methyl 6-chloro-1,2-dimethyl-1H-benzimidazole-5-carboxylate was obtained as colorless crystals (380 mg) from methyl 4-(N-acetyl-N-methylamino)-2-chloro-5-nitrobenzoate (489 mg).

$^1$H-NMR (CDCl$_3$): 2.62 (3H, s), 3.72 (3H, s), 3.95 (3H, s), 7.36 (1H, s), 8.18 (1H, s). MASS (ESI): m/z 239 (M+1).

PREPARATION EXAMPLE 45-3

In the same manner as in Preparation Example 23-1, 6-chloro-5-hydroxymethyl-1,2-dimethyl-1H-benzimidazole was obtained as colorless crystals (150 mg) from methyl 6-chloro-1,2-dimethyl-1H-benzimidazole-5-carboxylate (370 mg).

$^1$H-NMR (CDCl$_3$): 2.60 (3H, s), 3.70 (3H, s), 4.85 (2H, s), 7.30 (1H, s), 7.75 (1H, s). MASS (ESI): m/z 211 (M+1).

PREPARATION EXAMPLE 45-4

In the same manner as in Preparation Example 19-1, 6-chloro-5-chloromethyl-1,2-dimethyl-1H-benzimidazole was obtained as a yellow oil (150 mg) from 6-chloro-5-hydroxymethyl-1,2-dimethyl-1H-benzimidazole (140 mg).

$^1$H-NMR (CDCl$_3$): 2.66 (3H, s), 3.74 (3H, s), 4.83 (2H, s), 7.38 (1H, s), 7.79 (1H, s). MASS (ESI): m/z 229 (M+1).

PREPARATION EXAMPLE 45-5

In the same manner as in Preparation Example 18-4, methyl 3-((6-chloro-1,2-dimethyl-1H-benzimidazol-5-yl)methyl)-2-methyl-3H-imidazo[4,5-b]pyridine-5-carboxylate was obtained as pale-yellow crystals (135 mg), and methyl 1-((6-chloro-1,2-dimethyl-1H-benzimidazol-5-yl)methyl)-2-methyl-1H-imidazo[4,5-b]pyridine-5-carboxylate as a yellow oil, from methyl 2-methyl-3H-imidazo[4,5-b]pyridine-5-carboxylate (110 mg) and 6-chloro-5-chloromethyl-1,2-dimethyl-1H-benzimidazole (138 mg). methyl 3-((6-chloro-1,2-dimethyl-1H-benzimidazol-5-yl)methyl)-2-methyl-3H-imidazo[4,5-b]pyridine-5-carboxylate $^1$H-NMR (CDCl$_3$): 2.51 (3H, s), 2.52 (3H, s), 3.69 (3H, s), 3.97 (3H, s), 5.76 (2H, s), 6.85 (1H, s), 7.37 (1H, s), 8.07 (1H, d, J=8 Hz), 8.13 (1H, d, J=8 Hz). MS (ESI): m/z 384 (M+1).

PREPARATION EXAMPLE 45-6

In the same manner as in Preparation Example 14-7, 3-((6-chloro-1,2-dimethyl-1H-benzimidazol-5-yl)methyl)-2-methyl-3-imidazo[4,5-b]pyridine-5-carboxylic acid was obtained as pale-yellow crystals (70 mg) from methyl 3-((6-chloro-1,2-dimethyl-1H-benzimidazol-5-yl)methyl)-2-methyl-1H-imidazo[4,5-b]pyridine-5-carboxylate (85 mg).

$^1$H-NMR (DMSO-$d_6$): 2.56 (3H, s), 2.73 (3H, s), 3.90 (3H, s), 5.76 (2H, s), 6.95 (1H, s), 8.05 (1H, d, J=8 Hz), 8.20 (1H, d, J=8 Hz), 8.32 (1H, s). MS (ESI): m/z 370 (M+1).

PREPARATION EXAMPLE 46-1

In the same manner as in Preparation Example 49-1 to be mentioned later, ethyl 3,5-dichloropyridine-2-carboxylate was obtained as a pale-yellow oil (13.4 g) from 2,3,5-trichloropyridine (20 g).

$^1$H-NMR (CDCl$_3$): 1.44 (1H, t, J=7 Hz), 4.48 (2H, d, J=7 Hz), 7.84 (1H, d, J=1 Hz), 8.54 (1H, d, J=1 Hz).

PREPARATION EXAMPLE 46-2

In the same manner as in Preparation Example 31-2, 3,5-dichloro-2-(hydroxymethyl)pyridine was obtained as a colorless solid (1.43 g) from ethyl 3,5-dichloropyridine-2-carboxylate (2.0 g).

$^1$H-NMR (CDCl$_3$): 3.97 (1H, t, J=5 Hz), 4.78 (2H, d, J=5 Hz), 7.73 (1H, d, J=1 Hz), 8.47 (1H, d, J=1 Hz).

PREPARATION EXAMPLE 46-3

In the same manner as in Preparation Example 19-1, 3,5-dichloro-2-(methanesulfonyloxymethyl)pyridine was obtained as a pale-yellow solid (1.01 g) from 3,5-dichloro-2-(hydroxymethyl)pyridine (700 mg).

$^1$H-NMR (CDCl$_3$): 3.13 (3H, s), 5.44 (2H, s), 7.79 (1H, d, J=1 Hz), 8.51 (1H, d, J=1 Hz).

PREPARATION EXAMPLE 46-4

In the same manner as in Preparation Example 18-4, methyl 3-[(3,5-dichloropyridin-2-yl)methyl]-2-methyl-3H-imidazo[4,5-b]pyridine-5-carboxylate was obtained as pale-yellow crystals (476 mg), and methyl 1-[(3,5-dichloropyridin-2-yl)methyl]-2-methyl-3H-imidazo[4,5-b]pyridine-5-carboxylate as brown amorphous (193 mg), from methyl 2-methyl-3H-imidazo[4,5-b]pyridine-5-carboxylate (586 mg) and 3,5-dichloro-2-(methanesulfonyloxymethyl)pyridine (1.01 g).
Methyl 3-[(3,5-Dichloropyridin-2-yl)methyl]-2-methyl-3H-imidazo[4,5-b]pyridine-5-carboxylate:

$^1$H-NMR (CDCl$_3$): 2.54 (3H, s), 3.97 (3H, s), 5.74 (2H, s), 7.77 (1H, br s), 8.04 (1H, d, J=8 Hz), 8.11 (1H, d, J=8 Hz), 8.21 (1H, d, J=1 Hz). MASS (ESI): m/z 351 (M+1).
Methyl 1-[(3,5-Dichloropyridin-2-yl)methyl]-2-methyl-3H-imidazo[4,5-b]pyridine-5-carboxylate:

$^1$H-NMR (CDCl$_3$): 2.71 (3H, s), 4.00 (3H, s), 5.51 (2H, s), 7.64 (1H, d, J=8 Hz), 7.79 (1H, br s), 8.06 (1H, d, J=8 Hz), 8.31 (1H, br s). MASS (ESI): m/z 351 (M+1).

PREPARATION EXAMPLE 46-5

In the same manner as in Preparation Example 14-7, 3-[(3,5-dichloropyridin-2-yl)methyl]-2-methyl-3H-imidazo[4,5-b]pyridine-5-carboxylic acid was obtained as pale-brown crystals (346 mg) from methyl 3-[(3,5-dichloropyridin-2-yl)methyl]-2-methyl-3H-imidazo[4,5-b]pyridine-5-carboxylate (460 mg).

$^1$H-NMR (DMSO-d$_6$): 2.50 (3H, s), 5.78 (2H, s), 7.96 (1H, d, J=8 Hz), 8.09 (1H, d, J=8 Hz), 8.35–8.40 (2H, m). MASS (ESI): m/z 335 (M−1).

PREPARATION EXAMPLE 47-1

In the same manner as in Preparation Example 18-4, methyl 3-((3,5-dichloropyridin-2-yl)methyl)-2,7-dimethyl-3H-imidazo[4,5-b]pyridine-5-carboxylate (237 mg) was obtained as a white powder from methyl 2,7-dimethylimidazo[4,5-b]pyridine-5-carboxylate (150 mg) and 3,5-dichloro-2-(methanesulfonyloxymethyl)pyridine (225 mg).

$^1$H-NMR (CDCl$_3$): 2.54 (3H, s), 2.73 (3H, s), 3.96 (3H, s), 5.73 (2H, s), 7.75 (1H, d, J=1 Hz), 7.94 (1H, d, J=1 Hz), 8.21 (1H, d, J=1 Hz).

PREPARATION EXAMPLE 47-2

In the same manner as in Preparation Example 14-7, 3-((3,5-dichloropyridin-2-yl)methyl)-2,7-dimethyl-3H-imidazo[4,5-b]pyridine-5-carboxylic acid (207 mg) was obtained as a white powder from methyl 3-((3,5-dichloropyridin-2-yl)methyl)-2,7-dimethyl-3H-imidazo[4,5-b]pyridine-5-carboxylate (234 mg).

$^1$H-NMR (CDCl$_3$): 2.68 (3H, s), 2.75 (3H, s), 5.64 (2H, s), 7.80 (1H, d, J=1 Hz), 8.00 (1H, s), 8.26 (1H, d, J=1 Hz). MS (ESI): m/z 352 (M+1).

PREPARATION EXAMPLE 48-1

Ethyl 6-amino-5-nitronicotinate (9.2 g) was obtained as yellow crystals from 6-amino-5-nitronicotinic acid (18.2 g).

$^1$H-NMR (CDCl$_3$): 1.41 (3H, t, J=7 Hz), 4.40 (2H, q, J=7 Hz), 8.95 (1H, d, J=2 Hz), 9.01 (1H, s). MASS (ESI): m/z 210 (M−1).

PREPARATION EXAMPLE 48-2

In the same manner as in Preparation Example 31-2, 2-chloro-3-(hydroxymethyl)-6-phenylpyridine was obtained as a colorless solid (2.22 g) from methyl 2-chloro-6-phenylnicotinate (2.5 g).

$^1$H-NMR (CDCl$_3$): 2.04 (1H, t, J=5 Hz), 4.83 (2H, d, J=5 Hz), 7.39–7.53 (3H, m), 7.71 (1H, d, J=8 Hz), 7.92 (1H, d, J=8 Hz), 7.96–8.04 (2H, m).

PREPARATION EXAMPLE 48-3

In the same manner as in Preparation Example 19-1, 2-chloro-3-(methanesulfonyloxymethyl)-6-phenylpyridine was obtained as a colorless solid (1.10 g) from 2-chloro-3-(hydroxymethyl)-6-phenylpyridine (879 mg).

$^1$H-NMR (CDCl$_3$): 3.11 (3H, s), 5.37 (2H, s), 7.41–7.54 (3H, m), 7.74 (1H, d, J=8 Hz), 7.90 (1H, d, J=8 Hz), 7.97–8.05 (2H, m).

PREPARATION EXAMPLE 48-4

In the same manner as in Preparation Example 18-4, methyl 3-[(2-chloro-6-phenylpyridin-2-yl)methyl]-2-methyl-3H-imidazo[4,5-b]pyridine-5-carboxylate was obtained as colorless crystals (603 mg), and methyl 1-[(2-chloro-6-phenylpyridin-2-yl)methyl]-2-methyl-1H-imidazo[4,5-b]pyridine-5-carboxylate as pale-yellow crystals (400 mg), from methyl 2-methyl-3H-imidazo[4,5-b]pyridine-5-carboxylate (700 mg) and 2-chloro-3-(methanesulfonyloxymethyl)-6-phenylpyridine (1.20 g).
Methyl 3-[(2-Chloro-6-phenylpyridin-2-yl)methyl]-2-methyl-3H-imidazo[4,5-b]pyridine-5-carboxylate:

$^1$H-NMR (CDCl$_3$): 2.63 (3H, s), 4.00 (3H, s), 5.71 (2H, s), 7.15 (1H, d, J=8 Hz), 7.39–7.52 (3H, m), 7.54 (1H, d, J=8 Hz), 7.91–8.00 (2H, m), 8.09 (1H, d, J=8 Hz), 8.16 (1H, d, J=8 Hz). MASS (ESI): m/z 393 (M+1).
Methyl 1-[(2-Chloro-6-phenylpyridin-2-yl)methyl]-2-methyl-1H-imidazo[4,5-b]pyridine-5-carboxylate:

$^1$H-NMR (CDCl$_3$): 2.69 (3H, s), 4.03 (3H, s), 5.48 (2H, s), 6.82 (1H, d, J=8 Hz), 7.41–7.52 (3H, m), 7.54 (1H, d, J=8 Hz), 7.60 (1H, d, J=8 Hz), 7.94–8.00 (2H, m), 8.11 (1H, d, J=8 Hz). MASS (ESI): m/z 393 (M+1).

PREPARATION EXAMPLE 48-5

In the same manner as in Preparation Example 14-7, 3-[(2-chloro-6-phenylpyridin-2-yl)methyl]-2-methyl-3H-imidazo[4,5-b]pyridine-5-carboxylic acid was obtained as colorless crystals (523 mg) from methyl 3-[(2-chloro-6- phenylpyridin-2-yl)methyl]-2-methyl-3H-imidazo[4,5-b]pyridine-5-carboxylate (580 mg).

$^1$H-NMR (DMSO-d$_6$): 2.59 (3H, s), 5.66 (2H, s), 7.17 (1H, d, J=8 Hz), 7.43–7.54 (3H, m), 7.87 (1H, d, J=8 Hz), 7.97–8.05 (2H, m), 8.15 (1H, d, J=8 Hz). MASS (ESI): m/z 377 (M−1).

PREPARATION EXAMPLE 49-1

To a suspension of 5,6-dichloronicotinic acid (5.1 g) in tert-butyl alcohol (50 ml) were added triethylamine (2.7 g) and phosphorus diphenylazide (7.3 g) in a nitrogen atmosphere and the mixture was heated to 80° C. After 8 hr, the reaction mixture was cooled and water and ethyl acetate were added. The mixture was washed 3 times with water, saturated aqueous sodium hydrogen carbonate solution and saturated brine. The organic layer was dried over anhydrous magnesium sulfate, and the filtrate was concentrated. The residue was applied to flash silica gel chromatography (silica gel, 30 ml) and eluted with hexane:ethyl acetate=5:1–2:1 to give 3-(N-(tert-butoxycarbonyl)amino)-5,6-dichloropyridine as a colorless solid (6.49 g).

$^1$H-NMR (CDCl$_3$): 1.53 (9H, s), 6.58 (1H, br s), 8.10 (1H, d, J=1 Hz), 8.25 (1H, br s). MASS (ESI): m/z 263 (M+1).

PREPARATION EXAMPLE 49-2

To a solution of 3-(N-(tert-butoxycarbonyl)amino)-5,6-dichloropyridine (2.7 g) in anhydrous ethanol (50 ml) were added anhydrous triethylamine (7.38 g), palladium acetate (1.75 g) and 1,3-bis(diphenylphosphino)propane (3.21 g). The inside of the reaction vessel was substituted for 1 atm. carbon monoxide and the mixture was stirred at 60° C. After 10 hr, ethyl acetate (250 ml) was added to the reaction mixture, and an insoluble matter was filtered off. The filtrate was concentrated and the residue was applied to flash silica gel column chromatography (silica gel, 500 ml) and eluted with hexane:ethyl acetate=10:1–5:1–3:1–2:1 to give ethyl 5-(N-(tert-butoxycarbonyl)amino)-3-chloropyridine-2-carboxylate as a colorless solid (5.85 g).

$^1$H-NMR (CDCl$_3$): 1.43 (3H, t, J=7 Hz), 1.53 (9H, s), 4.46 (2H, q, J=7 Hz), 6.75 (1H, br s), 8.27–8.35 (2H, m). MASS (ESI): m/z 301 (M+1).

PREPARATION EXAMPLE 49-3

In the same manner as in Preparation Example 31-2, 5-(N-(tert-butoxycarbonyl)amino)-3-chloro-2-hydroxymethylpyridine was obtained as a colorless gum (4.65 g) from ethyl 5-(N-(tert-butoxycarbonyl)amino)-3-chloropyridine-2-carboxylate (5.84 g).

$^1$H-NMR (CDCl$_3$): 1.53 (9H, s), 4.04 (1H, t, J=5 Hz), 4.74 (2H, d, J=5 Hz), 6.59 (1H, br s), 8.14 (1H, br s), 8.27 (1H, d, J=1 Hz). MASS (ESI): m/z 259 (M+1).

PREPARATION EXAMPLE 49-4

In the same manner as in Preparation Example 19-1, 5-(N-(tert-butoxycarbonyl)amino)-3-chloro-2-(methanesulfonyloxymethyl)pyridine was obtained as a purple gum (5.7 g) from 5-(N-(tert-butoxycarbonyl)amino)-3-chloro-2-hydroxymethylpyridine (4.63 g).

$^1$H-NMR (CDCl$_3$) 1.53 (9H, s), 3.08 (3H, s), 5.41 (2H, s), 6.77 (1H, br s), 8.24 (1H, br d, J=1 Hz), 8.30 (1H, d, J=1 Hz).

PREPARATION EXAMPLE 49-5

In the same manner as in Preparation Example 18-4, methyl 3-[(5-(N-(tert-butoxycarbonyl)amino)-3-chloropyridin-2-yl)methyl]-2-methyl-3H-imidazo[4,5-b]pyridine-5-carboxylate was obtained as a pale-brown solid (1.45 g), and methyl 1-[(5-(N-(tert-butoxycarbonyl)amino)-3-chloropyridin-2-yl)methyl]-2-methyl-1H-imidazo[4,5-b]pyridine-5-carboxylate as pale-yellow crystals (400 mg), from methyl 2-methyl-3H-imidazo[4,5-b]pyridine-5-carboxylate (3.2 g) and 5-(N-(tert-butoxycarbonyl)amino)-3-chloro-2-(methanesulfonyloxymethyl)pyridine (5.04 g).

Methyl 3-[(5-(N-(tert-Butoxycarbonyl)amino)-3-chloropyridin-2-yl)methyl]-2-methyl-3H-imidazo[4,5-b]pyridine-5-carboxylate:

$^1$H-NMR (CDCl$_3$): 1.51 (9H, s), 2.48 (3H, s), 3.95 (3H, s), 5.66 (2H, s), 7.52 (1H, br s), 7.74 (1H, d, J=2 Hz), 8.03 (1H, d, J=8 Hz), 8.10 (1H, d, J=8 Hz), 8.24 (1H, br s). MASS (ESI): m/z 432 (M+1).

Methyl 1-[(5-(N-(tert-Butoxycarbonyl)amino)-3-chloropyridin-2-yl)methyl]-2-methyl-1H-imidazo[4,5-b]pyridine-5-carboxylate:

$^1$H-NMR (CDCl$_3$): 1.50 (9H, s), 2.72 (3H, s), 3.99 (3H, s), 5.48 (2H, s), 7.01 (1H, br s), 7.67 (1H, d, J=8 Hz), 8.03 (1H, d, J=8 Hz), 8.09 (1H, d, J=1 Hz), 8.29 (1H, br s). MASS (ESI): m/z 432 (M+1).

PREPARATION EXAMPLE 49-6

In the same manner as in Preparation Example 14-7, 3-[(5-(N-(tert-butoxycarbonyl)amino)-3-chloropyridin-2-yl)methyl]-2-methyl-3H-imidazo[4,5-b]pyridine-5-carboxylic acid was obtained as a colorless solid (384 mg) from methyl 3-[(5-(N-(tert-butoxycarbonyl)amino)-3-chloropyridin-2-yl)methyl]-2-methyl-3H-imidazo[4,5-b]pyridine-5-carboxylate (400 mg).

$^1$H-NMR (DMSO-d$_6$): 1.46 (9H, s), 2.48 (3H, s), 3.57 (3H, s), 5.70 (2H, s), 7.96 (1H, d, J=8 Hz), 8.08 (1H, d, J=8 Hz), 8.15 (1H, br s), 8.22 (1H, d, J=2 Hz), 9.82 (1H, br s). MASS (ESI): m/z 416 (M−1).

PREPARATION EXAMPLE 50-1

In the same manner as in Preparation Example 17-1, methyl 3-(5-amino-3-chloropyridin-2-yl)-2-methyl-3H-imidazo[4,5-b]pyridine-5-carboxylate trihydrochloride was obtained as pale-orange crystals (1.02 g) from methyl 3-((5-(N-(tert-butoxycarbonyl)amino)-3-chloropyridin-2-yl)methyl)-2-methyl-3H-imidazo[4,5-b]pyridine-5-carboxylate (1.04 g).

$^1$H-NMR (DMSO-d$_6$): 2.68 (3H, s), 3.89 (3H, s), 5.67 (2H, s), 7.13 (1H, d, J=1 Hz), 7.65 (1H, d, J=1 Hz), 8.13 (1H, d, J=8 Hz), 8.29 (1H, d, J=8 Hz). MS (ESI): m/z 332 (M+1).

PREPARATION EXAMPLE 50-2

In the same manner as in Example 65, methyl 3-((5-(N-(ethoxycarbonyl)amino)-3-chloropyridin-2-yl)methyl)-2-methyl-3H-imidazo[4,5-b]pyridine-5-carboxylate was obtained as pale-yellow crystals (326 mg) from methyl 3-((5-amino-3-chloropyridin-2-yl)methyl)-2-methyl-3H-imidazo[4,5-b]pyridine-5-carboxylate trihydrochloride (500 mg) and ethyl chlorocarbonate (245 mg).

$^1$H-NMR (CDCl$_3$): 1.32 (3H, t, J=7 Hz), 2.48 (3H, s), 3.94 (3H, s), 4.26 (2H, q, J=7 Hz), 5.64 (2H, s), 7.71 (1H, d, J=1 Hz), 8.03 (1H, d, J=8 Hz), 8.11 (1H, d, J=8 Hz), 8.23 (1H, s). MS (ESI): m/z 404 (M+1).

PREPARATION EXAMPLE 50-3

In the same manner as in Preparation Example 14-7, 3-((5-(N-(ethoxycarbonyl)amino)-3-chloropyridin-2-yl)methyl)-2-methyl-3H-imidazo[4,5-b]pyridine-5-carboxylic acid was obtained as pale-yellow crystals (240 mg) from methyl 3-((5-(N-(ethoxycarbonyl)amino)-3-chloropyridin-2-yl)methyl)-2-methyl-3H-imidazo[4,5-b]pyridine-5-carboxylate (326 mg).

$^1$H-NMR (DMSO-d$_6$): 1.23 (3H, t, J=7 Hz), 2.48 (3H, s), 4.14 (2H, q, J=7 Hz), 5.71 (2H, s), 7.97 (1H, d, J=8 Hz), 8.08 (1H, d, J=8 Hz), 8.14 (1H, s), 8.26 (1H, s). MS (ESI): m/z 390 (M+1).

PREPARATION EXAMPLE 51-1

In the same manner as in Example 65, methyl 3-((5-(N-(isopropoxycarbonyl)amino)-3-chloropyridin-2-yl)methyl)-2-methyl-3H-imidazo[4,5-b]pyridine-5-carboxylate was obtained as pale-yellow crystals (406 mg) from methyl 3-((5-amino-3-chloropyridin-2-yl)methyl)-2-methyl-3H-imidazo[4,5-b]pyridine-5-carboxylate trihydrochloride (500 mg) and isopropyl chlorocarbonate (277 mg).

$^1$H-NMR (CDCl$_3$): 1.30 (6H, d, J=7 Hz), 2.49 (3H, s), 3.94 (3H, s), 4.99–5.09 (1H, m), 5.66 (2H, s), 7.76 (1H, d, J=1 Hz), 8.03 (1H, d, J=8 Hz), 8.11 (1H, d, J=8 Hz), 8.23 (1H, s). MS (ESI): m/z 418 (M+1).

PREPARATION EXAMPLE 51-2

In the same manner as in Preparation Example 14-7, 3-((5-(N-(isopropoxycarbonyl)amino)-3-chloropyridin-2-yl)methyl)-2-methyl-3H-imidazo[4,5-b]pyridine-5-carboxylic acid was obtained as pale-yellow crystals (270 mg) from methyl 3-((5-(N-(isopropoxycarbonyl)amino)-3-chloropyridin-2-yl)methyl)-2-methyl-3H-imidazo[4,5-b]pyridine-5-carboxylate (397 mg).

$^1$H-NMR (DMSO-d$_6$): 1.24 (6H, d, J=7 Hz), 2.48 (3H, s), 4.81–4.95 (1H, m), 5.71 (2H, s), 7.97 (1H, d, J=8 Hz), 8.08 (1H, d, J=8 Hz), 8.14 (1H, s), 8.26 (1H, d, J=1 Hz). MS (ESI): m/z 404 (M+1).

PREPARATION EXAMPLE 52-1

In the same manner as in Preparation Example 31-2, 2,4-dichloro-5-hydroxymethylpyridine was obtained as colorless crystals (1.5 g) from ethyl 2,4-dichloropyridine-5-carboxylate (3 g).

$^1$H-NMR (CDCl$_3$): 4.82 (2H, d, J=5 Hz), 7.39 (1H, s), 8.48 (1H, s).

PREPARATION EXAMPLE 52-2

In the same manner as in Preparation Example 19-1, 5-chloromethyl-2,4-dichloropyridine was obtained as a yellow oil (725 mg) from 2,4-dichloro-5-hydroxymethylpyridine (660 mg).

$^1$H-NMR (CDCl$_3$): 4.66 (2H, s), 7.44 (1H, s), 8.44 (1H, s).

PREPARATION EXAMPLE 52-3

In the same manner as in Preparation Example 18-4, methyl 3-((2,4-dichloropyridin-5-yl)methyl)-2-methyl-1H-imidazo[4,5-b]pyridine-5-carboxylate was obtained as pale-yellow crystals (640 mg), and methyl 1-((2,4-dichloropyridin-5-yl)methyl)-2-methyl-1H-imidazo[4,5-b]pyridine-5-carboxylate as a yellow oil, from methyl 2-methyl-3H-imidazo[4,5-b]pyridine-5-carboxylate (650 mg) and 5-chloromethyl-2,4-dichloropyridine (723 mg).

Methyl 3-((2,4-Dichloropyridin-5-yl)methyl)-2-methyl-3H-imidazo[4,5-b]pyridine-5-carboxylate $^1$H-NMR (CDCl$_3$): 2.62 (3H, s), 4.00 (3H, s), 5.65 (2H, s), 7.45 (1H, s), 7.93 (1H, s), 8.07 (1H, d, J=8 Hz), 8.15 (1H, d, J=8 Hz). MS (ESI): m/z 351 (M+1).

PREPARATION EXAMPLE 52-4

In the same manner as in Preparation Example 14-7, 3-((2,4-dichloropyridin-5-yl)methyl)-2-methyl-3H-imidazo[4,5-b]pyridine-5-carboxylic acid was obtained as pale-yellow crystals (385 mg) from methyl 3-((2,4-dichloropyridin-5-yl)methyl)-2-methyl-3H-imidazo[4,5-b]pyridine-5-carboxylate (500 mg).

$^1$H-NMR (CDCl$_3$): 2.68 (3H, s), 5.59 (2H, s), 7.50 (1H, s), 7.84 (1H, s), 8.20 (1H, d, J=8 Hz), 8.25 (1H, d, J=8 Hz). MS (ESI): m/z 335 (M−1).

PREPARATION EXAMPLE 53-1

In the same manner as in Preparation Example 14-6, 2-chloro-4-(1-pentyloxy)toluene (16.3 g) was obtained as a pale-brown oil from 3-chloro-4-methylphenol (10.0 g).

$^1$H-NMR (CDCl$_3$): 0.93 (3H, t, J=6 Hz), 1.40 (4H, m), 1.76 (2H, m), 2.29 (3H, s), 3.90 (2H, t, J=6 Hz), 6.70 (1H, dd, J=8, 2 Hz), 6.90 (1H, d, J=2 Hz), 7.10 (1H, d, J=8 Hz).

PREPARATION EXAMPLE 53-2

In the same manner as in Preparation Example 4-2, 2-chloro-4-(1-pentyloxy)benzylbromide (21.9 g) was obtained as a pale-yellow solid from 2-chloro-4-(1-pentyloxy)toluene (16.2 g).

$^1$H-NMR (CDCl$_3$): 0.93 (3H, t, J=6 Hz), 1.40 (4H, m), 1.76 (2H, m), 3.93 (2H, t, J=6 Hz), 4.58 (2H, s), 6.77 (1H, dd, J=8, 2 Hz), 6.92 (1H, d, J=2 Hz), 7.32 (1H, d, J=8 Hz).

PREPARATION EXAMPLE 53-3

In the same manner as in Preparation Example 4-5, 2-{N-acetyl-N-[2-chloro-4-(1-pentyloxy)benzyl]amino}-6-bromo-3-nitropyridine (8.84 g) was obtained as a pale-yellow solid from 2-(acetamido)-6-bromo-3-nitropyridine (5.0 g) and 2-chloro-4-(1-pentyloxy)benzylbromide (8.97 g).

$^1$H-NMR (CDCl$_3$): 0.93 (3H, t, J=6 Hz), 1.30–1.48 (4H, m), 1.77 (2H, m), 2.23 (3H, br.s), 3.91 (2H, t, J=6 Hz), 5.29 (2H, br.s), 6.74–6.95 (2H, m), 7.38–7.52 (2H, m), 8.08 (1H, d, J=8 Hz).

PREPARATION EXAMPLE 53-4

In the same manner as in Preparation Example 4-6, 5-bromo-3-(2-chloro-4-(1-pentyloxy)benzyl)-2-methyl-3H-imidazo[4,5-b]pyridine (820 mg) was obtained as pale-brown crystals from 2-{N-acetyl-N-[2-chloro-4-(1-pentyloxy)benzyl]amino}-6-bromo-3-nitropyridine (1.38 g).

$^1$H-NMR (CDCl$_3$): 0.92 (3H, t, J=7 Hz), 1.28–1.49 (4H, m), 1.68–1.83 (2H, m), 2.48 (3H, s), 3.90 (2H, t, J=6 Hz), 5.49 (2H, s), 6.58 (1H, d, J=9 Hz), 6.66 (1H, dd, J=9, 2 Hz), 6.96 (1H, d, J=2 Hz), 7.37 (1H, d, J=8 Hz), 7.83 (1H, d, J=8 Hz). MASS (ESI): m/z 422, 424 (M+1).

PREPARATION EXAMPLE 54-1

In the same manner as in Example 65, 3-chloro-N-(ethoxycarbonyl)-4-methylaniline (227 g) was obtained as a gray powder from 3-chloro-4-methylaniline (158 g).

$^1$H-NMR (CDCl$_3$): 1.32 (3H, t, J=6 Hz), 2.32 (3H, s), 4.23 (2H, q, J=6 Hz), 6.50 (1H, br.s), 7.13 (2H, s), 7.46 (1H, s).

PREPARATION EXAMPLE 54-2

In the same manner as in Preparation Example 16-5, 3-chloro-N-(ethoxycarbonyl)-N,4-dimethylaniline (1 g) was obtained as a colorless oil from 3-chloro-N-(ethoxycarbonyl)-4-methylaniline (1 g).

$^1$H-NMR (CDCl$_3$): 1.24 (3H, t, J=7 Hz), 2.35 (3H, s), 3.27 (3H, s), 4.17 (2H, q, J=7 Hz), 7.05 (1H, dd, J=1, 8 Hz), 7.19 (1H, d, J=8 Hz), 7.25 (1H, d, J=1 Hz). MASS (ESI): m/z 228 (M+1).

PREPARATION EXAMPLE 54-3

In the same manner as in Preparation Example 4-2, a crude product of 4-bromomethyl-3-chloro-N-(ethoxycarbonyl)-N-methylaniline (1.49 g) was obtained as a brown oil from 3-chloro-N-(ethoxycarbonyl)-N,4-dimethylaniline (1.0 g).

$^1$H-NMR (CDCl$_3$): 1.29 (3H, t, J=6 Hz), 3.29 (3H, s), 4.20 (2H, q, J=6 Hz), 4.58 (2H, s), 7.18 (1H, dd, J=8, 2 Hz), 7.33 (1H, d, J=2 Hz), 7.40 (1H, d, J=8 Hz).

PREPARATION EXAMPLE 54-4

In the same manner as in Preparation Example 4-5, 6-bromo-2-(N-(2-chloro-4-(N-ethoxycarbonyl-N-methylamino)benzyl)-acetamido)-3-nitropyridine (20.8 g) was obtained as a brown oil from 2-(acetamido)-6-bromo-3-nitropyridine (13.2 g) and 4-bromomethyl-3-chloro-N-(ethoxycarbonyl)-N-methylaniline (26.8 g).

$^1$H-NMR (CDCl$_3$): 1.29 (3H, t, J=6 Hz), 2.20 (3H, br.s), 3.29 (3H, s), 4.20 (2H, q, J=6 Hz), 5.34 (2H, br.s), 7.10–7.65 (4H, m), 8.10 (1H, d, J=8 Hz).

PREPARATION EXAMPLE 54-5

In the same manner as in Preparation Example 3-4, 5-bromo-3-(2-chloro-4-(N-ethoxycarbonyl-N-methylamino)benzyl)-2-methyl-3H-imidazo[4,5-b]pyridine (15.5 g) was obtained as a pale-brown powder from 6-bromo-2-(N-(2-chloro-4-(N-ethoxycarbonyl-N-methylamino)benzyl)acetamido)-3-nitropyridine (20.8 g).

$^1$H-NMR (CDCl$_3$): 1.25 (3H, t, J=6 Hz), 2.50 (3H, s), 3.29 (3H, s), 4.19 (2H, q, J=6 Hz), 5.53 (2H, s), 6.56 (1H, d, J=8 Hz), 7.04 (1H, dd, J=8, 1 Hz), 7.35–7.45 (2H, m), 7.86 (1H, d, J=8 Hz).

PREPARATION EXAMPLE 55-1

In the same manner as in Example 65, methyl 3-(4-(N-benzyloxycarbonyl-N-methylamino)-2-chlorobenzyl)-2-methyl-3H-imidazo[4,5-b]pyridine-5-carboxylate (159 mg) was obtained as a yellow oil from methyl 3-(2-chloro-4-(methylamino)benzyl)-2-methyl-3H-imidazo[4,5-b]pyridine-5-carboxylate dihydrochloride (175 mg) and benzyl chloroformate (107 mg).

$^1$H-NMR (CDCl$_3$): 2.55 (3H, s), 3.28 (3H, s), 4.00 (3H, s), 5.16 (2H, s), 5.65 (2H, s), 6.60 (1H, d, J=8 Hz), 7.01 (1H, dd, J=1, 8 Hz), 7.27–7.44 (6H, m), 8.07 (1H, d, J=8 Hz), 8.15 (1H, d, J=8 Hz). MASS (ESI): m/z 479 (M+1).

PREPARATION EXAMPLE 55-2

In the same manner as in Preparation Example 14-7, 3-(4-(N-(benzyloxycarbonyl)-N-methylamino)-2-chlorobenzyl)-2-methyl-3H-imidazo[4,5-b]pyridine-5-carboxylic acid (132 mg) was obtained as a white powder from methyl 3-(4-(N-(benzyloxycarbonyl)-N-methylamino)-2-chlorobenzyl)-2-methyl-3H-imidazo[4,5-b]pyridine-5-carboxylate (207 mg).

$^1$H-NMR (CDCl$_3$): 2.63 (3H, s), 3.30 (3H, s), 5.17 (2H, s), 5.57 (2H, s), 6.60 (1H, d, J=8 Hz), 7.07 (1H, dd, J=8 and 2 Hz), 7.2–7.4 (5H, m), 7.45 (1H, d, J=2 Hz), 8.17 (1H, d, J=8 Hz), 8.24 (1H, d, J=8 Hz). MASS (ESI): m/e 463 (M–H)$^-$.

EXAMPLE 1

To a mixture of 3-(2-chloro-4-phenylbenzyl)-2-methyl-3H-imidazo[4,5-b]pyridine-5-carboxylic acid (200 mg) and N,N-dimethylformamide (2.0 ml) was added carbonyldiimidazole (129 mg) and the mixture was stirred at room temperature for 2 hr. To the reaction mixture were added (E)-2-(4-pyridyl)ethenesulfonamide (146 mg) and 1,8-diazabicyclo[5.4.0]undec-7-ene (0.12 ml) and the mixture was stirred at room temperature for 2.5 hr. 1N Hydrochloric acid was added to the reaction mixture under ice-cooling to adjust to pH 7, and water (2.0 ml) was added, which was followed by stirring at room temperature for 30 min. The precipitate was collected by filtration and washed with water to give a pale-gray powder (456 mg). This was suspended in ethanol (2.5 ml) and the suspension was heated to reflux, and then stirred at room temperature for 1 hr. The precipitate was collected by filtration and washed with ethanol to give 3-(2-chloro-4-phenylbenzyl)-2-methyl-5-[(E)-[2-(4-pyridyl)ethene]sulfonylcarbamoyl]-3H-imidazo[4,5-b]pyridine (254 mg) as a white powder.

$^1$H-NMR (CDCl$_3$): 2.68 (3H, s), 5.63 (2H, s), 6.81 (1H, d, J=8 Hz), 7.30–7.75 (11H), 8.13 (1H, d, J=8 Hz), 8.18 (1H, d, J=8 Hz), 8.67 (1H, J=6 Hz). MASS (ESI): m/z 543 (M−1).

EXAMPLE 2

In the same manner as in Example 1, 5-[(4-acetoxybutane)sulfonylcarbamoyl]-3-(2-chloro-4-phenylbenzyl)-2-methyl-3H-imidazo[4,5-b]pyridine (118 mg) was obtained from 3-(2-chloro-4-phenylbenzyl)-2-methyl-3H-imidazo[4,5-b]pyridine-5-carboxylic acid (100 mg) and 4-acetoxybutanesulfonamide (62 mg).

$^1$H-NMR (CDCl$_3$): 1.78 (2H, m), 1.96 (2H, m), 2.01 (3H, s), 2.69 (3H, s), 3.59 (2H, t, J=6 Hz), 4.05 (2H, t, J=6 Hz), 5.62 (2H, s), 6.81 (1H, d, J=8 Hz), 7.34–7.50 (4H), 7.55 (2H, d, J=8 Hz), 7.71 (1H, s), 8.15 (1H, d, J=8 Hz), 8.21 (1H, d, J=8 Hz), 9.88 (1H, s). MASS (ESI): m/z 556 (M+1).

EXAMPLE 3

In the same manner as in Example 1, 3-(2-chloro-4-phenylbenzyl)-2-methyl-5-[(4-ethoxycarbonylbenzene)sulfonylcarbamoyl]-3H-imidazo[4,5-b]pyridine was obtained as colorless crystals (1.01 g) from 3-(2-chloro-4-phenylbenzyl)-2-methyl-3H-imidazo[4,5-b]pyridine-5-carboxylic acid (1.00 g) and (4-ethoxycarbonylbenzene)sulfonamide (910 mg).

$^1$H-NMR (CDCl$_3$): 1.39 (3H, t, J=7 Hz), 2.68 (3H, s), 4.39 (2H, q, J=7 Hz), 5.62 (2H, s), 6.88 (1H, d, J=8 Hz), 7.37–7.53 (4H, m), 7.59 (2H, J=1,8 Hz), 7.74 (1H, J=1 Hz), 8.05–8.22 (6H, m). MS (ESI): m/z 587 (M−1).

EXAMPLE 4

In the same manner as in Preparation Example 14-7, 3-(2-chloro-4-phenylbenzyl)-2-methyl-5-[(4-carboxybenzene)sulfonylcarbamoyl]-3H-imidazo[4,5-b]pyridine was obtained as colorless crystals (809 mg) from 3-(2-chloro-4-phenylbenzyl)-2-methyl-5-[(4-ethoxycarbonylbenzene)sulfonylcarbamoyl]-3H-imidazo[4,5-b]pyridine (867 mg).

$^1$H-NMR (DMSO-d$_6$): 2.51 (3H, overlapped with DMSO-d$_6$), 5.88 (2H, s), 6.78 (1H, d, J=8 Hz), 7.36–7.51 (3H, m), 7.57 (1H, J=1,8 Hz), 7.70 (2H, J=1,8 Hz), 7.85–7.95 (2H, m), 8.10–8.20 (5H, m). MS (ESI): m/z 559 (M−1).

EXAMPLE 5

In the same manner as in Example 1, 3-(2-chloro-4-methoxybenzyl)-2-methyl-5-(1- pentanesulfonylcarbamoyl)-3H-imidazo[4,5-b]pyridine was obtained as colorless crystals (178 mg) from 3-(2-chloro-4-methoxybenzyl)-2-methyl-3H-imidazo[4,5-b]pyridine-5-carboxylic acid (180 mg) and 1-pentanesulfonamide (123 mg).

$^1$H-NMR (CDCl$_3$): 0.89 (3H, t, J=7 Hz), 1.25–1.50 (4H, m), 1.82–1.95 (2H, m), 2.66 (3H, s), 3.51–3.60 (2H, m), 3.80 (3H, s), 5.51 (2H, s), 6.74–6.83 (2H, m), 7.01 (1H, d, J=1 Hz), 8.11 (1H, d, J=8 Hz), 8.18 (1H, d, J=8 Hz). MASS (ESI): m/z 465 (M+1). m.p. 188–189° C.

EXAMPLE 6

In the same manner as in Example 1, 5-(1-butanesulfonylcarbamoyl)-3-(2-chloro-4-methoxybenzyl)-2-methyl-3H-imidazo[4,5-b]pyridine was obtained as colorless crystals (62 mg) from 3-(2-chloro-4-methoxybenzyl)-2-methyl-3H-imidazo[4,5-b]pyridine-5-carboxylic acid (80 mg) and 1-butanesulfonamide (50 mg).

$^1$H-NMR (CDCl$_3$): 0.94 (3H, t, J=7 Hz), 1.41–1.55 (2H, m), 1.80–1.93 (2H, m), 2.66 (3H, s), 3.52–3.60 (2H, m), 3.80 (3H, s), 5.51 (2H, s), 6.74–6.83 (2H, m), 7.01 (1H, d, J=1 Hz), 8.11 (1H, d, J=8 Hz), 8.18 (1H, d, J=8 Hz). MASS (ESI): m/z 451 (M+1). m.p. 175–177° C.

EXAMPLE 7

In the same manner as in Example 1, 3-(2-chloro-4-methoxybenzyl)-2-methyl-5-[(4-methylbenzene)sulfonylcarbamoyl]-3H-imidazo[4,5-b]pyridine was obtained as colorless crystals (202 mg) from 3-(2-chloro-4-methoxybenzyl)-2-methyl-3H-imidazo[4,5-b]pyridine-5-carboxylic acid (175 mg) and (4-methylbenzene)sulfonamide (135 mg).

$^1$H-NMR (CDCl$_3$): 2.42 (3H, s), 2.64 (3H, s), 3.82 (3H, s), 5.52 (2H, s), 6.80 (2H, s), 7.03 (1H, s), 7.34 (2H, d, J=8 Hz), 8.01–8.09 (4H, m). MASS (ESI): m/z 483 (M−1). m.p. 206–208° C.

EXAMPLE 8

In the same manner as in Example 1, 3-(2-chloro-4-ethoxybenzyl)-2-methyl-5-(1-pentanesulfonylcarbamoyl)-3H-imidazo[4,5-b]pyridine(47 mg) was obtained as a white powder from 3-(2-chloro-4-ethoxybenzyl)-2-methyl-3H-imidazo[4,5-b]pyridine-5-carboxylic acid (174 mg) and 1-pentanesulfonamide (115 mg).

$^1$H-NMR (CDCl$_3$): 0.89 (3H, t, J=7 Hz), 1.23–1.52 (4H, m), 1.40 (3H, t, J=7 Hz), 1.81–1.96 (2H, m), 2.65 (3H, s), 3.45–3.62 (2H, m), 4.01 (2H, q, J=7 Hz), 5.51 (2H, s), 6.68–6.82 (2H, m), 6.99 (1H, d, J=2 Hz), 8.11 (1H, d, J=8 Hz), 8.18 (1H, d, J=8 Hz), 9.85 (1H, br s). MASS (ESI): m/e 477 (M−H)$^-$. m.p. 165–166° C.

EXAMPLE 9

In the same manner as in Example 1, 5-(1-butanesulfonylcarbamoyl)-3-(2-chloro-4-ethoxybenzyl)-2-methyl-3H-imidazo[4,5-b]pyridine(70 mg) was obtained as a white powder from 3-(2-chloro-4-ethoxybenzyl)-2-methyl-3H-imidazo[4,5-b]pyridine-5-carboxylic acid (174 mg) and 1-butanesulfonamide (104 mg).

$^1$H-NMR (CDCl$_3$): 0.94 (3H, t, J=7 Hz), 1.38–1.58 (2H, m), 1.40 (3H, t, J=7 Hz), 1.77–1.94 (2H, m), 2.65 (3H, s), 3.49–3.62 (2H, m), 4.01 (2H, q, J=7 Hz), 5.51 (2H, s), 6.69–6.82 (2H, m), 6.99 (1H, d, J=2 Hz), 8.11 (1H, d, J=8 Hz), 8.18 (1H, d, J=8 Hz), 9.85 (1H, br s). MASS (ESI): m/e 463 (M−H)$^-$. m.p. 151–152° C.

EXAMPLE 10

In the same manner as in Example 1, 3-(2-chloro-4-ethoxybenzyl)-2-methyl-5-((1-propylaminosulfonyl)carbamoyl)-3H-imidazo[4,5-b]pyridine was obtained as colorless crystals (128 mg) from 3-(2-chloro-4-ethoxybenzyl)-2-methyl-3H-imidazo[4,5-b]pyridine-5-carboxylic acid (220 mg) and N-(1-propyl)sulfamide (132 mg).

$^1$H-NMR (CDCl$_3$): 0.94 (3H, t, J=7 Hz), 1.40 (3H, t, J=7 Hz), 1.53–1.67 (2H, m), 2.65 (3H, s), 3.03 (2H, q, J=7 Hz), 4.02 (2H, q, J=7 Hz), 5.52 (2H, s), 6.75 (2H, s), 7.00 (1H, s), 8.11 (1H, d, J=8 Hz), 8.16 (1H, d, J=8 Hz). MASS (ESI): m/z 464 (M−1). m.p. 152–155° C.

EXAMPLE 11

In the same manner as in Example 1, 5-((1-butylaminosulfonyl)carbamoyl)-3-(2-chloro-4-ethoxybenzyl)-2-methyl-3H-imidazo[4,5-b]pyridine was obtained as colorless crystals (188 mg) from 3-(2-chloro-4-ethoxybenzyl)-2-methyl-3H-imidazo[4,5-b]pyridine-5-carboxylic acid (200 mg) and N-(1-butyl)sulfamide (132 mg).

$^1$H-NMR (CDCl$_3$): 0.89 (3H, t, J=7 Hz), 1.30–1.45 (5H, m), 1.50–1.61 (2H, m), 2.65 (3H, s), 3.06 (2H, q, J=7 Hz), 4.01 (2H, q, J=7 Hz), 5.52 (2H, s), 6.75 (2H, s), 7.00 (1H, s), 8.10 (1H, d, J=8 Hz), 8.15 (1H, d, J=8 Hz). MASS (ESI): m/z 478 (M−1). m.p. 175–177° C.

EXAMPLE 12

In the same manner as in Example 1, 3-(2-chloro-4-(1-propoxy)benzyl)-2-methyl-5-(1-pentanesulfonylcarbamoyl)-3H-imidazo[4,5-b]pyridine was obtained as colorless crystals (169 mg) from 3-(2-chloro-4-(1-propoxy)benzyl)-2-methyl-3H-imidazo[4,5-b]pyridine-5-carboxylic acid (185 mg) and 1-pentanesulfonamide (112 mg).

$^1$H-NMR (CDCl$_3$): 0.89 (3H, t, J=7 Hz), 1.02 (3H, t, J=7 Hz), 1.25–1.50 (4H, m), 1.73–1.95 (4H, m), 2.65 (3H, s), 3.52–3.60 (2H, m), 3.90 (2H, t, J=7 Hz), 5.51 (2H, s), 6.76 (2H, s), 7.00 (1H, s), 8.11 (1H, d, J=8 Hz), 8.18 (1H, d, J=8 Hz). MASS (ESI): m/z 491 (M−1). m.p. 131–134° C.

EXAMPLE 13

In the same manner as in Example 1, 5-(1-butanesulfonylcarbamoyl)-3-(2-chloro-4-(1-propoxy)benzyl)-2-methyl-3H-imidazo[4,5-b]pyridine was obtained as colorless crystals (177 mg) from 3-(2-chloro-4-(1-propoxy)benzyl)-2-methyl-3H-imidazo[4,5-b]pyridine-5-carboxylic acid (190 mg) and 1-butanesulfonamide (106 mg).

$^1$H-NMR (CDCl$_3$): 0.94 (3H, t, J=7 Hz), 1.02 (3H, t, J=7 Hz), 1.41–1.57 (2H, m), 1.73–1.93 (4H, m), 2.65 (3H, s), 3.53–3.60 (2H, m), 3.90 (2H, t, J=7 Hz), 5.51 (2H, s), 6.76 (2H, s), 7.00 (1H, s), 8.11 (1H, d, J=8 Hz), 8.18 (1H, d, J=8 Hz). MASS (ESI): m/z 477 (M−1). m.p. 153–154° C.

EXAMPLE 14

In the same manner as in Example 1, 3-(2-chloro-4-isopropoxybenzyl)-2-methyl-5-(1-pentanesulfonylcarbamoyl)-3H-imidazo[4,5-b]pyridine was obtained as thin yellow crystals (140 mg) from 3-(2-chloro-4-isopropoxybenzyl)-2-methyl-3H-imidazo[4,5-b]pyridine-5-carboxylic acid (170 mg) and 1-pentanesulfonamide (107 mg).

$^1$H-NMR (CDCl$_3$): 0.89 (3H, t, J=7 Hz), 1.27–1.50 (4H, m), 1.32 (6H, d, J=7 Hz), 1.83–1.95 (2H, m), 2.65 (3H, s), 3.52–3.60 (2H, m), 4.52 (1H, sept, J=7 Hz), 5.51 (2H, s), 6.72 (2H, s), 6.99 (1H, s), 8.11 (1H, d, J=8 Hz), 8.19 (1H, d, J=8 Hz). MASS (ESI): m/z 491 (M−1). m.p. 130–133° C.

EXAMPLE 15

In the same manner as in Example 1, 5-(1-butanesulfonylcarbamoyl)-3-(2-chloro-4-isopropoxybenzyl)-2-methyl-3H-imidazo-[4,5-b]pyridine was obtained as thin yellow crystals (119 mg) from 3-(2-chloro-4-isopropoxybenzyl)-2-methyl-3H-imidazo[4,5-b]pyridine-5-carboxylic acid (180 mg) and 1-butanesulfonamide (103 mg).

$^1$H-NMR (CDCl$_3$): 0.94 (3H, t, J=7 Hz), 1.32 (6H, d, J=7 Hz), 1.42–1.60 (2H, m), 1.80–1.94 (2H, m) 2.65 (3H, s), 3.52–3.60 (2H, m), 4.53 (1H, sept, J=7 Hz), 5.51 (2H, s), 6.72 (2H, s), 6.99 (1H, d, J=1 Hz), 8.11 (1H, d, J=8 Hz), 8.19 (1H, d, J=8 Hz). MASS (ESI): m/z 477 (M−1). m.p. 138–141° C.

EXAMPLE 16

In the same manner as in Example 1, 3-(2-chloro-4-isopropoxybenzyl)-2-methyl-5-[(4-methylbenzene)sulfonyl-carbamoyl]-3H-imidazo[4,5-b]pyridine was obtained as thin yellow crystals (161 mg) from 3-(2-chloro-4-isopropoxybenzyl)-2-methyl-3H-imidazo[4,5-b]pyridine-5-carboxylic acid (155 mg) and (4-methylbenzene)sulfonamide (111 mg).

$^1$H-NMR (CDCl$_3$): 1.34 (6H, d, J=7 Hz), 2.42 (3H, s), 2.64 (3H, s), 4.54 (1H, sept, J=7 Hz), 5.51 (2H, s), 6.75 (2H, s), 7.01 (1H, s), 7.34 (2H, d, J=8 Hz), 8.00–8.10 (4H, m). MASS (ESI): m/z 511 (M−1). m.p. 202–204° C.

EXAMPLE 17

In the same manner as in Example 1, 3-(2-chloro-4-(1-butoxy)benzyl)-2-methyl-5-(1-pentanesulfonylcarbamoyl)-3H-imidazo[4,5-b]pyridine was obtained as colorless crystals (210 mg) from 3-(2-chloro-4-(1-butoxy)benzyl)-2-methyl-3H-imidazo[4,5-b]pyridine-5-carboxylic acid (220 mg) and 1-pentanesulfonamide (133 mg).

$^1$H-NMR (CDCl$_3$): 0.89 (3H, t, J=7 Hz), 0.96 (3H, t, J=7 Hz), 1.26–1.57 (6H, m), 1.70–1.95 (4H, m), 2.65 (3H, s), 3.50–3.60 (2H, m), 3.94 (2H, t, J=7 Hz), 5.51 (2H, s), 6.75 (2H, s), 7.00 (1H, s), 8.10 (1H, d, J=8 Hz), 8.18 (1H, d, J=8 Hz). MASS (ESI): m/z 505 (M−1). m.p. 133–136° C.

EXAMPLE 18

In the same manner as in Example 1, 5-(1-butanesulfonylcarbamoyl)-3-(2-chloro-4-(1-butoxy)benzyl)-2-methyl-3H-imidazo[4,5-b]pyridine was obtained as colorless crystals (196 mg) from 3-(2-chloro-4-(1-butoxy)benzyl)-2-methyl-3H-imidazo[4,5-b]pyridine-5-carboxylic acid (220 mg) and 1-butanesulfonamide (121 mg).

$^1$H-NMR (CDCl$_3$): 0.94 (3H, t, J=7 Hz), 0.96 (3H, t, J=7 Hz), 1.40–1.58 (4H, m), 1.70–1.93 (4H, m), 2.65 (3H, s), 3.52–3.60 (2H, m), 3.94 (2H, t, J=7 Hz), 5.51 (2H, s), 6.76 (2H, s), 7.00 (1H, s), 8.10 (1H, d, J=8 Hz), 8.18 (1H, d, J=8 Hz). MASS (ESI): m/z 491 (M−1). m.p. 144–145° C.

EXAMPLE 19

In the same manner as in Example 1, 3-(2-chloro-4-(1-butoxy)benzyl)-2-methyl-5-[(4-methylbenzene)sulfonylcarbamoyl]-3H-imidazo[4,5-b]pyridine was obtained as colorless crystals (185 mg) from 3-(2-chloro-4-(1-butoxy)benzyl)-2-methyl-3H-imidazo[4,5-b]pyridine-5-carboxylic acid (200 mg) and (4-methylbenzene)sulfonamide (137 mg).

$^1$H-NMR (CDCl$_3$): 0.97 (3H, t, J=7 Hz), 1.41–1.57 (2H, m), 1.70–1.84 (2H, m), 2.42 (3H, s), 2.64 (3H, s), 3.96 (2H, t, J=7 Hz), 5.51 (2H, s), 6.78 (2H, s), 7.02 (1H, s), 7.34 (2H, d, J=8 Hz), 8.00–8.10 (4H, m). MASS (ESI): m/z 525 (M−1). m.p. 150–153° C.

EXAMPLE 20

In the same manner as in Example 1, 3-(2-chloro-4-(1-pentyloxy)benzyl)-2-methyl-5-(1-pentanesulfonylcarbamoyl)-3H-imidazo[4,5-b]pyridine was obtained as thin yellow crystals (211 mg) from 3-(2-chloro-4-(1-pentyloxy)benzyl)-2-methyl-3H-imidazo[4,5-b]pyridine-5-carboxylic acid (200 mg) and 1-pentanesulfonamide (117 mg).

$^1$H-NMR (CDCl$_3$): 0.85–0.92 (6H, m), 1.25–1.50 (8H, m), 1.70–1.95 (4H, m), 2.65 (3H, s), 3.51–3.60 (2H, m), 3.93 (2H, t, J=7 Hz), 5.51 (2H, s), 6.75 (2H, s), 7.00 (1H, s), 8.11 (1H, d, J=8 Hz), 8.18 (1H, d, J=8 Hz). MASS (ESI): m/z 521 (M+1). m.p. 128–131° C.

EXAMPLE 21

In the same manner as in Example 1, 5-(1-butanesulfonylcarbamoyl)-3-(2-chloro-4-(1-pentyloxy)benzyl)-2-methyl-3H-imidazo[4,5-b]pyridine was obtained as thin yellow crystals (207 mg) from 3-(2-chloro-4-(1-pentyloxy)benzyl)-2-methyl-3H-imidazo[4,5-b]pyridine-5-carboxylic acid (220 mg) and 1-butanesulfonamide (117 mg).

$^1$H-NMR (CDCl$_3$): 0.92 (3H, t, J=7 Hz), 0.94 (3H, t, J=7 Hz), 1.30–1.62 (6H, m), 1.70–1.93 (4H, m), 2.65 (3H, s), 3.51–3.60 (2H, m), 3.93 (2H, t, J=7 Hz), 5.51 (2H, s), 6.75 (2H, s), 6.99 (1H, s), 8.10 (1H, d, J=8 Hz), 8.18 (1H, d, J=8 Hz). MASS (ESI): m/z 507 (M+1). m.p. 145–146° C.

EXAMPLE 22

In the same manner as in Example 1, 3-(2-chloro-4-(1-pentyloxy)benzyl)-2-methyl-5-((E)-(2-phenylethene)sulfonylcarbamoyl)-3H-imidazo[4,5-b]pyridine was obtained as colorless crystals (226 mg) from 3-(2-chloro-4-(1-pentyloxy)benzyl)-2-methyl-3H-imidazo[4,5-b]pyridine-5-carboxylic acid (200 mg) and (E)-(2-phenylethene)sulfonamide (142 mg).

$^1$H-NMR (CDCl$_3$): 0.92 (3H, t, J=7 Hz), 1.30–1.50 (4H, m), 1.71–1.83 (2H, m), 2.64 (3H, s), 3.94 (2H, t, J=7 Hz), 5.52 (2H, s), 6.68–6.79 (2H, m), 7.00 (1H, d, J=1 Hz), 7.16 (1H, d, J=15 Hz), 7.36–7.48 (3H, m), 7.50–7.59 (2H, m), 7.82 (1H, d, J=15 Hz), 8.08 (1H, d, J=8 Hz), 8.15 (1H, d, J=8 Hz). MASS (ESI): m/z 551 (M−1). m.p. 180–182° C.

EXAMPLE 23

In the same manner as in Example 1, 5-[(5-bromothiophen-2-yl)sulfonylcarbamoyl]-3-[2-chloro-4-(1-pentyloxy)benzyl]-2-methyl-3H-imidazo[4,5-b]pyridine was obtained as colorless crystals (175 mg) from 3-[2-chloro-4-(1-pentyloxy)benzyl]-2-methyl-3H-imidazo[4,5-b]pyridine-5-carboxylic acid (220 mg) and 5-bromothiophene-2-sulfonamide (206 mg).

$^1$H-NMR (CDCl$_3$): 0.93 (3H, t, J=7 Hz), 1.30–1.50 (4H, m), 1.73–1.85 (2H, m), 2.66 (3H, s), 3.95 (2H, t, J=7 Hz), 5.51 (2H, s), 6.74–6.83 (2H, m), 7.01 (1H, d, J=1 Hz), 7.09 (1H, d, J=5 Hz), 7.73 (1H, d, J=5 Hz), 8.07 (1H, d, J=8 Hz), 8.11 (1H, d, J=8 Hz). MASS (ESI): m/z 611 (M−1). m.p. 156–157° C.

EXAMPLE 24

In the same manner as in Example 1, 3-[2-chloro-4-(1-pentyloxy)benzyl]-2-methyl-5-[(5-chlorothiophen-2-yl)sulfonylcarbamoyl]-3H-imidazo[4,5-b]pyridine was obtained as colorless crystals (188 mg) from 3-[2-chloro-4-(1-pentyloxy)benzyl]-2-methyl-3H-imidazo[4,5-b]pyridine-5-carboxylic acid (220 mg) and 5-chlorothiophene-2-sulfonamide (168 mg).

$^1$H-NMR (CDCl$_3$): 0.93 (3H, t, J=7 Hz), 1.30–1.50 (4H, m), 1.73–1.85 (2H, m), 2.66 (3H, s), 3.95 (2H, t, J=7 Hz), 5.51 (2H, s), 6.74–6.84 (2H, m), 6.95 (1H, d, J=5 Hz), 7.00 (1H, d, J=1 Hz), 7.77 (1H, d, J=5 Hz), 8.07 (1H, d, J=8 Hz), 8.11 (1H, d, J=8 Hz). MASS (ESI): m/z 565 (M−1). m.p. 154–155° C.

EXAMPLE 25

In the same manner as in Example 1, 5-((1-propylaminosulfonyl)carbamoyl)-3-(2-chloro-4-(1-pentyloxy)benzyl)-2-methyl-3H-imidazo[4,5-b]pyridine was obtained as colorless crystals (193 mg) from 3-(2-chloro-4-(1-pentyloxy)benzyl)-2-methyl-3H-imidazo[4,5-b]pyridine-5-carboxylic acid (220 mg) and N-(1-propyl)sulfamide (118 mg).

$^1$H-NMR (CDCl$_3$): 0.92 (3H, t, J=7 Hz), 0.94 (3H, t, J=7 Hz), 1.30–1.49 (4H, m), 1.53–1.84 (4H, m), 2.64 (3H, s), 3.03 (2H, q, J=7 Hz), 3.93 (2H, t, J=7 Hz), 5.52 (2H, s), 6.74 (2H, s), 7.00 (1H, s), 8.10 (1H, d, J=8 Hz), 8.16 (1H, d, J=8 Hz). MASS (ESI): m/z 506 (M−1). m.p. 155–158° C.

EXAMPLE 26

In the same manner as in Example 1, 5-((1-butylaminosulfonyl)carbamoyl)-3-(2-chloro-4-(1-pentyloxy)benzyl)-2-methyl-3H-imidazo[4,5-b]pyridine was obtained as colorless crystals (202 mg) from 3-(2-chloro-4-(1-pentyloxy)benzyl)-2-methyl-3H-imidazo[4,5-b]pyridine-5-carboxylic acid (200 mg) and N-(1-butyl)sulfamide (118 mg).

$^1$H-NMR (CDCl$_3$): 0.84–0.97 (6H, m), 1.29–1.61 (8H, m), 1.70–1.83 (2H, m), 2.64 (3H, s), 3.05 (2H, q, J=7 Hz), 3.93 (2H, t, J=7 Hz), 5.51 (2H, s), 6.74 (2H, s), 7.00 (1H, s), 8.10 (1H, d, J=8 Hz), 8.15 (1H, d, J=8 Hz). MASS (ESI): m/z 520 (M−1). m.p. 136–138° C.

EXAMPLE 27

In the same manner as in Example 1, 3-(2-chloro-4-((cyclopentylmethyl)oxy)benzyl)-2-methyl-5-(1-pentanesulfonylcarbamoyl)-3H-imidazo[4,5-b]pyridine (160 mg) was obtained as a white powder from 3-(2-chloro-4-((cyclopentylmethyl)oxy)benzyl)-2-methyl-3H-imidazo[4,5-b]pyridine-5-carboxylic acid (164 mg) and 1-pentanesulfonamide (94 mg).

$^1$H-NMR (CDCl$_3$): 0.89 (3H, t, J=7 Hz), 1.24–1.97 (14H, m), 2.33 (11H, sept, J=7 Hz), 2.65 (3H, s), 3.49–3.63 (2H, m), 3.81 (2H, d, J=7 Hz), 5.51 (2H, s), 6.75 (2H, s), 7.00 (1H, s), 8.11 (1H, d, J=8 Hz), 8.18 (1H, d, J=8 Hz), 9.86 (1H, br s).

MASS (ESI): m/e 531 (M−H)$^-$. m.p. 160–161° C.

EXAMPLE 28

In the same manner as in Example 1, 5-(1-butanesulfonylcarbamoyl)-3-(2-chloro-4-((cyclopentylmethyl)oxy)benzyl)-2-methyl-3H-imidazo[4,5-b]pyridine (123 mg) was obtained as a white powder from 3-(2-chloro-4-((cyclopentylmethyl)oxy)benzyl)-2-methyl-3H-imidazo[4,5-b]pyridine-5-carboxylic acid (126 mg) and 1-butanesulfonamide (68 mg).

$^1$H-NMR (CDCl$_3$): 0.94 (3H, t, J=7 Hz), 1.23–1.95 (12H, m), 2.33 (1H, sept, J=7 Hz), 2.65 (3H, s), 3.50–3.63 (2H, m), 3.81 (2H, d, J=7 Hz), 5.51 (2H, s), 6.75 (2H, s), 7.00 (1H, s), 8.11 (1H, d, J=8 Hz), 8.18 (1H, d, J=8 Hz), 9.86 (11H, br s). MASS (ESI): m/e 517 (M−H)$^-$. m.p. 180–181° C.

EXAMPLE 29

In the same manner as in Example 1, 3-(2-chloro-4-ethoxybenzyl)-2-ethyl-5-(1-pentanesulfonylcarbamoyl)-3H-imidazo[4,5-b]pyridine was obtained as colorless crystals (175 mg) from 3-(2-chloro-4-ethoxybenzyl)-2-ethyl-3H-imidazo[4,5-b]pyridine-5-carboxylic acid (185 mg) and 1-pentanesulfonamide (117 mg).

$^1$H-NMR (CDCl$_3$): 0.89 (3H, t, J=7 Hz), 1.25–1.50 (10H, m), 1.81–1.95 (2H, m), 2.91 (2H, q, J=7 Hz), 3.50–3.60 (2H, m), 4.00 (2H, q, J=7 Hz), 5.52 (2H, s), 6.67–6.75 (2H, m), 7.00 (1H, d, J=1 Hz), 8.11–8.21 (2H, m). MASS (ESI): m/z 491 (M−1).

EXAMPLE 30

In the same manner as in Example 1, 3-(2-chloro-4-ethoxybenzyl)-2-ethyl-5-[(4-methylbenzene)sulfonylcarbamoyl]-3H-imidazo[4,5-b]pyridine was obtained as colorless crystals (196 mg) from 3-(2-chloro-4-ethoxybenzyl)-2-ethyl-3H-imidazo[4,5-b]pyridine-5-carboxylic acid (170 mg) and (4-methylbenzene)sulfonamide (121 mg).

$^1$H-NMR (CDCl$_3$): 1.37–1.47 (6H, m), 2.42 (3H, s), 2.90 (2H, q, J=7 Hz), 4.03 (2H, q, J=7 Hz), 5.52 (2H, s), 6.71 (1H, d, J=8 Hz), 6.75 (1H, dd, J=1,8 Hz), 7.01 (1H, d, J=1 Hz), 7.34 (2H, d, J=8 Hz), 8.00–8.10 (4H, m). MASS (ESI): m/z 511 (M−1).

EXAMPLE 31

In the same manner as in Example 1, 3-(2-chloro-4-(1-propoxy)benzyl)-2-ethyl-5-(1-pentanesulfonylcarbamoyl)-3H-imidazo[4,5-b]pyridine was obtained as colorless crystals (238 mg) from 3-(2-chloro-4-(1-propoxy)benzyl)-2-ethyl-3H-imidazo[4,5-b]pyridine-5-carboxylic acid (200 mg) and 1-pentanesulfonamide (121 mg).

$^1$H-NMR (CDCl$_3$): 0.89 (3H, t, J=7 Hz), 1.02 (3H, t, J=7 Hz), 1.20–1.51 (7H, m), 1.72–1.95 (4H, m), 2.95 (2H, q, J=7 Hz), 3.50–3.60 (2H, m), 3.90 (2H, t, J=7 Hz), 5.52 (2H, s), 6.69 (1H, d, J=8 Hz), 6.73 (1H, dd, J=1,8 Hz), is 7.00 (1H, d, J=1 Hz), 8.11–8.21 (2H, m). MASS (ESI): m/z 505 (M−1).

EXAMPLE 32

In the same manner as in Example 1, 3-(2-chloro-4-(1-propoxy)benzyl)-2-ethyl-5-[(4-methylbenzene)sulfonylcarbamoyl]-3H-imidazo[4,5-b]pyridine was obtained as colorless crystals (199 mg) from 3-(2-chloro-4-(1-propoxy)benzyl)-2-ethyl-3H-imidazo[4,5-b]pyridine-5-carboxylic acid (170 mg) and (4-methylbenzene)sulfonamide (117 mg).

$^1$H-NMR (CDCl$_3$): 1.03 (3H, t, J=7 Hz), 1.43 (3H, t, J=7 Hz), 1.80 (2H, tq, J=7, 7 Hz), 2.42 (3H, s), 2.90 (2H, q, J=7 Hz), 3.92 (2H, t, J=7 Hz), 5.52 (2H, s), 6.70 (1H, d, J=8 Hz), 6.76 (1H, dd, J=1,8 Hz), 7.02 (1H, d, J=1 Hz), 7.34 (2H, d, J=8 Hz), 8.00–8.10 (4H, m). MASS (ESI): m/z 525 (M−1).

EXAMPLE 33

In the same manner as in Example 1, 3-(2-chloro-4-(1-pentyloxy)benzyl)-2-ethyl-5-(1- pentanesulfonylcarbamoyl)-3H-imidazo[4,5-b]pyridine was obtained as colorless crystals (187 mg) from 3-(2-chloro-4-(1-pentyloxy)benzyl)-2-ethyl-3H-imidazo[4,5-b]pyridine-5-carboxylic acid (180 mg) and 1-pentanesulfonamide (102 mg).

$^1$H-NMR (CDCl$_3$): 0.84–0.97 (6H, m), 1.27–1.50 (11H, m), 1.70–1.95 (4H, m), 2.92 (2H, q, J=7 Hz), 3.50–3.60 (2H, m), 3.93 (2H, t, J=7 Hz), 5.52 (2H, s), 6.65–6.75 (2H, m), 7.00 (1H, d, J=1 Hz), 8.14 (1H, d, J=7 Hz), 8.24 (1H, d, J=7 Hz). MASS (ESI): m/z 533 (M−1).

EXAMPLE 34

In the same manner as in Example 1, 3-(2-chloro-4-(1-pentyloxy)benzyl)-2-ethyl-5-[(4-methylbenzene)sulfonylcarbamoyl]-3H-imidazo[4,5-b]pyridine was obtained as colorless crystals (180 mg) from 3-(2-chloro-74-(1-pentyloxy)benzyl)-2-ethyl-3H-imidazo[4,5-b]pyridine-5-carboxylic acid (160 mg) and (4-methylbenzene)sulfonamide (102 mg).

$^1$H-NMR (CDCl$_3$): 0.93 (3H, t, J=7 Hz), 1.30–1.50 (7H, m), 1.72–1.85 (2H, m), 2.42 (3H, s), 2.90 (2H, q, J=7 Hz), 3.95 (2H, t, J=7 Hz), 5.52 (2H, s), 6.70 (1H, d, J=8 Hz), 6.75 (1H, dd, J=1, 8 Hz), 7.01 (1H, d, J=1 Hz), 7.33 (2H, d, J=8 Hz), 8.00–8.10 (4H, m). MASS (ESI): m/z 553 (M−1).

EXAMPLE 35

In the same manner as in Example 1, 3-(2-chloro-4-(1-propoxy)benzyl)-2,7-dimethyl-5-(1-pentanesulfonylcarbamoyl)-3H-imidazo[4,5-b]pyridine was obtained as colorless crystals (220 mg) from 3-[2-chloro-4-(1-propoxy)benzyl]-2,7-dimethyl-3H-imidazo[4,5-b]pyridine-5-carboxylic acid (205 mg) and 1-pentanesulfonamide (124 mg).

$^1$H-NMR (CDCl$_3$): 0.88 (3H, t, J=7 Hz), 1.02 (3H, t, J=7 Hz), 1.26–1.50 (4H, m), 1.72–1.95 (4H, m), 2.64 (3H, s), 2.73 (3H, s), 3.50–3.60 (2H, m), 3.89 (2H, t, J=7 Hz), 5.49 (2H, s), 6.68–6.76 (2H, m), 7.00 (1H, d, J=1 Hz), 7.99 (1H, s). MASS (ESI): m/z 505 (M−1). m.p. 161–162° C.

EXAMPLE 36

In the same manner as in Example 1, 5-(1-butanesulfonylcarbamoyl)-3-[2-chloro-4-(1-propoxy)benzyl]-2,7-dimethyl-3H-imidazo[4,5-b]pyridine was obtained as colorless crystals (169 mg) from 3-[2-chloro-4-(1-propoxy)benzyl]-2,7-dimethyl-3H-imidazo[4,5-b]pyridine-5-carboxylic acid (180 mg).

$^1$H-NMR (CDCl$_3$): 0.94 (3H, t, J=7 Hz), 1.02 (3H, t, J=7 Hz), 1.40–1.56 (2H, m), 1.72–1.93 (4H, m), 2.64 (3H, s), 2.73 (3H, s), 3.50–3.60 (2H, m), 3.89 (2H, t, J=7 Hz), 5.49 (2H, s), 6.72 (2H, s), 6.99 (1H, br s), 7.99 (1H, s), 9.88 (1H, br s). MASS (ESI): m/z 491 (M−1). m.p. 164–166° C.

EXAMPLE 37

In the same manner as in Example 1, 3-(2-chloro-4-(1-propoxy)benzyl)-2,7-dimethyl-5-[(4-methylbenzene)sulfonylcarbamoyl]-3H-imidazo[4,5-b]pyridine was obtained as colorless crystals (222 mg) from 3-(2-chloro-4-(1-propoxy)benzyl)-2,7-dimethyl-3H-imidazo[4,5-b]pyridine-5-carboxylic acid (200 mg) and (4-methylbenzene)sulfonamide (137 mg).

$^1$H-NMR (CDCl$_3$): 1.03 (3H, t, J=7 Hz), 1.75–1.87 (2H, m), 2.42 (3H, s), 2.62 (3H, s), 2.66 (3H, s), 3.92 (2H, t, J=7 Hz), 5.49 (2H, s), 6.70–6.80 (2H, m), 7.01 (1H, d, J=1 Hz), 7.33 (2H, d, J=8 Hz), 7.88 (1H, s), 8.04 (2H, d, J=8 Hz). MASS (ESI): m/z 525 (M−1). m.p. 168–170° C.

EXAMPLE 38

In the same manner as in Example 1, 3-[2-chloro-4-(1-pentyloxy)benzyl]-2,7-dimethyl-5-(1-pentanesulfonylcarbamoyl)-3H-imidazo[4,5-b]pyridine was obtained as colorless crystals (198 mg) from 3-[2-chloro-4-(1-pentyloxy)benzyl]-2,7-dimethyl-3H-imidazo[4,5-b]pyridine-5-carboxylic acid (200 mg).

$^1$H-NMR (CDCl$_3$): 0.83–0.97 (6H, m), 1.26–1.49 (8H, m), 1.70–1.94 (4H, m), 2.64 (3H, s), 2.73 (3H, s), 3.50–3.59 (2H, m), 3.91 (2H, t, J=7 Hz), 5.49 (2H, s), 6.71 (2H, s), 6.99 (1H, br s), 7.99 (1H, br s), 9.88 (1H, br s). MASS (ESI): m/z 533 (M−1). m.p. 149–150° C.

EXAMPLE 39

In the same manner as in Example 1, 5-(1-butanesulfonylcarbamoyl)-3-[2-chloro-4-(1-pentyloxy)benzyl]-2,7-dimethyl-3H-imidazo[4,5-b]pyridine (177 mg) was obtained as colorless crystals from 3-[2-chloro-4-(1-pentyloxy)benzyl]-2,7-dimethyl-3H-imidazo[4,5-b]pyridine-5-carboxylic acid (200 mg).

$^1$H-NMR (CDCl$_3$): 0.86–1.00 (6H), 1.30–1.56 (6H), 1.70–1.93 (4H), 2.64 (3H, s), 2.74 (3H, s), 3.55 (2H, t, J=6 Hz), 3.93 (2H, t, J=6 Hz), 5.49 (2H, s), 6.72 (2H, s), 6.99 (1H, s), 7.99 (1H, s), 9.87 (1H, br s). MASS (ESI): m/z. m.p. 156–158° C.

EXAMPLE 40

In the same manner as in Example 1, 3-[2-chloro-4-(1-pentyloxy)benzyl]-2,7-dimethyl-5-[(4-methylbenzene)sulfonylcarbamoyl]-3H-imidazo[4,5-b]pyridine was obtained as colorless crystals (231 mg) from 3-[2-chloro-4-(1-pentyloxy)benzyl]-2,7-dimethyl-3H-imidazo[4,5-b]pyridine-5-carboxylic acid (200 mg).

$^1$H-NMR (CDCl$_3$): 0.94 (3H, t, J=7 Hz), 1.30–1.50 (4H, m), 1.71–1.84 (2H, m), 2.62 (3H, s), 2.66 (3H, s), 3.95 (2H, t, J=7 Hz), 5.49 (2H, s), 6.69–6.79 (2H, m), 6.78 (2H, s), 7.01 (1H, br s), 7.33 (2H, d, J=8 Hz), 7.88 (1H, s), 8.04 (2H, d, J=8 Hz), 10.14 (1H, br s). MASS (ESI): m/z 553 (M−1). m.p. 173–174° C.

EXAMPLE 41

In the same manner as in Example 1, 3-(4-(N-(tert-butoxycarbonyl)-N-methylamino)-2-chlorobenzyl)-2-methyl-5-(1-pentanesulfonylcarbamoyl)-3H-imidazo[4,5-b]pyridine (2.16 g) was obtained as a white powder from 3-(4-(N-(tert-butoxycarbonyl)-N-methylamino)-2-chlorobenzyl)-2-methyl-3H-imidazo[4 5-b]pyridine-5-carboxylic acid (1.89 g) and 1-pentanesulfonamide (1.00 g).

$^1$H-NMR (CDCl$_3$): 0.89 (3H, t, J=7 Hz), 1.23–1.53 (4H, m), 1.46 (9H, s), 1.82–1.97 (2H, m), 2.63 (3H, s), 3.25 (3H, s), 3.50–3.62 (2H, m), 5.56 (2H, s), 6.64 (1H, d, J=8 Hz), 7.10 (1H, dd, J=8 and 2 Hz), 7.46 (1H, d, J=2 Hz), 8.13 (1H, d, J=8 Hz), 8.21 (1H, d, J=8 Hz), 9.84 (1H, br s). MASS (ESI): m/e 562 (M−H)$^-$. m.p. 160–161° C.

EXAMPLE 42

To a solution of 3-(4-(N-(tert-butoxycarbonyl)-N-methylamino)-2-chlorobenzyl)-2-methyl-5-(1-pentanesulfonylcarbamoyl)-3H-imidazo[4,5-b]pyridine (1.91 g) in dichloromethane (19 ml) was added trifluoroacetic acid (14.5 ml) under ice-cooling, and the mixture was stirred for 1 hr. The solvent was evaporated and methanol (19 ml) was added to the residue for re-dissolution. Water (9.5 ml) was added and 1N aqueous sodium hydroxide solution was added dropwise under ice-cooling to adjust to about pH 4. The resulting precipitate was collected by filtration and dried under reduced pressure to give 3-(2-chloro-4-(methylamino)benzyl)-2-methyl-5-(1-pentanesulfonylcarbamoyl)-3H-imidazo[4,5-b]pyridine (1.53 g) as a white powder.

$^1$H-NMR (CDCl$_3$): 0.89 (3H, t, J=7 Hz), 1.25–1.52 (4H, m), 1.79–1.97 (2H, m), 2.68 (3H, s), 2.81 (3H, s), 3.48–3.62 (2H, m), 3.92 (1H, br s), 5.45 (2H, s), 6.46 (1H, dd, J=8 and 2 Hz), 6.63 (1H, d, J=2 Hz), 6.80 (1H, d, J=8 Hz), 8.08 (1H, d, J=8 Hz), 8.15 (1H, d, J=8 Hz), 9.86 (1H, br s). MASS (ESI): m/e 462 (M–H)$^-$. m.p. 185–186° C.

EXAMPLE 43

To a suspension of 3-(2-chloro-4-(methylamino)benzyl)-2-methyl-5-(1-pentanesulfonylcarbamoyl)-3H-imidazo[4,5-b]pyridine (232 mg) in tetrahydrofuran (1.2 ml)—methanol (1.2 ml) were added acetaldehyde (106 mg), sodium cyanoborohydride (65 mg) and acetic acid (60 mg) at room temperature, and the mixture was stirred. After 2 hr, acetaldehyde (80 mg) was added and the mixture was stirred for 2 hr. The reaction mixture was diluted A with chloroform/methanol (10/1) (10 ml), washed successively with water, 1N hydrochloric acid and saturated brine, and dried over anhydrous magnesium sulfate. The solvent was evaporated and the residue was recrystallized from acetone-water to give 3-(2-chloro-4-(ethylmethylamino)benzyl)-2-methyl-5-(1-pentanesulfonylcarbamoyl)-3H-imidazo[4,5-b]pyridine (197 mg) as a white powder.

$^1$H-NMR (CDCl$_3$): 0.89 (3H, t, J=7 Hz), 1.11 (3H, t, J=7 Hz), 1.24–1.53 (4H, m), 1.82–1.97 (2H, m), 2.69 (3H, s), 2.90 (3H, s), 3.37 (2H, q, J=7 Hz), 3.49–3.63 (2H, m), 5.46 (2H, s), 6.54 (1H, dd, J=8 and 2 Hz), 6.69 (1H, d, J=2 Hz), 6.82 (1H, d, J=8 Hz), 8.08 (1H, d, J=8 Hz), 8.16 (1H, d, J=8 Hz), 9.91 (1H, br s). MASS (ESI): m/e 490 (M–H)$^-$. m.p. 148–149° C.

EXAMPLE 44

In the same manner as in Example 43, 3-(2-chloro-4-(methyl-(1-propyl)amino)benzyl)-2-methyl-5-(1-pentanesulfonylcarbamoyl)-3H-imidazo[4,5-b]pyridine (204 mg) was obtained as a white powder from 3-(2-chloro-4-(methylamino)benzyl)-2-methyl-5-(1-pentanesulfonylcarbamoyl)-3H-imidazo[4,5-b]pyridine (208 mg) and propionaldehyde (267 mg).

$^1$H-NMR (CDCl$_3$): 0.89 (3H, t, J=7 Hz), 0.91 (3H, t, J=7 Hz), 1.26–1.68 (6H, m), 1.80–1.97 (2H, m), 2.69 (3H, s), 2.92 (3H, s), 3.17–3.30 (2H, m), 3.48–3.62 (2H, m), 5.46 (2H, s), 6.51 (1H, dd, J=8 and 2 Hz), 6.67 (1H, d, J=2 Hz), 6.80 (1H, d, J=8 Hz), 8.08 (1H, d, J=8 Hz), 8.15 (1H, d, J=8 Hz), 9.92 (1H, br s). MASS (ESI): m/e 504 (M–H)$^-$. m.p. 129–130° C.

EXAMPLE 45

In the same manner as in Example 43, 3-(4-((1-butyl)methylamino)-2-chlorobenzyl)-2-methyl-5-(1-pentanesulfonylcarbamoyl)-3H-imidazo[4,5-b]pyridine (144 mg) was obtained as a white powder from 3-(2-chloro-4-(methylamino)benzyl)-2-methyl-5-(1-pentanesulfonylcarbamoyl)-3H-imidazo[4,5-b]pyridine (206 mg) and butylaldehyde (305 mg).

$^1$H-NMR (CDCl$_3$): 0.89 (3H, t, J=7 Hz), 0.93 (3H, t, J=7 Hz), 1.23–1.65 (8H, m), 1.82–1.97 (2H, m), 2.68 (3H, s), 2.91 (3H, s), 3.22–3.34 (2H, m), 3.49–3.62 (2H, m), 5.46 (2H, s), 6.51 (1H, dd, J=9 and 2 Hz), 6.67 (1H, d, J=2 Hz), 6.80 (1H, d, J=9 Hz), 8.08 (1H, d, J=8 Hz), 8.16 (1H, d, J=8 Hz), 9.92 (1H, br s). MASS (ESI): m/e 518 (M–H)$^-$. m.p. 129–130° C.

EXAMPLE 46

In the same manner as in Example 1, 3-(4-(N-(tert-butoxycarbonyl)-N-methylamino)-2-chlorobenzyl)-2-methyl-5-((4-methylbenzene)sulfonylcarbamoyl)-3H-imidazo[4,5-b]pyridine (2.61 g) was obtained as a colorless powder from 3-(4-(N-(tert-butoxycarbonyl)-N-methylamino)-2-chlorobenzyl)-2-methyl-3H-imidazo[4,5-b]pyridine-5-carboxylic acid (1.90 g).

$^1$H-NMR (CDCl$_3$): 1.48 (9H, s), 2.44 (3H, s), 2.62 (3H, s), 3.28 (3H, s), 5,56 (2H, s), 6.65 (1H, d, J=8 Hz), 7.11 (1H, dd, J=8, 2 Hz), 7.34 (2H, d, J=8 Hz), 7.47 (1H, d, J=2 Hz), 8.03–8.10 (4H, m), 10.10 (1H, s). MASS (ESI): m/z 582 (M–H)$^-$.

EXAMPLE 47

In the same manner as in Example 42, 3-(2-chloro-4-(methylamino)benzyl)-2-methyl-5-((4-methylbenzene)sulfonylcarbamoyl)-3H-imidazo[4,5-b]pyridine (1.84 g) was obtained as a colorless powder from 3-(4-(N-(tert-butoxycarbonyl)-N-methylamino)-2-chlorobenzyl)-2-methyl-5-((4-methylbenzene)sulfonylcarbamoyl)-3H-imidazo[4,5-b]pyridine (2.30 g).

$^1$H-NMR (CDCl$_3$): 2.42 (3H, s), 2.67 (3H, s), 2.85 (3H, s), 3.96 (1H, br), 5.45 (2H, s), 6.50 (1H, dd, J=8, 2 Hz), 6.66 (1H, d, J=2 Hz), 6.82 (1H, d, J=8 Hz), 7.33 (2H, d, J=8 Hz), 7.98–8.05 (4H, m), 10.14 (1H, s). MASS (ESI): m/z 482 (M–H)$^-$. m.p. 210–212° C.

EXAMPLE 48

In the same manner as in Example 43, 3-(2-chloro-4-(dimethylamino)benzyl)-2-methyl-5-((4-methylbenzene)sulfonylcarbamoyl)-3H-imidazo[4,5-b]pyridine (55 mg) was obtained as a colorless powder from 3-(2-chloro-4-(methylamino)benzyl)-2-methyl-5-((4-methylbenzene)sulfonylcarbamoyl)-3H-imidazo[4,5-b]pyridine (220 mg) and 37% aqueous formaldehyde solution (184 mg).

$^1$H-NMR (CDCl$_3$): 2.42 (3H, s), 2.67 (3H, s), 2.97 (6H, s), 5.47 (2H, s), 6.60 (1H, dd, J=8, 2 Hz), 6.74 (1H, d, J=2 Hz), 6.86 (1H, d, J=8 Hz), 7.33 (2H, d, J=8 Hz), 7.98–8.05 (4H, m), 10.17 (1H, s). MASS (ESI): m/e 596 (M–H)$^-$. m.p. 218–220° C.

EXAMPLE 49

In the same manner as in Example 43, 3-(2-chloro-4-(ethylmethylamino)benzyl)-2-methyl-5-((4-methylbenzene)sulfonylcarbamoyl)-3H-imidazo[4,5-b]pyridine (176 mg) was obtained as pale-yellow crystals from 3-(2-chloro-4-(methylamino)benzyl)-2-methyl-5-((4-methylbenzene)sulfonylcarbamoyl)-3H-imidazo[4,5-b]pyridine (220 mg) and acetaldehyde (200 mg).

$^1$H-NMR (CDCl$_3$): 1.13 (3H, t, J=7 Hz), 2.42 (3H, s), 2.67 (3H, s), 2.92 (3H, s), 3.39 (2H, q, J=7 Hz), 5.46 (2H, s), 6.57 (1H, dd, J=8, 2 Hz), 6.71 (1H, d, J=2 Hz), 6.83 (1H, d, J=8 Hz), 7.33 (2H, d, J=8 Hz), 7.98–8.06 (4H, m), 10.19 (1H, s). MASS (ESI): m/z 511 (M–H)$^-$. m.p. 205–207° C.

EXAMPLE 50

In the same manner as in Example 43, 3-(2-chloro-4-(methyl-(1-propyl)amino)benzyl)-2-methyl-5-((4-methylbenzene)sulfonylcarbamoyl)-3H-imidazo[4,5-b]

pyridine (198 mg) was obtained as pale-yellow crystals from 3-(2-chloro-4-(methylamino)benzyl)-2-methyl-5-((4-methylbenzene)sulfonylcarbamoyl)-3H-imidazo[4,5-b]pyridine (220 mg) and propionealdehyde (343 mg).

$^1$H-NMR (CDCl$_3$): 0.92 (3H, t, J=7 Hz), 1.54–1.67 (2H, m), 2.42 (3H, s), 2.67 (3H, s), 2.94 (3H, s), 3.27 (2H, t, J=7 Hz), 5.46 (2H, s), 6.55 (1H, dd, J=8, 2 Hz), 6.69 (1H, d, J=2 Hz), 6.82 (1H, d, J=8 Hz), 7.33 (2H, d, J=8 Hz), 7.98–8.06 (4H, m), 10.19 (1H, s). MASS (ESI): m/z 524 (M–H)$^-$. m.p. 178–180° C.

EXAMPLE 51

In the same manner as in Example 43, 3-(2-chloro-4-((1-butyl)methylamino)benzyl)-2-methyl-5-((4-methylbenzene)sulfonylcarbamoyl)-3H-imidazo[4,5-b]pyridine (207 mg) was obtained as pale-yellow crystals from 3-(2-chloro-4-(methylamino)benzyl)-2-methyl-5-((4-methylbenzene)sulfonylcarbamoyl)-3H-imidazo[4,5-b]pyridine (220 mg) and butylaldehyde (426 mg).

$^1$H-NMR (CDCl$_3$): 0.94 (3H, t, J=7 Hz), 1.27–1.40 (2H, m), 1.50–1.60 (2H, m), 2.42 (3H, s), 2.67 (3H, s), 2.94 (3H, s), 3.30 (2H, t, J=7 Hz), 5.46 (2H, s), 6.54 (1H, dd, J=8, 2 Hz), 6.69 (1H, d, J=2 Hz), 6.81 (1H, d, J=8 Hz), 7.33 (2H, d, J=8 Hz), 7.98–8.05 (4H, m), 10.19 (1H, s). MASS (ESI): m/z 538 (M–H)$^-$. m.p. 129–132° C.

EXAMPLE 52

In the same manner as in Example 1, 3-(2-chloro-4-(methyl-(1-pentyl)amino)benzyl)-2-methyl-5-(1-pentanesulfonylcarbamoyl)-3H-imidazo[4,5-b]pyridine (137 mg) was obtained as pale-yellow crystals from 3-(2-chloro-4-(methyl-(1-pentyl)amino)benzyl)-2-methyl-3H-imidazo[4,5-b]pyridine-5-carboxylic acid (180 mg) and 1-pentanesulfonamide (306 mg).

$^1$H-NMR (CDCl$_3$): 0.88 (6H, t, J=7 Hz), 1.22–1.47 (8H, m), 1.47–1.60 (2H, m), 1.85–1.95 (2H, m), 2.68 (3H, s), 2.92 (3H, s), 3.26 (2H, t, J=7 Hz), 3.55 (2H, t, J=7 Hz), 5.46 (2H, s), 6.50 (1H, dd, J=8, 2 Hz), 6.67 (1H, d, J=2 Hz), 6.78 (1H, d, J=8 Hz), 8.06 (1H, d, J=8 Hz), 8.15 (1H, d, J=8 Hz), 9.92 (1H, s). MASS(ESI): m/z 532(M–H)$^{31}$. m.p. 83–85° C.

EXAMPLE 53

In the same manner as in Example 1, 3-(2-chloro-4-(N-(cyclohexylmethyl)methylamino)benzyl)-2-methyl-5-(1-pentanesulfonylcarbamoyl)-3H-imidazo[4,5-b]pyridine (105 mg) was obtained as a white powder from 3-(2-chloro-4-(N-(cyclohexylmethyl)methylamino)benzyl)-2-methyl-3H-imidazo[4,5-b]pyridine-5-carboxylic acid (106 mg) and 1-pentanesulfonamide (60 mg).

$^1$H-NMR (CDCl$_3$): 0.80–2.00 (17H, m), 0.89 (3H, t, J=7 Hz), 2.69 (3H, s), 2.93 (3H, s), 3.09 (2H, d, J=7 Hz), 3.49–3.64 (2H, m), 5.47 (2H, s), 6.48 (1H, dd, J=9 and 2 Hz), 6.65 (1H, d, J=2 Hz), 6.78 (1H, d, J=9 Hz), 8.08 (1H, d, J=8 Hz), 8.16 (1H, d, J=8 Hz), 9.92 (1H, br s). MASS (ESI): m/e 558 (M–H)$^-$. m.p. 169–170° C.

EXAMPLE 54

In the same manner as in Example 1, 3-(2-chloro-4-(N-(cyclohexylmethyl)methylamino)benzyl)-2-methyl-5-((4-methylbenzene)sulfonylcarbamoyl)-3H-imidazo[4,5-b]pyridine(101 mg) was obtained as a white powder from 3-(2-chloro-4-(N-(cyclohexylmethyl)methylamino)benzyl)-2-methyl-3H-imidazo[4,5-b]pyridine-5-carboxylic acid (99 mg) and (4-methylbenzene)sulfonamide (62 mg).

$^1$H-NMR (CDCl$_3$): 0.83–1.34 (6H, m), 1.60–1.82 (5H, m), 2.42 (3H, s), 2.67 (3H, s), 2.96 (3H, s), 3.12 (2H, d, J=7 Hz), 5.47 (2H, s), 6.52 (1H, dd, J=9 and 2 Hz), 6.67 (1H, d, J=2 Hz), 6.80 (1H, d, J=9 Hz), 7.33 (2H, d, J=8 Hz), 7.97–8.10 (4H, m), 10.20 (1H, br s). MASS (ESI): m/e 578 (M–H)$^{31}$. m.p. 194–195° C.

EXAMPLE 55

In the same manner as in Example 1, 3-(4-bromo-2-chlorobenzyl)-2,7-dimethyl-5-[(4-methylbenzene)sulfonylcarbamoyl]-3H-imidazo[4,5-b]pyridine was obtained as colorless crystals (161 mg) from 3-(4-bromo-2-chlorobenzyl)-2,7-dimethyl-3H-imidazo[4,5-b]pyridine-5-carboxylic acid (160 mg) and (4-methylbenzene)sulfonamide (104 mg).

$^1$H-NMR (CDCl$_3$): 2.41 (3H, s), 2.59 (3H, s), 2.68 (3H, s), 5.50 (2H, s), 6.59 (1H, d, J=8 Hz), 7.30–7.38 (3H, m), 7.68 (1H, d, J=2 Hz), 7.90 (1H, br s), 8.04 (2H, d, J=8 Hz). MASS (ESI): m/z 547 (M–1). m.p. 206–208° C.

EXAMPLE 56

3-(4-Bromo-2-chlorobenzyl)-2,7-dimethyl-5-[(4-methylbenzene)sulfonylcarbamoyl]-3H-imidazo[4,5-b]pyridine (400 mg) was dissolved in toluene (5 ml), and sodium tert-butylate (98 mg), N-methylethylamine (216 mg), (R)-(+)-2,2'-bis(diphenylphosphino)-1,1'-binaphthyl (3.4 mg) and tris(dibenzylideneacetone) dipalladium(0)(1.7 mg) were successively added in a nitrogen atmosphere. The mixture was stirred at 100° C. for 24 hr. The reaction mixture was concentrated under reduced pressure, and water was added. 1N Hydrochloric acid was added to adjust to pH 7 and the mixture was extracted with chlorform:methanol= 4:1. The organic layer was washed with saturated brine, dried over anhydrous magnesium sulfate, and concentrated under reduced pressure. To the residue was added ethanol (5.0 ml), and the mixture was heated and allowed to cool. The precipitated crystals were collected by filtration. The crystals were dissolved in N,N-dimethylformamide (1.8 ml) and water (1.2 ml) was gradually added on an oil bath at 80° C. The mixture was allowed to cool and precipitated crystals were collected by filtration and dried under reduced pressure with heating to give 3-(2-chloro-4-(ethylmethylamino) benzyl)-2,7-dimethyl-5-[(4-methylbenzene) sulfonylcarbamoyl]-3H-imidazo[4,5-b]pyridine (79 mg) as pale-yellow crystals.

$^1$H-NMR (CDCl$_3$): 1.14 (3H, t, J=7 Hz), 2.42 (3H, s), 2.65 (3H, s), 2.66 (3H, s), 2.92 (3H, s), 3.39 (2H, q, J=7 Hz), 5.44 (2H, s), 6.55 (1H, dd, J=8, 2 Hz), 6.72 (1H, d, J=2 Hz), 6.78 (1H, d, J=8 Hz), 7.32 (2H, d, J=8 Hz), 7.85 (1H, s), 8.04 (2H, d, J=8 Hz), 10.20 (1H, s). MASS (ESI): m/z 524 (M–H)$^{31}$. m.p. 212–215° C.

EXAMPLE 57

In the same manner as in Example 1, 3-[(3-chloro-5-(trifluoromethyl)-2-pyridyl)methyl]-2-methyl-5-(1-pentanesulfonylcarbamoyl)-3H-imidazo[4,5-b]pyridine was obtained as a colorless solid (108 mg) from 3-[(3-chloro-5-(trifluoromethyl)-2-pyridyl)methyl]-2-methyl-3H-imidazo[4,5-b]pyridine-5-carboxylic acid (130 mg) and 1-pentanesulfonamide (80 mg).

$^1$H-NMR (CDCl$_3$): 0.88 (3H, t, J=7 Hz), 1.26–1.49 (4H, m), 1.82–1.95 (2H, m), 2.69 (3H, s), 3.51–3.60 (2H, m), 5.76 (2H, s), 8.05 (1H, br s), 8.12 (1H, d, J=8 Hz), 8.19 (1H, d, J=8 Hz), 8.58 (1H, br s), 9.88 (1H, br s). MASS (ESI): m/z 502 (M–1). m.p. 169–170° C.

EXAMPLE 58

In the same manner as in Example 1, 3-[(3-chloro-5-(trifluoromethyl)-2-pyridyl)methyl]-2-methyl-5-[(4- methylbenzene)sulfonylcarbamoyl]-3H-imidazo[4,5-b]pyridine was obtained as a colorless solid (271 mg) from 3-[(3-chloro-5-(trifluoro-methyl)-2-pyridyl)methyl]-2-methyl-3H-imidazo[4,5-b]pyridine-5-carboxylic acid (130 mg) and (4-methylbenzene)sulfonamide (90 mg).

$^1$H-NMR (CDCl$_3$): 2.42 (3H, s), 2.67 (3H, s), 5.77 (2H, s), 7.33 (2H, d, J=8 Hz), 8.01–8.11 (4H, m), 8.59 (1H, br s), 10.16 (1H, br s). MASS (ESI): m/z 524 (M+1). m.p. 231–232° C.

EXAMPLE 59

In the same manner as in Example 1, 3-(2-chloro-4-phenylbenzyl)-2-ethoxy-5-(1-pentanesulfonylcarbamoyl)-3H-imidazo[4,5-b]pyridine was synthesized as a pale-brown powder (26 mg).

$^1$H-NMR (CDCl$_3$): 0.85 (3H, t, J=6 Hz), 1.20–1.45 (4H), 1.54 (3H, t, J=7 Hz), 1.85 (2H, m), 3.52 (2H, t, J=6 Hz), 4.74 (2H, q, J=7 Hz), 5.45 (2H, s), 7.20 (1H, d, J=8 Hz), 7.34–7.50 (4H), 7.56 (2H, d, J=8 Hz), 7.68 (1H, d, J=1 Hz), 7.88 (1H, d, J=8 Hz), 8.10 (1H, d, J=8 Hz). MASS (ESI): m/z 539 (M).

EXAMPLE 60

In the same manner as in Example 1, 3-(2-chloro-4-phenylbenzyl)-2-methyl-5-[(1-propylaminosulfonyl)carbamoyl]-3H-imidazo[4,5-b]pyridine was obtained as colorless crystals (209 mg) from 3-(2-chloro-4-phenylbenzyl)-2-methyl-3H-imidazo[4,5-b]pyridine-5-carboxylic acid (200 mg) and N-(1-propyl)sulfonamide (110 mg).

$^1$H-NMR (CDCl$_3$) 0.90 (3H, t, J=7 Hz), 1.48–1.64 (2H, m), 2.68 (3H, s), 2.94–3.05 (2H, m), 5.30 (1H, br s), 5.63 (2H, s), 6.80 (1H, d, J=8 Hz), 7.34–7.50 (4H, m), 7.55 (2H, br d, J=8 Hz), 7.71 (1H, br s), 8.12 (1H, d, J=8 Hz), 8.19 (1H, d, J=8 Hz), 9.95 (1H, br s). MASS (ESI): m/z 496 (M–1). m.p. 208–209° C.

EXAMPLE 61

In the same manner as in Example 1, 3-[(3-chloro-5-(trifluoromethyl)-2-pyridyl)methyl]-2,7-dimethyl-5-[(4-methylbenzene)sulfonylcarbamoyl]-3H-imidazo[4,5-b]pyridine was obtained as a colorless solid (173 mg) from 3-[(3-chloro-5-(trifluoromethyl)-2-pyridyl)methyl]-2,7-dimethyl-3H-imidazo[4,5-b]pyridine-5-carboxylic acid (180 mg) and p-toluenesulfonamide (120 mg).

$^1$H-NMR (CDCl$_3$): 2.42 (3H, s), 2.66 (3H, s), 2.67 (3H, s), 5.74 (2H, s), 7.32 (2H, br d, J=8 Hz), 7.88 (1H, s), 8.00–8.08 (3H, m), 8.58 (1H, br s), 10.16 (1H, br s). MASS (ESI): m/z 536 (M-1). m.p. 211–212° C.

EXAMPLE 62

In the same manner as in Example 1, 3-[(2,6-dichloro-3-pyridyl)methyl]-2-methyl-5-(1-pentanesulfonylcarbamoyl)-3H-imidazo[4,5-b]pyridine was obtained as a colorless solid (167 mg) from 3-[(2,6-dichloro-3-pyridyl)methyl]-2-methyl-3H-imidazo[4,5-b]pyridine-5-carboxylic acid (180 mg) and 1-pentanesulfonamide (121 mg).

$^1$H-NMR (CDCl$_3$): 0.89 (3H, t, J=7 Hz), 1.26–1.50 (4H, m), 1.82–1.95 (2H, m), 2.64 (3H, s), 3.51–3.61 (2H, m), 5.56 (2H, s), 7.03 (1H, d, J=8 Hz), 7.25 (1H, d, J=8 Hz), 8.17 (1H, d, J=8 Hz), 8.24 (1H, d, J=8 Hz), 9.73 (1H, br s). m.p. 233–234° C.

EXAMPLE 63

In the same manner as in Example 1, 3-[(2,6-dichloro-3-pyridyl)methyl]-2-methyl-5-[(4-methylbenzene)sulfonylcarbamoyl]-3H-imidazo[4,5-b]pyridine was obtained as a colorless solid (165 mg) from 3-[(2,6-dichloro-3-pyridyl)methyl]-2-methyl-3H-imidazo[4,5-b]pyridine-5-carboxylic acid (180 mg) and p-toluenesulfonamide (137 mg).

$^1$H-NMR (CDCl$_3$): 2.43 (3H, s), 2.63 (3H, s), 5.57 (2H, s), 7.05 (1H, d, J=8 Hz), 7.25 (1H, d, J=8 Hz), 7.35 (2H, br d, J=8 Hz), 8.05 (2H, br d, J=8 Hz), 8.09 (1H, d, J=8 Hz), 8.12 (1H, d, J=8 Hz), 10.05 (1H, br s). m.p. 226–227° C.

EXAMPLE 64

To a suspension of 3-(2-chloro-4-(methylamino)benzyl)-2-methyl-5-(1-pentanesulfonylcarbamoyl)-3H-imidazo[4,5-b]pyridine (188 mg) in dichloromethane (1.9 ml) were added pyridine (58 mg) and pivaloyl chloride (65 mg) at room temperature and the mixture was stirred for 2 days. The reaction mixture was diluted with chloroform, washed successively with water and saturated brine, and dried over anhydrous magnesium sulfate. The solvent was evaporated and ethanol was added to the residue to give crude crystals. Ethanol was evaporated, and the residue was recrystallized from acetone-water to give 3-(2-chloro-4-(methyl(pivaloyl)amino)benzyl)-2-methyl-5-(1-pentanesulfonylcarbamoyl)-3H-imidazo[4,5-b]pyridine (199 mg) as a white powder.

$^1$H-NMR (CDCl$_3$): 0.89 (3H, t, J=7 Hz), 1.09 (9H, s), 1.25–1.52 (4H, m), 1.82–1.97 (2H, m), 2.63 (3H, s), 3.23 (3H, s), 3.52–3.62 (2H, m), 5.61 (2H, s), 6.68 (1H, d, J=9 Hz), 7.07 (1H, dd, J=9 and 2 Hz), 7.39 (1H, d, J=2 Hz), 8.16 (1H, d, J=8 Hz), 8.23 (1H, d, J=8 Hz), 9.82 (1H, br s). MASS (ESI): m/e 546 (M–H)[31]. m.p. 207–208° C.

EXAMPLE 65

To a suspension of 3-(2-chloro-4-(methylamino)benzyl)-2-methyl-5-(1-pentanesulfonylcarbamoyl)-3H-imidazo[4,5-b]pyridine (278 mg) in dichloromethane (3 ml) were added pyridine (148 mg) and ethyl chlorocarbonate (129 mg) under ice-cooling, and the mixture was stirred for 24 hr. The solvent was evaporated and the residue was purified by silica gel column chromatography (ethyl acetate) and recrystallized from ethyl acetate-hexane to give 3-(4-(N-(ethoxycarbonyl)-N-methylamino)-2-chlorobenzyl)-2-methyl-5-(1-pentanesulfonylcarbamoyl)-3H-imidazo[4,5-b]pyridine (126 mg) as a white powder.

$^1$H-NMR (CDCl$_3$): 0.89 (3H, t, J=7 Hz), 1.25–1.52 (4H, m), 1.27 (3H, t, J=7 Hz), 1.83–198 (2H, m), 2.65 (3H, s), 3.30 (3H, s), 3.50–3.62 (2H, m), 4.19 (2H, q, J=7 Hz), 5.56 (2H, s), 6.65 (1H, d, J=8 Hz), 7.11 (1H, dd, J=8 and 2 Hz), 7.46 (1H, d, J=2 Hz), 8.14 (1H, d, J=8 Hz), 8.21 (1H, d, J=8 Hz), 9.82 (1H, br s). MASS (ESI): m/e 534 (M–H)[31]. m.p. 149–150° C.

EXAMPLE 66

In the same manner as in Example 1, 5-(1-butanesulfonylcarbamoyl)-3-(2-chloro-4-(1-pentyloxy)benzyl)-2-ethyl-3H-imidazo[4,5-b]pyridine was obtained as colorless crystals (147 mg) from 3-(2-chloro-4-(1-pentyloxy)benzyl)-2-ethyl-3H-imidazo[4,5-b]pyridine-5-carboxylic acid (200 mg) and 1-butanesulfonamide (102 mg).

$^1$H-NMR (CDCl$_3$): 0.87–0.99 (6H, m), 1.30–1.58 (9H, m), 1.70–1.93 (4H, m), 2.91 (2H, q, J=7 Hz), 3.50–3.60 (2H, m), 3.93 (2H, t, J=7 Hz), 5.51 (2H, s), 6.65–6.75 (2H, m), 7.00 (1H, s), 8.11–8.22 (2H, m). MS (ESI): m/z 519 (M–1). m.p. 140–142° C.

EXAMPLE 67

In the same manner as in Example 1, 5-(1-butanesulfonylcarbamoyl)-3-(2-chloro-4-

(cyclohexylmethyloxy)benzyl)-2-ethyl-3H-imidazo[4,5-b]pyridine was obtained as colorless crystals (184 mg) from 3-(2-chloro-4-(cyclohexylmethyloxy)benzyl)-2-ethyl-3H-imidazo[4,5-b]pyridine-5-carboxylic acid (200 mg) and 1-butanesulfonamide (96.2 mg).

$^1$H-NMR (CDCl$_3$): 0.94 (3H, t, J=7 Hz), 0.99–1.56 (11H, m), 1.65–1.94 (7H, m), 2.92 (2H, q, J=7 Hz), 3.52–3.60 (2H, m), 3.72 (2H, d, J=7 Hz), 5.52 (2H, s), 6.65–75 (2H, m), 7.00 (1H, d, J=1 Hz), 8.15 (1H, d, J=8 Hz), 8.19 (1H, d, J=8 Hz). MS (ESI): m/z 545 (M−1). m.p. 145–146° C.

EXAMPLE 68

In the same manner as in Example 1, 3-(2-chloro-4-(cyclohexylmethyloxy)benzyl)-2-ethyl-5-(1-pentanesulfonylcarbamoyl)-3H-imidazo[4,5-b]pyridine was obtained as colorless crystals (183 mg) from 3-(2-chloro-4-(cyclohexylmethyloxy)benzyl)-2-ethyl-3H-imidazo[4,5-b]pyridine-5-carboxylic acid (200 mg) and 1-pentanesulfonamide (106 mg).

$^1$H-NMR (CDCl$_3$): 0.89 (3H, t, J=7Hz), 0.95–1.50 (13H, m), 1.63–1.95 (7H, m), 2.92 (2H, q, J=7 Hz), 3.52–3.60 (2H, m), 3.72 (2H, d, J=7 Hz), 5.52 (2H, s), 6.65–75 (2H, m), 7.00 (1H, d, J=1 Hz), 8.15 (1H, d, J=8 Hz), 8.19 (1H, d, J=8 Hz). MS (ESI): m/z 559 (M−1). m.p. 137–139° C.

EXAMPLE 69

In the same manner as in Example 1, 5-(1-butanesulfonylcarbamoyl)-3-[2-chloro-4-(2-furyl)benzyl]-2-methyl-3H-imidazo[4,5-b]pyridine was obtained as colorless crystals (206 mg) from 3-[2-chloro-4-(2-furyl)benzyl]-2-methyl-3H-imidazo[4,5-b]pyridine-5-carboxylic acid (200 mg) and 1-butanesulfonamide (112 mg).

$^1$H-NMR (CDCl$_3$): 0.90 (3H, t, J=8 Hz), 1.36–1.52 (2H, m), 1.76–1.89 (2H, m), 2.66 (3H, s), 3.49–3.59 (2H, m), 5.58 (2H, s), 6.49 (1H, m), 6.70 (1H, d, J=5 Hz), 6.81 (1H, d, J=8 Hz), 7.46–7.51 (2H, m), 7.78 (1H, d, J=1 Hz), 8.13 (1H, d, J=8 Hz), 8.20 (1H, d, J=8 Hz), 9.83 (1H, br s). MASS (ESI): m/z 485 (M−1). m.p. 208–209° C.

EXAMPLE 70

In the same manner as in Example 1, 3-[2-chloro-4-(2-furyl)benzyl]-2-methyl-5-(1-pentanesulfonylcarbamoyl)-3H-imidazo[4,5-b]pyridine was obtained as colorless crystals (199 mg) from 3-[2-chloro-4-(2-furyl)benzyl]-2-methyl-3H-imidazo[4,5-b]pyridine-5-carboxylic acid (200 mg) and 1-pentanesulfonamide (120 mg).

$^1$H-NMR (CDCl$_3$): 0.86 (3H, t, J=8 Hz), 1.22–1.45 (4H, m), 1.78–1.90 (2H, m), 2.66 (3H, s), 3.49–3.56 (2H, m), 5.59 (2H, s), 6.49 (1H, m), 6.70 (1H, d, J=5 Hz), 6.80 (1H, d, J=8 Hz), 7.45–7.51 (2H, m), 7.77 (1H, d, J=1 Hz), 8.13 (1H, d, J=8 Hz), 8.20 (1H, d, J=8 Hz), 9.83 (1H, br 9). MASS (ESI): m/z 499 (M−1). m.p. 184–185° C.

EXAMPLE 71

In the same manner as in Example 1, 3-[2-chloro-4-(2-furyl)benzyl]-2-methyl-5-[(4-methylbenzene)sulfonylcarbamoyl]-3H-imidazo[4,5-b]pyridine was obtained as colorless crystals (205 mg) from 3-[2-chloro-4-(2-furyl)benzyl]-2-methyl-3H-imidazo[4,5-b]pyridine-5-carboxylic acid (200 mg) and p-toluenesulfonamide (140 mg).

$^1$H-NMR (CDCl$_3$): 2.39 (3H, s), 2.65 (3H, s), 5.58 (2H, s), 6.51 (1H, m), 6.73 (1H, d, J=5 Hz), 6.85 (1H, d, J=8 Hz), 7.27 (2H, d, J=8 Hz), 7.50–7.56 (2H, m), 7.79 (1H, d, J=1 Hz), 7.99 (2H, d, J=8 Hz), 8.05 (1H, d, J=8 Hz), 8.08 (1H, d, J=8 Hz), 10.09 (1H, br s). MASS (ESI): m/z 519 (M−1). m.p. 207–208° C.

EXAMPLE 72

In the same manner as in Example 1, 3-[4-(N-(tert-butoxycarbonyl)-N-ethylamino)-2-chlorobenzyl]-2-methyl-5-(1-pentanesulfonylcarbamoyl)-3H-imidazo[4,5-b]pyridine was obtained as a colorless solid (167 mg) from 3-[4-(N-(tert-butoxycarbonyl)-N-ethylamino)-2-chlorobenzyl]-2-methyl-3H-imidazo[4,5-b]pyridine-5-carboxylic acid (170 mg) and 1-pentanesulfonamide (100 mg).

$^1$H-NMR (CDCl$_3$): 0.90 (3H, t, J=7 Hz), 1.16 (3H, t, J=7 Hz), 1.27–1.53 (13H, m), 1.84–1.96 (2H, m), 2.62 (3H, s), 3.66 (3H, q, J=7 Hz), 5.57 (2H, s), 6.63 (1H, d, J=8 Hz), 7.05 (1H, dd, J=8 Hz), 7.41 (1H, d, J=1 Hz), 8.14 (1H, d, J=8 Hz), 8.21 (1H, d, J=8 Hz), 9.85 (1H, br s). MASS (ESI): m/z 576 (M−1). m.p. 131–132° C.

EXAMPLE 73

In the same manner as in Example 1, 3-(4-(N-(tert-butoxycarbonyl)-N-ethylamino)-2-chlorobenzyl)-2-methyl-5-((4-methylbenzene)sulfonylcarbamoyl)-3H-imidazo[4,5-b]pyridine(631 mg) was obtained as a pale-yellow powder from 3-(4-(N-(tert-butoxycarbonyl)-N-ethylamino)-2-chlorobenzyl)-2-methyl-3H-imidazo[4,5-b]pyridine-5-carboxylic acid (519 mg) and (4-methylbenzene)sulfonamide (300 mg).

$^1$H-NMR (CDCl$_3$): 1.17 (3H, t, J=7 Hz), 1.46 (9H, s), 2.42 (3H, s), 2.61 (3H, s), 3.68 (2H, q, J=7 Hz), 5.57 (2H, s), 6.63 (1H, d, J=8 Hz), 7.05 (1H, dd, J=8, 2 Hz), 7.34 (2H, d, J=8 Hz), 7.43 (1H, d, J=2 Hz), 8.04–8.12 (4H, m), 10.13 (1H, s). MASS (ESI): m/z 596 (M−H)[31]. m.p. 205–207° C.

EXAMPLE 74

In the same manner as in Example 42, 3-(2-chloro-4-(ethylamino)benzyl)-2-methyl-5-((4-methylbenzene)sulfonylcarbamoyl)-3H-imidazo[4,5-b]pyridine (349 mg) was obtained as colorless crystals from 3-(4-(N-(tert-butoxycarbonyl)-N-ethylamino)-2-chlorobenzyl)-2-methyl-5-((4-methylbenzene)sulfonylcarbamoyl)-3H-imidazo[4,5-b]pyridine (587 mg).

$^1$H-NMR (CDCl$_3$): 1.26 (3H, t, J=7 Hz), 2.42 (3H, s), 2.66 (3H, s), 3.17 (2H, q, J=7 Hz), 3.80 (1H, br s), 5.45 (2H, s), 6.49 (1H, dd, J=8, 2 Hz), 6.65 (1H, d, J=2 Hz), 6.80 (1H, d, J=8 Hz), 7.33 (2H, d, J=8 Hz), 7.98–8.17 (4H, m), 10.13 (1H, s). MASS (ESI): m/z 496 (M−H)[31]. m.p. 235–237° C.

EXAMPLE 75

In the same manner as in Example 43, 3-(2-chloro-4-(N,N-diethylamino)benzyl)-2-methyl-5-((4-methylbenzene)sulfonylcarbamoyl)-3H-imidazo[4,5-b]pyridine (125 mg) was obtained as colorless crystals from 3-(2-chloro-4-(ethylamino)benzyl)-2-methyl-5-((4-methylbenzene)sulfonylcarbamoyl)-3H-imidazo[4,5-b]pyridine (155 mg) and acetaldehyde (137 mg).

$^1$H-NMR (CDCl$_3$): 1.66 (6H, t, J=7 Hz), 2.42 (3H, s), 2.68 (3H, s), 3.34 (4H, q, J=7 Hz), 5.46 (2H, s), 6.52 (1H, dd, J=8, 2 Hz), 6.69 (1H, d, J=2 Hz), 6.80 (1H, d, J=8 Hz), 7.33 (2H, d, J=8 Hz), 7.99–8.07 (4H, m), 10.20 (1H, s). MASS (ESI): m/z 524 (M−H)[31]. m.p. 185–187° C.

EXAMPLE 76

In the same manner as in Example 43, 3-(2-chloro-4-(N-ethyl-N-(1-pentyl)amino)benzyl)-2-methyl-5-((4- methylbenzene)sulfonylcarbamoyl)-3H-imidazo[4,5-b]pyridine (80 mg) was obtained as colorless crystals from 3-(2-chloro-4-(ethylamino)benzyl)-2-methyl-5-((4-methylbenzene)sulfonylcarbamoyl)-3H-imidazo[4,5-b]pyridine (210 mg) and valeraldehyde (726 mg).

$^1$H-NMR (CDCl$_3$): 0.91 (3H, t, J=7 Hz), 0.15 (3H, t, J=7 Hz), 1.24–1.40 (4H, m), 1.54–1.64 (2H, m), 2.42 (3H, s), 2.67 (3H, s), 3.22 (2H, t, J=7 Hz), 3.34 (2H, q, J=7 Hz), 5.46 (2H, s), 6.49 (1H, dd, J=8, 2 Hz), 6.66 (1H, d, J=2 Hz), 6.77 (1H, d, J=8 Hz), 7.33 (2H, d, J=8 Hz), 7.98–8.07 (4H, m), 10.21 (1H, s). MASS (ESI): m/z 566 (M–H)$^{31}$. m.p. 162–164° C.

EXAMPLE 77

In the same manner as in Example 1, 3-(4-(N-(tert-butoxycarbonyl)-N-methylamino)-2-chlorobenzyl)-2,7-dimethyl-5-(1-pentanesulfonylcarbamoyl)-3H-imidazo[4,5-b]pyridine (185 mg) was obtained as pale-yellow crystals from 3-(4-(N-(tert-butoxycarbonyl)-N-methylamino)-2-chlorobenzyl)-2,7-dimethyl-3H-imidazo[4,5-b]pyridine-5-carboxylic acid (200 mg) and 1-pentanesulfonamide (102 mg).

$^1$H-NMR (CDCl$_3$): 0.89 (3H, t, J=7 Hz), 1.25–1.50 (4H, m), 1.46 (9H, s), 1.83–1.95 (2H, m), 2.62 (3H, s), 2.74 (3H, s), 3.25 (3H, s), 3.56 (2H, t, J=7 Hz), 5.53 (2H, s), 6.60 (1H, d, J=8 Hz), 7.08 (1H, dd, J=8, 2 Hz), 7.44 (1H, d, J=2 Hz), 8.02 (1H, s), 9.87 (1H, s). MASS (ESI): m/z 576 (M–H)$^{31}$. m.p. 193–194° C.

EXAMPLE 78

In the same manner as in Example 1, 3-(4-(N-(tert-butoxycarbonyl)-N-methylamino)-2-chlorobenzyl)-2,7-dimethyl-5-((4-methylbenzene)sulfonylcarbamoyl)-3H-imidazo[4,5-b]pyridine(625 mg) was obtained as pale-yellow crystals from 3-(4-(N-(tert-butoxycarbonyl)-N-methylamino)-2-chlorobenzyl)-2,7-dimethyl-3H-imidazo[4,5-b]pyridine-5-carboxylic acid (587 mg) and (4-methylbenzene)sulfonamide (339 mg).

$^1$H-NMR (CDCl$_3$): 1.47 (9H, s), 2.42 (3H, s), 2.60 (3H, s), 2.68 (3H, s), 3.26 (3H, s), 5.54 (2H, s), 6.60 (1H, d, J=8 Hz), 7.08 (1H, dd, J=8, 2 Hz), 7.33 (2H, d, J=8 Hz), 7.47 (1H, d, J=2 Hz), 7.91 (1H, s), 8.05 (2H, d, J=8 Hz), 10.13 (1H, s). MASS (ESI): m/z 596 (M–H)$^{31}$. m.p. 194–196° C.

EXAMPLE 79

In the same manner as in Example 42, 3-(2-chloro-4-(methylamino)benzyl)-2,7-dimethyl-5-((4-methylbenzene)sulfonylcarbamoyl)-3H-imidazo[4,5-b]pyridine (300 mg) was obtained as pale-yellow crystals from 3-(4-(N-(tert-butoxycarbonyl)-N-methylamino)-2-chlorobenzyl)-2,7-dimethyl-5-((4-methylbenzene)sulfonylcarbamoyl)-3H-imidazo[4,5-b]pyridine (420 mg).

$^1$H-NMR (CDCl$_3$): 2.42 (3H, s), 2.65 (3H, s), 2.65 (3H, s), 2.84 (3H, s), 3.95 (1H, br s), 5.43 (2H, s), 6.48 (1H, dd, J=8, 2 Hz), 6.65 (1H, d, J=2 Hz), 6.76 (1H, d, J=8 Hz), 7.32 (2H, d, J=8 Hz), 7.85 (1H, s), 8.04 (2H, d, J=8 Hz), 10.15 (1H, s). MASS (ESI): m/z 496 (M–H)$^{31}$.

EXAMPLE 80

In the same manner as in Example 43, 3-(2-chloro-4-(N-methyl-N-propylamino)benzyl)-2,7-dimethyl-5-((4-methylbenzene)sulfonylcarbamoyl)-3H-imidazo[4,5-b]pyridine (274 mg) was obtained as pale-yellow crystals from 3-(2-chloro-4-(methylamino)benzyl)-2,7-dimethyl-5-((4-methylbenzene)sulfonylcarbamoyl)-3H-imidazo[4,5-b]pyridine (286 mg) and propionealdehyde (1.00 g).

$^1$H-NMR (CDCl$_3$): 0.92 (3H, t, J=7 Hz), 1.54–1.66 (2H, m), 2.42 (3H, s), 2.65 (3H, s), 2.66 (3H, s), 2.94 (3H, s), 3.26 (2H, t, J=7 Hz), 5.44 (2H, s), 6.53 (1H, dd, J=8, 2 Hz), 6.69 (1H, d, J=2 Hz), 6.77 (1H, d, J=8 Hz), 7.32 (2H, d, J=8 Hz), 7.85 (1H, s), 8.04 (2H, d, J=8 Hz) MASS (ESI): m/z 538 (M–H)$^{31}$. m.p. 194–195° C.

EXAMPLE 81

In the same manner as in Example 1, 3-[4-(N-(tert-butoxycarbonyl)-N-ethylamino)-2-chlorobenzyl]-2,7-dimethyl-5-(1-pentanesulfonylcarbamoyl)-3H-imidazo[4,5-b]pyridine (185 mg) was obtained as pale-brown crystals from 3-[4-(N-(tert-butoxycarbonyl)-N-ethylamino)-2-chlorobenzyl]-2,7-dimethyl-3H-imidazo[4,5-b]pyridine-5-carboxylic acid (220 mg).

$^1$H-NMR (CDCl$_3$): 0.89 (3H, t, J=6 Hz), 1.15 (3H, t, J=6 Hz), 1.35 (4H, m), 1.45 (9H, s), 1.89 (2H, m), 2.62 (3H, s), 2.75 (3H, s), 3.55 (2H, m), 3.66 (2H, q, J=6 Hz), 5.55 (2H, s), 6.59 (1H, d, J=8 Hz), 7.03 (1H, dd, J=8, 2 Hz), 7.39 (1H, d, J=2 Hz), 8.03 (1H, s), 9.85 (1H, br. s). MASS (ESI): m/z 592 (M). m.p. 190–191° C.

EXAMPLE 82

In the same manner as in Example 1, 3-[4-(N-(tert-butoxycarbonyl)-N-ethylamino)-2-chlorobenzyl]-2,7-dimethyl-5-((4-methylbenzene)sulfonylcarbamoyl)-3H-imidazo[4,5-b]pyridine (170 mg) was obtained as pale-brown crystals from 3-[4-(N-(tert-butoxycarbonyl)-N-ethylamino)-2-chlorobenzyl]-2,7-dimethyl-3H-imidazo[4,5-b]pyridine-5-carboxylic acid 220 mg).

$^1$H-NMR (CDCl$_3$) 1.17 (3H, t, J=6 Hz), 1.45 (9H, s), 2.42 (3H, s), 2.60 (3H, s), 2.69 (3H, s), 3.68 (2H, q, J=6 Hz), 5.55 (2H, s), 6.59 (1H, d, J=8 Hz), 7.03 (1H, dd, J=8, 2 Hz), 7.33 (2H, d, J=8 Hz), 7.41 (1H, d, J=2 Hz), 7.92 (1H, s), 8.05 (2H, d, J=8 Hz), 10.12 (1H, br. s). MASS (ESI): m/z 612 (M). m.p. 163–165° C.

EXAMPLE 83

In the same manner as in Example 1, 3-(2-chloro-4-(1-pyrrolyl)benzyl)-2-methyl-5-(1-pentanesulfonylcarbamoyl)-3H-imidazo[4,5-b]pyridine (198 mg) was obtained as colorless crystals from 3-(2-chloro-4-(1-pyrrolyl)benzyl)-2-methyl-3H-imidazo[4,5-b]pyridine-5-carboxylic acid (200 mg) and 1-pentanesulfonamide (124 mg).

$^1$H-NMR (CDCl$_3$): 0.87 (3H, t, J=7Hz), 1.25–1.45 (4H, m), 1.80–1.90 (2H, m), 2.68 (3H, s), 3.54 (2H, t, J=7 Hz), 5.58 (2H, s), 6.35 (2H, t, J=2 Hz), 6.86 (1H, d, J=8 Hz), 7.07 (2H, t, J=2 Hz), 7.25 (1H, dd, J=8, 2 Hz), 7.52 (1H, d, J=2 Hz), 8.14 (1H, d, J=8 Hz), 8.20 (1H, d, J=8 Hz), 9.81 (1H, s). MASS (ESI): m/z 498 (M–H)$^{31}$. m.p. 171–172° C.

EXAMPLE 84

In the same manner as in Example 1, 3-(2-chloro-4-(1-pyrrolyl)benzyl)-2-methyl-5-((4-methylbenzene)sulfonylcarbamoyl)-3H-imidazo[4,5-b]pyridine (222 mg) was obtained as colorless crystals from 3-(2-chloro-4-(1-pyrrolyl)benzyl)-2-methyl-3H-imidazo[4,5-b]pyridine-5-carboxylic acid (200 mg) and 4-methylbenzenesulfonamide (140 mg).

$^1$H-NMR (CDCl$_3$): 2.40 (3H, s), 2.67 (3H, s), 5.58 (2H, s), 6.38 (2H, t, J=2 Hz), 6.92 (1H, d, J=8 Hz), 7.10 (2H, t, J=2 Hz), 7.24–7.30 (3H, m), 7.54 (1H, d, J=2 Hz), 7.94–7.98 (2H, m), 8.04–8.09 (2H, m), 10.05 (1H, s). MASS (ESI): m/z 518 (M–H)$^{31}$. m.p. 178–180° C.

EXAMPLE 85

To a solution of 3-[2-chloro-4-(cyclohexylmethyloxy) benzyl]-2-methyl-5-(1-pentanesulfonylcarbamoyl)-3H-imidazo[4,5-b]pyridine (50 mg) in N,N-dimethylformamide (0.25 ml) was added dropwise 1N aqueous sodium hydroxide solution (0.2 ml) at 80° C. Heating was immediately stopped and the mixture was stirred at room temperature. After 1 hr, the precipitated crystals were collected by filtration and washed 3 times with N,N-dimethylformamide:water=5:4 (0.5 ml) and 3 times with water (0.5 ml). The crystals were dried under reduced pressure at 50° C. for 5 hr to give 3-[2-chloro-4-(cyclohexylmethyloxy)benzyl]-2-methyl-5-(1-pentanesulfonylcarbamoyl)-3H-imidazo[4,5-b]pyridine sodium salt as colorless crystals (40 mg).

$^1$H-NMR (CDCl$_3$): 0.88 (3H, t, J=7 Hz), 0.95–1.90 (17H, m), 2.34 (3H, s), 2.55 (2h, br t, J=7 Hz), 3.67–3.70 (2H, m), 5.41–5.61 (2H, m), 6.30 (1H, dd, J=8, 2 Hz), 6.58 (1H, d, J=8 Hz), 6.83 (1H, d, J=8 Hz), 7.81 (1H, d, J=8 Hz), 8.06 (1H, d, J=8 Hz). MASS (ESI): m/z 545 (M−Na)$^-$. m.p.>250° C.

Results

3-[2-Chloro-4-(cyclohexylmethyloxy)benzyl]-2-methyl-5-(1-pentanesulfonylcarbamoyl)-3H-imidazo[4,5-b]pyridine sodium salt showed markedly improved oral absorption as compared to 3-[2-chloro-4-(cyclohexylmethyloxy)benzyl]-2-methyl-5-(1-pentanesulfonylcarbamoyl)-3H-imidazo[4,5-b]pyridine, which fact was demonstrated by $C_{max}$ that was 2 to 3 times greater in rats and about 16 times greater in dogs.

EXAMPLE 86

In the same manner as in Example 1, 3-[2-chloro-4-(2-furyl)benzyl]-2,7-dimethyl-5-(1-pentanesulfonylcarbamoyl)-3H-imidazo[4,5-b]pyridine was obtained as colorless crystals (212 mg) from 3-[2-chloro-4-(2-furyl)benzyl]-2,7-dimethyl-3H-imidazo[4,5-b]pyridine-5-carboxylic acid (200 mg) and 1-pentanesulfonamide (120 mg).

$^1$H-NMR (CDCl$_3$): 0.85 (3H, t, J=8 Hz), 1.22–1.46 (4H, m), 1.77–1.90 (2H, m), 2.65 (3H, s), 2.74 (3H, s), 3.48–3.56 (2H, m), 5.56 (2H, s), 6.48 (1H, m), 6.70 (1H, d, J=5 Hz), 6.76 (1H, d, J=8 Hz), 7.43–7.50 (2H, m), 7.77 (1H, d, J=1 Hz), 8.01 (1H, s), 9.86 (1H, br s). MASS (ESI): m/z 513 (M−1). m.p. 177–178° C.

EXAMPLE 87

In the same manner as in Example 1, 3-[2-chloro-4-(2-furyl)benzyl]-2,7-dimethyl-5-[(4-methylbenzene)sulfonylcarbamoyl]-3H-imidazo[4,5-b]pyridine was obtained as colorless crystals (212 mg) from 3-[2-chloro-4-(2-furyl)benzyl]-2,7-dimethyl-3H-imidazo[4,5-b]pyridine-5-carboxylic acid (200 mg) and p-toluenesulfonamide (140 mg).

$^1$H-NMR (CDCl$_3$): 2.39 (3H, s), 2.64 (3H, s), 2.67 (3H, s), 5.56 (2H, s), 6.50 (1H, m), 6.72 (1H, d, J=5 Hz), 6.80 (1H, d, J=8 Hz), 7.26 (2H, d, J=8Hz), 7.47–7.54 (2H, m), 7.78 (1H, d, J=1 Hz), 7.89 (1H, s), 7.99 (2H, d, J=8 Hz), 10.12 (1H, br s). MASS (ESI): m/z 533 (M−1). m.p. 189–190° C.

EXAMPLE 88

In the same manner as in Example 1, 3-[2-chloro-4-(2-furyl)benzyl]-2,7-dimethyl-5-(1-butanesulfonylcarbamoyl)-3H-imidazo[4,5-b]pyridine was obtained as colorless crystals (213 mg) from 3-[2-chloro-4-(2-furyl)benzyl]-2,7-dimethyl-3H-imidazo[4,5-b]pyridine-5-carboxylic acid (200 mg) and 1-butanesulfonamide (112 mg).

$^1$H-NMR (CDCl$_3$): 0.90 (3H, t, J=8 Hz), 1.36–1.51 (2H, m), 1.75–1.89 (2H, m), 2.65 (3H, s), 2.74 (3H, s), 3.49–3.58 (2H, m), 5.56 (2H, s), 6.48 (1H, m), 6.70 (1H, d, J=5 Hz), 6.77 (1H, d, J=8 Hz), 7.44–7.50 (2H, m), 7.77 (1H, d, J=1 Hz), 8.01 (1H, s), 9.86 (1H, br s). MASS (ESI): m/z 499 (M−1). m.p. 231–233° C.

EXAMPLE 89

In the same manner as in Example 1, 3-(2,4-dichloro-5-nitrobenzyl)-2-methyl-5-(1-pentanesulfonylcarbamoyl)-3H-imidazo[4,5-b]pyridine was obtained as colorless crystals (59 mg) from 3-[(2,4-dichloro-5-nitro)benzyl]-2-methyl-3H-imidazo[4,5-b]pyridine-5-carboxylic acid (170 mg) and 1-pentanesulfonamide (101 mg).

$^1$H-NMR (CDCl$_3$): 0.89 (3H, t, J=8 Hz), 1.24–1.50 (4H, m), 1.82–1.95 (2H, m), 2.65 (3H, s), 3.53–3.61 (2H, m), 5.60 (2H, s), 7.21 (1H, s), 7.77 (1H, s), 8.19 (1H, d, J=8 Hz), 8.27 (1H, d, J=8 Hz), 9.74 (1H, br s). MASS (ESI): m/z 514 (M−1).

EXAMPLE 90

In the same manner as in Example 1, 3-(2,4-dichloro-5-nitrobenzyl)-2-methyl-5-[(4-methylbenzene)sulfonylcarbamoyl]-3H-imidazo[4,5-b]pyridine was obtained as colorless crystals (205 mg) from 3-[(2,4-dichloro-5-nitro)benzyl]-2-methyl-3H-imidazo[4,5-b]pyridine-5-carboxylic acid (170 mg) and 4-methylbenzenesulfonamide (115 mg).

$^1$H-NMR (CDCl$_3$): 2.43 (3H, s), 2.62 (3H, s), 5.61 (2H, s), 7.23 (1H, s), 7.34 (2H, d, J=8 Hz), 7.77 (1H, s), 8.03 (2H, d, J=8 Hz), 8.11 (1H, d, J=8 Hz), 8.15 (1H, d, J=8 Hz), 10.09 (1H, br s). MASS (ESI): m/z 534 (M−1).

EXAMPLE 91

In the same manner as in Example 1, 3-[2,4-dichloro-5-(N,N-dimethylamino)benzyl]-2-methyl-5-(1-pentanesulfonylcarbamoyl)-3H-imidazo[4,5-b]pyridine was obtained as colorless crystals (174 mg) from 3-[2,4-dichloro-5-(N,N-dimethylamino)benzyl]-2-methyl-3H-imidazo[4,5-b]pyridine-5-carboxylic acid (190 mg) and 1-pentanesulfonamide (114 mg).

$^1$H-NMR (CDCl$_3$): 0.89 (3H, t, J=8 Hz), 1.27–1.50 (4H, m), 1.84–1.96 (2H, m), 2.59 (6H, s), 2.63 (3H, s), 3.52–3.62 (2H, m), 5.54 (2H, s), 6.33 (1H, s), 7.47 (1H, s), 8.15 (1H, d, J=8 Hz), 8.24 (1H, d, J=8 Hz), 9.90 (1H, br s). MASS (ESI): m/z 510 (M−1).

EXAMPLE 92

In the same manner as in Example 1, 3-[2,4-dichloro-5-(N,N-dimethylamino)benzyl]-2-methyl-5-[(4-methylbenzene)sulfonyl-carbamoyl]-3H-imidazo[4,5-b]pyridine was obtained as colorless crystals (213 mg) from 3-[2,4-dichloro-5-(N,N-dimethylamino)-benzyl]-2-methyl-3H-imidazo[4,5-b]pyridine-5-carboxylic acid (190 mg) and 4-methylbenzenesulfonamide (129 mg).

$^1$H-NMR (CDCl$_3$): 2.43 (3H, s), 2.57 (6H, s), 2.62 (3H, s), 5.55 (2H, s), 6.34 (1H, s), 7.35 (2H, d, J=8 Hz), 7.49 (1H, s), 8.04–8.15 (4H, m), 10.17 (1H, br s). MASS (ESI): m/z 530 (M−1).

EXAMPLE 93

3-(2-Chloro-4-(methylamino)benzyl)-2-methyl-5-((4-methylbenzene)sulfonylcarbamoyl)-3H-imidazo[4,5-b]

pyridine (220 mg) was dissolved in dichloromethane (200 ml), and pyridine (196 mg) and 1-butanesulfonyl chloride (453 mg) were added, which was followed by refluxing under heating for 12 hr. The reaction mixture was concentrated under reduced pressure, and water and 1N hydrochloric acid were added to adjust to pH 4. The mixture was extracted with chloroform. The organic layer was washed with saturated brine, dried over anhydrous magnesium sulfate, and concentrated under reduced pressure. The residue was purified by silica gel thin layer chromatography (chloroform:methanol=19:1) and lo ethanol (5 ml) was added to the purified product. The precipitated crystals were collected by filtration. The crystals were dissolved in N,N-dimethylformamide (1 ml) and water (0.85 ml) was added on an oil bath at 80° C. The mixture was allowed to cool and the precipitated crystals were collected by filtration to give 3-(4-(N-(1-butanesulfonyl)-N-methylamino)-2-chlorobenzyl)-2-methyl-5-((4-methylbenzene)sulfonylcarbamoyl)-3H-imidazo[4,5-b]pyridine (38 mg) as pale-yellow crystals.

$^1$H-NMR (CDCl$_3$): 0.92 (3H, t, J=7 Hz), 1.37–1.50 (2H, m), 1.74–1.85 (2H, m), 2.43 (3H, s), 2.64 (3H, s), 3.02 (2H, t, J=7 Hz), 3.35 (3H, s), 5.57 (2H, s), 6.72 (1H, d, J=8 Hz), 7.25 (1H, dd, J=8, 2Hz), 7.35 (2H, d, J=8 Hz), 7.56 (1H, d, J=2 Hz), 8.04–8.12 (4H, m), 10.05 (1H, s). MASS (ESI): m/z 602 (M−H)$^{31}$. m.p. 158–159° C.

EXAMPLE 94

In the same manner as in Example 85, 3-(4-(N-(tert-butoxycarbonyl)-N-methylamino)-2-chlorobenzyl)-2-methyl-5-(1-pentanesulfonylcarbamoyl)-3H-imidazo[4,5-b]pyridine sodium salt (175 mg) was obtained as colorless crystals from 3-(4-(N-(tert-butoxycarbonyl)-N-methylamino)-2-chlorobenzyl)-2-methyl-5-(1-pentanesulfonylcarbamoyl)-3H-imidazo[4,5-b]pyridine (233 mg).

$^1$H-NMR (DMSO-d$_6$): 0.83 (3H, t, J=7 Hz), 1.22–1.32 (4H, m), 1.38 (9H, s), 1.52–1.64 (2H, m), 2.46 (3H, s), 3.05 (2H, t, J=7 Hz), 3.15 (3H, s), 5.56 (2H, s), 6.43 (1H, d, J=8 Hz), 7.14 (1H, dd, J=8, 2 Hz), 7.54 (1H, d, J=2 Hz), 7.83 (1H, d, J=8 Hz), 7.98 (1H, d, J=8 Hz) MASS (ESI): m/z 562 (M−H)$^{31}$. m.p. 231–233° C.

EXAMPLE 95

In the same manner as in Example 65, 3-(2-chloro-4-(N-methyl-N-(1-propoxycarbonyl)amino)benzyl)-2-methyl-5-(1-pentanesulfonylcarbamoyl)-3H-imidazo[4,5-b]pyridine (175 mg) was obtained as colorless crystals from 3-(2-chloro-4-(methylamino)benzyl)-2-methyl-5-(1-pentanesulfonylcarbamoyl)-3H-imidazo[4,5-b]pyridine (299 mg) and 1-propyl chlorocarbonate (87 mg).

$^1$H-NMR (CDCl$_3$): 0.89 (3H, t, J=7 Hz), 0.91 (3H, t, J=7 Hz), 1.27–1.48 (4H, m), 1.60–1.72 (2H, m), 1.85–1.95 (2H, m), 2.64 (3H, s), 3.30 (3H, s), 3.57 (2H, t, J=7 Hz), 4.09 (2H, t, J=7 Hz), 5.56 (2H, s), 6.66 (1H, d, J=8 Hz), 7.12 (1H, dd, J=8, 2 Hz), 7.47 (1H, d, J=2 Hz), 8.14 (1H, d, J=8 Hz), 8.21 (1H, d, J=8 Hz), 9.84 (1H, s). MASS (ESI): m/z 548 (M−H)$^{31}$. m.p. 169–170° C.

EXAMPLE 96

In the same manner as in Example 65, 3-(2-chloro-4-(N-methyl-N-(isopropoxycarbonyl)amino)benzyl)-2-methyl-5-(1-pentanesulfonylcarbamoyl)-3H-imidazo[4,5-b]pyridine (173 mg) was obtained as colorless crystals from 3-(2-chloro-4-(methylamino)benzyl)-2-methyl-5-(1-pentanesulfonylcarbamoyl)-3H-imidazo[4,5-b]pyridine (299 mg) and isopropyl chlorocarbonate (87 mg).

$^1$H-NMR (CDCl$_3$): 0.89 (3H, t, J=7 Hz), 1.25 (6H, d, J=7 Hz), 1.31–1.48 (4H, m), 1.84–1.95 (2H, m), 2.64 (3H, s), 3.29 (3H, s), 3.57 (2H, t, J=7 Hz), 4.90–5.03 (1H, m), 5.56 (2H, s), 6.65 (1H, d, J=8 Hz), 7.11 (1H, dd, J=8, 2 Hz), 7.46 (1H, d, J=2 Hz), 8.14 (1H, d, J=8 Hz), 8.21 (1H, d, J=8 Hz), 25 9.84 (1H, s). MASS (ESI): m/z 548 (M−H)$^{31}$. m.p. 151–152° C.

EXAMPLE 97

In the same manner as in Example 1, 3-(4-(N-(tert-butoxycarbonyl)amino)-2-chlorobenzyl)-2-methyl-5-(1-pentanesulfonylcarbamoyl)-3H-imidazo[4,5-b]pyridine (217 mg) was obtained as pale-yellow crystals from 3-(4-(N-(tert-butoxycarbonyl)amino)-2-chlorobenzyl)-2-methyl-3H-imidazo[4,5-b]pyridine-5-carboxylic acid (234 mg) and 1-pentanesulfonamide (127 mg).

$^1$H-NMR (CDCl$_3$): 0.89 (3H, t, J=7 Hz), 1.27–1.48 (4H, m), 1.50 (9H, s), 1.83–1.94 (2H, m), 2.64 (3H, s), 3.55 (2H, t, J=7 Hz), 5.51 (2H, s), 6.58 (1H, s), 6.77 (1H, d, J=8 Hz), 7.03 (1H, dd, J=8, 2 Hz), 7.77 (1H, s), 8.11 (1H, d, J=8 Hz), 7.18 (1H, d, J=8 Hz), 9.79 (1H, s). MASS (ESI): m/z 548 (M−H)$^{31}$. m.p. 222–224° C.

EXAMPLE 98

In the same manner as in Example 1, 3-(2-chloro-4-(ethoxycarbonylamino)benzyl)-2-methyl-5-(1-pentanesulfonylcarbamoyl)-3H-imidazo[4,5-b]pyridine was obtained as thin yellow crystals (191 mg) from 3-(2-chloro-4-(ethoxycarbonylamino)benzyl)-2-methyl-3H-imidazo[4,5-b]pyridine-5-carboxylic acid (250 mg) and 1-pentanesulfonamide (146 mg).

$^1$H-NMR (CDCl$_3$): 0.89 (3H, t, J=7 Hz), 1.24–1.50 (4H, m), 1.31 (3H, t, J=7 Hz), 1.81–1.95 (2H, m), 2.65 (3H, s), 3.50–3.60 (2H, m), 4.22 (2H, q, J=7 Hz), 5.52 (2H, s), 6.79 (1H, d, J=8 Hz), 7.11 (1H, dd, J=i, 8 Hz), 7.74 (1H, d, J=1 Hz), 8.11 (1H, d, J=8 Hz), 8.18 (1H, d, J=8 Hz). MASS (ESI): m/z 520 (M−1).

EXAMPLE 99

In the same manner as in Example 1, 3-(2-chloro-4-(N-valerylamino)benzyl)-2-methyl-5-[(4-methylbenzene)sulfonylcarbamoyl]-3H-imidazo[4,5-b]pyridine was obtained as thin yellow crystals (196 mg) from 3-(2-chloro-4-(N-valerylamino)benzyl)-2-methyl-3H-imidazo[4,5-b]pyridine-5-carboxylic acid (200 mg) and (4-methylbenzene)sulfonamide (128 mg).

$^1$H-NMR (CDCl$_3$): 0.94 (3H, t, J=7 Hz), 1.33–1.48 (2H, m), 1.65–1.77 (2H, m), 2.37 (2H, t, J=7 Hz), 2.42 (3H, s), 2.65 (3H, s), 5.52 (2H, s), 6.85 (1H, d, J=8 Hz), 7.20–7.29 (2H, m), 7.34 (2H, d, J=8 Hz), 7.95–8.09 (4H, m). MASS (ESI): m/z 552 (M−1).

EXAMPLE 100

In the same manner as in Example 1, 3-(4-(N-(1-butanesulfonyl)amino)-2-chlorobenzyl)-2-methyl-5-[(4-methylbenzene)sulfonylcarbamoyl]-3H-imidazo[4,5-b]pyridine was obtained as thin ochroid crystals (201 mg) from 3-(4-(N-(1-butanesulfonyl)amino)-2-chlorobenzyl)-2-methyl-3H-imidazo[4,5-b]pyridine-5-carboxylic acid (200 mg) and 4-methylbenzenesulfonamide (118 mg).

$^1$H-NMR (CDCl$_3$): 0.91 (3H, t, J=7 Hz), 1.37–1.51 (2H, m), 1.75–1.89 (2H, m), 2.43 (3H, s), 2.65 (3H, s), 3.11–3.20

(2H, m), 5.52 (2H, s), 6.80 (1H, d, J=8 Hz), 7.04 (1H, dd, J=1, 8 Hz), 7.35 (2H, d, J=8 Hz), 7.42 (1H, d, J=1 Hz), 8.00–8.12 (4H, m). MASS (ESI): m/z 588 (M−1).

EXAMPLE 101

In the same manner as in Example 1, 3-(2-chloro-4-(N-(t-butylacetyl)amino)benzyl)-2-methyl-5-[(4-methylbenzene)sulfonylcarbamoyl]-3H-imidazo[4,5-b]pyridine was obtained as thin yellow crystals (204 mg) from 3-(2-chloro-4-(N-(t-butylacetyl)amino)benzyl)-2-methyl-3H-imidazo[4,5-b]pyridine-5-carboxylic acid (240 mg) and 4-methylbenzenesulfonamide (149 mg).

$^1$H-NMR (CDCl$_3$): 1.10 (9H, s), 2.23 (2H, s), 2.42 (3H, s), 2.65 (3H, s), 5.52 (2H, s), 6.83 (1H, d, J=8 Hz), 7.18–7.28 (2H, m), 7.34 (2H, d, J=8 Hz), 7.95–8.09 (4H, m). MASS (ESI): m/z 566 (M−1).

EXAMPLE 102

In the same manner as in Example 1, 3-(2-chloro-4-(N-(isopropoxycarbonyl)amino)benzyl)-2-methyl-5-((E)-1-penten-1-ylsulfonylcarbamoyl)-3H-imidazo[4,5-b]pyridine was obtained as colorless crystals (39 mg) from 3-(2-chloro-4-(N-(isopropoxycarbonyl)amino)benzyl)-2-methyl-3H-imidazo[4,5-b]pyridine-5-carboxylic acid (79 mg) and (E)-1-penten-1-ylsulfonamide (44 mg).

$^1$H-NMR (CDCl$_3$): 0.95 (3H, t, J=7 Hz), 1.29 (6H, d, J=7 Hz), 1.47–1.63 (2H, m), 2.22–2.33 (2H, m), 2.64 (3H, s), 4.95–5.05 (1H, m), 5.52 (2H, s), 6.58 (1H, d, J=16 Hz), 6.75 (1H, d, J=8 Hz), 7.05–7.20 (2H, m), 7.75 (1H, s), 8.09 (1H, d, J=8 Hz), 8.15 (1H, d, J=8 Hz). MS (ESI): m/z 532 (M−1). m.p. 187–189° C.

EXAMPLE 103

In the same manner as in Example 1, 5-(1-butanesulfonylcarbamoyl)-3-(2-chloro-4-(N-(isopropoxycarbonyl)amino)benzyl)-2-methyl-3H-imidazo[4,5-b]pyridine was obtained as colorless crystals (53 mg) from 3-(2-chloro-4-(N-(isopropoxycarbonyl)amino)benzyl)-2-methyl-3H-imidazo[4,5-b]pyridine-5-carboxylic acid (79 mg) and 1-butanesulfonamide (40 mg).

$^1$H-NMR (CDCl$_3$): 0.94 (3H, t, J=7 Hz), 1.29 (6H, d, J=7 Hz), 1.40–1.56 (2H, m), 1.80–1.91 (2H, m), 2.65 (3H, s), 3.51–3.60 (2H, m), 4.95–5.05 (1H, m), 5.52 (2H, s), 6.79 (1H, d, J=8 Hz), 7.10 (1H, dd, J=1, 8 Hz), 7.75 (1H, s), 8.10 (1H, d, J=8 Hz), 8.18 (1H, d, J=8 Hz). MS (ESI): m/z 520 (M−1). m.p. 181–182° C.

EXAMPLE 104

3-(2-Chloro-4-(N-ethoxycarbonyl-N-methylamino)benzyl)-2-methyl-3H-imidazo[4, 5-b]pyridine-5-carboxylic acid (150 mg) was dissolved in dry N,N-dimethylformamide (1.5 ml), and carbonyldiimidazole (91 mg) was added, which was followed by stirring at room temperature for 1.5 hr. To the reaction mixture was added 1-penten-1-ylsulfonamide sodium salt (96 mg) and the mixture was stirred at room temperature for 7 hr. 1N Hydrochloric acid was added dropwise under ice-cooling to adjust to pH 4. Water (1.5 ml) was added and the mixture was applied to ultrasonic washer for 15 min and then stirred for 15 min. The precipitate was collected by filtration, washed with water, suspended in ethanol (0.5 ml), heated in a boiling bath and stirred at room temperature for 30 min. The precipitate was collected by filtration, washed with ethanol, and recrystallized from N,N-dimethylformamide and water to give 3-(2-chloro-4-(N-ethoxycarbonyl-N-methylamino)benzyl)-2-methyl-5-((E)-1-penten-1-ylsulfonylcarbamoyl)-3H-imidazo[4,5-b]pyridine (165 mg) as colorless crystals. m.p.: 165–166° C.

$^1$H-NMR (CDCl$_3$): 0.95 (3H, t, J=6 Hz), 1.27 (3H, t, J=6 Hz), 1.55 (2H, m), 2.29 (2H, q, J=6 Hz), 2.65 (3H, s), 3.30 (3H, s), 4.19 (2H, q, J=6 Hz), 5.55 (2H, s), 6.56–6.66 (2H), 7.07–7.20 (2H), 7.46 (1H, d, J=2 Hz), 8.12 (1H, d, J=8 Hz), 8.19 (1H, d, J=8 Hz), 9.91 (1H, br. s). MS (ESI): m/z 535 (M+1).

EXAMPLE 105

In the same manner as in Example 1, 5-(1-butanesulfonylcarbamoyl)-3-(2-chloro-4-(N-ethoxycarbonyl-N-methylamino)benzyl)-2-methyl-3H-imidazo[4,5-b]pyridine (110 mg) was obtained as colorless crystals from 3-(2-chloro-4-(N-ethoxycarbonyl-N-methylamino)benzyl)-2-methyl-3H-imidazo[4,5-b]pyridine-5-carboxylic acid (128 mg). m.p.: 169–170° C.

$^1$H-NMR (CDCl$_3$): 0.95 (3H, t, J=6 Hz), 1.26 (3H, t, J=6 Hz), 1.49 (2H, m), 1.88 (2H, m), 2.65 (3H, s), 3.30 (3H, s), 3.58 (2H, t, J=6 Hz), 4.19 (2H, q, J=6 Hz), 5.55 (2H, s), 6.65 (1H, d, J=8 Hz), 7.11 (1H, dd, J=8, 2 Hz), 7.46 (1H, d, J=2 Hz), 8.14 (1H, d, J=8 Hz), 8.21 (1H, d, J=8 Hz), 9.82 (1H, br. s). MS (ESI): m/z 523 (M+1).

EXAMPLE 106

In the same manner as in Example 42, 3-(4-amino-2-chlorobenzyl)-2-methyl-5-(1-pentanesulfonylcarbamoyl)-3H-imidazo[4,5-b]pyridine (284 mg) was obtained as pale-yellow crystals from 3-(4-(N-t-butoxycarbonylamino)-2-chlorobenzyl)-2-methyl-5-(1-pentanesulfonylcarbamoyl)-3H-imidazo[4,5-b]pyridine (390 mg).

$^1$H-NMR (CDCl$_3$): 0.89 (3H, t, J=7 Hz), 1.30–1.50 (4H, m), 1.85–1.95 (2H, m), 2.67. (3H, s), 3.56 (2H, t, J=7 Hz), 3.83 (2H, s), 5.45 (2H, s), 6.53 (1H, dd, J=8, 2 Hz), 6.72–6.75 (2H, m), 8.08 (1H, d, J=8 Hz), 8.16 (1H, d, J=8 Hz), 9.84 (1H, s).

EXAMPLE 107

In the same manner as in Example 65, 3-(4-N-(1-propoxycarbonyl)amino)-2-chlorobenzyl)-2-methyl-5-(1-pentanesulfonylcarbamoyl)-3H-imidazo[4,5-b]pyridine (125 mg) was obtained as colorless crystals from 3-(4-amino-2-chlorobenzyl)-2-methyl-5-(1-pentanesulfonylcarbamoyl)-3H-imidazo[4,5-b]pyridine (130 mg) and n-propyl chlorocarbonate (39 mg).

$^1$H-NMR (CDCl$_3$): 0.88 (3H, t, J=7 Hz), 0.97 (3H, t, J=7 Hz), 1.30–1.48 (4H, m), 1.64–1.76 (2H, m), 1.83–1.93 (2H, m), 2.65 (3H, s), 3.55 (2H, t, J=7 Hz), 4.12 (2H, t, J=7 Hz), 5.52 (2H, s), 6.74 (1H, s), 6.78 (1H, d, J=8 Hz), 7.12 (1H, dd, J=8, 2 Hz), 7.75 (1H, d, J=2 Hz), 8.11 (1H, d, J=8 Hz), 8.18 (1H, d, J=8 Hz), 9.78 (1H, s). Mass (ESI): m/z 534 (M−H)$^-$. m.p. 215–216° C.

EXAMPLE 108

In the same manner as in Example 65, 3-(4-(N-(isopropoxycarbonyl)amino)-2-chlorobenzyl)-2-methyl-5-(1-pentanesulfonylcarbamoyl)-3H-imidazo[4,5-b]pyridine (120 mg) was obtained as pale-yellow crystals from 3-(4-amino-2-chlorobenzyl)-2-methyl-5-(1-pentanesulfonylcarbamoyl)-3H-imidazo[4,5-b]pyridine (130 mg) and isopropyl chlorocarbonate (39 mg).

$^1$H-NMR (CDCl$_3$): 0.88 (3H, t, J=7 Hz), 1.29 (6H, d, J=7 Hz), 1.32–1.46 (4H, m), 1.83–1.93 (2H, m), 2.65 (3H, s), 3.55 (2H, t, J=7 Hz), 4.94–5.06 (1H, m), 5.52 (2H, s), 6.67 (1H, s), 6.78 (1H, d, J=8 Hz), 7.11 (1H, dd, J=8, 2 Hz), 7.75 (1H, d, J=2 Hz), 8.11 (1H, d, J=8 Hz), 5 8.18 (1H, d, J=8 Hz), 9.78 (1H, s). Mass (ESI): m/z 534 (M−H)⁻. m.p. 198–199° C.

EXAMPLE 109

In the same manner as in Example 1, 5-(1-butanesulfonylcarbamoyl)-3-(4-(N-t-butoxycarbonylamino)-2-chlorobenzyl)-2-methyl-3H-imidazo[4,5-b]pyridine (270 mg) was obtained as pale-yellow crystals from 3-(4-(N-t-butoxycarbonylamino)-2-chlorobenzyl)-2-methyl-3H-imidazo[4,5-b]pyridine-5-carboxylic acid (300 mg) and 1-butanesulfonamide (148 mg).

¹H-NMR (CDCl₃): 0.94 (3H, t, J=7 Hz), 1.42–1.55 (2H, m), 1.50 (9H, s), 1.81–1.92 (2H, m), 2.65 (3H, s), 3.56 (2H, t, J=7 Hz), 5.52 (2H, s), 6.59 (1H, s), 6.77 (1H, d, J=8 Hz), 7.03 (1H, dd, J=8, 2 Hz), 7.78 (1H, s), 8.11 (1H, d, J=8 Hz), 8.18 (1H, d, J=8 Hz), 9.78 (1H, s). Mass (ESI): m/z 534 (M−H)⁻. m.p. 229–230° C.

EXAMPLE 110

In the same manner as in Example 42, 3-(4-amino-2-chlorobenzyl)-5-(1-butanesulfonylcarbamoyl)-2-methyl-3H-imidazo[4,5-b]pyridine (124 mg) was obtained as pale-yellow crystals from 5-(1-butanesulfonylcarbamoyl)-3-(4-(N-t-butoxycarbonylamino)-2-chlorobenzyl)-2-methyl-3H-imidazo[4,5-b]pyridine (207 mg).

¹H-NMR (CDCl₃): 0.95 (3H, t, J=7 Hz), 1.43–1.56 (2H, m), 1.82–1.92 (2H, m), 2.67 (3H, s), 3.57 (2H, t, J=7 Hz), 3.83 (2H, s), 5.45 (2H, s), 6.52 (1H, dd, J=8, 2 Hz), 6.73–6.76 (2H, m), 8.08 (1H, d, J=8 Hz), 8.16 (1H, d, J=8 Hz), 9.82 (1H, s).

EXAMPLE 111

In the same manner as in Example 65, 3-(4-ethoxycarbonylamino-2-chlorobenzyl)-2-methyl-5-(1-butanesulfonylcarbamoyl)-3H-imidazo[4,5-b]pyridine (100 mg) was obtained as colorless crystals from 3-(4-amino-2-chlorobenzyl)-5-(1-butanesulfonylcarbamoyl)-2-methyl-3H-imidazo[4,5-b]pyridine (102 mg) and ethyl chlorocarbonate (28 mg).

¹H-NMR (CDCl₃—CD₃OD): 0.94 (3H, t, J=7 Hz), 1.30 (3H, t, J=7 Hz), 1.42–1.55 (2H, m), 1.80–1.90 (2H, m), 2.53 (1H, s), 2.66 (3H, s), 3.56 (2H, t, J=7 Hz), 4.21 (2H, q, J=7 Hz), 5.53 (2H, s), 6.82 (1H, d, J=8 Hz), 7.16 (1H, dd, J=8, 2 Hz), 7.73 (1H, s), 8.11 (1H, d, J=8 Hz), 8.18 (1H, d, J=8 Hz). Mass (ESI): m/z 506 (M−H)⁻. m.p. 236–237° C.

EXAMPLE 112

In the same manner as in Example 1, 3-(4-(N-t-butoxycarbonylamino)-2-chlorobenzyl)-2-methyl-5-((E)-1-penten-1-ylsulfonylcarbamoyl)-3H-imidazo[4,5-b]pyridine (181 mg) was obtained as pale-yellow crystals from 3-(4-(N-t-butoxycarbonylamino)-2-chlorobenzyl)-2-methyl-3H-imidazo[4,5-b]pyridine-5-carboxylic acid (300 mg) and (E)-1-penten-1-ylsulfonamide (161 mg).

¹H-NMR (CDCl₃): 0.95 (3H, t, J=7 Hz), 1.51 (9H, s), 1.50–1.60 (2H, m), 2.28 (2H, q, J=7 Hz), 2.63 (3H, s), 5.51 (2H, s), 6.56–6.62 (2H, m), 6.72 (1H, d, J=8 Hz), 7.03 (1H, dd, J=8, 2 Hz), 7.08–7.19 (1H, m), 7.76 (1H, d, J=2 Hz), 8.08 (1H, d, J=8 Hz), 8.15 (1H, d, J=8 Hz), 9.87 (1H, s). Mass (ESI): m/z 546 (M−H)⁻. m.p. 215–216° C.

EXAMPLE 113

In the same manner as in Example 42, 3-(4-amino-2-chlorobenzyl)-2-methyl-5-((E)-1-penten-1-ylsulfonylcarbamoyl)-3H-imidazo[4,5-b]pyridine (170 mg) was obtained as pale-yellow crystals from 3-(4-(N-t-butoxycarbonylamino)-2-chlorobenzyl)-2-methyl-5-((E)-1-penten-1-ylsulfonylcarbamoyl)-3H-imidazo[4,5-b]pyridine (253 mg).

¹H-NMR (CDCl₃): 0.96 (3H, t, J=7 Hz), 1.48–1.60 (2H, m), 2.28 (2H, q, J=7 Hz), 2.66 (3H, s), 3.84 (2H, s), 5.45 (2H, s), 6.52 (1H, dd, J=8, 2 Hz), 6.60 (1H, d, J=16 Hz), 6.71 (1H, d, J=8 Hz), 6.76 (1H, d, J=2 Hz), 7.09–7.19 (1H, m), 8.07 (1H, d, J=8 Hz), 8.13 (1H, d, J=8 Hz), 9.92 (1H, s).

EXAMPLE 114

In the same manner as in Example 65, 3-(4-ethoxycarbonylamino-2-chlorobenzyl)-2-methyl-5-((E)-1-penten-1-ylsulfonylcarbamoyl)-3H-imidazo[4,5-b]pyridine (122 mg) was obtained as colorless crystals from 3-(4-amino-2-chlorobenzyl)-2-methyl-5-((E)-1-penten-1-ylsulfonylcarbamoyl)-3H-imidazo[4,5-b]pyridine (130 mg) and ethyl chlorocarbonate (35 mg).

¹H-NMR (CDCl₃): 0.95 (3H, t, J=7 Hz), 1.31 (3H, t, J=7 Hz), 1.48–1.60 (2H, m), 2.28 (2H, q, J=7 Hz), 2.64 (3H, s), 4.23 (2H, q, J=7 Hz), 5.52 (2H, s), 6.58 (1H, d, J=16 Hz), 6.72 (1H, s), 6.75 (1H, d, J=8 Hz), 7.10–7.19 (2H, m), 7.74 (1H, d, J=2 Hz), 8.09 (1H, d, J=8 Hz), 8.16 (1H, d, J=8 Hz), 9.86 (1H, s). Mass (ESI): m/z 518 (M−H)⁻; m.p. 233–234° C.

EXAMPLE 115

In the same manner as in Example 104, 3-(4-(N-(tert-butoxycarbonyl)-N-methylamino)-2-chlorobenzyl)-2-methyl-5-((E)-1-penten-1-ylsulfonylcarbamoyl)-3H-imidazo[4,5-b]pyridine (190 mg) was obtained as colorless crystals from 3-(4-(N-(tert-butoxycarbonyl)-N-methylamino)-2-chlorobenzyl)-2-methyl-3H-imidazo[4,5-b]pyridine-5-carboxylic acid (164 mg). m.p.: 154–155° C.

¹H-NMR (CDCl₃): 0.95 (3H, t, J=6 Hz), 1.46 (9H, s), 1.55 (2H, m), 2.28 (2H, q, J=6 Hz), 2.63 (3H, s), 3.25 (3H, s), 5.55 (2H, s), 6.55–6.65 (2H), 7.07–7.22 (2H), 7.46 (1H, d, J=2 Hz), 8.12 (1H, d, J=8 Hz), 8.19 (1H, d, J=8 Hz), 9.91 (1H, br. s). MS (ESI): m/z 561 (M−1).

EXAMPLE 116

In the same manner as in Example 1, 3-(2-chloro-4-(3-(1-propyl)ureido)benzyl)-2-methyl-5-[(4-methylbenzene)sulfonylcarbamoyl]-3H-imidazo[4,5-b]pyridine was obtained as thin yellow crystals (126 mg) from 3-(2-chloro-4-(3-(1-propyl)ureido)benzyl)-2-methyl-3H-imidazo[4,5-b]pyridine-5-carboxylic acid (130 mg) and (4-methylbenzene)sulfonamide (83 mg).

¹H-NMR (DMSO-d₆): 0.86 (3H, t, J=7 Hz), 1.36–1.50 (2H, m), 2.39 (3H, s), 2.47 (3H, s), 2.99–3.10 (2H, m), 5.73 (2H, s), 6.72 (1H, d, J=8 Hz), 7.05 (1H, dd, J=18 Hz), 7.43 (2H, d, J=8 Hz), 7.84–7.97 (4H, m), 8.11 (1H, d, J=8 Hz). MS (ESI): m/z 553 (M−1); m.p. 263–265° C.

EXAMPLE 117

3-(2-Chloro-4-(methylamino)benzyl)-2-methyl-5-((4-methylbenzene)sulfonylcarbamoyl)-3H-imidazo[4,5-b]pyridine (300 mg) was suspended in toluene (6 ml) and n-propyl isocyanate (264 mg) was added at room temperature, which was followed by stirring at 90° C. for 5 hr. The reaction mixture was concentrated under reduced pressure and ethanol (6 ml) was added to the residue. The mixture was heated and allowed to cool, and the precipitated crystals were collected by filtration. The crystals were dissolved in N,N-dimethylformamide (3.5 ml) and hot water (4.0 ml) was gradually added on an oil bath at 80° C. While stirring for 1 hr, the reaction mixture was allowed to cool, and the precipitated crystals were collected by filtration and dried by heating under reduced pressure to give 3-(4-(1-methyl-3-(1-propyl)ureido)-2-chlorobenzyl)-2-methyl-5-((4-methylbenzene)sulfonylcarbamoyl)-3H-imidazo[4,5-b]pyridine (309 mg) as colorless crystals.

$^1$H-NMR (CDCl$_3$): 0.86 (3H, t, J=7 Hz), 1.42–1.54 (2H, m), 2.43 (3H, s), 2.63 (3H, s), 3.17 (2H, q, J=7 Hz), 3.27 (3H, s), 4.46 (1H, t, J=7 Hz), 5.58 (2H, s), 6.66 (1H, d, J=8 Hz), 7.10 (1H, dd, J=8, 2 Hz), 7.35 (2H, d, J=8 Hz), 7.45 (1H, d, J=2 Hz), 8.03–8.14 (4H, m), 10.12 (1H, s). Mass (ESI): m/z 567 (M−H)$^{31}$. m.p. 190–191° C.

EXAMPLE 118

In the same manner as in Example 1, 3-(2-chloro-4-(2-oxo-1-pyrrolidinyl)benzyl)-2-methyl-5-((4-methylbenzene)sulfonylcarbamoyl)-3H-imidazo[4,5-b]pyridine (194 mg) was obtained as pale-yellow crystals from 3-(2-chloro-4-(2-oxotetrahydro-1H-pyrrol-1-yl)benzyl)-2-methyl-3H-imidazo[4,5-b]pyridine-5-carboxylic acid (173 mg) and (4-methylbenzene)sulfonamide (115 mg).

$^1$H-NMR (CDCl$_3$): 2.13–2.24 (2H, m), 2.42 (3H, s), 2.60–2.65 (5H, m), 3.87 (2H, t, J=7 Hz), 5.55 (2H, s), 6.82 (1H, d, J=8 Hz), 7.33 (2H, d, J=8 Hz), 7.45 (1H, dd, J=8, 2Hz), 7.96 (1H, d, J=2 Hz), 8.01–8.08 (4H, m), 10.07 (1H, s). Mass (ESI): m/z 536 (M−H)$^{31}$. m.p. 242–243° C.

EXAMPLE 119

In the same manner as in Example 1, 3-(2-chloro-4-(2-oxo-1,3-oxazolidin-3-yl)benzyl)-2-methyl-5-((4-methylbenzene)sulfonylcarbamoyl)-3H-imidazo[4,5-b]pyridine (158 mg) was obtained as pale-yellow crystals and 3-(2-chloro-4-(((2-(4-methylbenzene)sulfonylcarbamoyloxy)ethyl)amino)benzyl)-2-methyl-5-((4-methylbenzene)sulfonylcarbamoyl)-3H-imidazo[4,5-b]pyridine (37 mg) as a yellow powder, from a mixture of 3-(2-chloro-4-(2-oxo-1,3-oxazolidin-3-yl)benzyl)-2-methyl-3H-imidazo[4,5-b]pyridine-5-carboxylic acid and methyl 3-(2-chloro-4-((2-hydroxyethyl)amino)benzyl)-2-methyl-3H-imidazo[4,5-b]pyridine-5-carboxylate, and (4-methylbenzene)sulfonamide (282 mg).

3-(2-Chloro-4-(2-oxo-1,3-oxazolidin-3-yl)benzyl)-2-methyl-5-((4-methylbenzene)sulfonylcarbamoyl)-3H-imidazo[4,5-b]pyridine $^1$H-NMR (CDCl$_3$): 2.42 (3H, s), 2.66 (3H, s), 4.09 (2H, t, J=7 Hz), 4.51 (2H, t, J=7 Hz), 5.54 (2H, s), 6.92 (1H, d, J=8 Hz), 7.34–7.47 (3H, m), 7.89 (1H, d, J=2 Hz), 8.00–8.07 (4H, m), 10.03 (1H, s); Mass (ESI): m/z 538 (M−H)$^{31}$. m.p. 243–245° C.

3-(2-Chloro-4-(((2-(4-methylbenzene)sulfonylcarbamoyloxy)ethyl)amino)benzyl)-2-methyl-5-((4-methylbenzene)sulfonylcarbamoyl)-3H-imidazo[4,5-b]pyridine.

$^1$H-NMR (CDCl$_3$): 2.40 (3H, s), 2.43 (3H, s), 2.67 (3H, s), 3.30 (2H, t, J=7 Hz), 3.67 (1H, t, J=7 Hz), 4.21 (2H, t, J=7 Hz), 5.47 (2H, s), 6.48 (1H, dd, J=8, 2 Hz), 6.63 (1H, d, J=2 Hz), 6.81 (1H, d, J=8 Hz), 7.27–7.37 (4H, m), 7.85 (2H, d, J=8 Hz), 7.98–8.05 (4H, m); Mass (ESI): m/z 709 (M−H)$^−$.

EXAMPLE 120

In the same manner as in Example 1, 3-[(4-chloro-1,2-dimethyl-1H-benzimidazol-5-yl)methyl]-2-methyl-5-(1-pentanesulfonylcarbamoyl)-3H-imidazo[4,5-b]pyridine (69 mg) was obtained as pale-yellow crystals from 3-[(4-chloro-1,2-dimethyl-1H-benzimidazol-5-yl)methyl]-2-methyl-3H-imidazo[4,5-b]pyridine-5-carboxylic acid (100 mg) and 1-pentanesulfonamide (245 mg). m.p. 229–231° C.

$^1$H-NMR (CDCl$_3$): 0.88 (3H, t, J=7 Hz), 1.24–1.49 (4H, m), 1.79–1.93 (2H, m), 2.65 (3H, s), 2.68 (3H, s), 3.49–3.59 (2H, m), 3.74 (3H, s), 5.71 (2H, s), 6.96 (1H, d, J=8 Hz), 7.23 (1H, d, J=8 Hz), 8.08 (1H, d, J=8 Hz), 8.15 (1H, d, J=8 Hz), 9.70 (1H, br s). MASS (ESI): m/z 501 (M−1).

EXAMPLE 121

In the same manner as in Example 1, 3-[(4-chloro-1,2-dimethyl-1H-benzimidazol-5-yl)methyl]-2-methyl-5-[(4-methylbenzene)sulfonylcarbamoyl]-3H-imidazo[4,5-b]pyridine (76 mg) was obtained as pale-yellow crystals from 3-[(4-chloro-1,2-dimethyl-1H-benzimidazol-5-yl)methyl]-2-methyl-3H-imidazo[4,5-b]pyridine-5-carboxylic acid (100 mg) and (4-methylbenzene)sulfonamide (278 mg). m.p. >250° C.

$^1$H-NMR (CDCl$_3$): 2.42 (3H, s), 2.66 (3H, s), 2.67 (3H, s), 3.76 (3H, s), 5.72 (2H, s), 6.96 (1H, d, J=8 Hz), 7.25 (1H, d, J=8 Hz), 7.32 (2H, d, J=8 Hz), 7.95–8.04 (4H, m), 10.00 (1H, br s). MASS (ESI): m/z 521 (M−1).

EXAMPLE 122

In the same manner as in Example 1, 3-((6-chloro-1,2-dimethyl-1H-benzimidazol-5-yl)methyl)-2-methyl-5-((4-methylbenzene)sulfonylcarbamoyl)-3H-imidazo[4,5-b]pyridine was obtained as colorless crystals (22 mg) from 3-((6-chloro-1, 2-dimethyl-1H-benzimidazol-5-yl)methyl)-2-methyl-3H-imidazo[4,5-b]pyridine-5-carboxylic acid (60 mg) and (4-methylbenzene)sulfonamide (42 mg).

$^1$H-NMR (CDCl$_3$): 2.41 (3H, s), 2.56 (3H, s), 2.59 (3H, s), 3.74 (3H, s), 5.68 (2H, s), 6.88 (1H, s), 7.32 (2H, d, J=8 Hz), 7.48 (1H, s), 8.01 (2H, d, J=8 Hz), 8.05 (2H, d, J=1 Hz). MS (ESI): m/z 521 (M−1). m.p. 279–280° C.

EXAMPLE 123

In the same manner as in Example 1, 3-[(3,5-dichloropyridin-2-yl)methyl]-2-methyl-5-(1-pentanesulfonylcarbamoyl)-3H-imidazo[4,5-b]pyridine was obtained as colorless crystals (165 mg) from 3-[(3,5-dichloropyridin-2-yl)methyl]-2-methyl-3H-imidazo[4,5-b]pyridine-5-carboxylic acid (160 mg) and 1-pentanesulfonamide (108 mg). m.p. 155–156° C.

$^1$H-NMR (CDCl$_3$): 0.89 (3H, t, J=7 Hz), 1.24–1.50 (4H, m), 1.82–1.96 (2H, m), 2.70 (3H, s), 3.51–3.61 (2H, m), 5.67 (2H, s), 7.82 (1H, d, J=1 Hz), 8.10 (1H, d, J=8 Hz), 8.17 (1H, d, J=8 Hz), 8.29 (1H, d, J=1 Hz), 9.93 (1H, br s). MASS (ESI): m/z 468 (M−1).

EXAMPLE 124

In the same manner as in Example 1, 3-[(3,5-dichloropyridin-2-yl)methyl]-2-methyl-5-[(4-methylbenzene)sulfonylcarbamoyl]-3H-imidazo[4,5-b]pyridine was obtained as a colorless solid (175 mg) from 3-[(3,5-dichloropyridin-2-yl)methyl]-2-methyl-3H-imidazo[4,5-b]pyridine-5-carboxylic acid (160 mg) and (4-methylbenzene)sulfonamide (122 mg). m.p. 197–199° C.

$^1$H-NMR (CDCl$_3$): 2.43 (3H, s), 2.67 (3H, s), 5.67 (2H, s), 7.34 (2H, d, J=8 Hz), 7.85 (1H, d, J=1 Hz), 7.99–8.09 (4H, m), 8.30 (1H, d, J=8 Hz), 10.20 (1H, br s). MASS (ESI): m/z 488 (M−1).

EXAMPLE 125

In the same manner as in Example 1, 3-((3,5-dichloropyridin-2-yl)methyl)-2,7-dimethyl-5-((4- methylbenzenesulfonyl)carbamoyl)-3H-imidazo[4,5-b]pyridine (114 mg) was obtained as colorless crystals from 3-((3,5-dichloropyridin-2-yl)methyl)-2,17-dimethyl-3H-imidazo[4,5-b]pyridine-5-carboxylic acid (102 mg) and (4-methylbenzene)sulfonamide (75 mg). m.p. 235–236° C.

$^1$H-NMR (CDCl$_3$): 2.41 (3H, s), 2.66 (3H, s), 2.68 (3H, s), 5.64 (2H, s), 7.33 (2H, d, J=8 Hz), 7.83 (1H, d, J=1 Hz), 7.86 (1H, s), 8.04 (2H, d, J=8 Hz), 8.30 (1H, d, J=1 Hz). MS (ESI): m/z 503 (M−1).

EXAMPLE 126

In the same manner as in Example 1, 3-((3,5-dichloropyridin-2-yl)methyl)-2,7-dimethyl-5-(((E)-2-phenylethenesulfonyl)carbamoyl)-3H-imidazo[4,5-b]pyridine (113 mg) was obtained as colorless crystals from 3-((3,5-dichloropyridin-2-yl)methyl)-2,7-dimethyl-3H-imidazo[4,5-b]pyridine-5-carboxylic acid (102 mg) and (E)-2-phenylethenesulfonamide (75 mg). m.p. 219–220° C.

$^1$H-NMR (CDCl$_3$): 2.67 (3H, s), 2.70 (3H, s), 5.64 (2H, s), 7.14 (1H, d, J=16 Hz), 7.36–7.57 (5H), 7.76–7.84 (2H), 7.95 (1H, s), 8.28 (1H, d, J=1 Hz). MS (ESI): m/z 515 (M−1).

EXAMPLE 127

In the same manner as in Example 1, 3-[(2-chloro-6-phenylpyridin-3-yl)methyl]-2-methyl-5-(1-pentanesulfonylcarbamoyl)-3H-imidazo[4,5-b]pyridine was obtained as colorless crystals (206 mg) from 3-[(2-chloro-6-phenylpyridin-3-yl)methyl]-2-methyl-3H-imidazo[4,5-b]pyridine-5-carboxylic acid (180 mg) and 1-pentanesulfonamide (108 mg). m.p. 224–225° C.

$^1$H-NMR (CDCl$_3$): 0.85 (3H, t, J=7 Hz), 1.20–1.45 (4H, m), 1.86–1.90 (2H, m), 2.70 (3H, s), 3.49–3,57 (2H, m), 5.61 (2H, s), 7.20 (1H, d, J=8 Hz), 7.40–7.51 (3H, m), 7.65 (1H, d, J=8 Hz), 7.96–8.04 (2H, m), 8.15 (1H, d, J=8 Hz), 8.22 (1H, d, J=8 Hz), 9.76 (1H, br s). MASS (ESI): m/z 510 (M−1).

EXAMPLE 128

In the same manner as in Example 1, 3-[(2-chloro-6-phenylpyridin-3-yl)methyl]-2-methyl-5-[(4-methylbenzene)sulfonylcarbamoyl]-3H-imidazo[4,5-b]pyridine was obtained as colorless crystals (210 mg) from 3-[(2-chloro-6-phenylpyridin-3-yl)methyl]-2-methyl-3H-imidazo[4,5-b]pyridine-5-carboxylic acid (180 mg) and (4-methylbenzene)sulfonamide (122 mg). m.p. 236–238° C.

$^1$H-NMR (CDCl$_3$): 2.38 (3H, s), 2.69 (3H, s), 5.61 (2H, s), 7.21–7.28 (3H, m), 7.43–7.53 (3H, m), 7.69 (1H, d, J=8 Hz), 7.94–8.14 (6H, m), 10.04 (1H, br s). MASS (ESI): m/z 530 (M−1).

EXAMPLE 129

In the same manner as in Example 1, 3-[(5-(N-(tert-butoxycarbonyl)amino)-3-chloropyridin-2-yl)methyl]-2-methyl-5-(1-pentanesulfonylcarbamoyl)-3H-imidazo[4,5-b]pyridine was obtained as colorless crystals (126 mg) from 3-[(5-(N-(tert-butoxycarbonyl)amino)-3-chloropyridin-2-yl)methyl]-2-methyl-3H-imidazo[4,5-b]pyridine-5-carboxylic acid (128 mg) and 1-pentanesulfonamide (70 mg). m.p. 193–194° C.

$^1$H-NMR (CDCl$_3$): 0.89 (3H, t, J=7 Hz), 1.25–1.50 (4H, m), 1.51 (9H, s), 1.84–1.96 (2H, m), 2.72 (3H, s), 3.51–3.59 (2H, m), 5.63 (2H, s), 6.65 (1H, br s), 7.06 (1H, d, J=8 Hz), 8.09–8.15 (2H, m), 8.25 (1H, br s), 9.55 (1H, br s). MASS (ESI): m/z 549 (M−1).

EXAMPLE 130

In the same manner as in Example 104, 3-[(5-(N-(tert-butoxycarbonyl)amino)-3-chloropyridin-2-yl)methyl]-2-methyl-5-((E)-1-penten-1-ylsulfonylcarbamoyl)-3H-imidazo[4,5-b]pyridine was obtained as pale-brown crystals (133 mg) from 3-[(5-(N-(tert-butoxycarbonyl)amino)-3-chloropyridin-2-yl)methyl]-2-methyl-3H-imidazo[4,5-b]pyridine-5-carboxylic acid (128 mg) and (E)-1-penten-1-ylsulfonamide sodium salt (79 mg). m.p. 202–204° C.

$^1$H-NMR (CDCl$_3$): 0.95 (3H, t, J=7 Hz), 1.47–1.61 (11H, m), 2.23–2.33 (2H, m), 2.70 (3H, s), 5.62 (2H, s), 6.59 (1H, d, J=15 Hz), 6.67 (1H, br s), 7.15 (1H, dt, J=15, 7 Hz), 8.04 (1H, d, J=8 Hz), 8.08–8.13 (2H, m), 8.26 (1H, br s), 10.03 (1H, br s). MASS (ESI): m/z 547 (M−1).

EXAMPLE 131

In the same manner as in Example 1, 3-[(5-(N-(tert-butoxycarbonyl)amino)-3-chloropyridin-2-yl)methyl]-2-methyl-5-[(4-methylbenzene)sulfonylcarbamoyl]-3H-imidazo[4,5-b]pyridine was obtained as pale-brown crystals (119 mg) from 3-[(5-(N-(tert-butoxycarbonyl)amino)-3-chloropyridin-2-yl)methyl]-2-methyl-3H-imidazo[4,5-b]pyridine-5-carboxylic acid (128 mg) and (4-methylbenzene)sulfonamide (79 mg). m.p. 163–165° C.

$^1$H-NMR (CDCl$_3$): 1.52 (9H, s), 2.42 (3H, s), 2.71 (3H, s), 5.63 (2H, s), 6.67 (1H, br s), 7.34 (2H, d, J=8 Hz), 7.96–8.09 (4H, m), 8.13 (1H, d, J=1 Hz), 8.30 (1H, br s). MASS (ESI): m/z 569 (M−1).

EXAMPLE 132

In the same manner as in Example 1, 3-[(3-chloro-5-(N-(ethoxycarbonyl)amino)pyridin-2-yl)methyl]-2-methyl-5-(1-pentanesulfonylcarbamoyl)-3H-imidazo[4,5-b]pyridine was obtained as colorless crystals (75 mg) from 3-[3-chloro (5-(N-(ethoxycarbonyl)amino)pyridin-2-yl)methyl]-2-methyl-3H-imidazo[4,5-b]pyridine-5-carboxylic acid (78 mg) and 1-pentanesulfonamide (47 mg). m.p. 232–233° C.

$^1$H-NMR (CDCl$_3$): 0.89 (3H, t, J=7 Hz), 1.24–1.50 (7H, m), 1.83–1.96 (2H, m), 2.72 (3H, s), 3.50–3.59 (2H, m), 4.24 (2H, q, J=7 Hz), 5.63 (2H, s), 6.84 (1H, br s), 8.06 (1H, d, J=8 Hz), 8.14 (1H, d, J=8 Hz), 8.18 (1H, d, J=2 Hz), 8.24 (1H, br s), 9.92 (1H, br s). MASS (ESI): m/z 521 (M−1).

EXAMPLE 133

In the same manner as in Example 104, 3-[(3-chloro-5-(N-(ethoxycarbonyl)amino)pyridin-2-yl)methyl]-2-methyl-5-((E)-1-penten-1-ylsulfonylcarbamoyl)-3H-imidazo[4,5-b]pyridine was obtained as colorless crystals (84 mg) from 3-[(3-chloro-5-(N-(ethoxycarbonyl)amino)pyridin-2-yl)methyl]-2-methyl-3H-imidazo[4,5-b]pyridine-5-carboxylic acid (78 mg) and (E)-1-penten-1-ylsulfonamide sodium salt (53 mg). m.p. 236–239° C.

$^1$H-NMR (CDCl$_3$): 0.95 (3H, t, J=7 Hz), 1.32 (3H, t, J=7 Hz), 1.54 (2H, q, J=7 Hz), 2.22–2.33 (2H, m), 2.71 (3H, s), 4.24 (2H, q, J=7 Hz), 5.63 (2H, s), 6.58 (1H, d, J=15 Hz), 6.86 (1H, br s), 7.14 (1H, dt, J=15, 7 Hz), 8.04 (1H, d, J=8 Hz), 8.10 (1H, d, J=8 Hz), 8.17 (1H, d, J=2 Hz), 8.24 (1H, br s), 10.01 (1H, br s). MASS (ESI): m/z 519 (M−1).

EXAMPLE 134

In the same manner as in Example 1, 3-[(3-chloro-5-(N-(ethoxycarbonyl)amino)pyridin-2-yl)methyl]-2-methyl-5-[(4-methylbenzene)sulfonylcarbamoyl]-3H-imidazo[4,5-b]pyridine was obtained as colorless crystals (71 mg) from 3-[3-chloro(5-(N-(ethoxycarbonyl)amino)pyridin-2-yl)methyl]-2-methyl-3H-imidazo[4,5-b]pyridine-5-carboxylic acid (78 mg) and (4-methylbenzene)sulfonamide (53 mg). m.p. 244–246° C.

$^1$H-NMR (CDCl$_3$): 1.32 (3H, t, J=7 Hz), 2.42 (3H, s), 2.71 (3H, s), 4.25 (2H, q, J=7 Hz), 5.64 (2H, s), 6.87 (1H, br s), 7.33 (2H, d, J=8 Hz), 7.96–8.08 (4H, m), 8.19 (1H, d, J=2 Hz), 8.26 (1H, br s). MASS (ESI): m/z 41 (M−1).

EXAMPLE 135

In the same manner as in Example 1, 3-[(5-(N-(isopropoxycarbonyl)amino)-3-chloropyridin-2-yl)methyl]-2-methyl-5-(1-pentanesulfonylcarbamoyl)-3H-imidazo[4,5-b]pyridine was obtained as colorless crystals (82 mg) from 3-[(5-(N-(isopropoxycarbonyl)amino)-3-chloropyridin-2-yl)methyl]-2-methyl-3H-imidazo[4,5-b]pyridine-5-carboxylic acid (90 mg) and 1-pentanesulfonamide (51 mg).

$^1$H-NMR (DMSO-d$_6$): 0.79 (3H, t, J=7 Hz), 1.16–1.40 (4H, m), 1.24 (6H, d, J=7 Hz), 1.62–1.75 (2H, m), 2.45 (3H, s), 3.46–3.56 (2H, m), 4.82–4.95 (1H, m), 5.90 (2H, s), 7.97 (1H, d, J=8 Hz), 8.11–8.18 (2H, m), 8.28 (1H, d, J=1 Hz). MS (ESI): m/z 535 (M−1). m.p. 228–230° C.

EXAMPLE 136

In the same manner as in Example 104, 3-[(5-(N-(isopropoxycarbonyl)amino)-3-chloropyridin-2-yl)methyl]-2-methyl-5-((E)-1-penten-1-ylsulfonylcarbamoyl)-3H-imidazo[4,5-b]pyridine was obtained as pale-yellow crystals (101 mg) from 3-[(5-(N-(isopropoxycarbonyl)amino)-3-chloropyridin-2-yl)methyl]-2-methyl-3H-imidazo[4,5-b]pyridine-5-carboxylic acid (90 mg) and (E)-1-penten-1-ylsulfonamide sodium salt (57 mg).

$^1$H-NMR (DMSO-d$_6$): 0.86 (3H, t, J=7 Hz), 1.24 (6H, d, J=7 Hz), 1.37–1.51 (2H, m), 2.20–2.30 (2H, m), 2.43 (3H, s), 4.84–4.95 (1H, m), 5.90 (2H, s), 6.78 (1H, d, J=8 Hz), 6.85–6.98 (1H, m), 7.94 (1H, d, J=8 Hz), 8.13 (2H, d, J=8 Hz), 8.28 (1H, d, J=1 Hz). MS (ESI): m/z 533 (M−1). m.p. 242–244° C.

EXAMPLE 137

In the same manner as in Example 1, 3-[(5-(N-(isopropoxycarbonyl)amino)-3-chloropyridin-2-yl)methyl]-2-methyl-5-((4-methylbenzene)sulfonylcarbamoyl)-3H-imidazo[4,5-b]pyridine was obtained as colorless crystals (68 mg) from 3-[(5-(N-(isopropoxycarbonyl)amino)-3-chloropyridin-2-yl)methyl]-2-methyl-3H-imidazo[4,5-b]pyridine-5-carboxylic acid (80 mg) and (4-methylbenzene)sulfonamide (51 mg).

$^1$H-NMR (CDCl$_3$): 1.31 (6H, d, J=7 Hz), 2.42 (3H, s), 2.71 (3H, s), 4.98–5.09 (1H, m), 5.64 (2H, s), 7.34 (2H, d, J=8 Hz), 8.00 (2H, d, J=1 Hz), 8.05 (2H, d, J=8 Hz), 8.18 (1H, d, J=1 Hz), 8.29 (1H, s). MS (ESI): m/z 555 (M−1). m.p. 229–231° C.

EXAMPLE 138

In the same manner as in Example 1, 3-((2,4-dichloropyridin-5-yl)methyl)-2-methyl-5-(1-pentanesulfonylcarbamoyl)-3H-imidazo[4,5-b]pyridine was obtained as pale-yellow crystals (182 mg) from 3-((2,4-dichloropyridin-5-yl)methyl)-2-methyl-3H-imidazo[4,5-b]pyridine-5-carboxylic acid (190 mg) and 1-pentanesulfonamide (128 mg).

$^1$H-NMR (CDCl$_3$): 0.89 (3H, t, J=7 Hz), 1.28–1.50 (4H, m), 1.83–1.95 (2H, m), 2.65 (3H, s), 3.53–3.60 (2H, m), 5.60 (2H, s), 7.53 (1H, s), 7.74 (1H, s), 8.16 (1H, d, J=8 Hz), 8.25 (1H, d, J=8 Hz). MS (ESI): m/z 468 (M−1). m.p. 161–163° C.

EXAMPLE 139

In the same manner as in Example 1, 3-((2,4-dichloropyridin-5-yl)methyl)-2-methyl-5-((4-methylbenzene)sulfonylcarbamoyl)-3H-imidazo[4,5-b]pyridine was obtained as pale-yellow crystals (195 mg) from 3-((2,4-dichloropyridin-5-yl)methyl)-2-methyl-3H-imidazo[4,5-b]pyridine-5-carboxylic acid (180 mg) and (4-methylbenzene)sulfonamide (137 mg).

$^1$H-NMR (DMSO-d$_6$): 2.39 (3H, s), 2.56 (3H, s), 5.83 (2H, s), 7.45 (2H, d, J=8 Hz), 7.86 (1H, d, J=8 Hz), 7.91 (1H, s), 7.94 (2H, s), 8.11 (1H, d, J=8 Hz), 8.23 (1H, s). MS (ESI): m/z 488 (M−1). m.p. 248–250° C.

EXAMPLE 140

In the same manner as in Example 85, 3-(2-chloro-4-(phenylethynyl)benzyl)-2,7-dimethyl-5-(1-pentanesulfonylcarbamoyl)-3H-imidazo[4,5-b]pyridine sodium salt was obtained as colorless crystals (133 mg) from 3-(2-chloro-4-(phenylethynyl)benzyl)-2,7-dimethyl-5-(1-pentanesulfonylcarbamoyl)-3H-imidazo[4,5-b]pyridine (172 mg). m.p. 175–178° C.

$^1$H-NMR (DMSO-d$_6$) 0.83 (3H, t, J=8 Hz), 1.18–1.46 (4H, m), 1.50–1.64 (2H, m), 2.46 (3H, s), 2.58 (3H, s), 2.99–3.09 (2H, m), 5.59 (2H, s), 6.45 (1H, d, J=8 Hz), 7.35–7.46 (4H, m), 7.51–7.60 (2H, m), 7.78 (1H, d, J=1 Hz), 7.85 (1H, s). MASS (ESI): m/z 547 (M−Na−1).

EXAMPLE 141

In the same manner as in Example 85, 3-[2-chloro-4-(5-chlorothiophen-2-yl)benzyl]-2-methyl-5-(1-pentanesulfonylcarbamoyl)-3H-imidazo[4,5-b]pyridine sodium salt was obtained as colorless crystals (78 mg) from 3-[2-chloro-4-(5-chlorothiophen-2-yl)benzyl]-2-methyl-5-(1-pentanesulfonylcarbamoyl)-3H-imidazo[4,5-b]pyridine (77 mg). m.p.:>250° C.

$^1$H-NMR (DMSO-d$_6$): 0.82 (3H, t, J=8 Hz), 1.27–1.36 (4H, m), 1.50–1.65 (2H, m), 2.48 (3H, s), 2.99–3.09 (2H, m), 5.59 (2H, s), 6.50 (1H, d, J=8 Hz), 7.17 (1H, d, J=4 Hz), 7.43 (1H, dd, J=8, 1 Hz), 7.47 (1H, d, J=4 Hz), 7.86 (1H, d, J=8 Hz), 7.94 (1H, d, J=8 Hz), 7.99 (1H, s). MASS (ESI): m/z 549 (M−Na−1).

EXAMPLE 142

In the same manner as in Example 85, 3-(2-chloro-4-(phenylethynyl)benzyl)-2,7-dimethyl-5-[(4-methylbenzene)sulfonylcarbamoyl]-3H-imidazo[4,5-b]pyridine sodium salt was obtained as colorless crystals (77 mg) from 3-(2-chloro-4-(phenylethynyl)-benzyl)-2,7-dimethyl-5-[(4-methylbenzene)sulfonylcarbamoyl]-3H-imidazo[4,5-b]pyridine (85 mg). m.p.:>250° C.

$^1$H-NMR (DMSO-d$_6$): 2.30–2.44 (3H, s), 2.57 (3H, s), 5.55 (2H, s), 6.41 (1H, d, J=8 Hz), 7.15 (2H, d, J=8 Hz), 7.36 (1H, dd, J=8, 1 Hz), 7.39–7.47 (3H, m), 7.51–7.60 (2H, m), 7.70 (2H, d, J=8 Hz), 7.77 (1H, d, J=1 Hz), 7.84 (1H, s). MASS (ESI): m/z 567 (M−Na−1).

EXAMPLE 143

In the same manner as in Example 85, 5-[(5-bromothiophen-2-yl)sulfonylcarbamoyl]-3-(2-chloro-4-phenylbenzyl)-2,7-dimethyl-3H-imidazo[4,5-b]pyridine sodium salt was obtained as colorless crystals (105 mg) from 5-[(5-bromothiophen-2-yl)sulfonylcarbamoyl]-3-(2-chloro-4-phenylbenzyl)-2,7-dimethyl-3H-imidazo[4,5-b]pyridine (134 mg). m.p. >250° C.

$^1$H-NMR (DMSO-d$_6$): 2.49 (3H, s), 2.58 (3H, s), 5.59 (2H, s), 6.47 (1H, d, J=8 Hz), 7.08 (1H, d, J=4 Hz), 7.27 (1H, d, J=4 Hz), 7.34–7.54 (4H, m), 7.65 (2H, d, J=8 Hz), 7.82–7.86 (2H, m). MASS (ESI): m/z 615 (M−Na−1).

EXAMPLE 144

3-[2-Chloro-4-(1-pentyloxy)benzyl]-2-methyl-5-[(4-methylbenzene)sulfonylcarbamoyl]-3H-imidazo[4,5-b]pyridine (200 mg) was dissolved in N,N-dimethylformamide (1.5 ml) at 80° C. and 1N sodium hydroxide (0.7 ml) was added dropwise at the same temperature, which was followed by stirring at room temperature for 1.5 hr. The precipitated crystals were collected by filtration and washed with a mixed solvent (1.5 ml) of N,N-dimethylformamide:water=2:1 and water (0.5 ml) to give 3-[2-chloro-4-(1-pentyloxy)benzyl]-2-methyl-5-[(4-methylbenzene)sulfonylcarbamoyl]-3H-imidazo[4,5-b]pyridine sodium salt (199 mg) as colorless crystals. m.p.: 308–310° C.

$^1$H-NMR (DMSO-d$_6$): 0.88 (3H, t, J=6 Hz), 1.20–1.42 (4H, m), 1.67 (2H, m), 2.30 (3H, s), 2.42 (3H, s), 3.92 (2H, t, J=6 Hz), 5.46 (2H, s), 6.43 (1H, d, J=8 Hz), 6.80 (1H, dd, J=8, 2 Hz), 7.10 (1H, d, J=2 Hz), 7.18 (2H, d, J=8 Hz), 7.74 (2H, d, J=8 Hz), 7.90 (1H, d, J=8 Hz), 8.00 (1H, d, J=8 Hz).

EXAMPLE 145

In the same manner as in Example 1, 3-(4-(N-(ethoxycarbonyl)-N-methylamino)-2-chlorobenzyl)-2-methyl-5-(1-pentanesulfonylcarbamoyl)-3H-imidazo[4,5-b]pyridine (210 mg) was obtained as a white powder from 3-(4-(N-(ethoxycarbonyl)-N-methylamino)-2-chlorobenzyl)-2-methyl-3H-imidazo[4,5-b]pyridine-5-carboxylic acid (177 mg). m.p.: 149–150° C.

$^1$H-NMR (CDCl$_3$): 0.89 (3H, t, J=7 Hz), 1.26 (3H, t, J=7 Hz), 1.24–1.52 (4H, m), 1.78–2.02 (2H, m), 2.65 (3H, s), 3.30 (3H, s), 3.44–3.66 (2H, m), 4.19 (2H, q, J=7 Hz), 5.56 (2H, s), 6.66 (1H, d, J=8 Hz), 7.11 (1H, dd, J=8 and 2 Hz), 7.46 (1H, d, J=2 Hz), 8.13 (1H, d, J=8 Hz), 8.21 (1H, d, J=8 Hz), 9.85 (1H, br. s). MASS (APCI): m/e 536 (M+H)$^+$.

EXAMPLE 146

In the same manner as in Example 1, 3-(4-(N-(benzyloxycarbonyl)-N-methylamino)-2-chlorobenzyl)-2-methyl-5-(1-pentanesulfonylcarbamoyl)-3H-imidazo[4,5-b]pyridine (107 mg) was obtained as a white powder from 3-(4-(N-(benzyloxycarbonyl)-N-methylamino)-2-chlorobenzyl)-2-methyl-3H-imidazo[4,5-b]pyridine-5-carboxylic acid (102 mg). m.p.: 120–121° C.

$^1$H-NMR (CDCl$_3$): 0.89 (3H, t, J=7 Hz), 1.18–1.55 (4H, m), 1.78–2.02 (2H, m), 2.63 (3H, s), 3.32 (3H, s), 3.45–3.65 (2H, m), 5.17 (2H, m), 5.56 (2H, s), 6.66 (1H, d, J=8 Hz), 7.12 (1H, dd, J=8 and 2 Hz), 7.22–7.44 (5H, m), 7.47 (1H, d, J=2 Hz), 8.13 (1H, d, J=8 Hz), 8.21 (1H, d, J=8 Hz), 9.83 (1H, br. s). MASS (APCI): m/e 598 (M+H)$^+$.

Industrial Applicability

The above-mentioned sulfonamide compounds and pharmaceutically acceptable salts thereof of the present invention are useful as pharmaceutical preparations which, based on the hypoglycemic action, are used for the prophylaxis and treatment of, for example, impaired glucose tolerance disorder, diabetes (e.g., type II diabetes), gestational diabetes, diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy and the like), insulin resistance syndrome (e.g., insulin receptor abnormality, Rabson-Mendenhall syndrome, leprechaunism, Kobberling-Dunnigan syndrome, Seip syndrome, Lawrence syndrome, Cushing syndrome, acromegaly and the like), polycystic ovary syndrome, hyperlipidemia, atherosclerosis, cardiovascular diseases (e.g., stenocardia, cardiac failure and the like), hyperglycemia (e.g., those characterized by abnormal saccharometabolism such as eating disorders), pancreatitis, osteoporosis, hyperuricemia, hypertension, inflammatory bowel diseases, skin disorders related to an anomaly of differentiation of epidermic cells; and which, based on the cGMP-PDE (particularly PDE-V) inhibitory action, smooth muscle relaxing action, bronchodilating action, vasodilating action, smooth muscle cell inhibitory action, allergy suppressing action and the like, are used for angina pectoris, pulmonary hypertension, congestive heart failure, glomerulopathy (e.g., diabetic glomerulosclerosis), tubulointerstitial disorders (e.g., kidney diseases induced by FK506, cyclosporine and the like), renal failure, angiostenosis (e.g., after percutaneous arterioplasty), peripheral vascular diseases, cerebral apoplexy, chronic reversible obstructive impairment (e.g., bronchitis, asthma inclusive of chronic asthma and allergic asthma), autoimmune diseases, allergic rhinitis, urticaria, glaucoma, diseases characterized by impaired intestinal motility (e.g., irritable bowel syndrome), impotence (e.g., organic impotence, psychic impotence and the like), nephritis, cancer cachexia, restenosis after PTCA, cachexia (e.g., progressive weight loss due to lipolysis, myolysis, anemia, edema, anorexia and the like in chronic diseases such as cancer, tuberculosis, endocrine diseases and AIDS, and the like. A combination of a compound of formula (I) or pharmaceutically acceptable salts thereof and a retinoid is useful for treating disease states caused by uncontrolled cell proliferation, including cancer, restenosis and atherosclerosis.

This application is based on application Ser. Nos. 259283/1999, 367540/1998 and 346175/1998 filed in Japan on Aug. 9, 1999, Dec. 24, 1998 and Dec. 4, 1998, respectively, the contents of which are incorporated hereinto by reference.

What is claimed is:

1. The sulfonamide compound of formula (I) comprising:

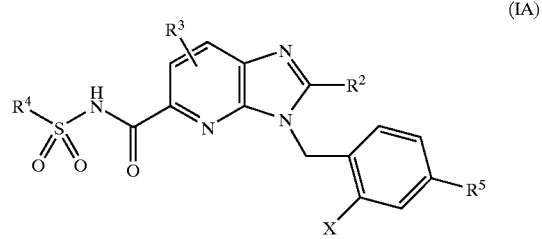

(IA)

wherein R$^2$ is lower alkyl or lower alkoxy,
R$^3$ is hydrogen or lower alkyl,
R$^4$ is lower alkenyl optionally substituted by aryl or heterocyclic group, aryl optionally substituted by carboxy or protected carboxy, lower alkyl optionally substituted by acyloxy, amino optionally substituted by lower alkyl, or heterocyclic group optionally substituted by halogen, $R^5$ is pyrrolyl, furyl, or amino substituted by protected carboxy and optionally substituted by lower alkyl, X is halogen, and Y is CH or N, or a salt or a solvate thereof.

2. The sulfonamide compound of claim 1, wherein $R^5$ is amino substituted by protected carboxy and lower alkyl, or a salt thereof.

3. The sulfonamide compound of claim 2, wherein $R^2$ is lower alkyl, and $R^4$ is lower alkyl or amino optionally substituted by lower alkyl, or a salt thereof.

4. The sulfonamide compound of claim 1, which is:

3-(4-(N-(tert-butoxycarbonyl)-N-methylamino)-2-chlorobenzyl)-2-methyl-5-(1-pentanesulfonylcarbamoyl)-3H-imidazo[4,5-b]pyridine, 3-(4-(N-(tert-butoxycarbonyl)-N-methylamino)-2-chlorobenzyl)-2-methyl-5-((4-methylbenzene)sulfonylcarbamoyl)-3H-imidazo[4,5-b]pyridine, 3-(4-(N-(tert-butoxycarbonyl)-N-methylamino)-2-chlorobenzyl)-2-methyl-5-(1-pentane-sulfonylcarbamoyl)-3H-imidazo[4,5-b]pyridine, 5-(1-butanesulfonylcarbamoyl)-3-[2-chloro-4-(2-furyl)benzyl]-2-methyl-3H-imidazol[4,5-b]pyridine, 3-[2-chloro-4-(2-furyl)benzyl]-2-methyl-5-(1-pentanesulfonylcarbamoyl)-3H-imidazo[4,5-b]pyridine, 3-[2-chloro-4-(2-furyl)benzyl]-2-methyl-5-(4-methylbenzene)sulfonylcarbamoyl]-3H-imidazo[4,5-b]pyridine, 3-[4-(N-(tert-butoxycarbonyl)-N-ethylamino-2-chlorobenzyl]-2-methyl-5-(1-pentanesulfonylcarbamoyl)-3H-imidazo[4,5-b]pyridine, 3-(4-(N-(tert-butoxycarbonyl)-N-ethylamino)-2-chlorobenzyl)-2-methyl-5-((4-methyl-benzene)sulfonylcarbamoyl)-3H-imidazo[4,5-b]pyridine, 3-(4-(N-(tert-butoxycarbonyl)-N-methylamino)-2-chlorobenzyl)-2,7-dimethyl-5-(1pentanesulfonylcarbamoyl)-3H-imidazo[4,5-b]pyridine, 3-(4-(N-(tert-butoxycarbonyl)-N-methylamino)-2-chlorobenzyl)-2,7-dimethyl-5-((4methylbenzene)sulfonylcarbamoyl)-3H-imidazo[4,5-b]pyridine, 3-[4-(N-(tert-butoxycarbonyl)-N-ethylamino)-2-chlorobenzyl]-2,7-dimethyl-5-(1pentanesulfonylcarbamoyl)-3H-imidazo[4,5-b]pyridine, 3-[4-(N-(tert-butoxycarbonyl)-N-ethylamino)-2-chlorobenzyl]-2,7-dimethyl-5-((4methylbenzene)sulfonylcarbamoyl)-3H-imidazo[4,5-b]pyridine, 3-(2-chloro-4-(1-pyrrolyl)benzyl)-2-methyl-5-((4-methylbenzene)sulfonylcarbamoyl)-3H-imidazo[4,5-b]pyridine, 3-[2-chloro-4-(2-furyl)benzyl]-2,7-dimethyl-5-(1-pentanesulfonylcarbamoyl)-3H-imidazo[4,5-b]pyridine, 3-[2-chloro-4-(2-furyl)benzyl]-2,7-dimethyl-5-[(4-methylbenzene)sulfonylcarbamoyl]-3H-imidazo[4,5-b]pyridine, 3-[2-chloro-4-(2-furyl)benzyl]-2,7-dimethyl-5-(1-butanesulfonylcarbamoyl)-3H-imidazo[4,5-b]pyridine, 3-(4-(N-(tert-butoxycarbonyl)-N-methylamino)-2-chlorobenzyl)-2-methyl-5-(1-pentanesulfonylcarbamoyl)-3H-imidazo[4,5-b]pyridine sodium salt, 3-(2-chloro-4-(N-methyl-N-(1-propoxycarbonyl)amino)benzyl)-2-methyl-5-(1-pentanesulfonylcarbamoyl)-3H-imidazo]4,5-b]pyridine, 3-(2-chloro-4-(N-methyl-N-(1-isopropoxycarbonyl)amino)benzyl)-2-methyl-5-(1-pentanesulfonylcarbamoyl)-3H-imidazo]4,5-b]pyridine, 3-(4-(N-(tert-butoxycarbonyl)amino)-2-chlorobenzyl)-2-methyl-5-(1-pentane-sulfonylcarbamoyl)-3H-imidazo[4,5-b]pyridine, 3-(2-chloro-4-(N-(isopropoxycarbonyl)amino)benzyl)-2-methyl-5-((E)1-penten-1-ylsulfonylcarbamoyl)-3H-imidazo]4,5-b]pyridine, 5-(1-butanesulfonylcarbamoyl)-3-(2-chloro-4-(N-(isopropoxycarbonyl)amino)benzyl)-2-methyl-3H-imidazo[4,5-b]pyridine, 3-(2-chloro-4-(N-(ethoxycarbonyl-N-methylamino)benzyl)-2-methyl-5-((E)1-penten-1-ylsulfonylcarbamoyl)-3H-imidazo]4,5-b]pyridine, 5-(1-butanesulfonylcarbamoyl)-3-(2-chloro-4-(N-(ethoxycarbonyl-N-methylamino)benzyl)-2-methyl-3H-imidazo[4,5-b]pyridine, 3-(4-(N-(1-propoxycarbonyl)amino)-2-chlorobenzyl)-2-methyl-5-(1-pentanesulfonyl-carbamoyl)-3H-imidazo[4,5-b]pyridine, 3-(4-(N-(1-isopropoxycarbonyl)amino)-2-chlorobenzyl)-2-methyl-5-(1-pentanesulfonyl-carbamoyl)-3H-imidazo[4,5-b]pyridine, 5-(1-butanesulfonylcarbamoyl)-3-(4-(N-(t-butoxycarbonylamino)-2-chlorobenzyl-2-methyl-3H-imidazo[4,5-b]pyridine, 3-(4-ethoxycarbonylamino-2-chlorobenzyl)-2-methyl-5-(1-butanesulfonylcarbamoyl)-3H-imidazo[4,5-b]pyridine, 3-(4-(N-t-butoxycarbonylamino)-2-chlorobenzyl)-2-methyl-5-((E)-1-penten-1-ylsulfonylcarbamoyl)-3H-imidazo[4,5-b]pyridine, 3-(4-ethoxycarbonylamino-2-chlorobenzyl)-2-methyl-5-((E)-1-penten-1-ylsulfonyl-carbamoyl)-3H-imidazo[4,5-b]pyridine, 3-(4-(N-(tert-butoxycarbonyl)-N-methylamino)-2-chlorobenzyl)-2-methyl-5-((E)-1-penten-1-ylsulfonyl-carbamoyl)-3H-imidazo[4,5-b]pyridine, 3-[(5-(N-(tert-butoxycarbonyl)amino)-3-chloropyridin-2-yl)methyl]-2-methyl-5-(1-pentanesulfonylcarbamoyl)-3H-imidazo[4,5-b]pyridine, 3-[(5-(N-(tert-butoxycarbonyl)amino)-3-chloropyridin-2-yl)methyl]-2-methyl-5-((E)-1-penten-1-ylsulfonylcabamoyl)-3H-imidazo[4,5-b]pyridine, 3-[(5-(N-(tert-butoxycarbonyl)amino)-3-chloropyridin-2-yl)methyl]-2-methyl-5-[(5methylbenzene)sulfonylcarbamoyl]-3H-imidazo[4,5-b]pyridine, 3-[(3-chloro-5-(N-(ethoxycarbonyl)amino)pyridin-2-yl)methyl]-2-methyl-5-(1-pentanesulfonylcarbamoyl)-3H-imidazo[4,5-b]pyridine, 3-[(3-chloro-5-(N-(ethoxycarbonyl)amino)pyridin-2-yl)methyl]-2-methyl-5-((E)-1-penten-1-ylsulfonylcarbamoyl)-3H-imidazo[4,5-b]pyridine, 3-[(3-chloro-5-(N-(ethoxycarbonyl)amino)pyridin-2-yl)methyl]-2-methyl-5-[(4-methylbenzene)sulfonylcarbamoyl]-3H-imidazo[4,5-b]pyridine, 3-[(5-(N-(isopropoxycarbonyl)amino)-3-chloropyridin-2-yl)methyl]-2-methyl-5-(1-pentanesulfonylcarbamoyl)-3H-imidazo[4,5-b]pyridine, 3-[(5-(N-(isopropoxycarbonyl)amino)-3-chloropyridin-2-yl)methyl]-2-methyl-5-((E)-1-penten-1-ylsulfonylcarbamoyl)-3H-imidazo[4,5-b]pyridine, 3-[(5-(N-(isopropoxycarbonyl)amino)-3-chloropyridin-2-yl)methyl]-2-methyl-5-((4-methylbenzene)sulfonylcarbamoyl)-3H-imidazo[4,5-b]pyridine, 3-(4-(N-(ethoxycarbonyl)-N-methylamino)-2-chlorobenzyl)-2-methyl-5-(1-pentane-sulfonylcarbamoyl)-3H-imidazo[4,5-b]pyridine, or 3-(4-(N-(benzyloxycarbonyl)-N-methylamino)-2-chlorobenzyl)-2-methyl-5-(1-pentanesulfonylcarbamoyl)-3H-imidazo[4,5-b]pyridine, or a salt thereof.

5. The sulfonamide compound of claim 4, which is:

3-(4-N-(ethoxycarbonyl)-N-methylamino)-2-chlorobenzyl)-2-methyl-5-(1-pentanesulfonylcarbamoyl)-3H-imidazo[4,5-b]pyridine, 3-[2-chloro-4-(2-furyl)benzyl]-2-methyl-5-[(4-methylbenzene)sulfonylcarbamoyl]-3H-imidazo[4,5-b]pyridine, 3-(2-chloro-4-(1-pyrrolyl)benzyl)-2-methyl-5-(1-pentanesulfonylcarbamoyl)-3H-imidazo[4,5-b]pyridine, 3-(4-N-(isopropoxycarbonyl)amino)-2-chlorobenzyl)-2-methyl-5-(1-pentane-sulfonylcarbamoyl)-3H-imidazo[4,5-b]pyridine, 3-[(5-(N-(tert-butoxycarbonyl)amino)-3-chloropyridin-2-yl)methyl]-5-[(4-methylbenzene)sulfonylcarbamoyl]-3H-imidazo[4,5-b]pyridine, or a salt thereof.

6. A method of preventing and/or treating impaired glucose tolerance disorder, diabetes, gestational diabetes, a diabetic complication, insulin resistance syndrome, polycystic ovary syndrome, hyperlipidemia, atherosclerosis, a cardiovascular disease, hyperglycemia, pancreatitis, osteoporosis, hyperuricemia, hypertension, an inflammatory bowel disease, a skin disorder related to an anomaly of differentiation of epidermic cells in a mammal, that comprises administering to said mammal, a therapeutically effective amount of the sulfonamide compound of claim 1 or a pharmaceutically acceptable salt thereof.

7. A composition comprising the compound of claim 1.

8. The composition of claim 7 further comprising a pharmaceutically acceptable carrier or excipient.

9. The composition of claim 7 that comprises an adjuvant, auxiliary substance, stabilizer, moistening agent, emulsifier, or buffering agent, or a combination of two or more thereof.

10. The composition of claim 7 in the form of a capsule, tablet, sugar-coated tablet, or granule.

11. The composition of claim 7 in the form of a suppository, gel or ointment.

12. The composition of claim 7 in the form of a liquid or lotion.

13. The composition of claim 7 in the form of a suspension or emulsion.

14. The composition of claim 7 comprising a unit dose of said compound ranging from 0.1 mg to 1000 mg.

15. A method of reducing blood sugar level in a mammal comprising:

administering a therapeutically effective amount of the sulfonamide compound of claim 1 or a pharmaceutically acceptable salt thereof to said mammal.

16. The method of claim 15 that comprises treating a human.

17. The method of claim 15 comprising administering to said mammal a daily dose of said sulfonamide compound ranging from 0.1 mg to about 1000 mg.

18. A method for preventing and/or treating a disease associated with a high blood sugar level comprising administering to a mammal in need thereof a therapeutically effective amount of the compound of claim 1.

19. The method of claim 18 that comprises treating a human.

20. The method of claim 18 comprising administering to said mammal a daily dose of said compound ranging from 0.1 mg to about 1000 mg.

21. The method of claim 18 that comprises preventing and/or treating impaired glucose tolerance disorder, diabetes, gestational diabetes, diabetic complications, insulin resistance syndrome, or hyperglycemia.

22. A method for producing the sulfonamide compound of claim 1 or a salt thereof, comprising reacting a compound of formula (II):

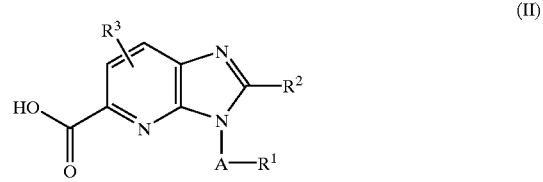

(II)

wherein $R^1$ is an aryl or heterocyclic group substituted by at least one substituent selected from the group consisting of (1) unsubstituted aryl, (2) a heterocyclic group optionally substituted by oxo or halogen, (3) halogen, (4) halo(lower)alkyl, (5) lower alkoxy optionally substituted by cyclo(lower)alkyl, (6) amino optionally substituted by at least one substituent selected from the group consisting of lower alkyl optionally substituted by cyclo(lower)alkyl, protected carboxy, acyl, lower alkylcarbamoyl, and lower alkanesulfonyl, (7) nitro and (8) lower alkynyl optionally substituted by aryl, $R^2$ is a lower alkyl or lower alkoxy, $R^3$ is hydrogen or lower alkyl, and A is a lower alkylene, or reactive derivative at the carboxy thereof or a salt thereof, with a compound of formula (III):

$R^4—SO_2NH_2$ (III)

wherein $R^4$ is a lower alkenyl optionally substituted by aryl or heterocyclic group, aryl optionally substituted by carboxy or protected carboxy, lower alkyl optionally substituted by acyloxy, amino optionally substituted by lower alkyl, or heterocyclic group optionally substituted by halogen, or a salt thereof.

23. A method of treatment according to claim 6.
24. A method of treatment according to claim 15.
25. A method of treatment according to claim 18.
26. A method for inhibiting cGMP-PDE or PDE-V in a mammal comprising administering to said mammal an amount of the compound of claim 1 effective to inhibit cGMP-PDE or PDE-V.
27. A method for relaxing smooth muscle in a mammal comprising administering to said mammal an amount of the compound of claim 1 effective to relax smooth muscle.

28. A method for bronchodilation or vasodilation in a mammal comprising administering to said mammal an amount of the compound of claim 1 effective to provide brochodilation or vasodilation.

29. A method for making a therapeutic agent comprising admixing the compound of claim 1 or a pharmaceutically acceptable salt thereof, with a pharmaceutically acceptable excipient or carrier.

30. A salt of the compound of claim 1.

31. The salt of claim 30 that is an alkali metal salt.

32. The salt of claim 30 that is an alkaline earth metal salt.

33. The salt of claim 30 that is a salt with an inorganic base.

34. The salt of claim 30 that is a salt with an organic amine.

35. The salt of claim 30 that is a salt with an inorganic acid.

36. The salt of claim 30 that is a salt with an organic carboxylic acid.

37. The salt of claim 30 that is a salt with an sulfonic acid.

38. The salt of claim 30 that is a salt with an amino acid.

39. A solvate of the compound of claim 1.

40. A hydrate of the compound of claim 1.

41. An ethanol solvate of the compound of claim 1.

42. An isomer of the compound of claim 1.

43. A mixture of isomers of the compound of claim 1.

44. An enantiomer of the compound of claim 1.

45. A diasteromer of the compound of claim 1.

* * * * *